United States Patent
Yuen et al.

(10) Patent No.: US 8,454,528 B2
(45) Date of Patent: Jun. 4, 2013

(54) NON-CONTACT PHYSIOLOGIC MOTION SENSORS AND METHODS FOR USE

(75) Inventors: Andrea Yuen, Honolulu, HI (US); Amy Droitcour, San Francisco, CA (US); Anders Host Madsen, Honolulu, HI (US); Byung Kwon Park, Honolulu, HI (US); Charles El Hourani, Honolulu, HI (US); Tommy Shing, Honolulu, HI (US)

(73) Assignee: Kai Medical, Inc., Honolulu, HI (US)

( * ) Notice: Subject to any disclaimer, the term of this patent is extended or adjusted under 35 U.S.C. 154(b) by 937 days.

(21) Appl. No.: 12/418,518

(22) Filed: Apr. 3, 2009
(Under 37 CFR 1.47)

(65) Prior Publication Data
US 2010/0130873 A1  May 27, 2010

Related U.S. Application Data

(60) Provisional application No. 61/072,983, filed on Apr. 3, 2008, provisional application No. 61/072,982, filed on Apr. 3, 2008, provisional application No.
(Continued)

(51) Int. Cl.
*A61B 5/08* (2006.01)
*G01S 13/58* (2006.01)
*G01S 13/00* (2006.01)

(52) U.S. Cl.
USPC ...... 600/534; 340/539.12; 342/114; 342/115; 342/152; 600/407

(58) Field of Classification Search
USPC .......... 600/407, 534; 340/447, 539.1, 539.12, 340/539.15; 342/28, 114, 115
See application file for complete search history.

(56) References Cited

U.S. PATENT DOCUMENTS
3,796,208 A   3/1974   Bloice
4,438,771 A   3/1984   Friesen et al.
(Continued)

FOREIGN PATENT DOCUMENTS
WO   WO 2007/143535   12/2007
WO   WO 2008/105837    9/2008

OTHER PUBLICATIONS

Droitcour, Amy, "Non-Contact Measurement of Heart and Respiration Rates With a Single-Chip Microwave Doppler Radar", Nov. 2006, Proquest, DAI-B 67/05, p. 2736, ISBN: 9780542706615, ProQuest document ID: 1216744471.*

(Continued)

*Primary Examiner* — Navin Natnithithadha
*Assistant Examiner* — Eric Messersmith
(74) *Attorney, Agent, or Firm* — Knobbe, Martens, Olson & Bear LLP

(57) ABSTRACT

A radar-based physiological motion sensor is disclosed. Doppler-shifted signals can be extracted from the signals received by the sensor. The Doppler-shifted signals can be digitized and processed subsequently to extract information related to the cardiopulmonary motion in one or more subjects. The information can include respiratory rates, heart rates, waveforms due to respiratory and cardiac activity, direction of arrival, abnormal or paradoxical breathing, etc. In various embodiments, the extracted information can be displayed on a display.

46 Claims, 71 Drawing Sheets

Related U.S. Application Data

61/123,017, filed on Apr. 3, 2008, provisional application No. 61/123,135, filed on Apr. 3, 2008, provisional application No. 61/125,021, filed on Apr. 21, 2008, provisional application No. 61/125,019, filed on Apr. 21, 2008, provisional application No. 61/125,018, filed on Apr. 21, 2008, provisional application No. 61/125,023, filed on Apr. 21, 2008, provisional application No. 61/125,027, filed on Apr. 21, 2008, provisional application No. 61/125,022, filed on Apr. 21, 2008, provisional application No. 61/125,020, filed on Apr. 21, 2008, provisional application No. 61/125,164, filed on Apr. 22, 2008, provisional application No. 61/128,743, filed on May 23, 2008, provisional application No. 61/137,519, filed on Jul. 30, 2008, provisional application No. 61/137,532, filed on Jul. 30, 2008, provisional application No. 61/194,838, filed on Sep. 29, 2008, provisional application No. 61/194,836, filed on Sep. 29, 2008, provisional application No. 61/194,839, filed on Sep. 29, 2008, provisional application No. 61/194,840, filed on Sep. 29, 2008, provisional application No. 61/194,848, filed on Sep. 30, 2008, provisional application No. 61/196,762, filed on Oct. 17, 2008, provisional application No. 61/200,761, filed on Dec. 2, 2008, provisional application No. 61/200,876, filed on Dec. 3, 2008, provisional application No. 61/141,213, filed on Dec. 29, 2008, provisional application No. 61/204,881, filed on Jan. 9, 2009, provisional application No. 61/204,880, filed on Jan. 9, 2009, provisional application No. 61/206,356, filed on Jan. 30, 2009, provisional application No. 61/154,176, filed on Feb. 20, 2009, provisional application No. 61/154,728, filed on Feb. 23, 2009, provisional application No. 61/154,732, filed on Feb. 23, 2009.

(56) References Cited

U.S. PATENT DOCUMENTS

| | | | |
|---|---|---|---|
| 4,757,825 | A | 7/1988 | Diamond |
| 5,230,094 | A | 7/1993 | Kitching et al. |
| 5,348,008 | A | 9/1994 | Bornn et al. |
| 5,349,524 | A | 9/1994 | Daft et al. |
| 5,445,156 | A | 8/1995 | Daft et al. |
| 5,619,995 | A | 4/1997 | Lobodzinski |
| 5,683,424 | A | 11/1997 | Brown et al. |
| 5,706,013 | A * | 1/1998 | Melvin et al. ............... 342/159 |
| 6,031,482 | A | 2/2000 | Lemaitre |
| 6,062,216 | A | 5/2000 | Corn |
| 6,150,941 | A | 11/2000 | Geiger et al. |
| 6,208,286 | B1 | 3/2001 | Rostislavovich |
| 6,661,345 | B1 | 12/2003 | Bevan et al. |
| 6,679,830 | B2 | 1/2004 | Kolarovic et al. |
| 6,840,907 | B1 | 1/2005 | Brydon |
| 6,875,176 | B2 | 4/2005 | Mourad et al. |
| 6,909,397 | B1 | 6/2005 | Greneker, III et al. |
| 6,984,207 | B1 | 1/2006 | Sullivan et al. |
| 7,025,729 | B2 | 4/2006 | de Chazal et al. |
| 7,155,171 | B2 | 12/2006 | Ebert et al. |
| 7,345,618 | B1 | 3/2008 | Cole et al. |
| 7,361,146 | B1 | 4/2008 | Bharmi |
| 7,417,727 | B2 | 8/2008 | Polonskiy |
| 7,432,847 | B2 | 10/2008 | Fedotov et al. |
| 7,435,221 | B1 | 10/2008 | Bharmi |
| 7,567,200 | B1 | 7/2009 | Osterweil |
| 8,130,862 | B2 * | 3/2012 | Forenza et al. ............... 375/295 |
| 2002/0042565 | A1 | 4/2002 | Cooper et al. |
| 2002/0058875 | A1 | 5/2002 | Doten et al. |
| 2005/0128123 | A1 | 6/2005 | Greneker, III et al. |
| 2006/0079773 | A1 | 4/2006 | Mourad |
| 2006/0172860 | A1 | 8/2006 | Estrella |
| 2006/0184056 | A1 | 8/2006 | de Chazal et al. |
| 2007/0197881 | A1 | 8/2007 | Wolf et al. |
| 2008/0074307 | A1 | 3/2008 | Boric-Lubecke et al. |
| 2008/0077015 | A1 | 3/2008 | Boric-Lubecke et al. |
| 2008/0119716 | A1 * | 5/2008 | Boric-Lubecke et al. .... 600/407 |
| 2008/0238757 | A1 * | 10/2008 | Lin et al. ...................... 342/22 |
| 2008/0275349 | A1 | 11/2008 | Halperin et al. |
| 2009/0278728 | A1 | 11/2009 | Morgan |
| 2010/0152600 | A1 | 6/2010 | Droitcour et al. |
| 2010/0201572 | A1 * | 8/2010 | Lackey et al. ............... 342/373 |
| 2010/0204550 | A1 | 8/2010 | Heneghan et al. |
| 2010/0204587 | A1 | 8/2010 | Lin et al. |
| 2010/0240999 | A1 | 9/2010 | Droitcour et al. |
| 2010/0249630 | A1 | 9/2010 | Droitcour et al. |
| 2010/0249633 | A1 | 9/2010 | Droitcour et al. |
| 2010/0292568 | A1 | 11/2010 | Droitcour et al. |

OTHER PUBLICATIONS

Massagram, et al., "Feasibility of Heart Rate Variability Measurement from Quadrature Doppler Radar Using Arctangent Demodulation with DC Offset Compensation," Aug. 26, 2007, Engineering in Medicine and Biology Society, 2007. EMBS 2007. 29th Annual International Conference of the IEEE, pp. 1643-1646.*

Lubecke, O.B., "10 GHz Doppler radar sensing of respiration and heart movement," 2002, Bioengineering Conference. Proceedings of the IEEE 28th Annual Northeast, pp. 55-56.*

Droitcour, et al., "Range Correlation and I/Q Performance Benefits in Single-Chip Silicon Doppler Radars for Noncontact Cardiopulmonary Monitoring," Mar. 2004, IEEE Transactions on Microwave Theory and Techniques, vol. 52, No. 3, pp. 838-848.*

Park, "Design and Development of a Doppler Radar System for Robust Cardiopulmonary Monitoring," Aug. 2008, Proquest, DAI-B 69/02, ISBN: 9780549482383, ProQuest document ID: 1481670141.*

Li and Lin, "Complex signal demodulation and random body movement cancellation techniques for non-contact vital sign detection," Jun. 20, 2008, Microwave Symposium Digest, 2008 IEEE MTT-S International, pp. 567-570.*

Park et al., "Center Tracking Quadrature Demodulation for a Doppler Radar Motion Detector," Jun. 8, 2007, Microwave Symposium. IEEE/MTT-S International, pp. 1323-1326.*

International Search Report in Application No. PCT/US2009/039560 dated Jun. 15, 2009.

Fox, et al.,"An Evaluation of a Non-contact Biomotion Sensor with Actimetry," Proc. 29th IEEE EMBS Conference, Aug. 2007.

International Search Report in Application No. PCT/US2010/035023 dated Oct. 5, 2010.

* cited by examiner

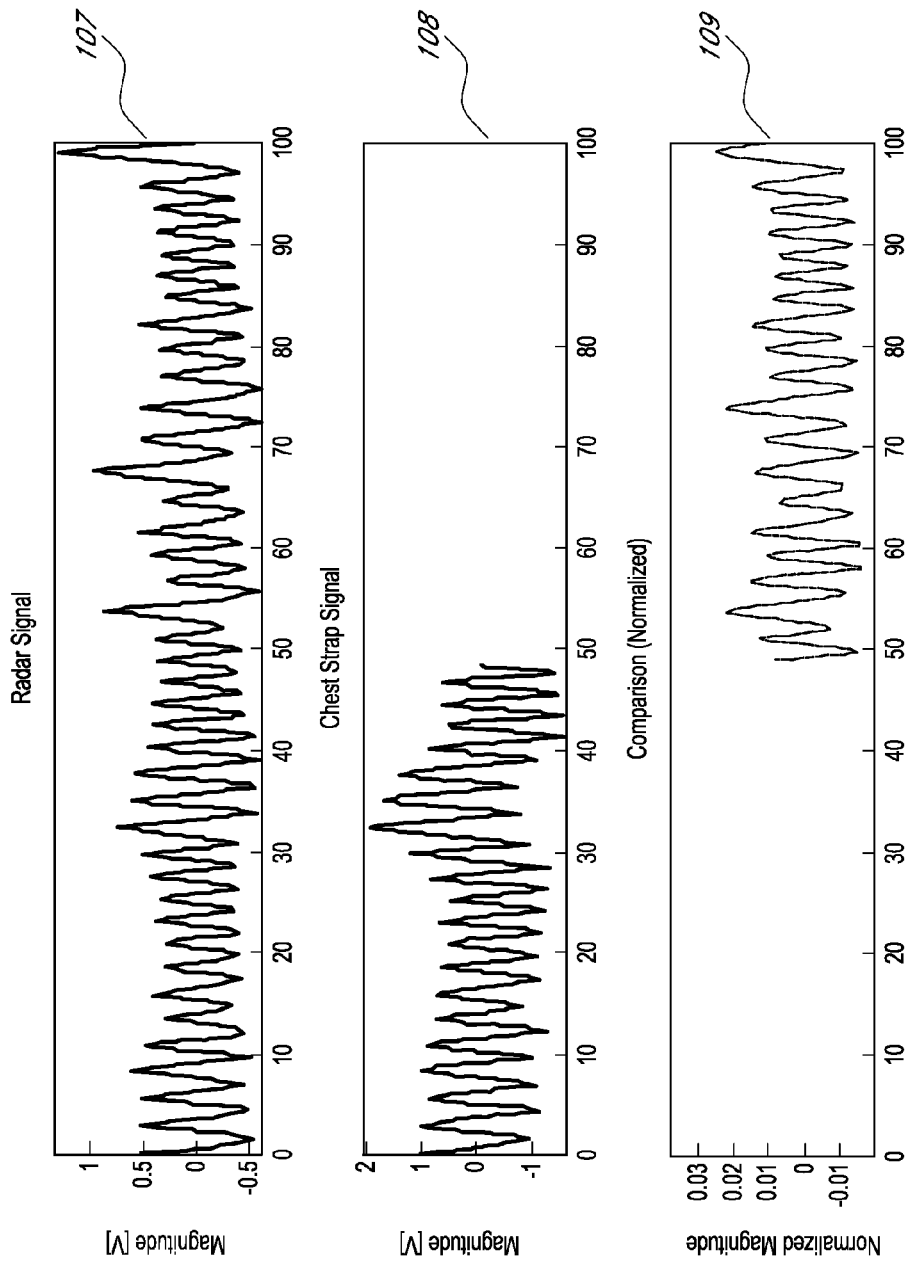

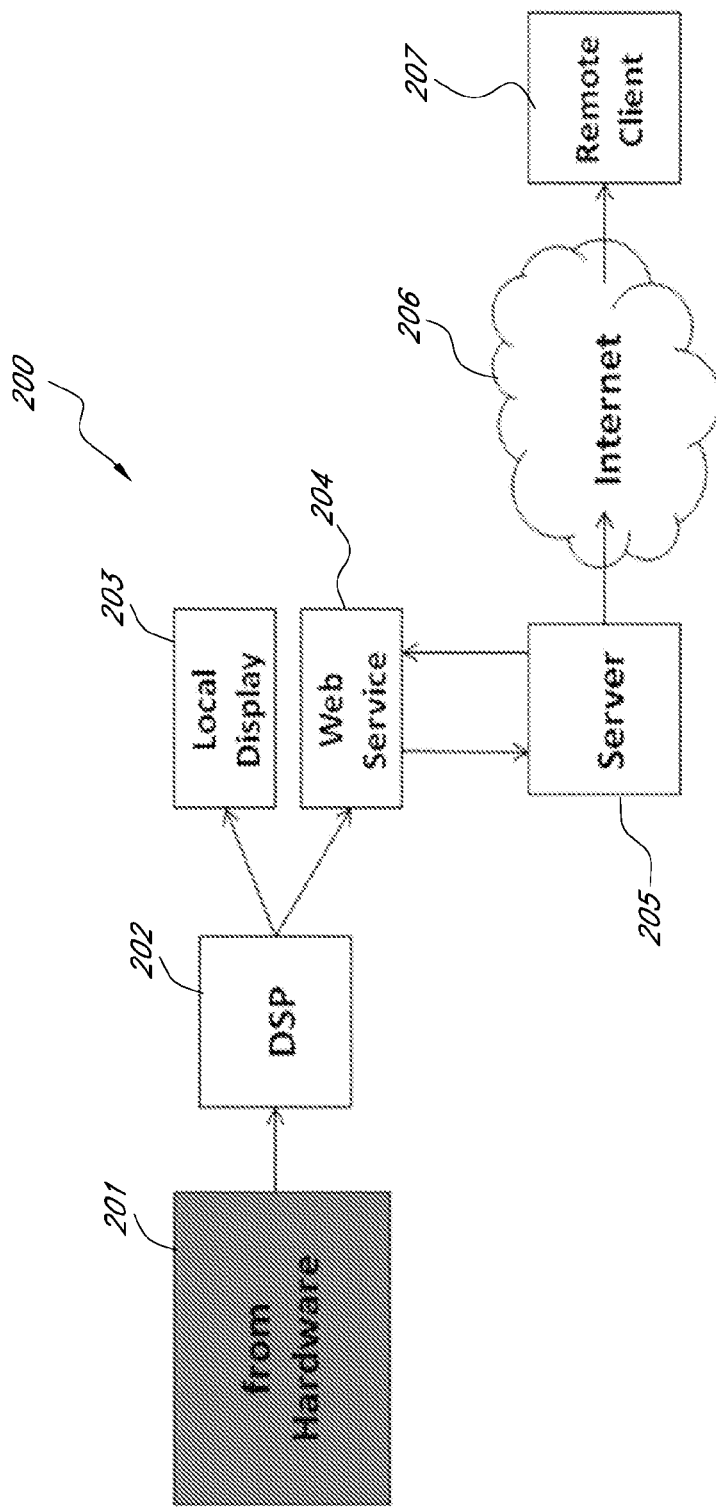

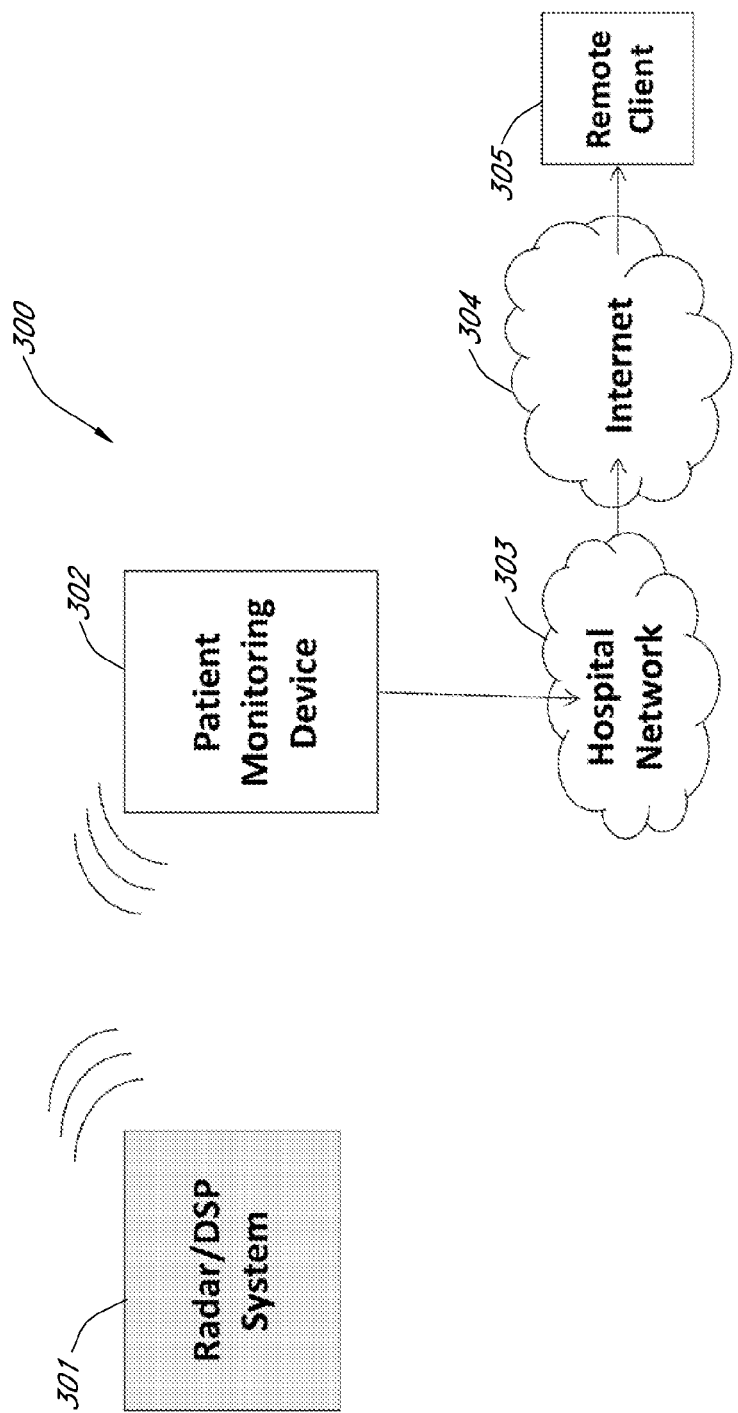

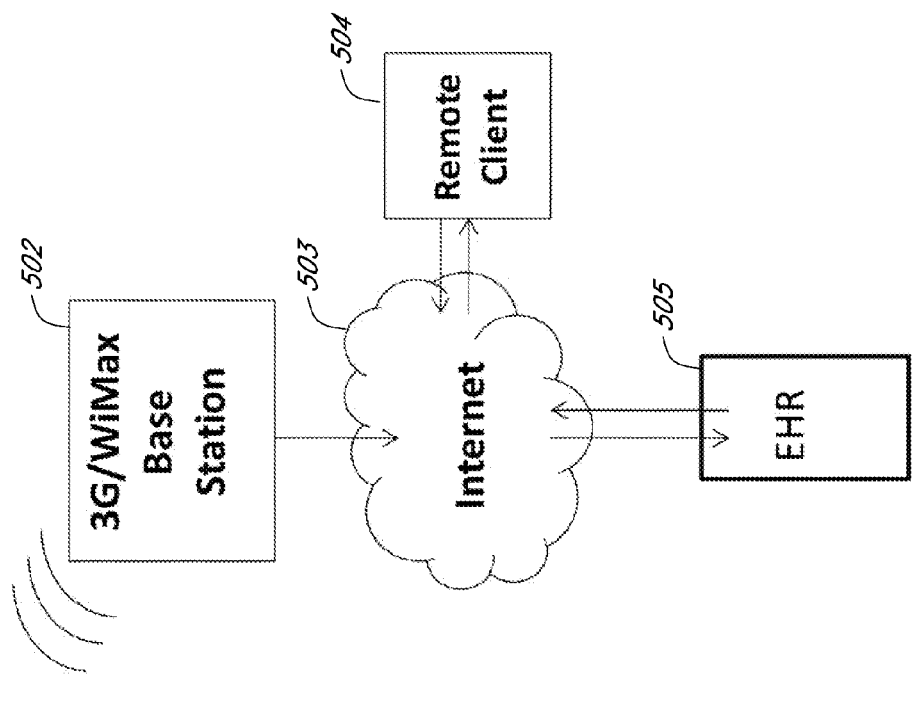
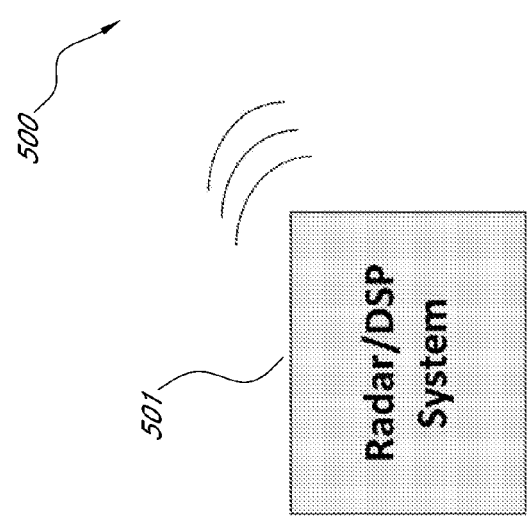
FIG. 5

Rate estimation (frequency domain):

Rate estimation (time domain, zero crossings with frequency domain check):

FIG. 10D

Rate estimation (time domain, peak delution)

1001s: Let $pv(n)$ denote the "interest points" as follows:

$$pv(n) = \begin{cases} x(n) & \text{if (I or II) and III and IV} \\ 0 & \text{otherwise} \end{cases}$$

(I) $|x(n)| > |x(n-1)|$ and $|x(n)| > |x(n+1)|$
(II) $|x(n)| = |x(n-1)|$
(III) $u(k) = 1$ for $n-T \leq k \leq n+T$
(IV) $v(k) = 1$ for $n-T \leq k \leq n+T$ where $u(n)$ and $v(n)$ are motion and clipping windows respectively.

1001t: Non-maxima suppression for every sample in a neighborhood of length $2W$:

For every n, find $\gamma_m = \max_{n-W \leq k \leq n+W} pv(k)$, where $\gamma_m = pv(m)$ $$\widehat{pv}(k) = \begin{cases} \gamma_m & k = m \\ 0 & n-W < k < n+W, k \neq m \end{cases}$$

1001u: Classify interest points as either peaks or valleys:

$$pvid(n) = \begin{cases} 1 & \widehat{pv}(n) > 0 \text{ (peak)} \\ -1 & \widehat{pv}(n) < 0 \text{ (valley)} \\ 0 & \widehat{pv}(n) = 0 \text{ (not an interest point)} \end{cases}$$

1001v: Resolve consecutive peaks and consecutive valleys (because a breathing signal should have alternating peaks and valleys):

i. $pvid(k_1) > 0, pvid(k_2) > 0$ are consecutive peaks when $\nexists\, k$ such that $pvid(k) < 0$ and $k_1 < k < k_2$. Similarly for consecutive valleys.

ii. For 2 or more consecutive interest points with same polarity, retain only the largest if the interest point was a peak or otherwise the smallest if the interest point was a valley.

iii. The resulting interest points should have alternating polarity.

1001w: Let $\lambda$ be the largest number of peaks in sequence

1001x: 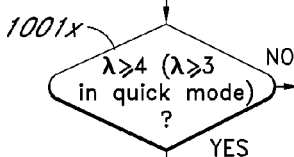 $\lambda \geq 4$ ($\lambda \geq 3$ in quick mode)?

NO → 1001y: Rate cannot be determined

YES → 1001z: Rate (R3) is given by $(60 \cdot 100 \cdot (\lambda - 1))/L$ breaths per minute, where $L$ is the length of the interval bounded by the first and last peak. A rate could be determined similarly by considering the valleys.

Flowchart (B)

Flowchart (C)

Flowchart (D)

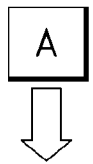

1403b

Form an M x N array matrix A whose $i^{th}$ column is $g(\theta_i) = \begin{bmatrix} 1 & \exp[jkd\ \sin(\theta_i)] & \ldots & \exp[jkd\ (M-1)\sin(\theta_i)] \end{bmatrix}^T$ where $d = \lambda/2$ and $\theta$ are the receive antenna separation and angle from the normal vector of antenna array to corresponding the corresponding reflecting signal source respectively, while M and N are the number of received antennas and reflecting signal sources respectively.

1405

Smoothing the DOA vectors with a weighted average of the current DOA vectors and previous DOA vectors in a buffer. If non-cardiopulmonary motion, clearing the buffer of DOA vectors

1404

Signal separation can be achieved by steering spatial nulls toward unwanted signal sources by applying inverse of matrix A, to the conditioned channel data.

Repeating the DOA tracking algorithm periodically and updating the DOA vector

Executing linear or non linear demodulation to each separated signal to get individual cardiopulmonary signal

FIG. 14B

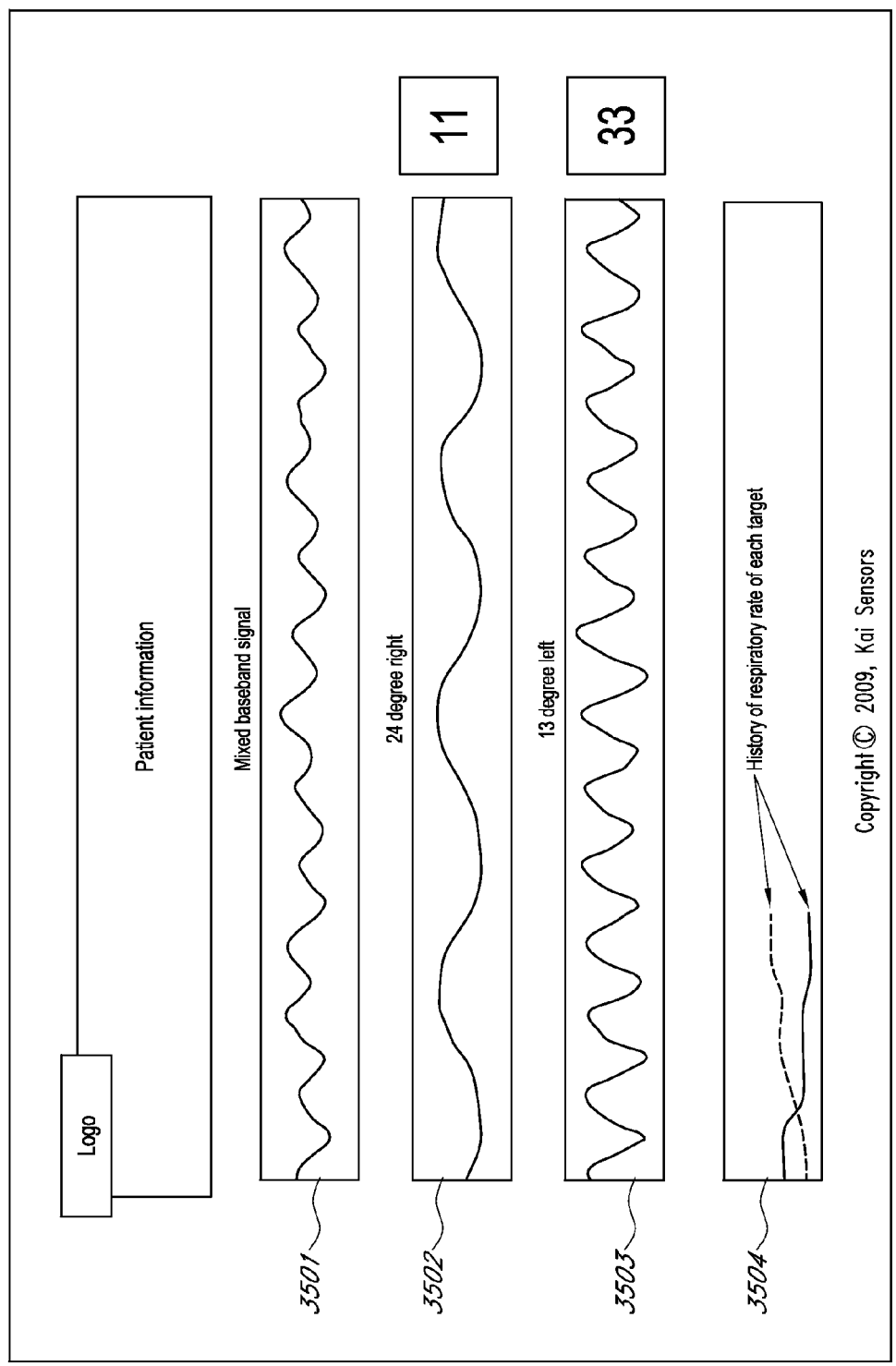

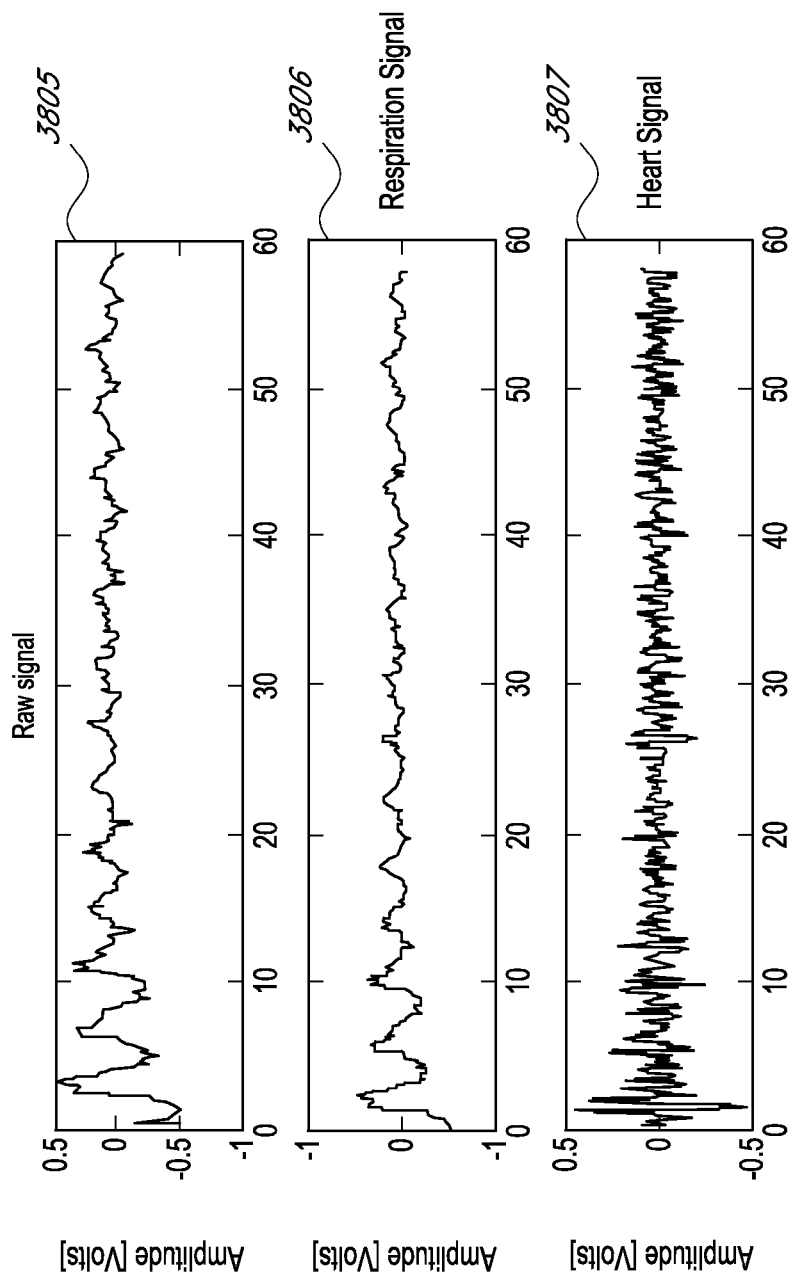

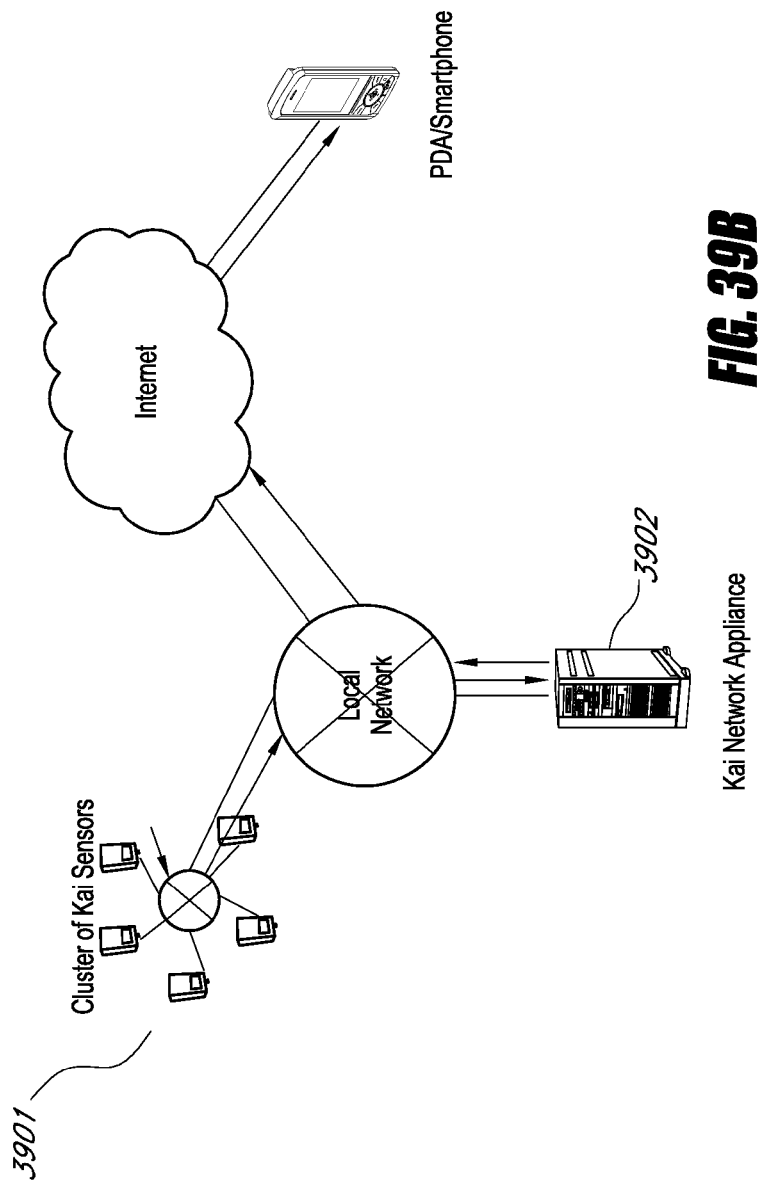

NON-CONTACT PHYSIOLOGIC MOTION SENSORS AND METHODS FOR USE

CROSS-REFERENCE TO RELATED APPLICATIONS

This application claims the benefit under 35 U.S.C. §119(e) of U.S. Provisional Application No. 61/072,983, filed on Apr. 3, 2008, titled "Doppler Radar System for Local and Remote Respiration Signals Monitoring"; U.S. Provisional Application No. 61/072,982, filed on Apr. 3, 2008, titled "Method for Detection of Cessation of Breathing"; U.S. Provisional Application No. 61/123,017, filed on Apr. 3, 2008, titled "Method for Detection of Motion Interfering with Respiration"; U.S. Provisional Application No. 61/123,135, filed on Apr. 3, 2008, titled "Method for Detection of Presence of Subject"; U.S. Provisional Application No. 61/125,021, filed on Apr. 21, 2008, titled "Non-contact Spirometry with a Doppler Radar"; U.S. Provisional Application No. 61/125,019, filed on Apr. 21, 2008, titled "Monitoring Physical Activity with a Physiologic Monitor"; U.S. Provisional Application No. 61/125,018, filed on Apr. 21, 2008, titled "Non-contact Method for Calibrating Tidal Volume Measured with Displacement Sensors"; U.S. Provisional Application No. 61/125,023, filed on Apr. 21, 2008, titled "Use of Empirical Mode Decomposition to Extract Physiological Signals from Motion Measured with a Doppler Radar"; U.S. Provisional Application No. 61/125,027, filed on Apr. 21, 2008, titled "Use of Direction of Arrival and Empirical Mode Decomposition Algorithms to Isolate and Extract Physiological Motion Measured with a Doppler Radar"; U.S. Provisional Application No. 61/125,022, filed on Apr. 21, 2008, titled "Data Access Architectures for Doppler Radar Patient Monitoring Systems"; U.S. Provisional Application No. 61/125,020, filed on Apr. 21, 2008, titled "Use of Direction of Arrival Algorithms to Isolate and Separate Physiological Motion Measured with a Doppler Radar"; U.S. Provisional Application No. 61/125,164, filed on Apr. 22, 2008, titled "Biometric Signature Collection Using Doppler Radar System"; U.S. Provisional Application No. 61/128,743, filed on May 23, 2008, titled "Doppler Radar Based Vital Signs Spot Checker"; U.S. Provisional Application No. 61/137,519, filed on Jul. 30, 2008, titled "Doppler Radar Based Monitoring of Physiological Motion Using Direction of Arrival"; U.S. Provisional Application No. 61/137,532, filed on Jul. 30, 2008, titled "Doppler Radar Respiration Spot Checker with Narrow Bean Antenna Array"; U.S. Provisional Application No. 61/194,838, filed on Sep. 29, 2008, titled "Doppler Radar-Based Body Worn Respiration Sensor"; U.S. Provisional Application No. 61/194,836, filed on Sep. 29, 2008, titled "Wireless Sleep Monitor Utilizing Non-Contact Monitoring of Respiration Motion"; U.S. Provisional Application No. 61/194,839, filed on Sep. 29, 2008, titled "Continuous Respiratory Rate and Pulse Oximetry Monitoring System"; U.S. Provisional Application No. 61/194,840, filed on Sep. 29, 2008, titled "Separation of Multiple Targets' Physiological Signals Using Doppler Radar with DOA Processing"; U.S. Provisional Application No. 61/194,848, filed on Sep. 30, 2008, titled "Detection of Paradoxical Breathing with a Doppler Radar System"; U.S. Provisional Application No. 61/196,762, filed on Oct. 17, 2008, titled "Monitoring of Chronic Illness Using a Non-contact Respiration Monitor"; U.S. Provisional Application No. 61/200,761, filed on Dec. 2, 2008, titled "Detection of Paradoxical Breathing with a Paradoxical Breathing Indicator with a Doppler Radar System"; U.S. Provisional Application No. 61/200,876, filed on Dec. 3, 2008, titled "Doppler Radar Based Monitoring of Physiological Motion Using Direction of Arrival and An Identification Tag"; U.S. Provisional Application No. 61/141,213, filed on Dec. 29, 2008, titled "A Non-Contact Cardiopulmonary Sensor Device for Medical and Security Applications"; U.S. Provisional Application No. 61/204,881, filed on Jan. 9, 2009, titled "Doppler Radar Based Continuous Monitoring of Physiological Motion"; U.S. Provisional Application No. 61/204,880, filed on Jan. 9, 2009, titled "Doppler Radar Respiration Spot Checker with Narrow Beam Antenna Array"; U.S. Provisional Application No. 61/206,356, filed on Jan. 30, 2009, titled "Doppler Radar Respiration Spot Check Device with Narrow Beam Antenna Array: Kai Sensors Non-Contact Respiratory Rate Spot Check"; U.S. Provisional Application No. 61/154,176, filed on Feb. 20, 2009, titled "A Non-Contact Cardiopulmonary Monitoring Device for Medical Imaging System Applications"; U.S. Provisional Application No. 61/154,728, filed on Feb. 23, 2009, titled "Doppler Radar-Based Measurement of Vital Signs for Battlefield Triage"; U.S. Provisional Application No. 61/154,732, filed on Feb. 23, 2009, titled "Doppler Radar-Based Measurement of Presence and Vital Signs of Subjects for Home Healthcare". Each of the foregoing applications is incorporated herein by reference in its entirety.

BACKGROUND

1. Field of the Invention

This application in general relates to monitors that can assess the physiological and psychological state of a subject and, in particular, relates to non-contact and radar-based physiologic sensors and their method of use.

2. Description of the Related Art

Motion sensors that can obtain physiological information of a subject, such as respiratory activity, cardiac activity, cardiovascular activity, and cardiopulmonary activity on a continuous or intermittent basis can be useful in various medical applications. Unfortunately, such physiologic activity often occurs in the presence of various other motions, such as, for example, rolling over while sleeping, etc. Thus, data from such motion sensors will typically include desired components corresponding to the physiological activity being measured, and undesired components corresponding to other motions, noise, etc. Existing systems do not adequately separate the desired components from the undesired components.

SUMMARY

These and other problems are solved by a system that uses a radar-based sensor to sense physiological motion and a processing system that analyzes the data from the radar to distinguish desired data components corresponding to various physiological activity from undesired data components due to other activity, motions, noise, etc. The system can be used to obtain respiratory rate, heart rate, and physiological waveforms including, but not limited to, heart waveforms, pulse waveform, and/or a respiratory waveform. These rates and waveforms can be analyzed to assess various physiological and medical parameters such as, for example, respiratory rates, cardiac rates, respiratory effort, depth of breath, tidal volume, vital signs, medical conditions, psychological state, or location of the subject, etc. These waveforms can also be used to synchronize ventilation or medical imaging with respiratory and/or cardiac motion. The information in these rates and waveforms can be used in many embodiments, including vital signs assessments, apnea monitors, general patient monitoring, neonatal monitoring, burn victim monitoring, home monitoring of the elderly or disabled, triage, chronic illness management, post-surgical monitoring, monitoring of patients during medical imaging scans, disease detection, assessment of psychological state, psychological or psychiatric evaluation, pre-resuscitation assessment, post-resuscitation assessment, and/or lie detection. Various embodiments of the motion sensors can be used in medical applications in various environments including, but not limited to, hospitals, clinics, homes, skilled nursing facilities, assisted living facilities, health kiosks, emergency rooms, emergency transport, patient transport, disaster areas, and battlefields. Various embodiments of the motion sensors can be used for security applications including, but not limited to, security screening at airports, borders, sporting events and other public events, or as a lie detector. Various embodiments of the physiological motion sensors can distinguish valid measurement of heart and respiratory activity from interference, noise, or other motion, and it can provide continuous, point in time, intermittent and/or piecemeal data from which rates, signatures, and key variations can be recognized. Various embodiments of the physiological motion sensor can operate with no contact and work at a distance from a subject. Some embodiments of the physiological motion sensor can also operate when placed on the subject's chest in contact with the body. Various embodiments of the physiological motion sensor can operate on subjects in any position, including lying down, reclined, sitting, or standing. Various embodiments of the physiological motion sensor can operate on subjects from different positions relative to the subject, including from the subject's, from the subject's side, from the subject's back, from above the subject, and from below the subject.

One embodiment includes a method of sensing motion using a motion sensor, the method that includes generating electromagnetic radiation from a source of radiation, wherein the frequency of the electromagnetic radiation is in the radio frequency range, transmitting the electromagnetic radiation towards a subject using one or more transmitters, receiving a radiation scattered at least by the subject using one or more receivers, extracting a Doppler shifted signal from the scattered radiation, transforming the Doppler shifted signal to a digitized motion signal, the digitized motion signal comprising one or more frames, wherein the one or more frames include time sampled quadrature values of the digitized motion signal, demodulating the one or more frames using a demodulation algorithm executed by a processor to isolate a signal corresponding to a physiological movement of the subject or a part of the subject, analyzing the signal to obtain information corresponding to a non-cardiopulmonary motion or other signal interference, processing the signal to obtain information corresponding to the physiological movement of the subject or a part of the subject, substantially separate from the non-cardiopulmonary motion or other signal interference, and communicating the information to an output system that is configured to perform an output action.

In one embodiment, the output system includes a display unit configured to display the information. In one embodiment, the output system includes an audible system that is configured to report information or alerts audibly based on the information. In one embodiment, the output system includes an external medical system that is configured to perform an action based on the information. In one embodiment, the demodulating algorithm includes a linear demodulation algorithm, an arc-based demodulation algorithm or a non-linear demodulation algorithm. In one embodiment, the information is displayed at least alphanumerically, graphically and as a waveform.

In one embodiment, the subject is a human being or an animal and the physiological movement includes at least one of a motion due to respiratory activity of the subject, motion due to a cardiopulmonary activity of the subject, motion due to a cardiac activity of the subject, motion due to a cardiovascular activity of the subject, and motion due to a physical activity of the subject.

In various embodiment the demodulating algorithm includes projecting the signal in a complex plane on a best-fit line, projecting the signal in a complex plane on a principal eigenvector, or aligning a signal arc to a best-fit circle and using the best-fit circle parameters to extract the angular information from the signal arc.

In various embodiment demodulating includes computing in the processor a first set of covariance matrices of a first subset of frames selected from the one or more frames, determining a first A-matrix, wherein the first A-matrix includes a weighted sum of the first set of covariance matrices, determining a first parameter vector corresponding to a first primary value of the first A matrix, storing the first parameter vector in a memory device which is in communication with the processor. In one embodiment, demodulation includes, computing in the processor a second set of covariance matrices of a second subset of frames selected from the one or more frames, determining a second A-matrix, wherein the second A-matrix includes a weighted sum of the second set of covariance matrices, determining a second parameter vector corresponding to a second primary value of the second A-matrix, calculating an inner product of the first parameter vector and the second parameter vector, multiplying the second parameter vector by the sign of the inner product, and projecting the values of the second frame on the second parameter vector to obtain the demodulated signal. In one embodiment, the first primary value includes the largest eigenvalue of the first A-matrix and the first primary vector includes an eigenvector corresponding to the eigenvalue. In one embodiment, the second primary value includes the largest eigenvalue of the second A-matrix and the second primary vector includes an eigenvector corresponding to the eigenvalue.

In one embodiment, the source of radiation includes an oscillator. In one embodiment, the one or more transmitters include one or more antennae. In one embodiment, the one or more receivers include one or more antennae or arrays of antennae. In one embodiment, the transmitting and receiving antennae are the same antennae. In one embodiment, the receiver includes a homodyne receiver. In one embodiment, the receiver includes a heterodyne receiver. In one embodiment, the receiver includes a low-IF receiver configured to transform the Doppler-shifted signal to a Doppler-shifted signal comprising frequencies in a low intermediate frequency range, which is digitized and digitally transformed to a digitized motion signal.

In one embodiment, the processor includes at least one of a digital signal processor, a microprocessor and a computer.

In one embodiment, the output system includes a display unit configured to display information regarding the physiological movement of a user at a remote location.

In one embodiment, analyzing the signal includes executing a non-cardiopulmonary motion detection algorithm configured to detect the absence of non-cardiopulmonary motion is detected if the signal includes a single stable source or the presence of non-cardiopulmonary signal if at least the signal is unstable or at least the signal has multiple sources.

In one embodiment, analyzing the signal includes executing a non-cardiopulmonary motion detection algorithm configured to detect the presence of non-cardiopulmonary motion if the signal indicates an excursion larger than the subject's maximum chest excursion from cardiopulmonary activity.

In one embodiment, analyzing the signal includes executing a non-cardiopulmonary motion detection algorithm configured to detect the presence of non-cardiopulmonary motion if a best-fit vector related to linear demodulation changes significantly.

In one embodiment, analyzing the signal includes executing a non-cardiopulmonary motion detection algorithm configured to detect the presence of non-cardiopulmonary motion if a RMS difference between a complex constellation of the signal and a best fit vector related to linear demodulation changes significantly.

In one embodiment, analyzing the signal includes executing a non-cardiopulmonary motion detection algorithm configured to detect the presence of non-cardiopulmonary motion if an origin or radius of a best-fit circle related to arc-based demodulation changes significantly.

In one embodiment, analyzing the signal includes executing a non-cardiopulmonary motion detection algorithm configured to detect the presence of non-cardiopulmonary motion if a RMS difference between a complex constellation of the signal and a best-fit circle related to arc-based demodulation changes significantly.

In one embodiment, analyzing the signal includes executing a non-cardiopulmonary motion detection algorithm by a processor to detect the presence or absence of non-cardiopulmonary motion or other signal interference from the digitized motion signal, wherein the non-cardiopulmonary motion detection algorithm includes a first mode which detects a presence of non-cardiopulmonary motion or other signal interference and a second mode which detects a cessation of non-cardiopulmonary motion or other signal interference.

One embodiment includes communicating information related to a signal quality of a cardiopulmonary motion signal, based on at least one of: a presence of non-cardiopulmonary motion or other signal interference, an absence of non-cardiopulmonary motion or other signal interference, a degree of non-cardiopulmonary motion or other signal interference, an assessment of the signal-to-noise ratio, a detection of low signal power, or a detection of signal clipping or other signal interference, to an output system configured to output the information.

In one embodiment, the first mode includes selecting a first subset of frames from the one or more frames and computing in the processor a first set of covariance matrices of the first subset of frames filtered by a low-pass filter, determining a first A-matrix wherein the A-matrix includes a weighted sum of the first set of covariance matrices, determining a first parameter vector corresponding to a first primary value of the first A matrix, storing the first parameter vector in a memory device which is in communication with the processor. One embodiment further includes computing in the processor a second set of covariance matrices of a second subset of frames filtered by the low-pass filter, determining a second A-matrix, wherein the A-matrix includes a weighted sum value of the second set of covariance matrices, determining a first and a second primary value of the second A-matrix, determining a second parameter vector corresponding to the first primary value of the second A-matrix, calculating an inner product of the first parameter vector and the second parameter vector, calculating a ratio of the first primary value of the second A matrix to the second primary value of the second A matrix, calculating a first energy corresponding to the average energy of a third subset of frames filtered by a high-pass filter and a second energy corresponding to the average energy of a fourth subset of frames filtered by a high-pass filter, and calculating a ratio of the second energy to the first energy. In one embodiment, the first primary value includes the largest eigenvalue of the first A-matrix and the first primary vector includes an eigenvector corresponding to the eigenvalue. In one embodiment, the first primary value of the second A-matrix includes the second largest eigenvalue of the second A-matrix, the second primary value of the second A-matrix includes the largest eigenvalue of the second A-matrix and the second primary vector of the second A-matrix includes an eigenvector corresponding to the first primary value of the second A-matrix.

One embodiment includes computing in the processor a first condition, the first condition being the inner product is less than a first threshold value or the ratio of the first primary value of the second A matrix to the second primary value of the second A matrix is less than a second threshold value or the ratio of the second energy to the first energy is greater than a third threshold value, wherein the presence of non-cardiopulmonary motion or other signal interference is detected if the first condition is true and the ratio of the second energy to the first energy is greater than a fourth threshold value. In one embodiment, the first threshold value is approximately between 0.6 and 1. In one embodiment, the second threshold value is approximately between 4 and 12. In one embodiment, the third threshold value is approximately between 4 and 20. In one embodiment, the fourth threshold value is approximately between 0.1 and 0.8.

In one embodiment, the second mode includes selecting in the processor each and every consecutive subset of frames within a fifth subset of frames, computing in the processor covariance matrices for every subset of frames computing in the processor an A'-matrix for each subset of frames, wherein the A'-matrix is the weighted average of the covariance matrices in the subset, computing in the processor a rho-matrix, wherein each element of the rho-matrix corresponds to a first primary vector of the corresponding A'-matrix, computing the inner product of each pair of primary vectors in the rho-matrix and selecting a minimum absolute value of the inner products, calculating an A matrix which is the sum of the covariance matrices in a sixth subset of frames, determining the first primary value of the A-matrix and the second primary value of the A matrix, calculating the ratio of the first primary value of the A matrix to the second primary value of the A matrix, One embodiment includes computing in the processor a second condition, the second condition being the minimum absolute value of the inner products is greater than a first threshold value and the ratio of the first primary value to the second primary value is greater than a second threshold value, wherein the cessation of non-cardiopulmonary motion or other signal interference is detected if the second condition is true. In one embodiment, the fifth threshold value is approximately between 0.6 and 1. In one embodiment, the sixth threshold value is approximately between 4 and 12. In one embodiment, the first primary vector includes an eigenvector corresponding to the largest eigenvalue of the corresponding A'-matrix. In one embodiment, the first primary value includes the largest eigenvalue of the A-matrix and the second primary value includes the second largest eigenvalue of the A-matrix. One embodiment includes computing a frame from the one or more frames when the non-cardiopulmonary motion substantially ceased. In one embodiment, one or more frames preceding the frame are discarded.

One embodiment includes a method of estimating the rate of a physiological motion using a motion sensor, generating an electromagnetic radiation from a source of radiation, wherein the frequency of the electromagnetic radiation is in the radio frequency range, transmitting the electromagnetic radiation towards a subject using one or more transmitters, receiving a radiation scattered at least by the subject using one or more receivers, extracting a Doppler shifted signal from the scattered radiation, transforming and digitizing the Doppler shifted signal to a digitized motion signal, the digitized motion signal comprising one or more frames, wherein the one or more frames include time sampled quadrature values of the digitized motion signal, demodulating the one or more frames using a demodulation algorithm executed by a processor to isolate a signal corresponding to a physiological movement of the subject or a part of the subject, executing a non-cardiopulmonary motion detection algorithm by the processor to identify from the digitized motion signal one or more non-cardiopulmonary motion detection events or other signal interference events corresponding to the presence or absence of a non-cardiopulmonary motion or other signal interference, executing by a processor a rate estimation algorithm to estimate a rate of the physiological movement, and providing information related to at least the rate of the physiological movement of the subject or a part of the subject to an output unit that is configured to output the information.

In one embodiment, the rate estimation algorithm includes collecting a plurality of samples from the demodulated frames, identifying one or more samples from the plurality of samples corresponding to non-cardiopulmonary motion detection events and setting to zero the one or more samples from the plurality of samples to obtain at least a first subset of the plurality of samples, and subtracting in the processor a mean of the first subset from the first subset. One embodiment includes calculating in the processor a Fourier transform of the samples included in the first subset to obtain a magnitude spectrum of the samples in the first subset. In one embodiment, the estimated frequency domain rate of the physiological movement corresponds to the largest magnitude component in the spectrum of the samples in the first subset. One embodiment includes identifying either at least three positive zero crossings or at least three negative zero crossings in the first subset, identifying at least a first value for the samples within a first and a second zero crossing, the first value being the largest magnitude positive value or largest magnitude negative value, identifying at least a second value for the samples within a second and a third zero crossing, the second value being the largest magnitude positive value or largest magnitude negative value comparing the first and second values against a threshold value, identifying at least a first breathing event if the first value is greater than a threshold value, identifying at least a second breathing event if the second value is greater than a threshold value, and estimating a time domain respiration rate based on at least the first and second breathing events and the time interval between the first, second and third zero crossings. One embodiment includes calculating in the processor a Fourier transform of the samples included in the first subset to obtain a magnitude spectrum of the samples in the first subset, estimating a frequency domain respiration rate of the physiological movement that corresponds to the largest magnitude spectrum of the samples in the first subset, and comparing the time domain rate and the frequency domain rate to verify an accuracy of the time domain rate and the frequency domain rate.

In one embodiment, the rate estimation algorithm includes identifying at least three consecutive peaks from the plurality of samples, such that a valley is included between two consecutive peaks, and determining a respiration rate based on a number of consecutive peaks detected and the time interval between a first and a last peak.

In one embodiment, the rate estimation algorithm includes identifying at least three consecutive valleys from the plurality of samples, such that a peak is included between two consecutive valleys, and determining a respiration rate based on a number of consecutive valleys detected and the time interval between a first and a last valley. In one embodiment, the rate algorithm selects whether to identify peaks or valleys depending on which occurs first. In one embodiment, the rate estimation algorithm averages the respiration rate based on a number of consecutive peaks and the respiration rate based on a number of consecutive valleys to improve the robustness of the rate estimate.

One embodiment includes a system for sensing a physiological motion including one or more antennas configured to transmit electromagnetic radiation, one or more antennas configured to receive electromagnetic radiation, at least one processor configured to extract information related to cardiopulmonary motion by executing at least one of a demodulation algorithm, a non-cardiopulmonary motion detection algorithm, a rate estimation algorithm, a paradoxical breathing algorithm and a direction of arrival algorithm, and a communications system configured to communicate with an output device, the output device configured to output information related to the cardiopulmonary motion. In one embodiment, a vital signs monitor is configured to monitor at least one of a respiration rate, a heart rate, a depth of breath, respiratory waveform, heart waveform, tidal volume activity and degree of asynchronous breathing in one or more subjects. In one embodiment, an apnea detection system is configured to monitor at least one of a respiration rate, a heart rate, a depth of breath, tidal volume and paradoxical breathing and the presence or absence of breathing in one or more subjects. In one embodiment, a sleep monitor is configured to monitor at least one of a respiration rate, respiratory effort, a heart rate, a depth of breath, tidal volume, paradoxical breathing, activity, position, and physical movement in one or more subjects. In one embodiment, a vital signs measurement system is configured to measure at least one of respiration rate, heart rate, ratio of inhale time to exhale time, tidal volume, and depth of breath in one or more subjects. In one embodiment, a vital signs measurement system is configured to perform a measurement at a point in time or at intermittent points in time.

One embodiment includes a psycho-physiological state monitor configured to monitor at least one of a respiration rate, a heart rate, respiratory waveform, heart waveform, activity, a depth of breath, tidal volume, inhale time, exhale time, and inhale time to exhale time ratio in one or more subjects in response to one or more external stimuli.

In one embodiment, the system sends information to an imaging system, the imaging system configured to image a subject, the information configured to synchronize the imaging system to a physiological motion in the subject.

In one embodiment, the system is configured to send information to a medical device, the information configured to operate the medical device. In one embodiment, the medical device includes a defibrillator. In one embodiment, the system is configured to assess at least one of the presence or absence of respiratory motion and the presence or absence of heart motion.

One embodiment includes a physical activity monitor configured to monitor at least one of a respiration rate, a heart rate, a depth of breath, tidal volume, frequency of non-cardiopulmonary motion, and duration of non-cardiopulmonary motion in one or more subjects.

In one embodiment, the weighted sum includes an arithmetic mean.

In one embodiment, the medical device includes a ventilator.

One embodiment includes a method of estimating the presence or absence of paradoxical breathing using a motion sensor by generating an electromagnetic radiation from a source of radiation, wherein the frequency of the electromagnetic radiation is in the radio frequency range, transmitting the electromagnetic radiation towards a subject using one or more transmitters, receiving a radiation scattered at least by the subject using one or more receivers, extracting a Doppler shifted signal from the scattered radiation, transforming the Doppler shifted signal to a digitized quadrature motion signal, the digitized quadrature motion signal comprising one or more frames, wherein the one or more frames include time sampled quadrature values of the digitized motion signal, executing a non-cardiopulmonary motion detection algorithm by the processor to identify from the digitized motion signal one or more non-cardiopulmonary motion detection events or other signal interference events corresponding to the presence or absence of a non-cardiopulmonary motion or other signal interference, executing by a processor a paradoxical breathing indication algorithm to estimate the presence or absence of paradoxical breathing, and providing information related to at least the presence, absence, or degree of paradoxical breathing. In one embodiment, the paradoxical breathing indication algorithm includes selecting a subset of the frames, filtering the frames using a low-pass filter, and obtaining a complex constellation plot of the filtered frames.

In one embodiment, an absence of paradoxical breathing is detected if the complex constellation plot is approximately linear, such that the magnitude of a first dimension of the complex constellation plot is greater than a second dimension of the complex constellation plot.

In one embodiment, a presence of paradoxical breathing is detected if the complex constellation plot has a first and a second dimension, such that the first and second dimensions have comparable magnitude.

In one embodiment, a paradoxical factor is calculated to estimate a degree of paradoxical breathing. In one embodiment, the paradoxical factor can be estimated by calculating in the processor a covariance matrix of the subset, calculating a first primary value and a second primary value of the covariance matrix, calculating a first primary vector corresponding to the first primary value and a second primary vector corresponding to the second primary value, projecting the signal on the first primary vector and determining a first amplitude corresponding to the largest peak-to-peak value of the projected signal on the first primary vector, projecting the signal on the second primary vector and determining a second amplitude corresponding to the largest peak-to-peak value of the projected signal on the second primary vector, calculating a first ratio of the first amplitude to the second amplitude, calculating a second ratio of the first primary value to the second primary value, and calculating a product of the first ratio to the second ratio. In one embodiment, the first and second primary value include eigenvalues of the covariance matrix and the first and second primary vectors include eigenvectors corresponding to the first and second primary value.

In one embodiment, the paradoxical indicator is calculated with a cost function performed on the paradoxical factor. In one embodiment, the presence or absence of paradoxical breathing is determined by comparing the output of the cost function to a threshold.

In one embodiment, the paradoxical indicator is analyzed to provide a first indication for absence of paradoxical breathing, a second indication for uncertain results and a third indication for the presence of paradoxical breathing.

One embodiment includes a method of estimating the direction of arrival using a motion sensor by generating an electromagnetic radiation from a source of radiation, wherein the frequency of the electromagnetic radiation is in the radio frequency range, transmitting the electromagnetic radiation towards a subject using one or more transmitters, receiving a radiation scattered at least by the subject using one or more receivers, extracting a Doppler shifted signal from the scattered radiation, transforming the Doppler shifted signal to a digitized quadrature motion signal, the digitized quadrature motion signal comprising one or more frames, wherein the one or more frames include time sampled quadrature values of the digitized motion signal from each receiver, executing by a processor a direction of arrival algorithm to estimate the number of targets and corresponding angles, and providing information corresponding to at least one of the cardiopulmonary movement of one or more subjects or a part of one or more subjects, the number of subjects, and the direction of one or more subjects to an output unit that is configured to output the information. In one embodiment, the direction of arrival algorithm includes filtering a subset of frames selected from the one or more frames using a low pass filter, each frame consisting of signals from a plurality of receive channels in the multiple receive antenna array, calculating the power spectrum density of all the channels for the low pass filtered subset of frames, using the power of the frequency components in the calculated power spectrum density to determine the frequency components that are most likely to contain a cardiopulmonary signals from one or more subjects, identifying the angular direction of each frequency component, identifying at least a first and a second angular direction such that each angular direction is separated from the other angular direction by an angular distance greater than or equal to an angular resolution of the one or more receivers, eliminating one or more angles that are separated by an angular distance less than the angular resolution of the one or more receivers, and generating one or more DOA vectors with unity magnitude for each target in the angular direction, and smoothing the DOA vectors with a weighted average of a current DOA vector and a previous DOA vectors in a buffer. One embodiment further includes separating the signal from each angular direction by steering spatial nulls towards the other angular directions, executing by the processor a non-cardiopulmonary motion detection algorithm to detect a presence or absence of non-cardiopulmonary motion or other signal interference in each separated signal, and executing by the processor a demodulation algorithm to demodulate each of the separated signals, and process each demodulated signal to obtain information corresponding to the cardiopulmonary motion if absence of non-cardiopulmonary motion is detected. One embodiment further includes isolating the signal from the desired subject by steering spatial nulls toward the other angular directions, executing by the processor a non-cardiopulmonary motion detection algorithm to detect a presence or absence of non-cardiopulmonary motion or other signal interference in the isolated signal, and executing by the processor a demodulation algorithm to demodulate the isolated signal, and process the demodulated signal to obtain information corresponding to the subject's cardiopulmonary motion if absence of non-cardiopulmonary motion is detected.

In one embodiment, the direction of arrival algorithm includes filtering a subset of frames selected from the one or more frames using a low pass filter, each frame consisting of signals from a plurality of receive channels included in the multiple receiver antenna array, calculating the power spectrum density of all the channels for the low pass filtered subset of frames, using the power of the frequency components in the calculated power spectrum density to determine the frequency components that are most likely to contain the cardiopulmonary signals from one or more subjects, identifying an angular direction of each frequency component, identifying at least a first and a second angular direction such that each angular direction is separated from the other angular direction by an angular distance greater than or equal to an angular resolution of the multiple receiver antenna array, eliminating one or more angles that are separated by an angular distance less than the angular resolution of the multiple receiver antenna array, generating a DOA vector with unity magnitude for each target in the the angular direction, smoothing the DOA vectors with a weighted average of the current DOA vectors and previous DOA vectors in a buffer, repeating the DOA algorithm periodically and updating the DOA vectors, and communicating angles corresponding to the DOA vectors to the output unit.

BRIEF DESCRIPTION OF THE DRAWINGS

FIGS. 1B-1F illustrates measurements obtained by the system illustrated in FIG. 1A.

FIG. 2 schematically illustrates a block diagram of a radar-based physiological motion sensor system integrated with a remote interface.

FIG. 3 schematically illustrates a block diagram of a system including radar-based physiological motion sensor including an add-on module.

FIG. 5 schematically illustrates another embodiment of a standalone radar-based sensor device with wireless connectivity.

FIGS. 10A-10D illustrate an embodiment of a rate estimation algorithm including frequency domain rate estimation and time domain rate estimation.

FIG. 35 illustrates a screen shot of a display device configured to display the respiratory motion waveforms for two people.

FIGS. 38A-38C illustrate information related to cardiopulmonary activity as measured by a wearable Doppler radar system in contact with a subject.

FIGS. 39A and 39B describe embodiments of a network topology of a plurality of clusters including a radar-based physiological motion sensors.

DETAILED DESCRIPTION

Figure 1A:
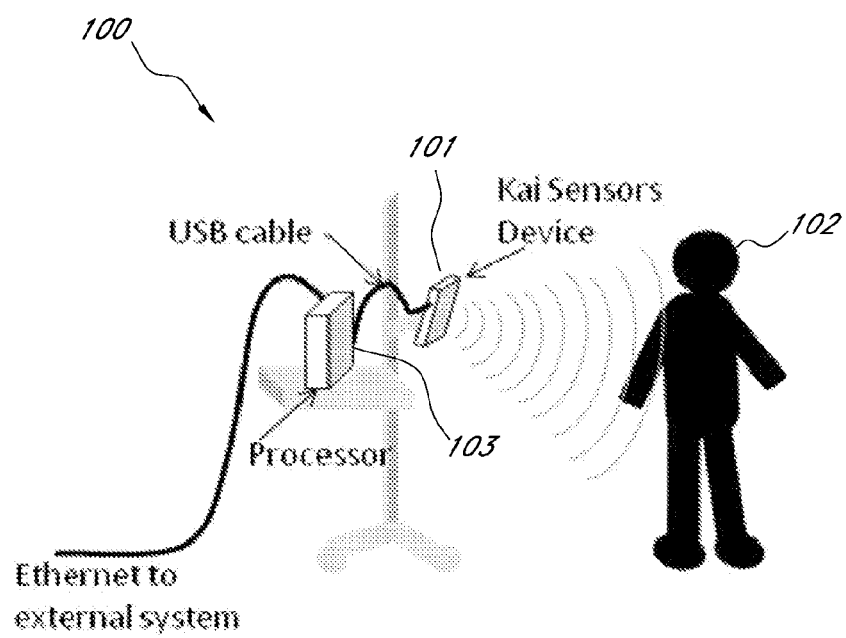
FIG. 1A schematically illustrates an embodiment of a physiological motion sensor system comprising radar.
Figure 1B:
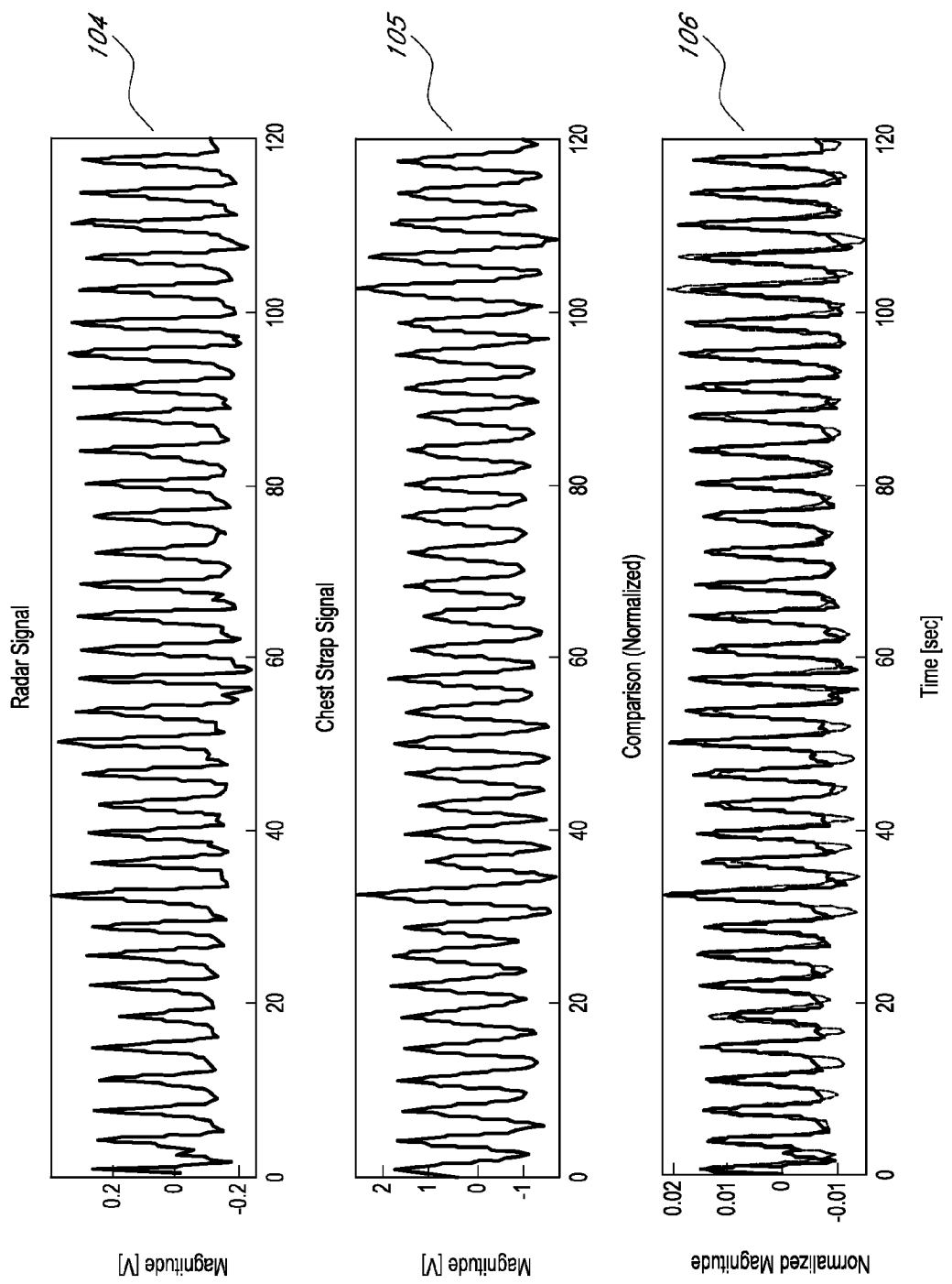

FIG. 1A shows a physiological motion sensor system 100 wherein a radar 101 senses motion and/or physiologic activity of a subject 102. Data from the radar 101 is provided to a processing system 103 that analyzes the radar data to determine various desired physiological parameters and provide output information regarding the physiological parameters to an output system or device configured to perform an output action. In various embodiments, the output device can include a display system configured to display an audible system configured to report information or issue alerts or a medical device configured to perform a function based on the information. The system 100 can further include a communications system configured to communicate using wired or wireless communication links. The communications system can use standard or proprietary protocols. FIG. 1B shows an example of a measurement obtained by the system 100 as displayed on a display unit.

FIGS. 1B-1F illustrate examples of the measurement obtained by the system 100. The measurements can include waveforms due to cardiopulmonary activity of a subject 102 displayed on a display unit.

FIG. 1B illustrates the waveforms obtained by embodiments of the system 100 described above for a 54-year-old male subject with a body mass index (BMI) of 23 with Hypertension and Congestive Heart Failure. Plot 104 of FIG. 1B shows the physiological motion signal (e.g., respiratory rate and the amplitude of respiration) detected by the radar-based physiological motion sensor system. Plot 105 illustrates the physiological motion signal detected by a conventional contact physiological motion sensor (e.g., a chest strap). Plot 106 shows the comparison between the normalized motion signal detected by the radar-based physiological motion sensor and the normalized conventional sensor. Plot 106 shows good correspondence between the two signals.

FIG. 1C illustrates variations in the respiratory rate and the amplitude of respiration obtained by embodiments of the system described above for a 44-year-old male with a BMI of 40, with Diabetes, Hypertension, and CAD. Plot 107 of FIG. 1C shows the physiological motion signal (e.g., respiratory rate and the amplitude of respiration) detected by the radar-based physiological motion sensor system. Plot 108 illustrates the physiological motion signal detected by a conventional contact physiological motion sensor (e.g., a chest strap). Plot 109 shows the comparison between the normalized motion signal detected by the radar-based physiological motion sensor and the normalized conventional sensor. As observed earlier, plot 109 shows good correspondence between the two signals.

Figure 1D:
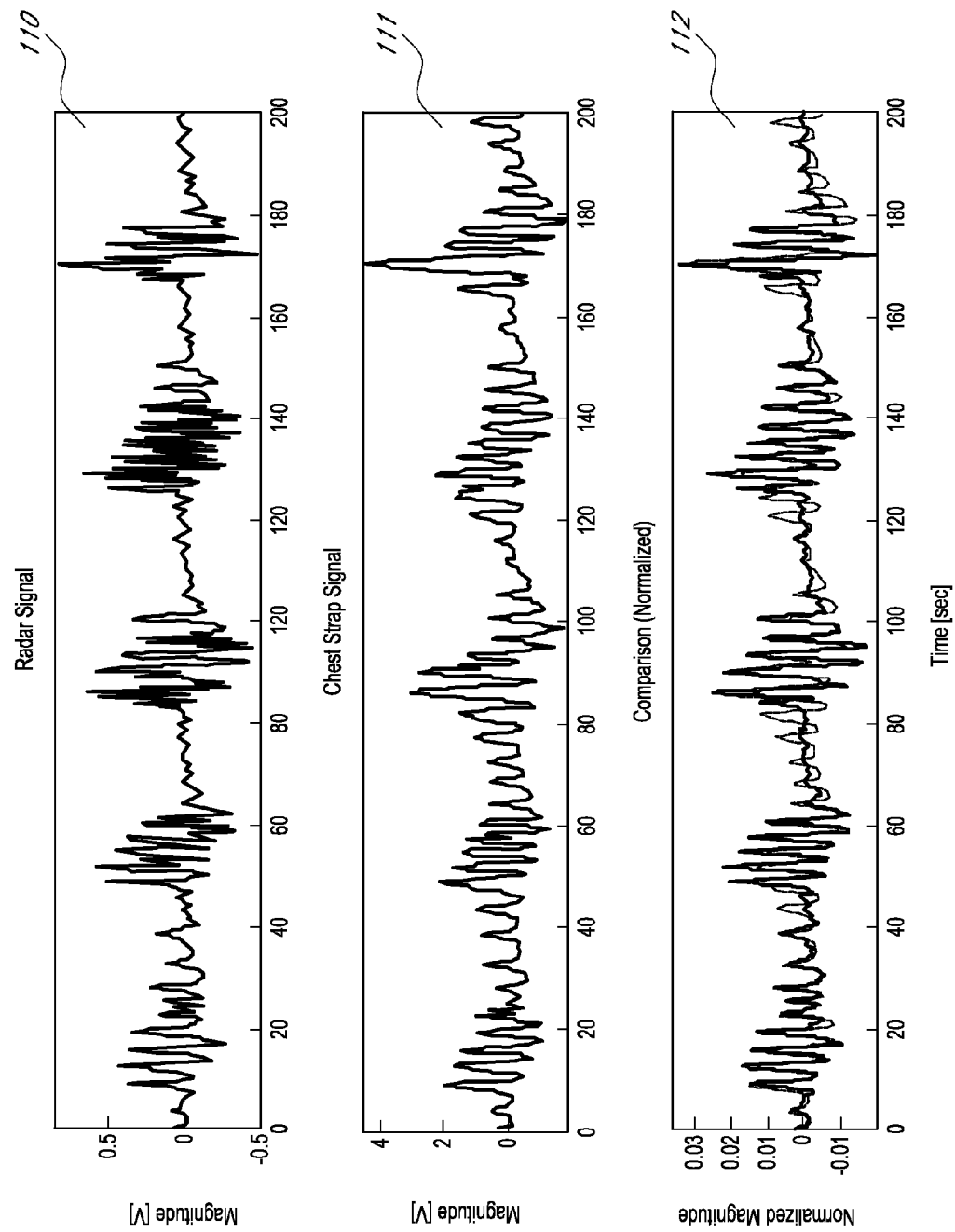

FIG. 1D illustrates the physiological motion signal for a 55-year-old male with a BMI of 40, with High Cholesterol, Hypertension, and CAD, while he was snoring. Plot 110 shows the motion signal detected by the radar-based physiological motion sensor and illustrates detection of apnea (cessation of breathing) and variation in the respiration signal baseline. Plot 111 is a corresponding measurement obtained by a conventional monitor while plot 112 illustrates the comparison between the conventional monitor and the system 100.

Figure 1E:
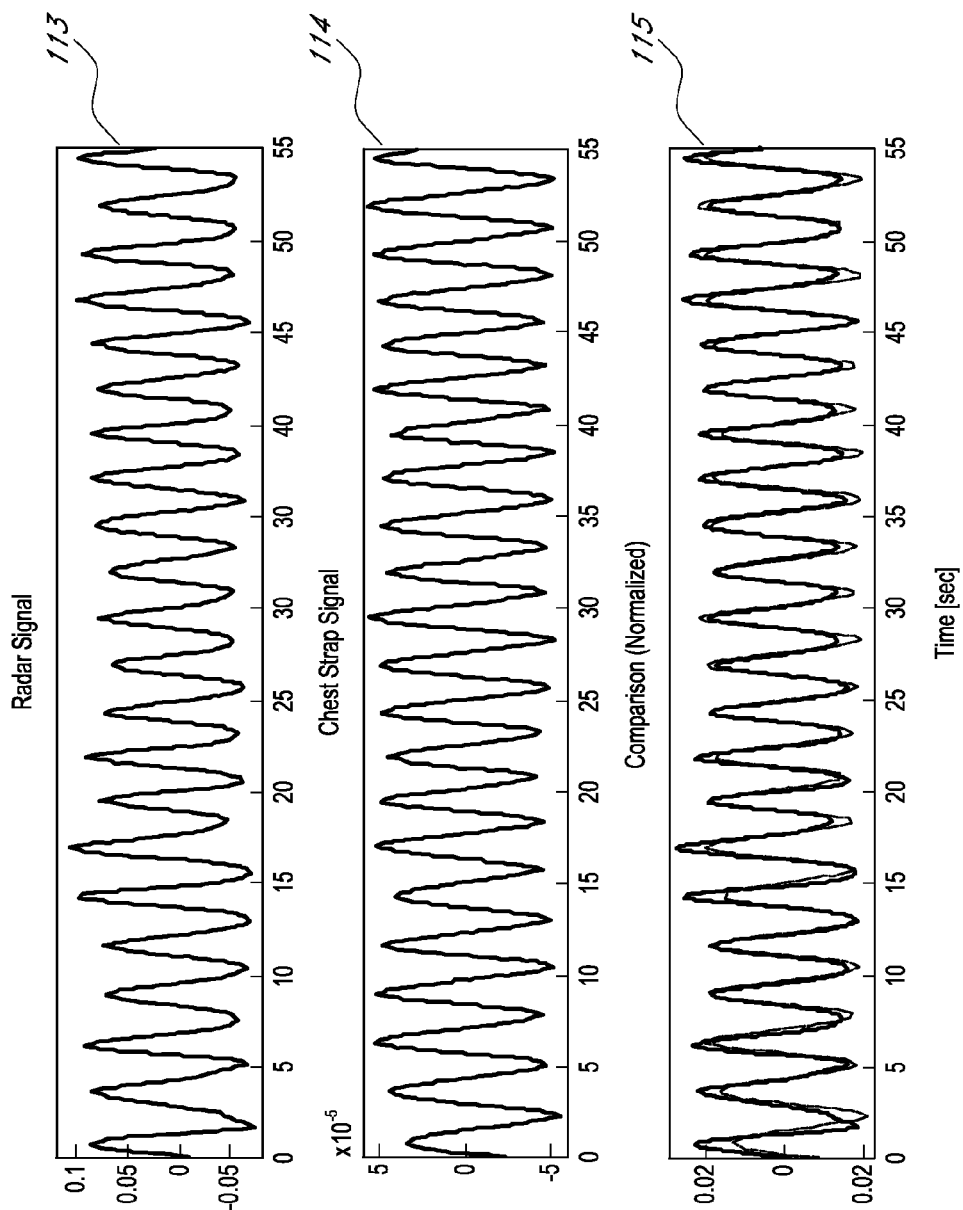

FIG. 1E illustrates the physiological motion signal for a 59-year-old female with a BMI of 30, with COPD and CHF. Plot 113 shows the measurement obtained by the physiological motion sensor of system 100. Plot 114 shows the corresponding measurement obtained by a conventional sensor and plot 115 shows the comparison between the two measurements.

Figure 1F:
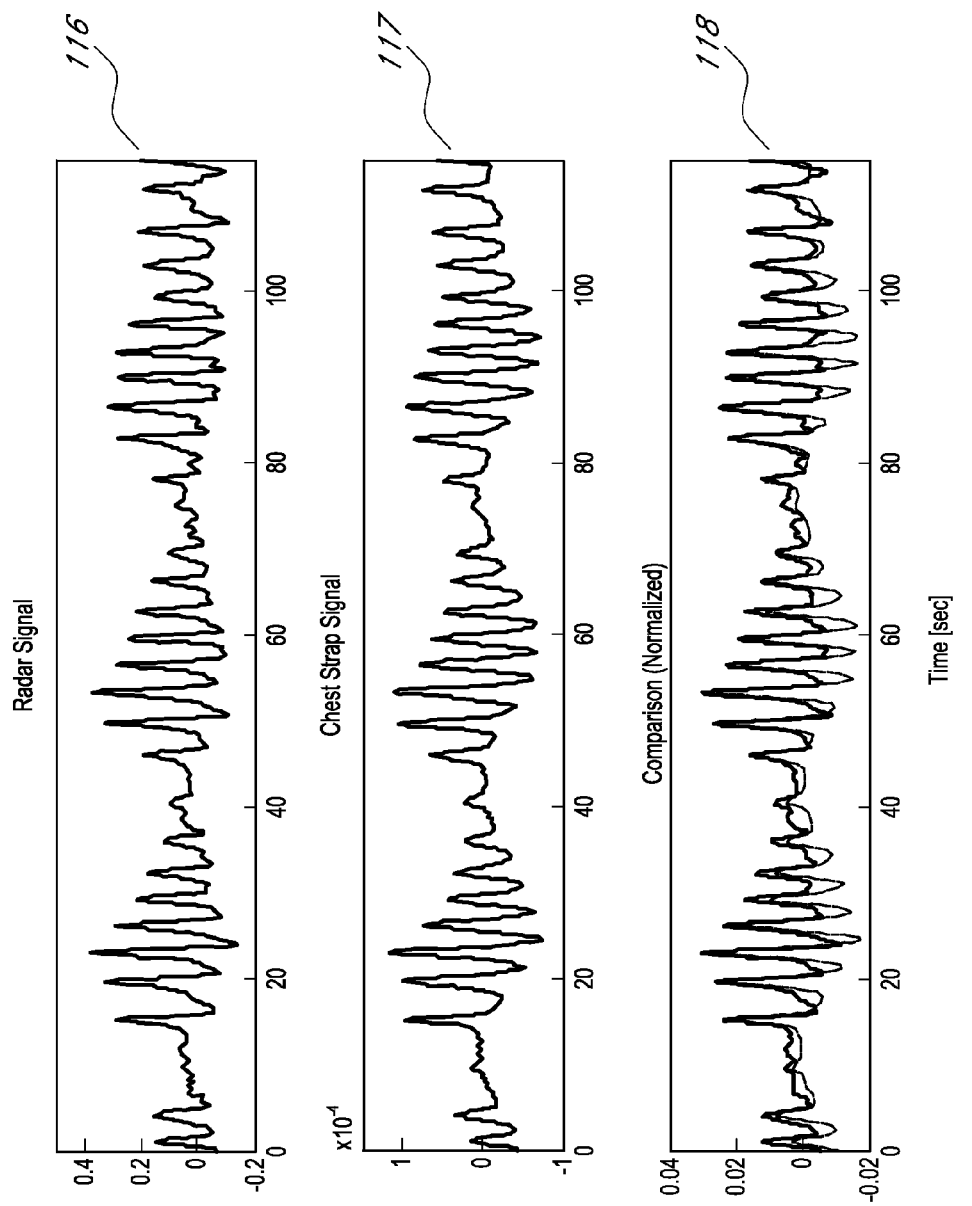

FIG. 1F illustrates the physiological motion signal for a 57-year-old Female with a BMI of 38, with CHF and CAD. Plot 116 illustrates detection of apnea (cessation of breathing) and variation in the respiration signal baseline for the subject. Plot 117 illustrates a corresponding measurement obtained by a conventional sensor and plot 118 shows the comparison between the two.

In various embodiments, the radar-based physiological sensor can include a user interface to allow a user to enter information or to allow the user to enter commands and/or instructions. In various embodiments, the user interface can include a start button and a stop button as disclosed in U.S. Provisional App. No. 61/128,743 which is incorporated herein in its entirety, said starting and stopping buttons. In various embodiments, the user interface can include a clear button. In various embodiments, the user interface can include additional buttons (e.g., a save button, a print button, etc.) or a keypad.

In various embodiments, the system 100 can communicate the information to a remote display and/or a central server or a computer. In some embodiments, SOAP web service can communicate data to a server. From the server, the respiration data can be accessed by a remote client with a browser and an internet connection as disclosed in U.S. Provisional App. No. 61/072,983, which is incorporated herein by reference in its entirety. FIG. 2 illustrates a block diagram of a system integrated with a remote interface 200. The system illustrated in FIG. 2 includes a radar-based physiological sensor 201 in electrical communication with a signal processor 202. The information from the signal processor can be displayed locally on a local display 203 or can be stored in a server 205 over a web service 204. A remote client 207 can access the information stored on the server using the internet 206 or some other communication protocol.

In various embodiments, the system 100 can include an add-on module with wireless connectivity as disclosed in U.S. Provisional App. No. 61/125,022, which is incorporated herein by reference in its entirety. FIG. 3 illustrates a block diagram of a system 300 including radar-based physiological sensor including an add-on module. As illustrated in FIG. 3, the device 301 is networked to a patient monitoring system 302 using a personal area network technology such as Bluetooth, Ultra Wide Band, Wireless USB, etc. The patient monitoring system 302 can display the cardiopulmonary motion information on its local interface and/or forward the data to a remote database over the internet 304 or a hospital network 303 such that it can be accessed by a remote client 305.

Figure 4:
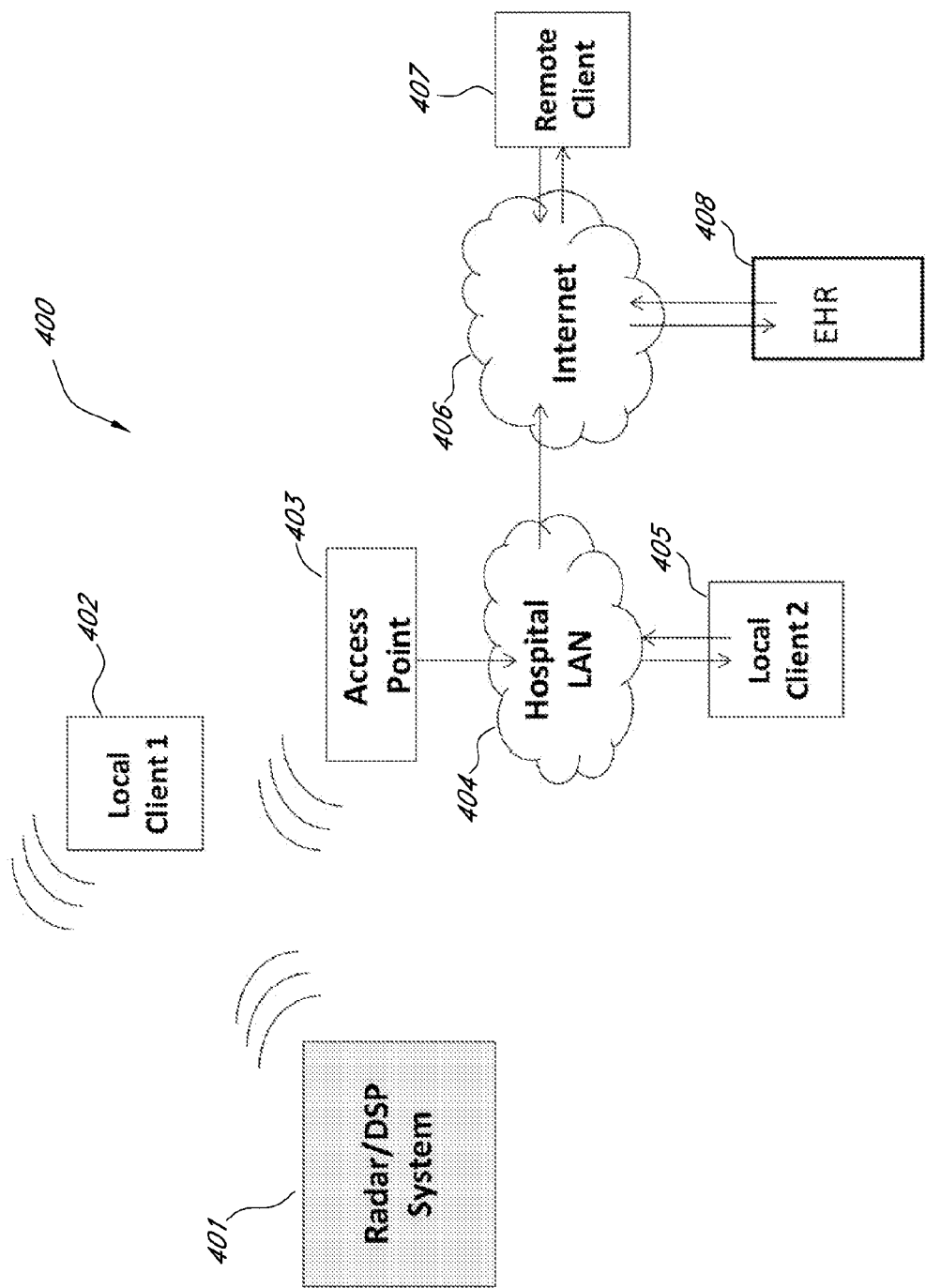
FIG. 4 schematically illustrates the block diagram of a standalone radar-based sensor device configured to communicate with a hospital network.

FIG. 4 illustrates the block diagram of a Standalone Device configured to communicate with a hospital network. The system 400 illustrated in FIG. 4 includes a radar-based physiological sensor system 401 similar to the system 100 described above including a digital signal processor. The system 401 is in wireless communication to an access point 403. The radar-based physiological sensor system 401 can communicate information related to the physiological or cardiopulmonary motion to a remote server, connected to the hospital network 404, via the access point 403 using a wireless communication technology such as Bluetooth, Wireless USB, etc. The access point 403 can be connected to the hospital network 404 (e.g., the hospital LAN) over a wired or a wireless network. A local client 402 or 405 can access the information from the system 401 or the server wirelessly or over the hospital network 404. A remote client 407 can also have access to the information over the internet 406. In various embodiments, the information from the system 401 can be communicated to a central database 408 maintaining electronic health records over the internet 406.

Various embodiments of the system 100 can communicate information using TCP/IP over Ethernet Connectivity or with Serial RS-232 Connectivity. FIG. 5 illustrates another embodiment of a standalone device with wireless connectivity 500 as disclosed in in U.S. Provisional App. No. 61/125,022, which is incorporated herein by reference in its entirety. A radar system 501 similar to system 100 described above can use any of several wireless technologies to connect with a central healthcare practitioner's station, a patient information database, and/or an electronic medical record 505. The network can be configured to forward or display the data on PC's, PDA's or medical tablets of a remote client 504 over the internet 503. In a hospital setting, the system 501 can use communication protocols such 802.11 or any other communication protocol the hospital uses for networking. If the system 501 is used in a home or field setting, a 3G cellular or WiMax connection can be used in lieu of a LAN technology to send the data to the electronic health record 505 or a remote client 504 or other databases via the internet 503. In various embodiments, the information sent by the system 501 can be viewed by a healthcare practitioner.

In various embodiments, the device 501 can also be made to conform with the standards set forth by the Continua health alliance by following a scheme such that the device uses Bluetooth or USB to connect with a managing computer which will disseminate the data to a healthcare provider's network for storage or examination.

Figure 6:
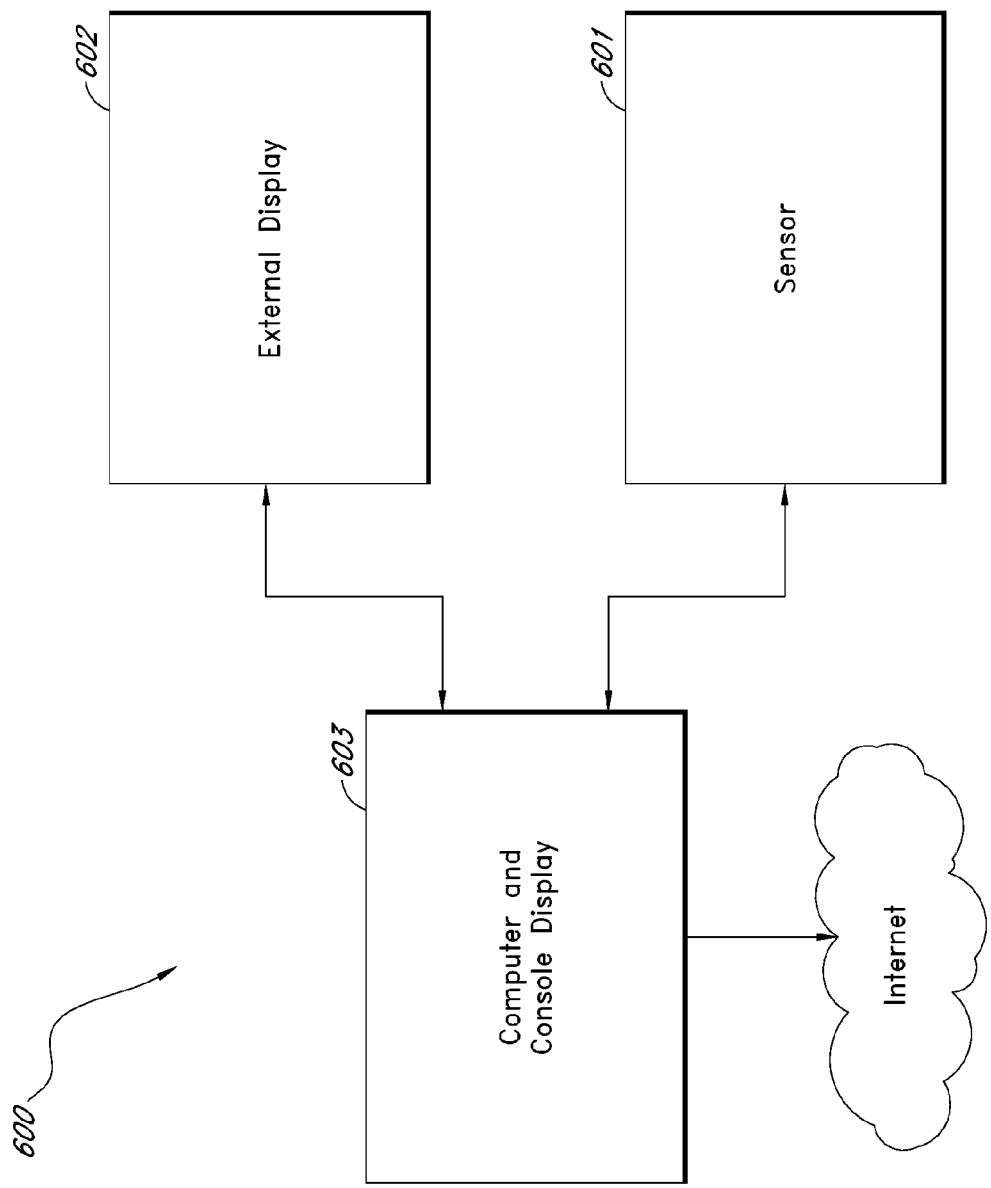
FIG. 6 schematically illustrates another embodiment of a radar-based physiological motion sensor comprising a processor and a display.

FIG. 6 illustrates a system 600 including a physiological motion sensor 601 similar to system 100 described above in communication with a computer including a console display 603. In some embodiments, the computer 603 can be in communication with an external display 602. In some embodiments, the sensor 601 can communicate information related to the physiological motion to the computer for storage and/or display. A remote client can be able to access the information from the computer over the internet.

Various embodiments of the physiological motion sensor system 100 described herein can be used as continuous monitoring devices and systems. Various embodiments of the system 100 can be used to measure cardiopulmonary motion from a distance ranging from many meters to the point of contact with body. Various embodiments of the system 100 provide physiological waveforms, displays of physiological variables, history plots of physiological variables, indications of signal quality and/or indications of specific conditions. Various embodiments can include physiological waveforms including respiratory waveforms, heart waveforms, and/or pulse waveforms. Various embodiments can include physiological variables including respiratory rate, heart rate, tidal volume, depth of breath, inhale time, exhale time, inhale time to exhale time ratio, airflow rate, heart beat-to-beat interval, and/or heart rate variability. Various embodiments can include indications of signal quality, which can be general such as good quality, or poor quality, or which can be specific, including indication of low signal power, signal interference, non-cardiopulmonary motion, or circuit noise. Indications of specific conditions can include general indications of health, warnings of physiological variables that are outside the normal range, indication of abnormal breathing patterns, or indication of paradoxical breathing.

As shown below in FIG. 21, in various embodiments, the continuous vital signs monitor can have a local interface, including buttons and display, and it can have electronic communications to a central monitoring site (such as a central nurse's station) or to a central database (such as an electronic medical record). In various embodiments, the system 100 can be a stand-alone device, or it can be a module integrated in another vital signs monitoring device (e.g., a hospital monitoring system). Various embodiments of the continuous vital signs monitor can be used in the hospital or clinic for general patient monitoring, for monitoring of post-surgical patients, for monitoring of patients receiving pain medications that put them at high risk of respiratory depression, for monitoring patients with respiratory diseases or disorders, for monitoring patients using invasive or non-invasive ventilators, and for monitoring of patients during medical imaging scans as disclosed in U.S. Provisional App. No. 61/154,176 which is incorporated herein by reference in its entirety. Various embodiments of the continuous vital signs monitoring system 100 can be used in pediatric and/or neonatal wards in hospitals.

Various embodiments of the continuous vital signs monitor can be used in the home as disclosed in U.S. Provisional App. No. 61/072,983, which is incorporated herein by reference in its entirety and in U.S. Provisional App. No. 61/196,762 which is incorporated herein by reference in its entirety. Various embodiments of the device can operate locally, remotely or both. Various embodiments of the device can connect to another device, including, but not limited to, a personal health system, another home healthcare device, a personal computer, a mobile phone, a set-top box, or a data aggregator. Various embodiments of the device can connect via a wired or wireless connection to a central station at a remote location (away from the home). In various embodiments, the system 100 can have a local display which displays some or all of the obtained data on the display. In various embodiments, the system 100 can communicate the information to another device in the home, and/or it can communicate the information via a wired or wireless connection to a central database that is remote (e.g., away from the home). In various embodiments, the device can operate with local control, can be controlled by another device via a wired or wireless connection, can operate automatically, or can be controlled by a central system that is remote (e.g., away from the home). In various embodiments, this home device can be used for general vital signs monitoring, or it can be used to monitor chronic illnesses that affect the cardiopulmonary system including, but not limited to, Diabetes, Chronic Obstructive Pulmonary Disease, and Congestive Heart Failure. In various embodiments, the non-contact continuous vital signs monitor can be a module that is integrated into a personal health system or another home healthcare device, sharing its display and communications. Various embodiments of the system 100 can conform to Continua Health Alliance guidelines.

In various embodiments, the continuous vital signs monitor can also be used in a skilled nursing facility, in a similar embodiment to the hospital monitor. Embodiments of this device can be used for general vital signs monitoring of the elderly or ill, and can also be used for early detection of pneumonia. Embodiments of the continuous vital signs monitor can also be used in emergency vehicles (e.g., ambulances, helicopters, etc.) to monitor a patient during emergency transport. Various embodiments of the system 100 can also determine the duration of subject activity or the percentage of time the subject is active. This information can be used to provide an activity index. Changes in the activity index can be used as indicators of a change in health state. In various embodiments, the physiological motion sensor can be used to detect battlefield survivors and monitor their physiological signals as disclosed in U.S. Provisional App. No. 61/001,995 which is incorporated herein by reference in its entirety. In various embodiments, a software based array configuration that is executable by a processor can be applied to Doppler radar to search for survivors in detecting mode, and to track them in target mode by focusing the beam. Survivor location can be determined from DOA processing at dual or multiple frequencies.

As described in more detail below, the system 100 can include algorithms for calculating respiratory rate, accuracy of the respiratory rate, algorithms to recognize inaccurate data, to recognize interfering motion, to recognize electrical signal interference, to recognize electrical noise, to report varying rates, to analyze the regularity or irregularity of the respiratory rate and to signal or alert a user if the respiratory rate is high or low, etc.

As described in more detail below, the system 100 can include hardware and/or software which is executable by a processor to improve signal quality, such as, for example, RF leakage cancellation, DC cancellation, noise cancellation, low IF architecture, homodyne system balancing, etc. Various embodiments of the system 100 described herein can have the capability to discern between cardiopulmonary and other motions. In various embodiments of the system 100, methods and algorithms for motion discrimination and detection can enable increased accuracy of cardiopulmonary data. Various embodiments described herein employ methods of decreasing the delay between the occurrence of an event and the reporting and display of that event by DC cancellation and high speed data acquisition. A low time delay is typically important for applications in which another device uses the reported event to initiate or trigger another action. A low time delay also improves synchronization with other measurements. The respiration or heart waveforms that are generated by the various embodiments described herein can be used to trigger actions by other systems. For example, various embodiments describe triggering medical imaging (e.g., with CT or MRI scans) based on cardiac or respiratory displacement and triggering assistive ventilation based on spontaneous respiratory effort. The respiration or heart waveforms that are generated by the various embodiments described herein can be used to provide physiological synchronization with other systems. For example, various embodiments describe synchronizing cardiopulmonary motion or other motion to medical imaging (e.g., CT scans or MRI) systems, assistive ventilation systems, polygraph systems, security screening systems, biofeedback systems, chronic disease management systems and exercise equipment.

Various embodiments of the system 100 can automatically, using the algorithms related to Direction of Arrival (DOA), track a subject's physiological signals as the subject moves around e.g., up and down in a bed. Various embodiments of the system 100 can automatically, using the algorithms related to DOA, track a subject's location as the subject moves around e.g., up and down in a bed. Various embodiments of the system 100 can be configured to cancel extraneous motion when extracting cardiopulmonary motion which can result in greater accuracy of the readings. Various embodiments of the system 100 can also, using algorithms such as DOA, separate and monitor or measure secondary or multiple cardiopulmonary motion sources (e.g., cardiopulmonary motion of a second or multiple subjects nearby can be reported simultaneously). Various embodiments of the system 100 can also, using algorithms such as DOA, separate and suppress secondary or multiple cardiopulmonary motion sources (e.g., cardiopulmonary motion of a second or multiple subjects nearby can be suppressed such that only the intended subject is measured). Various embodiments of the system 100 can include a radio frequency identification (RFID) tag in conjunction with DOA to ensure tracking of the desired subject.

Various embodiments described herein can use various approaches for motion compensation such as empirical mode decomposition (EMD), suppression of secondary motion sources with direction of arrival (DOA) processing, blind signal separation (BSS), independent component analysis (ICA), and suppression of motion in the direction of high-frequency received signals.

Various embodiments of the system 100 can include radio frequency identification (RFID) tag configured to enable positive identification of a monitored subject. Various embodiments of the system 100 can be adapted to have various sizes, form factors and physical dimensions suitable for including in a bedside unit, a hand held unit, in a PDA, a module as part of larger medical system, etc. Various embodiments of the system 100 can include one or more outputs such that information can be viewed and controlled either locally or remotely. In various embodiments, the system 100 can be a thin client application such that the system 100 will include the sensor, data acquisition, and communications, and demodulation, processing, and output systems would be in another device. For example, in some embodiments, the system 100 is provided to a network system where controls and processing are centralized for a network of sensors and the sensor and networking/communications part is onsite, near the subject. In some embodiments, the system 100 automates the initiation of measurements under certain predefined circumstances e.g., when person is detected in a room, at set time intervals, etc. In various embodiments, the system 100 can be used to perform non-contact measurement of depth of breath and relative tidal volume or absolute tidal volume. Various embodiments of the system 100 can be used as a cardiopulmonary and/or activity monitor.

In various embodiments, the system 100 can be integrated with other contact or non-contact medical monitoring devices, such as, for example, pulse oximeters, blood pressure cuffs, etc. In various embodiments, the system 100 can be integrated with an air flow sensor and a pulse oximeter to meet requirements of Type 3 Home Sleep Test. In various embodiments, sleep apnea detection can be performed, either with the system 100 alone or in combination with other devices. In some embodiments, the system 100 can be used to measure physiological response to particular stimuli e.g., questions, images, sounds, entertainment, activities, education. In various embodiments, the system 100 can be used by veterinarians as a non-contact cardiopulmonary monitor for animals. In various embodiments, the system 100 can be used by researchers as a non-contact cardiopulmonary monitor in animals, for example, to study vital signs during hibernation or for post surgery monitoring of animals. Some embodiments of the system 100 can be used in triage applications e.g., battlefield triage or disaster area triage. Various embodiments of the system 100 can be used to monitor cardiac, cardiopulmonary, and/or respiratory activity in infants and neonates.

Non-contact physiological motion sensors, according to various embodiments described herein can be used to obtain a measurement of respiratory motion, which can be used as a continuous respiratory monitor. This continuous respiratory monitor can be a stand-alone device, with its own display, buttons and/or external communications, or it can be a module integrated with other vital signs monitoring devices or other medical devices. This continuous respiratory monitor can provide respiratory waveforms. This continuous respiratory monitor can provide current values and historical plots for respiratory values including respiratory rate, tidal volume, inhale time, exhale time, inhale time ratio to exhale time ratio, depth of breath, abdominal excursion to chest excursion ratio, and/or airflow rate. This continuous respiratory monitor can provide information on the variability and historical variability, each in various frequency bands, of respiratory rate, tidal volume, inhale time, exhale time, inhale time ratio to exhale time ratio, depth of breath, abdominal excursion ratio, and/or airflow rate. This continuous respiratory monitor can provide indications and history of indications of the presence and degree of paradoxical breathing, the presence and degree of obstructed breathing, and/or the presence and degree of distressed breathing. This continuous respiratory monitor can provide information on the frequency, depth, and length of gasps and sighs. This continuous respiratory monitor can provide information on the frequency and duration of non-cardiopulmonary motion. This continuous respiratory monitor can provide information on changes in the shape of the breathing waveform, or changes in the harmonic content of the breathing waveform. Various embodiments of the continuous respiratory monitor system include an interface that provides alerts for high and low respiratory rates, rate history, tidal volume history, information related to inhalation/exhalation intervals, indication of paradoxical breathing, indication of obstructed breathing, subject position, activity level/monitoring, for distinguishing between motion and measured cardiopulmonary activity, health ranking (e.g., high, medium, and low) and signal quality ranking (e.g., alerts when signal is too low). Various embodiments of the system 100 can provide alerts for high respiratory rates, low respiratory rates, high variability of respiratory rates, low variability of respiratory rates, irregularity of breathing pattern, changes in breathing pattern, high inhale time to exhale time ratio, low inhale time to exhale time ratio, and changes in inhale time to exhale time ratio. Thresholds for these alerts can be values that are pre-set, values that can are set by the user, values that are calculated based on a patient's baseline respiratory rates, or values that are calculated based on a patient's baseline rates and historical variability of a patient's rates.

The system 100 can be used in systems that monitor sleep in subjects. For example, in some embodiments, the system 100 can provide a non-contact approach to replace piezoelectric or inductive chest straps for measuring respiratory effort and/or respiratory rates. In various embodiments, the system 100 can provide a non-contact approach to replace piezoelectric or inductive chest straps for measuring the difference in respiratory related motion for different parts of the body (e.g., as a paradoxical breathing indicator). In various embodiments, the physiological motion sensor can be used either alone or in combination with other devices to detect obstructive sleep apnea, central sleep apnea or other sleep disorders. In various embodiments, the system 100 can be used with an air flow sensor and/or a pulse oximeter for a Type 3 Home Sleep test. In various embodiments, the system 100 can be used with a wireless air flow sensor and/or a wireless pulse oximeter for a wireless Type 3 Home Sleep test with minimal patient contact. In various embodiments, the system 100 can be used alone as a Type 4 Home Sleep Test. In various embodiments, the system 100 can be used alone as a Type 4 Home Sleep Test that involves no contact with the subject and operates from a distance. In various embodiments, the system 100 can provide a non-contact way of measuring cardiopulmonary activity as well as limb and other body motion during sleep. Various embodiments of the system 100 can conform to Continua Health Alliance guidelines. In various embodiments, the system 100 can be used for sudden infant death syndrome (SIDS) monitoring or screening (e.g., in infants or neonates). Various embodiments of the system 100 can be used to monitor cardiopulmonary and/or cardiac activity in infants and newborns. Various embodiments of the system 100 can be used on neonates, infants, children, adults, and elderly subjects.

Various embodiments of the physiological motion sensors described herein can be used to obtain respiratory effort waveforms. As such, they can be used as part of a home sleep test as disclosed in U.S. Provisional App. No. 61/194,836 which is incorporated herein by reference in its entirety that includes pulse-oximetry and nasal airflow sensors to detect both central apnea and obstructive sleep apnea, and to differentiate between the two. Various embodiments of the respiratory effort sensor can also be used as part of a sleep assessment in a sleep laboratory or as part of a sleep apnea screening device used in the home. The respiratory effort information can also contain information about the degree of paradoxical breathing as disclosed in U.S. Provisional App. No. 61/200,761 which is incorporated herein by reference in its entirety. Various embodiments of the non-contact physiological motion sensors described herein can be used to obtain respiratory effort waveforms, respiratory rate, indication of paradoxical breathing, indication of activity, and heart rate. Various embodiments of the system 100 can be used as a home screening test for obstructive sleep apnea as disclosed in U.S. Provisional App. No. 61/194,836 which is incorporated herein by reference in its entirety and in U.S. Provisional App. No. 61/200,761 which is incorporated herein by reference in its entirety.

In various embodiments described herein, it can be possible to measure respiratory motion without any contact to the subject with a radar-based system specifically configured to measure physiological motion, and respiratory motion can be derived from the physiological motion signal. In addition to detecting respiratory rates from the motion, respiratory motion can also provide a measure of respiratory effort similar to that provided by piezoelectric or inductive chest belts designed to measure respiratory effort. In various embodiments, measurements of respiratory effort can be necessary to determine whether an event is a central apnea or an obstructive apnea. In various embodiments, respiratory motion can be measured with a radar-based system described herein overnight irrespective of the position of the subject in the bed.

In various embodiments, the physiological motion sensor can include a radar-based device that can be configured to detect paradoxical breathing (e.g., when the abdomen contracts as the rib cage expands or the rib cage contracts as the abdomen expands). In most cases, during obstructive apnea paradoxical breathing can be exhibited, although paradoxical breathing cannot indicate an airway obstruction. In various embodiments, an indication of paradoxical breathing and of the level of paradoxical breathing can be useful in detecting obstructive apnea.

Various embodiments of the radar-based physiological motion sensor can also measure non-cardiopulmonary motion (e.g., activity such as tossing and turning in bed, wakefulness, or involuntary movement during sleep). The level of activity can be used to estimate the quality of sleep, and it can be helpful in determining the sleep state of the subject. Various embodiments of the system 100 can also be used to determine when the person is in the bed or out of the bed, to track how often the subject is getting out of bed during the night, etc. Various embodiments of the system 100 can also measure the heart rate. During apneaic events, the heart rate can increase, and in some embodiments, the heart rate can be used to confirm an apnea that is indicated by other measurements.

Various embodiments of the system 100 can be used to estimate the tidal volume, or the amount of air inhaled and exhaled with each breath. When the tidal volume is accurately measured, it can be used to estimate the airflow. Various embodiments of the system 100 can include multiple-antenna hardware and software that is executable by a processor such that it can track the subject as he/she moves in bed during the night. This can provide information about how much the subject is moving within the bed, and it can improve the radar-based measurement of respiration and activity. The physiological motion sensor can be used in conjunction with other sensors to provide a more complete picture of respiration during sleep. Various embodiments of the system 100 can include additional sensors including, but not limited to, a nasal/oral airflow sensor and a pulse oximeter.

In various embodiments, the nasal/oral airflow sensor can provide either an indication of whether the patient is breathing, or with a more advanced sensor, an estimate of the velocity of the airflow. This can be used to accurately detect apnea, and with the more advanced sensors, it can also be used to detect hypopnea (reduction in airflow). An accurate measurement of airflow is critical to determine whether an event is a hypopnea or an apnea. The nasal/oral airflow sensor can include one or more thermistors, hot-wire anemometers, or pressure sensors. In some embodiments, a nasal/oral airflow sensor can be provided to measure the air flow through each nostril and the mouth independently. In most embodiments, an airflow sensor alone cannot determine whether an apnea is central or obstructive.

In various embodiments, the pulse oximeter can provide information on the effectiveness of respiration by arterial hemoglobin saturation or an estimate of blood oxygenation. Decreases in blood oxygenation can indicate the severity of an apneaic or hypopneaic event, and are important for clinical decisions. The pulse oximeter can also provide a heart rate. In various embodiments, pulse oximetry can be recorded on the finger or on the ear though in most embodiments, the finger measurements are generally considered more accurate.

In various embodiments, the pulse oximeter and oral/nasal airflow sensors can require contact with the patient. In various embodiments, the pulse oximeter and oral/nasal airflow sensors can be configured to transmit data wirelessly to the data recording device. In various embodiments, this recording device can be integrated with the radar-based physiological motion sensor device.

Various embodiments of the system 100 can include a wireless home sleep monitor, including a radar-based physiological motion sensor, a pulse oximeter with wireless communications, and a nasal/oral airflow sensor with wireless communications, operating without wires on the patient and with minimal contact to the patient. Various embodiments of the home sleep monitor can provide a complete picture of respiration during sleep (e.g., airflow, respiratory effort, and oxygenation). In various embodiments, the home sleep monitor system 100 can also provide a heart rate, variability in the heart rate, and information about motion during sleep. In various embodiments, the pulse oximeter and oral/nasal airflow sensor can be configured to independently send their data wirelessly to the hub, such that no wires would be required. This can provide an advantage over other commercially available home sleep monitors, which requires wires to the recording device or wires to a single body-worn device with then wirelessly, transmits data to the recording device.

Various embodiments of the physiological motion sensor system 100 can be used to obtain a spot check of vital signs, such as respiratory rate and heart rate, at a point in time or intermittently (e.g., at regular intervals, at specified times, on demand, etc.). In various embodiments, the system 100 can have different user-selectable time intervals over which the breathing rate can be measured (e.g., 15 seconds, 30 seconds, 60 seconds, etc.), a chosen number of breathing cycles (e.g., 2, 3, 5, etc.), or a more general indication of the measurement length (e.g., "quick," "normal," "extended"). In various embodiments, the system 100 can use signal quality, respiratory rate, respiratory rate variability, and respiratory waveform shape variability to automatically select a measurement interval. In various embodiments, the system 100 can recognize data with interference from non-cardiopulmonary motion, vibration, other radio-frequency signals, or circuit noise, and can not include it in rate calculation. This can improve the accuracy of rate readings. In various embodiments, the accuracy of rate readings can be further improved through rate estimation algorithms that include accuracy checks. Various embodiments of the system 100 can be configured to identify non-cardiopulmonary motion by the subject or other motion near the subject when extracting cardiopulmonary motion, which can result in greater accuracy of the readings and/or avoid displaying an error due to non-cardiopulmonary motion detection.

In various embodiments, both time and frequency domain approaches can be used for assessment of validity of respiratory rate calculations. In various embodiments, the system 100 can provide a signal quality feedback system during and after the measurement. The signal quality feedback can indicate non-cardiopulmonary motion, signal interference, low signal power and/or clipping due to signal overload. In various embodiments, system self-test and environment-checks before measurement can be performed. In various embodiments, the system 100 can use a free-running signal source to reject RF interference, e.g., random frequency drifts can provide immunity against interference from sources operating in the same frequency band. In various embodiments, the system 100 can be integrated with other devices, approaches and peripherals used for chronic disease management in homes and other remote settings. For example, the system 100 can be used with blood pressure cuffs, thermometers in a home health management unit. Various embodiments of the system 100 can provide cardiopulmonary information as part of a health kiosk. Various embodiments of the system 100 can be used to measure the amount of air inhaled/exhaled with each breath (relative tidal volume) and the depth of breadth. Various embodiments of the system 100 can provide alerts of high or low heart or respiratory rates or irregular heart or respiratory rates. In various embodiments, the system 100 can be used to detect heart arrhythmia or respiratory sinus arrhythmia. Various embodiments of the system 100 can have an aiming or a focusing element to help the user aim the system properly for accurate measurements. In various embodiments, on-demand spot check measurements are provided. In various embodiments, the measurements can be initiated locally or remotely. Various embodiments of the system 100 can be integrated with audiovisual or other multimedia devices.

The system 100 can be used as a non-contact vital signs spot check to obtain respiratory rate and/or heart rate in one or more subjects. Embodiments of the vital signs spot check system 100 can be used in a hospital or skilled nursing facility for regular vital signs assessment of in-patients, or in any clinical setting for vital signs assessment of patients checking in for treatment of checkups. Embodiments of the vital signs spot check system 100 can be used in pediatric or neonatal wards for monitoring cardiopulmonary activity in infants and newborns. Various embodiments of the system 100 can include a local interface, including' buttons and display, and can have electronic communications to a central site (such as a central nurse's station) or to a central database (such as an electronic medical record). In various embodiments, the system 100 can be a stand-alone device, or it can be a module providing one measurement (such as respiratory rate) or multiple measurements (such as either respiratory rate and tidal volume or respiratory rate and heart rate) integrated with another vital signs spot check device. In various embodiments, the vital signs spot check system 100 can display only a rate or rates that are measured. In some embodiments, the system 100 can be configured to display a snapshot of the heart and/or respiratory waveforms. In various embodiments, the non-contact vital signs spot check can be used for triage in an emergency room, a disaster area, or a battlefield as disclosed in U.S. Provisional App. No. 61/154,728 which is incorporated herein by reference in its entirety.

Various embodiments of the vital signs spot check system described herein can be used in the home for management of chronic illnesses as disclosed in U.S. Provisional App. No. 61/196,762 which is incorporated herein by reference in its entirety, including COPD, diabetes, and congestive heart failure. As described above, in various embodiments, the system 100 can be connected to another device, including, but not limited to, a personal health system, another home healthcare device, a personal computer, a cellular phone, a set-top box, or a data aggregator. In various embodiments of the system, the device can connect via a wired or wireless connection to a central station that is remote (e.g., away from the home). In various embodiments, the system 100 can have a local display with some or all of the obtained data displayed on it. In some embodiments, the system 100 can communicate the information to another device via a wired or wireless connection to a central database that is remote (e.g., away from the home). In various embodiments, the device can operate with local control or can be controlled by another device via a wired or wireless connection. In various embodiments, the system 100 can operate automatically, or can be controlled by a central system that is remote (e.g., away from home). In various embodiments of the system, the vital signs spot check system 100 can be a module that is integrated into a personal health system or another home healthcare device, sharing its display and communications.

In various embodiments, the vital signs spot check system 100 can be included in a health kiosk as disclosed in U.S. Provisional App. No. 61/128,743 which is incorporated herein in its entirety. Various embodiments of the kiosk vital signs spot check system 100 can be a standalone device that sends vital signs information to a kiosk computer. Various embodiments of the system 100 can require a local person to press the buttons on the device to initiate operation. In some embodiments, the system 100 can be controlled by a remote healthcare practitioner with a start signal sent to the device through the kiosk computer. In some embodiments, the system 100 can initiate the measurement automatically when the patient enters the kiosk area; the system 100 can sense the presence of the patient, or the system 100 can use data from another device that senses the presence of the patient. Various embodiments of the kiosk vital signs spot check system 100 can be a module that is integrated into the kiosk such that the patient is not aware of its presence. In such embodiments, the system 100 can be controlled by the kiosk computer, either with a remote healthcare practitioner initiating the measurement, or a measurement being initiated automatically, possibly a fixed time after the patient enters the kiosk or sits down. In various embodiments, the system 100 can measure respiratory rate only once, or it can continue to measure intermittently while the patient is at the kiosk, providing a rate history for the time the patient was in the kiosk to the remote healthcare provider.

In various embodiments, the cardiopulmonary information, activity and other physiological motion data collected by the system 100 can be used to assess and monitor psychological or psycho-physiological state or changes in psychological or psycho-physiological state. In various embodiments, the system 100 can monitor changes in psycho-physiological state induced by external stimuli (e.g., questions, sounds, images, etc.)

Various embodiments of the non-contact physiological sensor system 100 can be used to obtain respiratory rate, heart rate, and physiological waveforms that can be analyzed to help assess the psychological state of the measurement subject as disclosed in U.S. Provisional App. No. 61/141,213 which is incorporated herein by reference in its entirety. The psychological information can be used for many applications, including, but not limited to, various medical applications, security screening of subjects at airports, borders, and sporting events and other public areas, lie detection, and psychological or psychiatric evaluation. In various embodiments of the system 100 used in security screening applications information output from the system 100 can be used to help detect malintent.

Various embodiments of the physiological motion sensor system 100 can be used to provide physiological motion waveforms that can be used for synchronization of medical imaging with chest or organ motion as disclosed in U.S. Provisional App. No. 61/154,176 which is incorporated herein by reference in its entirety.

Various embodiments of the system described herein can be used to provide physiological motion waveforms that can be used for synchronization of mechanical ventilation, including non-invasive ventilation, with respiratory effort.

Various embodiments, the system 100 can be integrated with a pulse oximeter. The various embodiments described herein, the physiological motion sensor 100 can be used to sense respiratory information and can be operated in connection with a pulse oximeter that measures the patient's oxygen saturation. In various embodiments, the combination of the two sensor systems can provide information on ventilation and oxygenation, giving a more complete measurement of respiratory efficacy than either could alone as disclosed in U.S. Provisional App. No. 61/194,839 which is incorporated herein by reference in its entirety. These embodiments have applications in the monitoring of post-surgical patients, patients using opioid-based medications, patients at risk of respiratory depression, etc.

Various embodiments of the system 100 can be integrated with or connected to a patient-controlled analgesia system, and prevent additional doses of analgesia if the respiratory rate drops below a threshold, indicating the onset of opioid-induced respiratory depression. Various embodiments can also use additional respiratory variables in the calculation of when to prevent additional doses of analgesia, including tidal volume, inhale time to exhale time ratio, depth of breath, frequency of non-cardiopulmonary motion, duration of non-cardiopulmonary motion, length of pauses in breathing, frequency, depth, and length of gasps, frequency, depth, and length of signs, and/or shape of the breathing waveform. The thresholds in such embodiments can be at least one of pre-set in the factory, set by the healthcare professional, calculated based on patient baseline values. Various embodiments can also include alerts.

In various embodiments, the system 100 can be used to determine if a subject is breathing and/or if his/her heart is beating. In various embodiments, the system 100 can detect presence of and/or monitor cardiopulmonary information (respiratory and/or cardiac) from several meters away from a subject to the point of contact. In various embodiments, the system 100 can detect and monitor cardiopulmonary information (respiratory and cardiac) while in contact with the subject's body. In various embodiments, the system 100 can measure body surface motion associated with cardiopulmonary activity. In various embodiments, the system 100 can measure internal body motion associated with cardiopulmonary activity. In various embodiments, the system 100 can measure electromagnetically measureable internal and/or external body changes associated with cardiopulmonary activity, including but not limited to impedance changes. In various embodiments, the system 100 can perform the above described functions by itself or in combination with other monitoring devices.

In various embodiments, the physiological motion sensor described herein can be used to determine whether a subject requires cardiopulmonary resuscitation or use of a defibrillator (either an automated external defibrillator or a hospital defibrillator) by detecting whether the patient has a heartbeat as disclosed in U.S. Provisional App. No. 61/194,838 which is incorporated herein by reference in its entirety. In various embodiments, the system 100 can send a signal to an external medical device such that it can integrate information from the system with information from other sensors to determine whether resuscitation is required. This determination can be indicated to the user visually or audibly. In various embodiments, the system 100 can provide a signal to a defibrillator, such that if a heartbeat is detected, it is not possible to deliver an electrical shock to the patient. In various embodiments, the system 100 can send a signal to trigger external medical devices (e.g., defibrillator, ventilators, oxygen pumps, external respirators, etc.). The non-contact physiological motion sensor can be used after a defibrillator is used on a patient to determine if mechanical heart activity has resumed.

In various embodiments, the physiological motion sensor system 100 can be used to detect human motion at a distance and/or through radar-penetrable barriers. In various embodiments, this motion can include gross motion, such as walking, as well as small motion due to fidgeting or speech, and minute surface displacements resulting from cardiopulmonary activity. In various embodiments, the signals from the different sources can be separated by sophisticated signal processing and classified into biometric signatures unique for each individual as disclosed in U.S. Provisional App. No. 61/125,164, which is incorporated herein by reference in its entirety. In various embodiments, empirical mode decomposition as disclosed in U.S. Provisional App. No. 61/125,023, which is incorporated herein by reference in its entirety can be used for identifying individual signatures of physiological motion, including heart and respiratory motion waveforms. In some embodiments, empirical mode decomposition as disclosed in U.S. Provisional App. No. 61/125,023, which is incorporated herein by reference in its entirety can be used for identifying patterns in the variability of the amplitude of physiological motion. In various embodiments, empirical mode decomposition as disclosed in U.S. Provisional App. No. 61/125,023, which is incorporated herein by reference in its entirety can be used for identifying patterns in the variability of rate of physiological processes, such as heart rate variability and respiratory rate variability. In various embodiments, empirical mode decomposition as disclosed in U.S. Provisional App. No. 61/125,023, which is incorporated herein by reference in its entirety can be used for analyzing the interaction.

In various embodiments, many variables extracted from the cardiopulmonary motion signal can be used for biometric identification of individuals. In various embodiments, these variables include respiratory rate, inhale time, exhale time, inhale time to exhale time ratio, frequency of gasps, depth of gasps, length of gasps, frequency of signs, depth of signs, length of signs, depth of breath, presence of paradoxical breathing, degree of paradoxical breathing, tidal volume, ratio of abdominal excursion to chest excursion, harmonic content of breathing signal, ratio of the powers of different harmonics of the breathing signal, airflow rate, heart rate, and heart beat-to-beat interval. In various embodiments, the biometric identification would also include the variability of some or all of the above-mentioned variables in any number of frequency bands. In various embodiments, the biometric identification would also include the correlation between heart variables and respiratory variables. In various embodiments, the biometric identification would also include the frequency, duration, and amount of activity, and/or the frequency, duration, and amount of fidgeting.

Various embodiments of the system 100 can be used to determine the patient's tidal volume. Various embodiments of the system 100 can determine the relationship between displacement and tidal volume from medical record information, such that an accurately measured displacement can be converted to a tidal volume estimate as disclosed in U.S. Provisional App. No. 61/125,021, which is incorporated herein by reference in its entirety. In various embodiments, the system 100 can be used to determine the relationship between displacement and tidal volume based on patient maneuvers and medical record information, such that no contacting devices would be required to perform a calibration as disclosed in U.S. Provisional App. No. 61/125,018, which is incorporated herein by reference in its entirety. In some embodiments of the system, published formulae and the medical record can be used to predict the patient's vital capacity, such that if the patient performs a vital capacity maneuver by inhaling as deeply as possible and exhaling as fully as possible, the relationship between chest displacement and tidal volume can be calculated. In various embodiments, the system 100 can be calibrated before measurement, such that a tidal volume can be estimated. In various embodiments, the system 100 can be used to determine relationship between displacement and tidal volume via direct measurement: calibration with a spirometer or other device that accurately measures tidal volume as disclosed in U.S. Provisional App. No. 61/125,021, which is incorporated herein by reference in its entirety.

In various embodiments, relative tidal volume can be measured without calibration by providing information about whether the tidal volume is increasing or decreasing from a baseline value during continuous monitoring of a patient. In various embodiments of the relative tidal volume measurement, the relative tidal volume can be reset each time non-cardiopulmonary motion is detected, thereby avoiding errors in the relative tidal volume that result from changes in the relationship between chest displacement and tidal volume with the patient in different positions and with different spatial relationships between the sensor and the patient. Such an embodiment can be useful in non-ventilated or non-invasively ventilated critical care patients.

In various embodiments, data from the system 100 can be used to generate an activity index. In various embodiments, the system 100 can use the non-cardiopulmonary motion detection algorithm to determine the frequency and duration of subject activity or the percentage of time the subject is active. This information can be used to provide an activity index. In some embodiments, changes in the activity index can be used as indicators of a change in health state (e.g., if a patient's activity one day is significantly less than their baseline, it can indicate an illness). In various embodiments, the activity index can also be used during measurement of sleeping subjects to assess sleeping vs. waking states, insomnia, restless leg syndrome. In various embodiments, the activity index can be used to assess circadian rhythm disorders, alertness, metabolic activity, energy expenditure, and daytime sleepiness.

Various embodiments of the system 100 can be used to detect apnea, or the cessation of respiratory activity. For example, in some embodiments, if the physiological motion sensor detects no local maximum above a specified threshold, the system 100 can detect cessation of breathing as disclosed in U.S. Provisional Application No. 61/072,982 which is incorporated herein by reference in its entirety.

In various embodiments, the device can use an algorithm to determine whether there are no local maxima above specified threshold because breathing has ceased or because the subject is no longer present as disclosed in U.S. Provisional App. No. 61/072,983 which is incorporated herein by reference in its entirety and in U.S. Provisional App. No. 61/123,135, which is incorporated herein by reference in its entirety. In some embodiments, this algorithm can include analyzing two frequency bands: a high-frequency band and a low-frequency band, which are separated by software filters that is executable by a processor. If a breathing subject exists, the device can tell presence of a subject from the breathing signal which is mostly located in the low frequency band (below approximately 0.8 Hz). However, if the subject is not breathing, the device can still detect other motion including heart or other involuntary motion containing higher frequency components. Consequently, the device can determine presence of a non-breathing subject or the absence of a subject by comparing average power of different frequency bands with a threshold power level.

Various embodiments of the device can differentiate between the presence or absence of a subject based on frequency analysis and thresholds of the cardiopulmonary and non-cardiopulmonary signals obtained by the motion sensor. In various embodiments, the non-contact physiological motion sensor could be used to determine whether a subject is present as disclosed in U.S. Provisional App. No. 61/123,135, which is incorporated herein by reference in its entirety and in U.S. Provisional App. No. 61/001,996 which is incorporated herein by reference in its entirety and in U.S. Provisional App. No. 61/154,732 which is incorporated herein by reference in its entirety. For example, in a home monitoring scenario, the system 100 can be used to track how long the patient is in a specific position or a specific room. For example, in a kiosk scenario, the system could determine when a subject is present in the kiosk.

In various embodiments, the non-contact physiological motion sensor can also be used in security applications in a through-the-wall mode to determine whether there are people present in a container, or in a room. Because the sensor can be used to detect heart rate, it can be used to detect people who are hiding and/or holding their breath.

In various embodiments, the device can detect the presence or absence of a subject based on an algorithm as disclosed in U.S. Provisional App. No. 61/072,983, which is incorporated herein by reference in its entirety and in U.S. Provisional App. No. 61/123,135, which is incorporated herein by reference in its entirety. In some embodiments, this algorithm can include analyzing two frequency bands: a high-frequency band and a low-frequency band, which are separated by software filters that are executable by a processor. If a breathing subject exists, the device can tell presence of a subject from the breathing signal which is mostly located in the low frequency band (below approximately 0.8 Hz). However, if the subject is not breathing, the device can still detect other motion including heart or other involuntary motion containing higher frequency components. Consequently, the device can determine presence or absence of a subject by comparing average power of different frequency bands from threshold power level. In some embodiments, when the device is directed towards a specific bed or chair, subject presence can be detected by whether or not the physiological motion activity is above a threshold, wherein the threshold is set based on baseline measurements. In some embodiments, respiration processing can be switched off if no subject is present.

Various embodiments of the system 100 described herein include a radar-based physiological motion sensor. Various embodiments of the system 100 can include a source of radiation, one or more receivers to receive radiation scattered by the subject, a system (e.g., an analog to digital converter) to digitize the received signal. Various embodiments of the system 100 can also include a processor, a computer or a microprocessor to process the digital signal and extract information related to the physiological motion. In various embodiments, the processor can be controlled by a controller. The information related to the physiological motion can be communicated to a user in various ways (e.g., displayed visually or graphically, transmitted electronically over a wired or a wireless communications link or network, communicated audibly through an internal voice or an alarm, etc.).

Various embodiments of the system 100 described herein can operate with no contact and work at a distance from a subject. Various embodiments of the system 100 can operate on subjects that are in any position, including lying down, reclined, sitting, or standing. Various embodiments of the system 100 can work at various distances from the subject, from, for example, 0.1 to 4.0 meters. In some embodiments, the system 100 can be positioned in various locations relative to the subject, including, but not limited to, in front of the subject, behind the subject, above the subject, below the subject, to the side of the subject, or at various angles to the subject. In some embodiments, the system 100 can operate while being positioned on the subject's (e.g., patient's) chest. In these embodiments, the system 100 can be laid on the subject's chest, held to the subject's chest by a user, or worn on the subject's chest with a strap, necklace, or harness.

Various embodiments of the system 100 can use multiple receiver channels in combination with specialized algorithms to determine the direction of the target, to isolate physiological motion from spatially separated non-physiological motion, to simultaneously detect physiological motion from different subjects, to track the angle of a single subject, or to isolate the physiological motion from a first subject when one or more other subjects are within the field of view In various embodiments, multiple receive antennas and receive channels can be added to provide multi-channel outputs. These additional receive channels can be used to determine the direction of the target, to isolate physiological motion from spatially separated non-physiological motion, to simultaneously detect physiological motion from different subjects, or to isolate the physiological motion from a first subject when a second subject is within the field of view. Algorithms used to provide this information from multiple antennas include, but are not limited to, direction-of-arrival, independent component analysis, and blind source separation as disclosed in U.S. Provisional App. No. 61/141,213 which is incorporated herein by reference in its entirety and in U.S. Provisional App. No. 61/204,881 which is incorporated herein by reference in its entirety as disclosed in U.S. Provisional App. No. 61/137,519 which is incorporated herein by reference in its entirety.

In various embodiments, the physiological motion sensor system 100 can be a stand-alone device, with its own display, user interface, clock, recording hardware and software, signal processing hardware and software, and/or communications hardware and software; this can all be integrated in one unit, or can include multiple units, connected by a cable, such as USB. Alternatively, the physiological sensor can be integrated as part of a system that can include additional monitoring devices (physiological and/or non-physiological), and use that system's display, user interface, clock, recording hardware and software, signal processing hardware and software, and/or communications hardware. In various embodiments, the sensor can receive an analog or digital synchronization signal from the system, such that data from the sensor can be synchronized with signals from other sensors and events, or it can transmit an analog or digital synchronization signal to the system, or it can have an internal clock that is synchronized with the system clock and use time stamps on the data for synchronization. In some embodiments, the sensor can be a device with its own signal processing hardware and software, with two way communication to the system which includes display, recording, and/or communications beyond the system, and possibly additional signal processing of the waveforms from the device and, if included, waveforms from other sensors. In this case, the device would receive commands from the system for starting measurements, stopping measurements, and other hardware control signals. In some embodiments, the device can perform the initial signal processing and provide a waveform that is analyzed by the system. The data can be analyzed in real time or through post-processing as disclosed in U.S. Provisional App. No. 61/204,880 which is incorporated herein by reference in its entirety.

In various embodiments, the senor system 100 can be provided with alarms which can issue alerts if irregularities or abnormalities in the patient's breathing are detected. In some embodiments, the system 100 can also activate alarms (e.g., when the subject is not breathing for more than 10 seconds or is breathing faster than approximately 20 breaths/minute for more than 10 seconds).

In various embodiments, physiological waveforms related to respiratory effort, chest wall movement due to the underlying heart motion, and peripheral pulse movement, etc., can be obtained by the physiological motion sensor as disclosed in U.S. Provisional App. No. 61/141,213 which is incorporated herein by reference in its entirety. Information derived from these waveforms can include, but is not limited to, respiratory rate, inhale time as disclosed in U.S. Provisional App. No. 61/141,213 which is incorporated herein by reference in its entirety, exhale time as disclosed in U.S. Provisional App. No. 61/141,213 which is incorporated herein by reference in its entirety, inhale time to exhale time ratio as disclosed in U.S. Provisional App. No. 61/141,213 which is incorporated herein by reference in its entirety, frequency, depth, and length of gasps as disclosed in U.S. Provisional App. No. 61/141,213 which is incorporated herein by reference in its entirety, frequency, depth, and length of sighs as disclosed in U.S. Provisional App. No. 61/141,213 which is incorporated herein by reference in its entirety, depth of breath as disclosed in U.S. Provisional App. No. 61/072,983, which is incorporated herein by reference in its entirety, presence of and degree of paradoxical breathing as disclosed in U.S. Provisional App. No. 61/194,836 which is incorporated herein by reference in its entirety and in U.S. Provisional App. No. 61/194,848 which is incorporated herein by reference in its entirety and in U.S. Provisional App. No. 61/200,761 which is incorporated herein by reference in its entirety, tidal volume as disclosed in U.S. Provisional App. No. 61/125,021 which is incorporated herein by reference in its entirety and in U.S. Provisional App. No. 61/125,018, which is incorporated herein by reference in its entirety, abdominal excursion to chest excursion ratio as disclosed in U.S. Provisional App. No. 61/141,213 which is incorporated herein by reference in its entirety, harmonic content of breathing signal as disclosed in U.S. Provisional App. No. 61/141,213 which is incorporated herein by reference in its entirety, shape of the breathing waveform as disclosed in U.S. Provisional App. No. 61/141,213 which is incorporated herein by reference in its entirety, airflow rate as disclosed in U.S. Provisional App. No. 61/072,983, which is incorporated herein by reference in its entirety and in U.S. Provisional App. No. 61/125,021 which is hereby incorporated by reference in its entirety, distressed breathing indication as disclosed in U.S. Provisional App. No. 61/072,983, which is incorporated herein by reference in its entirety, unforced vital capacity as disclosed in U.S. Provisional App. No. 61/125,021, which is incorporated herein by reference in its entirety, heart and pulse rate, average heart, pulse and breath rate, beat-to-beat interval, heart rate variability, blood pressure, pulse transit time, cardiac output, other respiratory signals, correlation between heart and respiratory rates or waveforms, frequency, duration, and amount of activity as disclosed in U.S. Provisional App. No. 61/125,019, which is incorporated herein by reference in its entirety, frequency, duration, and amount of fidgeting and lung fluid content The variability of these variables in various frequency bands is also subject to analysis, including heart rate variability and respiratory rate variability, but also variability of changes of the shape of the heart or respiratory waveform, changes in the depth of breathing, and changes in the degree of paradoxical breathing. These can be measured as a spot check, monitored continuously while a patient is at rest, monitored at specific times related to questions being asked, statements being made, or specific tasks being performed, or they can be monitored in subjects going about their normal activities.

The information derived from these waveforms can be displayed on a display unit. In various embodiments, information provided on screen can include, but is not limited to, respiratory rate, inhale time, exhale time, inhale time to exhale time ratio, depth of breath, presence of and degree of paradoxical breathing, tidal volume, abdominal excursion to chest excursion ratio, heart or pulse rate, average heart rate, average pulse rate and average breath rate, beat-to-beat interval. In various embodiments, information provided in waveforms can include, but is not limited to, respiratory waveform, heart waveform obtained non-contact, heart waveform obtained with the device contacting the chest, and pulse waveform. In various embodiments, the analysis provided on-screen can include respiratory rate history, heart rate history, activity index (the percentage of time the subject is physically active) as disclosed in U.S. Provisional App. No. 61/125,019, which is incorporated herein by reference in its entirety, tidal volume vs. time as disclosed in U.S. Provisional App. No. 61/125,021, which is incorporated herein by reference in its entirety, air flow rate vs. lung volume as disclosed in U.S. Provisional App. No. 61/125,021, which is incorporated herein by reference in its entirety.

Figure 7:
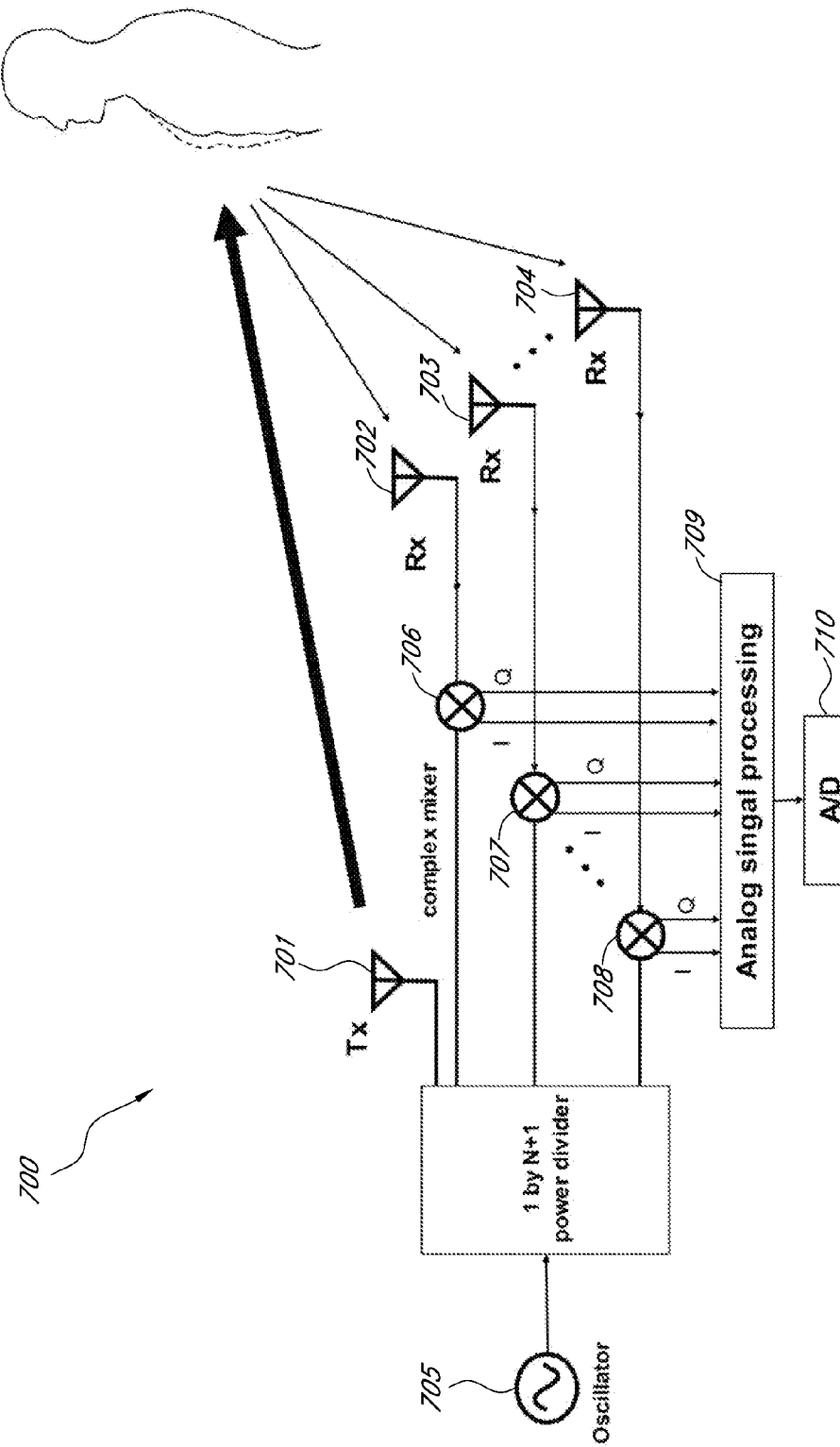
FIG. 7 schematically illustrates an embodiment of a radar-based physiological motion sensor comprising a transmitter and multiple receivers.

As described above, in various embodiments, the physiological motion sensor 700 can be implemented as a continuous wave radar transceiver. In various embodiments, the transceiver can be a single transmitter with a single quadrature receive channel as disclosed in U.S. Provisional App. No. 61/072,983, which is incorporated herein by reference in its entirety as shown in FIG. 7. In some embodiments, the sensor 700 can include a single transmitter 701 with multiple receiver channels or antennas 702, 703, 704 (e.g., a SIMO system) as disclosed in U.S. Provisional App. No. 61/072,983, which is incorporated herein by reference in its entirety and in U.S. Provisional App. No. 61/125,027, which is incorporated herein by reference in its entirety. In some embodiments, the sensor 700 can include multiple transmitters, each at a different frequency, and multiple receiver channels, or antennas each which can receive each frequency as disclosed in U.S. Provisional App. No. 61/125,027, which is incorporated herein by reference in its entirety and in U.S. Provisional App. No. 61/137,519 which is incorporated herein by reference in its entirety.

In various embodiments, the transceiver includes a transmitter and a receiver. In a continuous wave implementation, a transceiver can generate a single-frequency signal which is fed to the antenna. The transceiver can operate at any frequency from 100 MHz to 100 GHZ, including, but not limited to, frequencies in the 902-928 MHz ISM band, the 2.400-2.500 GHz ISM band, the 5.725-5.875 GHz ISM band, the 10.475-10.575 GHz motion detection band, and the 24.00-24.25 GHz ISM band. This signal can be generated internally with a voltage controlled oscillator (VCO) 705, which can either be phase-locked or to optionally not phase-locked a crystal or external clock. In some embodiments, if the device is integrated in an external system, the signal can be supplied by the external system. In various embodiments, the signal source can be generated internally and synchronized with an external signal, or it can be generated in an external system. In various embodiments, the board can include an RF switch, which can change the amount of RF power transmitted by approximately 10 dB or more.

In various embodiments, the receiver can be homodyne (also known as direct-conversion) with complex mixers 706, 707, 708 that can generate quadrature outputs (also known as quadrature demodulation) as disclosed in U.S. Provisional App. No. 61/072,983, which is incorporated herein by reference in its entirety as disclosed in U.S. Provisional App. No. 61/128,743 which is incorporated herein in by reference in its entirety and in U.S. Provisional App. No. 61/137,519 which is incorporated herein by reference in its entirety. In various embodiments, the receiver can also be a low-IF receiver as disclosed in U.S. Provisional App. No. 61/128,743 which is incorporated herein by reference in its entirety, which includes a heterodyne receiver in which the intermediate frequency (IF) can be directly digitized. In various embodiments, the intermediate frequency can be in the range from approximately a few Hz to approximately 200 kHz. In some embodiments, the intermediate frequency can be greater than 200 kHz. In various embodiments, the transceiver can also use a heterodyne or super-heterodyne receiver as disclosed in U.S. Provisional App. No. 61/128,743 which is incorporated herein by reference in its entirety. In various embodiments, the transmitter and receiver can include a single antenna or an array of antennas acting as a single antenna. The quadrature outputs from the receivers can be processed by an analog signal processor 709 before being digitized by an analog to digital converter 710.

In various embodiments, the DC offset can be eliminated through AC coupling or other DC-cancellation methods. In some embodiments, the DC-cancellation method can utilize a digitally controlled signal source to act as a non-time-varying (DC) reference that the original signal is compared against. In some embodiments, the digitally controlled signal source is a voltage divider with a digitally controlled potentiometer. When the comparison is performed with a difference function, this approach can remove the DC offset while preserving the time-varying signal. In some embodiments, DC cancellation is initiated with a search function, which iteratively searches for the correct DC-offset value, at the start of the DC-cancellation cycle. In some embodiments, DC cancellation is initiated by using an additional acquisition device to instantly provide the rough initial estimate of the DC-offset by acquiring the full signal before amplification and compensation. Once the initial DC-offset value is found and subtracted from the signal, the digitally-controlled reference can be fine-tuned by analyzing the newly compensated and amplified signal and then optimizing to find a better DC-offset value. The new DC-offset value can be found utilizing several methods including, but not limited to: the first read value, the median over a respiration cycle, the mean over a respiration cycle, or the center point find of a respiration arc in a complex constellation (found by calculating the mean of the in-phase signal and the mean of the quadrature signal, and setting the DC-offset values for the I and Q channels respectively). Using the above described method, the DC-offset-cancelling reference signal can be dynamically adjusted in response to large or subtle changes in the radar view to ensure minimal signal loss or distortion while maintaining proper resolution of the acquisition device. In various embodiments, DC-cancellation can include modulation of the transmitted or received RF signal. Utilizing a phase-sensitive synchronized demodulator, amplifier and low-pass filtering, signals can be extracted from high-noise, large DC-offset environments. In some embodiments, this can be similar to signal chopping with a lock-in amplifier. Modulation can be achieved in several ways, including but not limited to: physical means such as vibration or electrical means such as modulating phase, amplitude or frequency of the transmitted or received signal.

Figure 8:
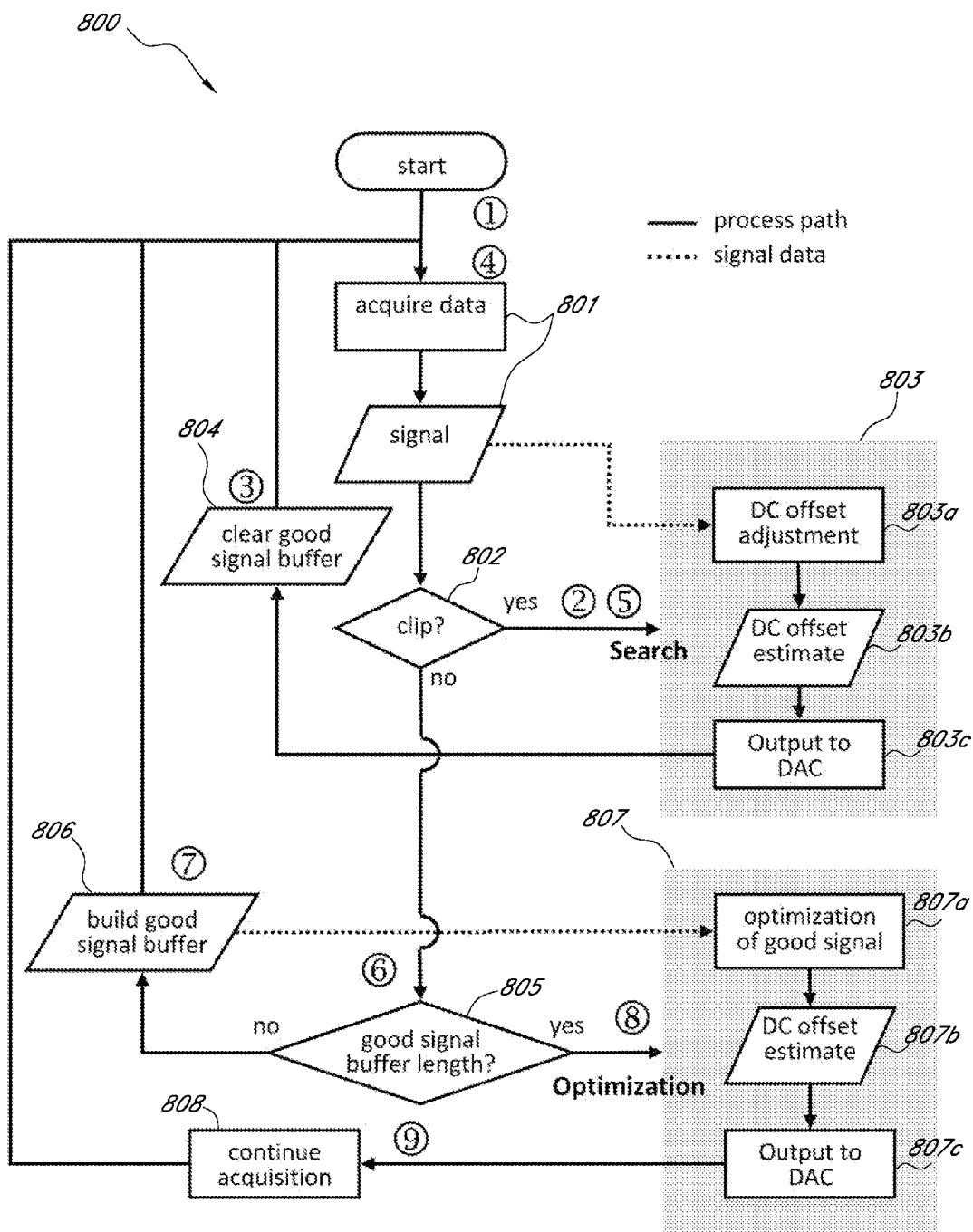
FIG. 8 illustrates a flowchart of an embodiment of a method configured to perform DC cancellation.

FIG. 8 illustrates a flowchart of an embodiment of a method configured to perform DC cancellation 800. At the beginning, an analog-to-digital converter (ADC) acquires the motion signal obtained by transforming the Doppler shifted received signal as shown in block 801. If in block 802, it is determined that the signal is being clipped, then the method proceeds to block 803. In block 803, the estimated DC offset is adjusted depending on at least one of the following factors gain of the system, input range of the ADC and various other factors as shown in blocks 803a and 803b. The estimated DC offset value is output to a digital-to-analog converter (DAC) as shown in block 803c. A good signal buffer configured to store continuously acquired signal that has no clipping is cleared as shown in block 804, the method returns to block 801 and the signal is re-acquired.

If in block 802, it is determined that the signal is not being clipped, then the method proceeds to step 805 wherein the good signal buffer length is checked against a threshold length. In various embodiments, the threshold length can be set by a user or a system designer. In various embodiments, the threshold length can be at least the number of samples in a full respiration cycle which can be greater than approximately 6 s. If the good signal buffer length is less than the threshold length then method proceeds to block 806 wherein the good signal buffer is built by acquiring more signal. However, if the good signal buffer length is greater than the threshold length then the method proceeds to block 807 wherein the estimated DC offset value is optimized as shown in blocks 807*a* and 807*b*. During optimization, the good signal buffer is analyzed in several ways, for example by calculating the average, median or midrange voltage value. For quadrature systems, the arc-center point can be optimized. After optimization, the DC offset value is output to the DAC as shown in block 807*c* and the method proceeds to block 808 to continue signal acquisition.

In various embodiments of the system 100, the signal transmitted by the one or more transmitters described above is scattered by the subject and the surrounding and subsequently received by said one or more receivers described above as a radar-based cardiopulmonary motion sensor. In various embodiments, the Doppler-shifted signal can be transformed to a to an analog motion signal with a homodyne receiver or a heterodyne receiver. Alternatively, the Doppler-shifted signal can be down converted to an intermediate frequency which can be directly digitized, and the motion signal can be generated digitally. In various embodiments, the analog motion signal requires signal and the low-intermediate frequency conditioning before it is digitized. In various embodiments, the signal conditioning system 100 can include one or more baseband amplifiers. In various embodiments, the signal conditioning system 100 can include one or more analog anti-aliasing filters. In various embodiments the signal conditioning system 100 can include a method to remove DC offset, including, but not limited to, high-pass filtering, AC-coupling, or DC-offset removal as described in this document. In various embodiments, one or more of the baseband amplifiers are fixed amplifiers. In various embodiments, one of more of the baseband amplifiers is variable gain amplifiers (VGA). In various embodiments, the VGA can have two or more stages. In various embodiments, the VGA can have continuously tunable gain. A VGA is controlled by digital control signals. In various embodiments, the gain levels of the VGA can be determined by the user or dynamically by the processor through signal analysis as disclosed in U.S. Provisional App. No. 61/141,213 which is incorporated herein by reference in its entirety.

In some embodiments, the receiver can have one quadrature output per antenna or an array of antennae. In some embodiments, the receiver can have multiple outputs with different analog filtering and/or amplification, to isolate different information before digitization and digital signal processing. This can be advantageous in improving the dynamic range for each physiological motion signal. For example, each baseband signal would be split to have different gain and filtering for the heart signal than for the respiration signal as disclosed in U.S. Provisional App. No. 61/141,213 which is incorporated herein by reference in its entirety. In various embodiments, the system 100 can include digital signaling or a digital-to-analog converter (DAC) and hardware such that the hardware is controllable by software. In various embodiments, the hardware can be controlled in several ways, which can include but are not limited to: turning sections or components of the transceiver and the signal conditioning system on and off, which can be used in various embodiments to conserve power, for a controlled power-up, or for self-tests; turning the received and/or transmitted RF signal on and off, which can be used in various embodiments to decrease exposure to radio signals or for self-tests; setting the receiver gain, which can be used to increase the dynamic range of the system; compensation for DC offsets in the signal conditioning; controlling amount of gain in signal conditioning before acquisition; modifying the range of the data acquisition, which can be used to increase the dynamic range of the system; modifying the antenna pattern of the system, which can change the area covered by the antenna beam; and changing the frequency of the transmitted signal. In various embodiments, the hardware settings can be selected automatically by the software, manually by the user, or a combination of automatically and manually for different settings as disclosed in U.S. Provisional App. No. 61/141,213 which is incorporated herein by reference in its entirety.

Various embodiments of the system including the radar-based physiological motion sensor can include wired or wireless communication systems. The various embodiments can use standard or proprietary communication protocols, or combinations thereof. Such protocols can include technologies from all layers of the TCP/IP networking model, including, but not limited to, serial, USB, Bluetooth, Zigbee, Wi-Fi, Cellular, TCP/IP, Ethernet, SOAP, etc. For example, Ethernet can be used as the link layer protocol while TCP/IP is used for routing, and SOAP is used as an Application layer protocol. On the other hand, only TCP/IP over Ethernet can be used, without additional packaging at the Application level. In the later case, data collected from the radar system 100 can be formatted and directly packaged as TCP payload. In some embodiments, this can include a timestamp for when the data was collected, the data, and an indicator for the quality of the data. This data is attached with a TCP header and then becomes the IP payload. The IP header (addresses) is attached to the payload and then is encapsulated by Link layer headers and footers. Finally, physical layer header and footers are added and the packet is sent via the Ethernet connection. To access data from the connection, a user or a client should have a program to listen to a specified port on their Ethernet connection where the packets are being sent.

In various embodiments, the digitized quadrature signals can be processed using various algorithms to provide respiratory and pulse waveforms.

In various embodiments, the quadrature signals can be demodulated using any of several algorithms, including but not limited to linear demodulation, arc-based demodulation algorithm (e.g., arc-tangent demodulation with center tracking) or non-linear demodulation algorithm. Demodulation algorithms can include any of the following methods, but not limited to, projecting the signal in the complex plane on a best-fit line, projecting the signal in the complex plane on the principal eigenvector, or aligning the signal arc to a best-fit circle and using the circle parameters to extract angular information from the signal arc. Linear demodulation can use any of many algorithms, including projecting the signal in the complex plane on the principal eigenvector, or projecting the signal on the best-fit line. Arctangent demodulation can extract phase information which is corresponding to the chest motion associated with cardiopulmonary activity as explained herein. In quadrature systems, data collected by two orthogonal channels (e.g., In-phase (I) and quadrature phase (Q)) lie on a circle centered at a DC vector of the channels. After tracking center vector of the corresponding circle and subtracting it from the data samples, phase information of received signal can be extracted through an arctangent function.

Figure 9:
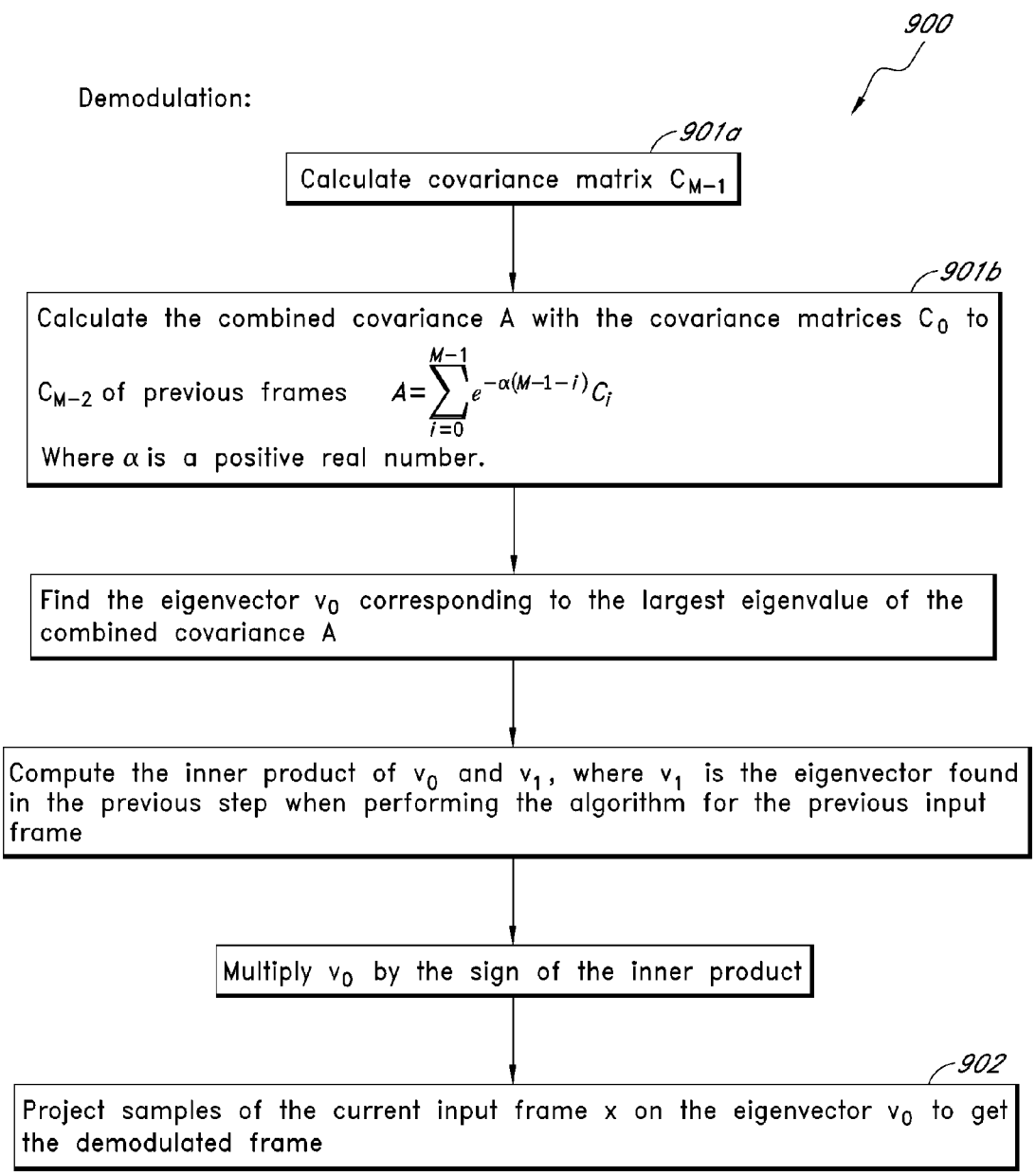
FIG. 9 illustrates an embodiment of a linear demodulation algorithm.

An embodiment of a linear demodulation algorithm is further described below and illustrated in FIG. 9. In one embodiment, the algorithm comprises computing covariance matrices for a subset of input frames as shown in block 901*a* including the most recent frame and projecting the data on a primary vector or an eigenvector of said covariance matrix as shown in block 902. If it is determined that the current eigenvector is in a reverse direction as compared to a previously determined eigenvector then the algorithm is configured to rotate the current eigenvector by 180 degrees.

In various embodiments, the linear demodulation algorithm comprises the following steps:

1. Compute covariance matrix $C_{M-1}$ of the current input frame x as shown in block 901a.
2. Using $C_{M-1}$ and covariance matrices $C_0$ to $C_{M-2}$ of previous frames, compute an A-matrix as shown in block 901b given by the equation:

$$A = \sum_{i=0}^{M-1} e^{-\alpha \cdot (M-1-i)} C_i$$

where α corresponds to a damping factor and can be a positive real number. In various embodiments, the value of α can range from approximately 0.1 to approximately 0.5. In one embodiment, α can be 0.2. M corresponds to the number of frames in the buffer and can range from 2 to 15. In one embodiment, M can be 10.

3. Find the primary vector or eigenvector $v_0$ corresponding to the largest primary value or eigenvalue of A as shown in block 901c.
4. Compute the inner product of $v_0$ and $v_1$, where $v_1$ is the eigenvector found in step 3 when performing the algorithm for the previous input frame as shown in block 901d.
5. Multiply $v_0$ by the sign of the inner product found in step 4 as shown in block 901e.
6. Project samples of the current input frame x on the eigenvector $v_0$ calculated in step 5 to get the demodulated frame as shown in block 902.

In various embodiments, many different algorithms can be used alone or in combination to isolate different physiological motion signals from the combined physiological motion signal and surrounding noise. These include, but are not limited to fixed filters as disclosed in U.S. Provisional App. No. 61/141,213 which is incorporated herein by reference in its entirety, adaptive filters as disclosed in U.S. Provisional App. No. 61/141,213 which is incorporated herein by reference in its entirety, matched filter, wavelet, empirical mode decomposition as disclosed in U.S. Provisional App. No. 61/125,023, which is incorporated herein by reference in its entirety, blind source separation as disclosed in U.S. Provisional App. No. 61/141,213 which is incorporated herein by reference in its entirety, Direction of Arrival (DOA) information as disclosed in U.S. Provisional App. No. 61/125,020, which is incorporated herein by reference in its entirety and in as disclosed in U.S. Provisional App. No. 61/141,213 which is incorporated herein by reference in its entirety, independent component analysis as disclosed in U.S. Provisional App. No. 61/141,213 which is incorporated herein by reference in its entirety, smart antennas as disclosed in U.S. Provisional App. No. 61/141,213 which is incorporated herein by reference in its entirety, and empirical mode decomposition as disclosed in U.S. Provisional App. No. 61/125,023, which is incorporated herein by reference in its entirety as disclosed in U.S. Provisional App. No. 61/141,213 which is incorporated herein by reference in its entirety. One embodiment used to isolate the heart signal from the combined signal is first extracting the respiratory signal, then subtracting this from the combined signal, and then filtering (either fixed or adaptive filtering) the remainder signal to obtain the relatively smaller heart signal. Another embodiment used to isolate the heart signal is cancelling harmonics of respiration signal combined with minimum mean squared error estimation.

For some applications, it is important to determine the beginning and end of breaths or beats, or to determine the peak of each breath or beat, such that breath-to-breath or beat-to-beat intervals can be calculated. Peak detection involves finding local maxima and minima that meet various defined properties in a signal. There are many variations of peak detection that can be used in various embodiments of this device, including, but not limited to maxima above a threshold preceded and followed by minima below a threshold (in various embodiments, the threshold can be fixed or can be based on previous peaks and valleys); perform a least-squares quadratic fit between peaks, valleys, and/or zero-crossings and determine the peak of this function (this method provides interpolation). In some embodiments, the above algorithms can be performed after removing the baseline variation of the signal. In some embodiments, the peak detection algorithm can include finding zero-crossings of the derivative of the signal. In some embodiments, it is also possible to use zero-crossings to estimate the interval of each breathing cycle, by selecting either the positive or negative zero-crossings. In some embodiments, valley detection can replace peak detection.

For some applications, it is desirable to estimate the rate of the cardiopulmonary signals. In some embodiments, the rate of the signals can be estimated in the time domain, using peak detection as disclosed in U.S. Provisional App. No. 61/128,743 which is incorporated herein by reference in its entirety as described above or zero-crossing detection as disclosed in U.S. Provisional App. No. 61/141,213 which is incorporated herein by reference in its entirety, and calculating either the time required for a specific number of peaks, by calculating the average peak-to-peak interval, or by determining the number of peaks in a specified time period. The rate can also be estimated in the frequency domain. This can be calculated as the Short Time Fourier Transform, using a window that can be of predetermined length or a variable length depending on the signal. The respiration rate can also be calculated in the frequency domain using the instantaneous frequency as calculated with the Hilbert-Huang Transform after applying empirical mode decomposition as disclosed in U.S. Provisional App. No. 61/125,023, which is incorporated herein by reference in its entirety.

Figure 10A:
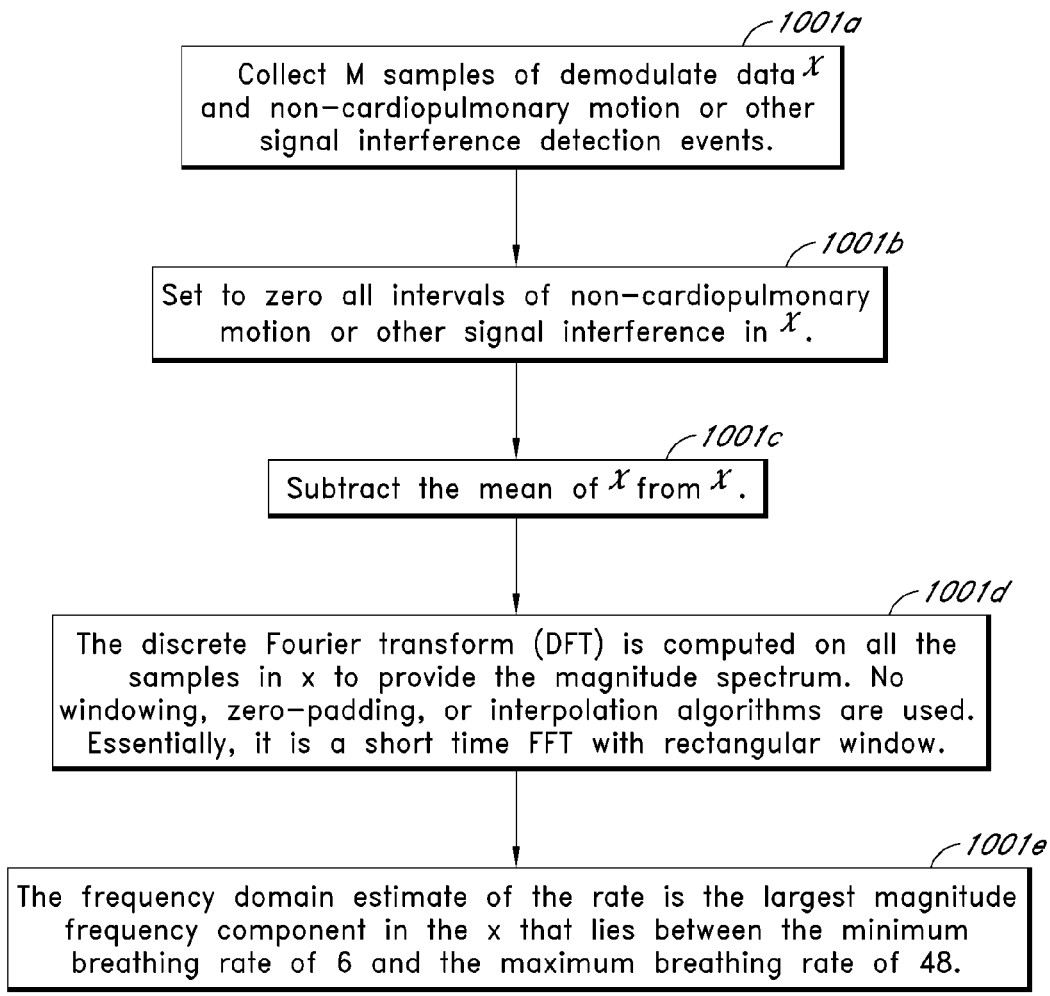

An embodiment of a frequency domain rate estimation algorithm is further described below and illustrated in FIG. 10A. The frequency domain rate estimation comprises the following steps:

1. Collect M samples of demodulated data x and non-cardiopulmonary motion or other signal interference detection events as shown in block 1001a, where M is the number of samples for rate estimation and in various embodiments can be 1440, 2880, 4320 or some other number.
2. Set to zero all intervals of non-cardiopulmonary motion or other signal interference in x as shown in block 1001b.
3. Subtract the mean of x from x as shown in block 1001c.
4. Determine the rate using frequency domain information as follows:
    i. A Fourier transform (e.g., discrete Fourier transform) is computed for all the samples in x to provide the magnitude spectrum as shown in block 1001d. No windowing, zero-padding, or interpolation algorithms are used. In some embodiments, the Fourier transform can include a short time fast Fourier transform with rectangular window.

ii. The frequency domain estimate of the rate is the largest magnitude frequency component in x as shown in block 1001e. In various embodiments, the frequency domain estimate of the rate can be the largest magnitude frequency component that lies between a breathing rate of 6 and a breathing rate of 48.

Figure 10B:
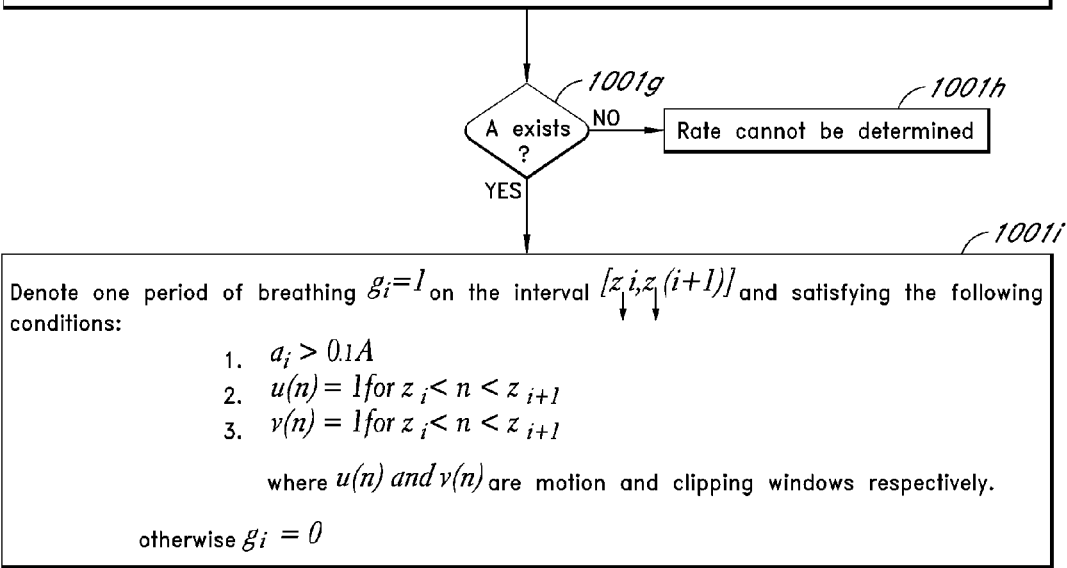

An embodiment of a time domain rate estimation algorithm is further described below and illustrated in FIG. 10B. The time domain rate estimation comprises the following steps:

1. Collect M samples of demodulated data x and non-cardiopulmonary motion or other signal interference detection events as shown in block 1001a of FIG. 10A, where M is the number of samples for rate estimation and in various embodiments can be 1440, 2880, 4320 or some other number.

2. Set to zero all intervals of non-cardiopulmonary motion or other signal interference in x as shown in block 1001b of FIG. 10A.

3. Subtract the mean of x from x as shown in block 1001c of FIG. 10A.

4. Determine the rate using time domain information as follows:

a) Let $z_i$ be the index of the sample such that $x(z_i) \leq 0$ and $x(z_{i+1}) > 0$ thereby identifying positive zero crossings in the input frame as shown in block 1001f. In various embodiments, negative zero crossings can also be identified.

b) Let $a_i$ be the largest amplitude in the interval $z_i$ and $z_{i+1}$.

c) Let $A = \max a_i$ for all i, such that there exists three (two in quick mode) distinct numbers i, j, k where:
  i) $a_i > 0.1A$
  ii) $a_j > 0.1A$
  iii) $a_k > 0.1A$ d) If in block 1001g it is determined that there exists no such A, then the rate cannot be determined as shown in block 1001h.

e) Otherwise denote one period of breathing $g_i = 1$ on the interval $[z_i, z_i + 1.]$ and satisfying the following conditions as shown in block 1001i:
  i) $a_i > 0.1A$
  ii) $u(n) = 1$ for $z_i < n < Z_{i+1}$
  iii) $v(n) = 1$ for $z_i < n <_{i+1}$
  where u(n) and v(n) are motion and clipping windows respectively.

f) Otherwise $g_i = 0$.

g) Let $\lambda$ be the largest number of consecutive breaths where $g_i = 1$. That is $\lambda$ is the largest number such that $g_i, g_{i+1}, g_{i+2}, g_{i+3}, \ldots, g_{i+\lambda-1} = 1$ for some i, as shown in block 1001j.

h) If in block 1001k, it is determined that $\lambda < 3$ ($\lambda < 2$ in quick mode), then the rate cannot be determined, otherwise the rate is given by $(60 \times 100 \times \lambda)/(z_{i+\lambda} - z_i)$ breaths per minute as shown in block 1001m.

Figure 10C:
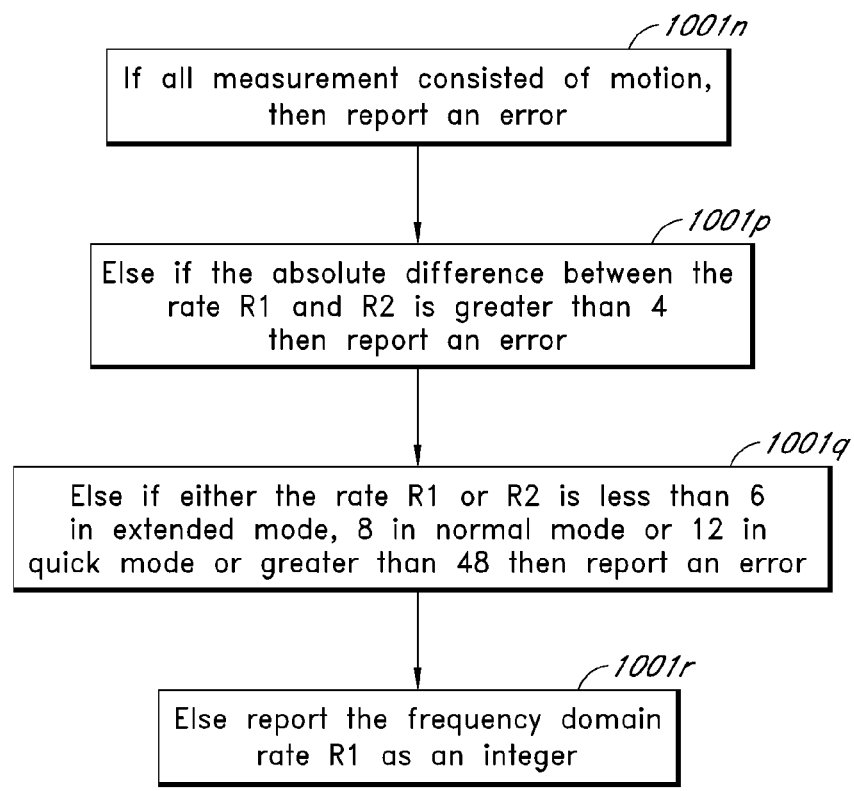

In various embodiments, the rate estimation algorithm can use both the frequency domain estimate and the time domain estimate to determine the respiration rate as illustrated in FIG. 10C. An advantage of employing the two methods simultaneously is two-fold. First, comparing the result of these two approaches will help determine if breathing is regular. Secondly, the redundancy introduced by employing two algorithms can help in mitigating risk of inaccuracies in determining the respiratory rates. For example, with reference to the embodiments of the time domain rate estimation algorithm and the frequency domain rate estimation algorithm described above, if the algorithms determined that all measurements consisted of non-cardiopulmonary motion as shown in block 1001n or other signal interference then an error message is reported. In some embodiments, if the difference between the rates estimated by the two algorithms is greater than 4 as shown in block 1001p then an error is reported. In some embodiments, if the rate estimated by either the frequency domain rate algorithm or the time domain rate algorithm is less than 6, then an error is reported as shown in block 1001q. In some embodiments, if the rate estimated by either the frequency domain rate algorithm or the time domain rate algorithm is less than 8 or 12, then an error is reported as shown in block 1001q. In some embodiments, if the rate estimated by either the frequency domain rate algorithm or the time domain rate algorithm is greater than 48, then an error is reported. In various embodiments if the rate estimated by the either the frequency domain rate algorithm or the time domain rate algorithm is between the range of 12 and 48, then the frequency domain rate is reported. In some embodiments, the rate estimated by the either the frequency domain rate algorithm or the time domain rate algorithm can be between the range of 8 and 48 or 6 and 48 to be considered as accurate.

An embodiment of a peak detection algorithm to estimate a rate is further described below and illustrated in FIG. 10D.

1. Collect M samples of demodulated data x and motion detection events as shown in block 1001a of FIG. 10A, where M is the number of samples for rate estimation and in various embodiments can be 1440, 2880, 4320 or some other number.

2. Set to zero all intervals of non-cardiopulmonary motion or other signal interference in x as shown in block 1001b of FIG. 10B.

3. Subtract the mean of x from x, as shown in block 1001c of FIG. 10C.

4. The time domain estimate of the rate is found as follows:

(a) Let pv(n) denote the interest points as follows:

$$pv(n) = \begin{cases} x(n) & \text{if (I or II) and III and IV} \\ 0 & \text{otherwise} \end{cases}$$

(I) $|x(n)| > |x(n-1)|$ and $|x(n)| > |x(n+1)|$ (II) $|x(n)| = |x(n-1)|$ (III) $u(k) = 1$ for $n - \tau \leq k \leq n + \tau$ (IV) $v(k) = 1$ for $n - \tau \leq k \leq n + \tau$ where u(k) and v(k) are motion and clipping windows respectively, as shown in block 1001s.

(b) Non-maxima suppression for every sample in a neighborhood of length 2W is performed, as shown in block 1001t by the following method:

For every n, find $$\gamma_m = \max_{n-W \leq k \leq n+W} pv(k),$$

where $\gamma_m = pv(m)$ $$\hat{pv}(k) = \begin{cases} \gamma_m & k = m \\ 0 & n - W \leq k \leq n + W \cdot k \neq m \end{cases}$$

(c) Classify interest points as either peaks or valleys, as shown in block 1001u, by using the following equation:

$$pvid(n) = \begin{cases} 1 & pv(n) > o \text{ (peak)} \\ -1 & pv(n) < o \text{ (valley)} \\ 0 & pv(n) = 0 \text{ (not an interest point)} \end{cases}$$

(d) Resolve consecutive peaks and consecutive valleys, as shown in block 1001v, since a breathing signal should have alternating peaks and valleys. In various embodiments, the resolution can be done as follows:

pvid($k_1$)>9, pvid($k_2$)>0 are consecutive peaks when ∃k such that pvid(k)<0 and $k_1$<k<$k_2$. A similar method can be followed to identify consecutive peaks.

(ii) For 2 or more consecutive interest points with same polarity, retain only the largest if the interest point was a peak or otherwise the smallest if the interest point was a valley.

(iii) The resulting interest points should have alternating polarity.

(e) Let λ be the largest number of peaks in sequence. If λ<4 (λ<3 in quick mode), then the rate cannot be determined, otherwise the rate is given by 60×100×λ/L breaths per minute, where L is the length of the interval bounded by the first and last peak. A rate could be determined similarly by considering the valleys.

In various embodiments, signal processing can determine both the points of inhalation and exhalation and count them over time. For every block of data, a respiration rate can be calculated and buffered based on detected inhalation or exhalation events. The rates can be stored until a designated number of consecutive inhalation events or exhalation events are detected (e.g., 3, 5, 10, 15, 20). In some embodiments, 3 can be set as the default rate. In some embodiments, the device can be configured to return or display the median value of the inhalation and exhalation events found. In various embodiments, if an interruption (e.g., non-physiological motion or other interfering signal) is detected during the reading, any respiration rate values stored in the buffer will be cleared and no values will be buffered until the interruption has ceased as disclosed in U.S. Provisional App. No. 61/128,743 which is incorporated herein by reference in its entirety.

In various embodiments, instead of calculating the respiration based on blocks of data, it is also possible to calculate the respiration based on each inspiration peak to inspiration peak interval as disclosed in U.S. Provisional App. No. 61/128,743 which is incorporated herein by reference in its entirety. In some embodiments the system (e.g., a spot-check monitor) could measure a specified number of peaks before displaying a respiration rate, or it could measure for a specified time interval. In various embodiments, the time interval or the number of peaks could be automatically extended if the measured respiration rate is varying more than a few breaths per minute to ensure an accurate reading of in irregular rate as disclosed in U.S. Provisional App. No. 61/204,880 which is incorporated herein by reference in its entirety.

In some embodiments, a spot-check monitor including the radar-based physiological motion sensor could measure a specified number of peaks before displaying a rate as disclosed in U.S. Provisional App. No. 61/128,743 which is incorporated herein by reference in its entirety and in U.S. Provisional App. No. 61/137,532 which is incorporated herein by reference in its entirety. The spot-check monitor could measure a user-selectable number of peaks (e.g., 3, 5, 10, 15) for a certain time interval (e.g., 10 seconds, 15 seconds, 20 seconds, 30 seconds, 45 seconds, 60 seconds, or other time interval) as disclosed in U.S. Provisional App. No. 61/128,743 which is incorporated herein by reference in its entirety and in in U.S. Provisional App. No. 61/137,532 which is incorporated herein by reference in its entirety.

In various embodiments of the system, the software that is executable by a processor can automatically extend the time interval or number of peaks included for a rate estimate if respiration is irregular or varying more than a few breaths per minute as disclosed in U.S. Provisional App. No. 61/128,743 which is incorporated herein by reference in its entirety. In some embodiments, the software that is executable by a processor can only provide a respiratory rate if variability in rates is low over the measurement interval as disclosed in U.S. Provisional App. No. 61/128,743 which is incorporated herein by reference in its entirety. In some embodiments, the software that is executable by a processor can provide an indication of the level of variability as disclosed in U.S. Provisional App. No. 61/128,743 which is incorporated herein by reference in its entirety.

In some embodiments, the software that is executable by a processor can make an assessment of signal quality to prevent the display of incorrect rates. In various embodiments, the assessment can include four steps. In various embodiments, the first step can employ the non-respiratory signal detection algorithm to suppress any portions of the signal with motion other than respiration. In the second step, the software that is executable by a processor can compute the respiration rate using a time domain approach and a frequency domain approach, described above, separately, thereby producing two respiration rates for the same signal. The third step includes comparing the two rates resulting from the time and frequency domain approaches and determining if they are close to a certain number of breaths. In various embodiments, a smaller difference between the two rates can imply regular breathing intervals and regular breathing depths. In various embodiments, the software that is executable by a processor can regard regular breathing intervals and regular breathing depths as the two signal quality measures upon which it can confidently provide an accurate rate. In various embodiments, the fourth step includes checking if either one of the rates lies outside of a pre-determined interval for respiration rates in which case the software that is executable by a processor cannot provide a rate. Otherwise, the respiration rate can then be computed in various embodiments as the average of the two rates or by simply choosing either one of the rates.

In various embodiments described herein, a Doppler radar system with complex signal processing can monitor paradoxical breathing based on the complex constellation of the received motion signal based on target motion, including both chest and abdomen motion. The complex constellation is the plot of the quadrature signal vs. the in-phase signal. In various embodiments, paradoxical breathing can be an important sign of obstructed breathing, respiratory muscle weakness, or respiratory failure. Paradoxical breathing can also occur with some types of paralysis. With paradoxical breathing, the abdomen and rib cage move in opposite directions rather than in unison, example when the rib cage expands, the abdomen contracts, and when the abdomen expands, the rib cage contracts.

Obstructive apnea is commonly defined as an 80-100% reduction in airflow signal amplitude for a minimum of 10 seconds with continued respiratory effort. The rib cage and abdomen can move out of phase as the patient tries to breathe, but the airway is blocked. A quadrature Doppler radar system, such as the one described above, can monitor this paradoxical breathing based on the complex constellation due to the target's chest and abdomen motion. Since a human's physiological signal such as breathing is a very narrow band signal (~less than 1 KHz) compared to the radar carrier signal, all the reflected signals will be phase modulated on a coherent carrier signal. Therefore, if human body parts, for example the chest and abdomen, are expanding or contracting simultaneously, the received reflecting signals from different paths (reflecting from different body parts) will only shift the phasor of the carrier signal but not the phase modulated narrow band carrier signals. Shift of the phasor of phase modulated narrow band carrier signals can also occur when different body parts are moving at the same frequency but with different amplitude or phase delay, as is the case in paradoxical breathing. Consequently, in the former case, the shape of the complex plot at the baseband due to the respiration will not change and will form a fraction of a circle (an arc) which is similar to the one from the a single source, while in the latter case the phasor of the baseband signal changes during the periodic motion (such as breathing), resulting in distortion of the complex constellation. This fact can be used to detect paradoxical breathing. Simplified phasor diagrams of those the two cases in the previous paragraph are described in FIGS. 11A and 11B as disclosed in U.S. Provisional App. No. 61/194,836 which is incorporated herein by reference in its entirety and in U.S. Provisional App. No. 61/194,848 which is incorporated herein by reference in its entirety and in U.S. Provisional App. No. 61/200,761 which is incorporated herein by reference in its entirety.

Figure 11A:
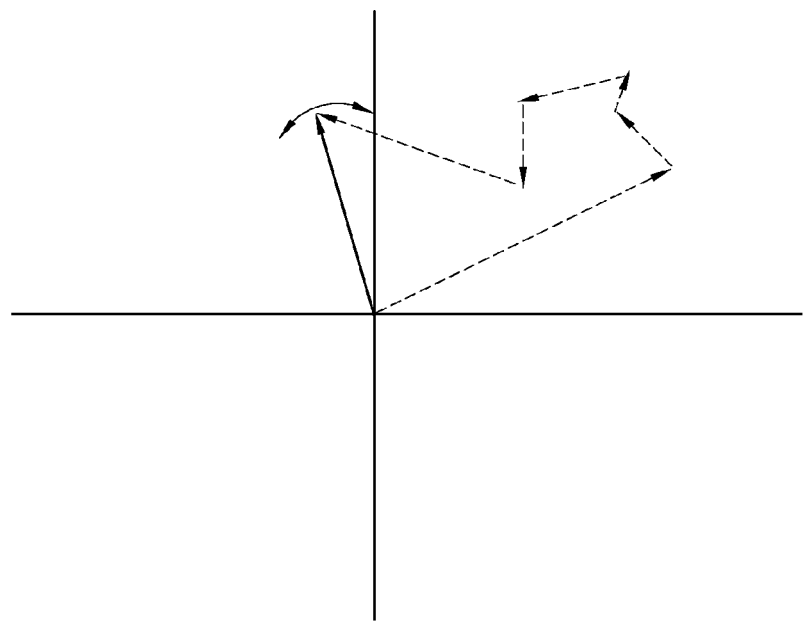
FIGS. 11A and 11B illustrate the phasor diagrams for normal breathing and paradoxical breathing.
Figure 11B:
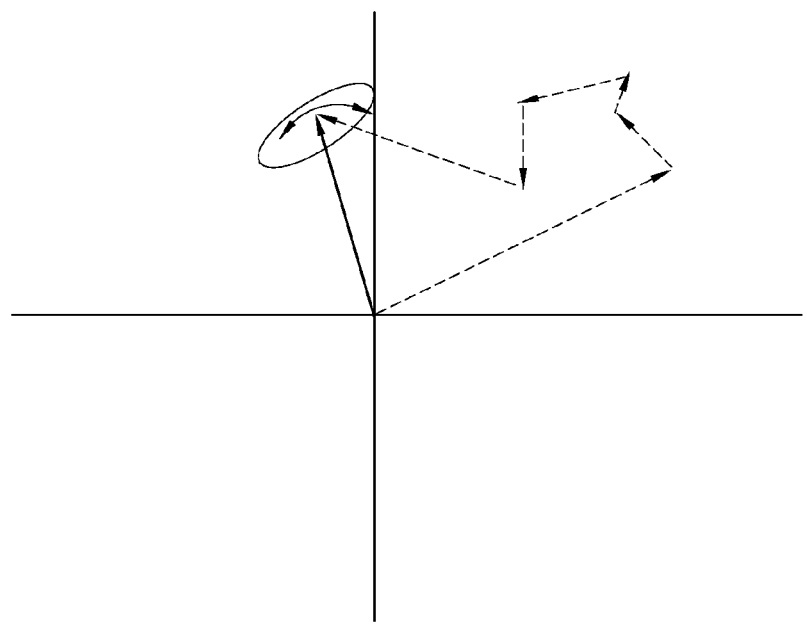

FIG. 11A illustrates the phasor diagrams for normal breathing and FIG. 11B illustrates the phasor diagrams for paradoxical breathing. During the normal breathing, only the phasor of carrier signal is shifted as different phase delayed carrier signals represented by the dashed vector are superimposed, while during the paradoxical breathing, not only the phasor of carrier signal but also that of baseband signal are shifted thus resulting in different complex constellation shape from FIG. 11A.

In various embodiments, comprising measurement of a motion causing a Doppler shift that is narrowband compared to the carrier signal (<<1%), multiple reflections from synchronized sources do not distort the shape of the complex motion signal, but reflections can change the signal power due to destructive or constructive interference of reflected carrier signals with different time delays. In various embodiments, comprising measurement of a motion signal causing a Doppler shift that is narrowband compared to the carrier signal (<<1%), multiple reflections from synchronized sources do not result in distortion of the complex motion signal unless the multi-path occurs over a range that is comparable (>1%) to the electrical wavelength (>300 km) corresponding to the frequency of the cardiopulmonary signal (<1 kHz), which is the frequency of the phase modulation on the carrier signal. In various embodiments, the signals reflected from different body parts can be handled as multi-path signals causing Doppler shifts on the carrier signal with a very narrow signal band and with time delays much less than those corresponding to the wavelength of the phase modulation frequency (>300 km), and consequently there is no shape change of the complex signal as long as all the body parts expand or contract simultaneously. However, if there is time delay (or phase shift) between the expanding or contracting motion of different body parts, such as in paradoxical breathing, the complex constellation is distorted and becomes an elliptic or ribbon shape rather than a small arc or line shape. Paradoxical breathing can be detected by comparing the ratio of two primary vectors (e.g., eigenvectors) and amplitudes of the signals projected on each primary vector. A dedicated cost function given by the equation can identify paradoxical breathing events from the processed outputs and provide indication of paradoxical breathing.

The paradoxical factor can be calculated as the ratio of the largest eigenvalue to the second largest eigenvalue multiplied by the ratio of the maximum amplitude of the signal projected on the principal vector to the maximum amplitude of the signal projected onto the vector orthogonal to the principal eigenvector. A cost function can convert the paradoxical factor to a paradox indicator, which can be used to indicate paradoxical breathing.

The input to the cost function will be the paradoxical factor and the cost function will transform it to a value which is between 0 and 1. In some embodiments, the cost function can be given by the following equation $$\text{Cost(input)} = \frac{1}{v \times \sqrt{2\pi}} \int_{x1}^{x2} \exp\left(\frac{-(\text{input}-m)^2}{2 \times v^2}\right) dx,$$

where x1, x2 are range of paradoxical factor which may be 0 and 1, while m and v are boundary input values between paradoxical and non-paradoxical and v is emphasizing factor of paradoxical factor. For example, if m is close to x1 then paradoxical indicator threshold is set to lower paradoxical factor. On the other hand, as v increases paradoxical indicator changes more dramatically as paradoxical factor changes. If the paradoxical indicator is near one, it is likely that there is paradoxical breathing; if the paradoxical indicator is near zero, it is unlikely that there is paradoxical breathing. A threshold may be set on the paradoxical indicator to provide a yes/no output, or two thresholds may be applied to achieve a green-yellow-red output corresponding to likely paradoxical breathing, uncertain output, and unlikely paradoxical breathing.

Figure 11C:
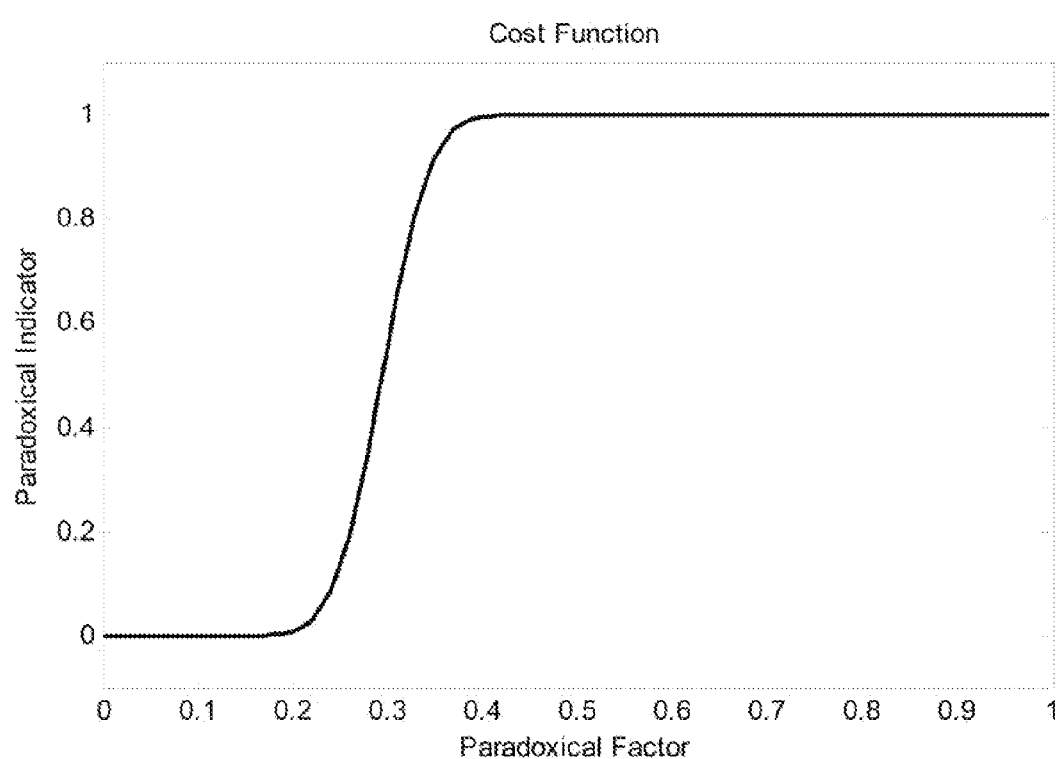
FIG. 11C shows an embodiment of a cost function configured to convert the paradoxical factor to a paradoxical indicator.

In one embodiment, of this invention, m is set to 0.3 and v is set 0.04. The cost function with these values of m and v is shown in FIG. 11C.

Figure 11D:
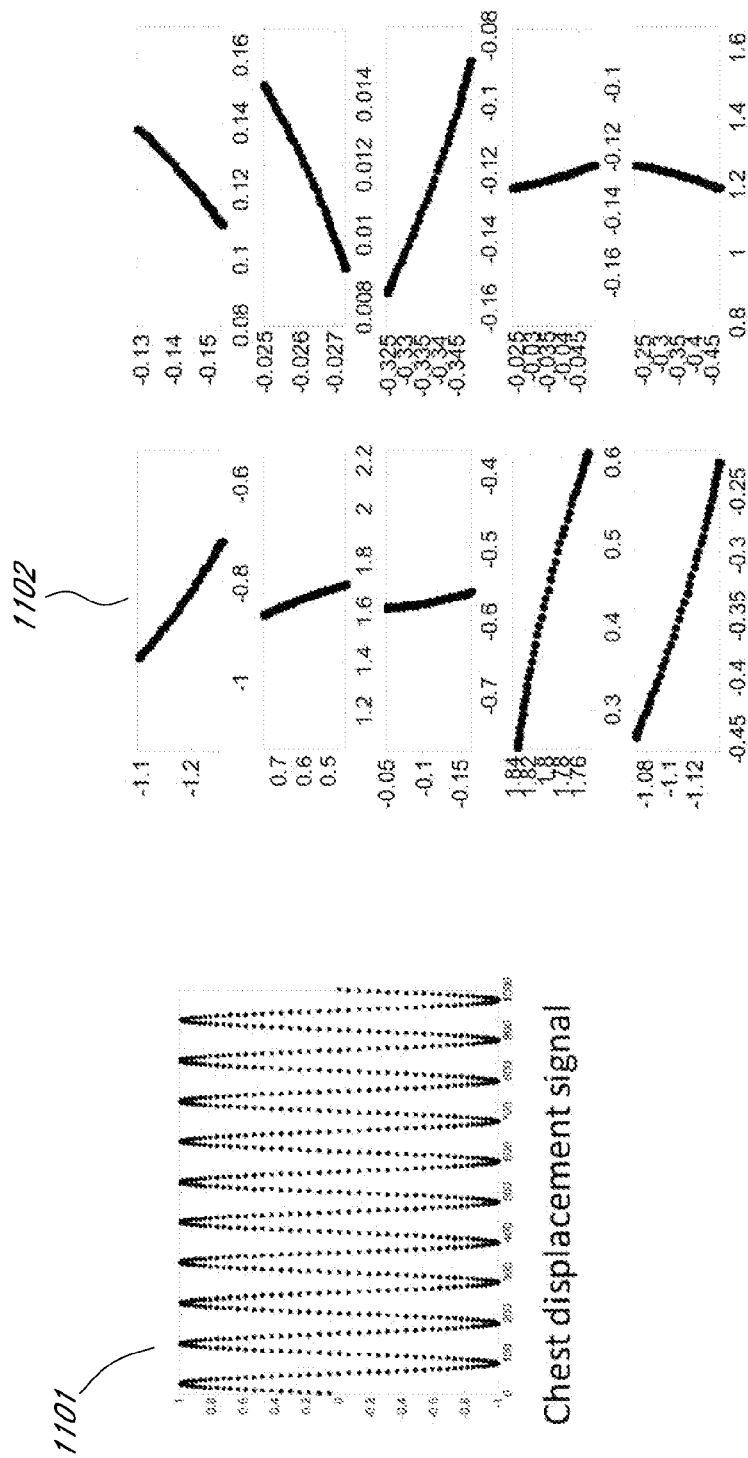
FIGS. 11D and 11E illustrate the baseband outputs with multi-path delayed signals when the body parts exhibit simultaneous expansion and contraction.
Figure 11E:
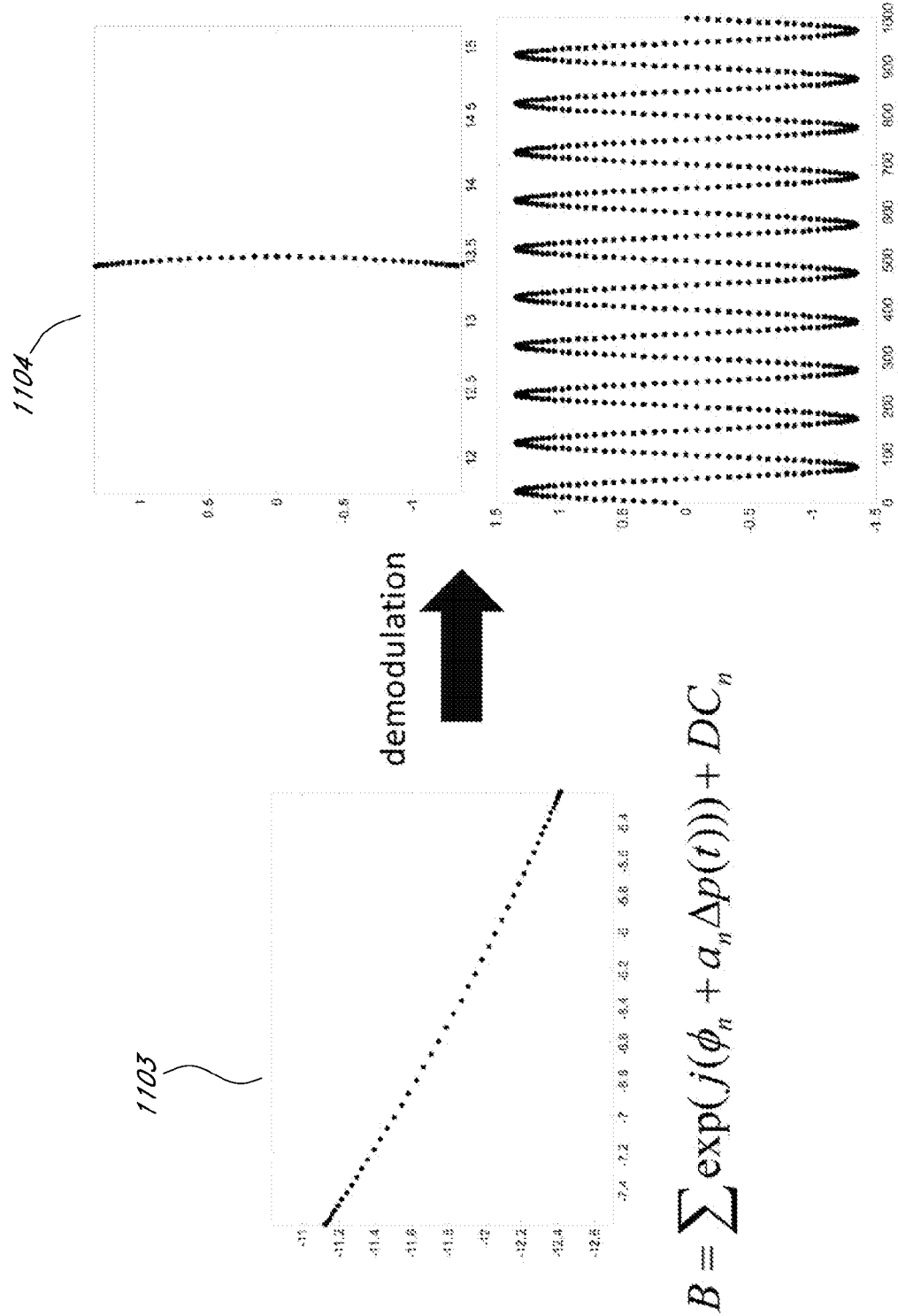
Figure 11F:
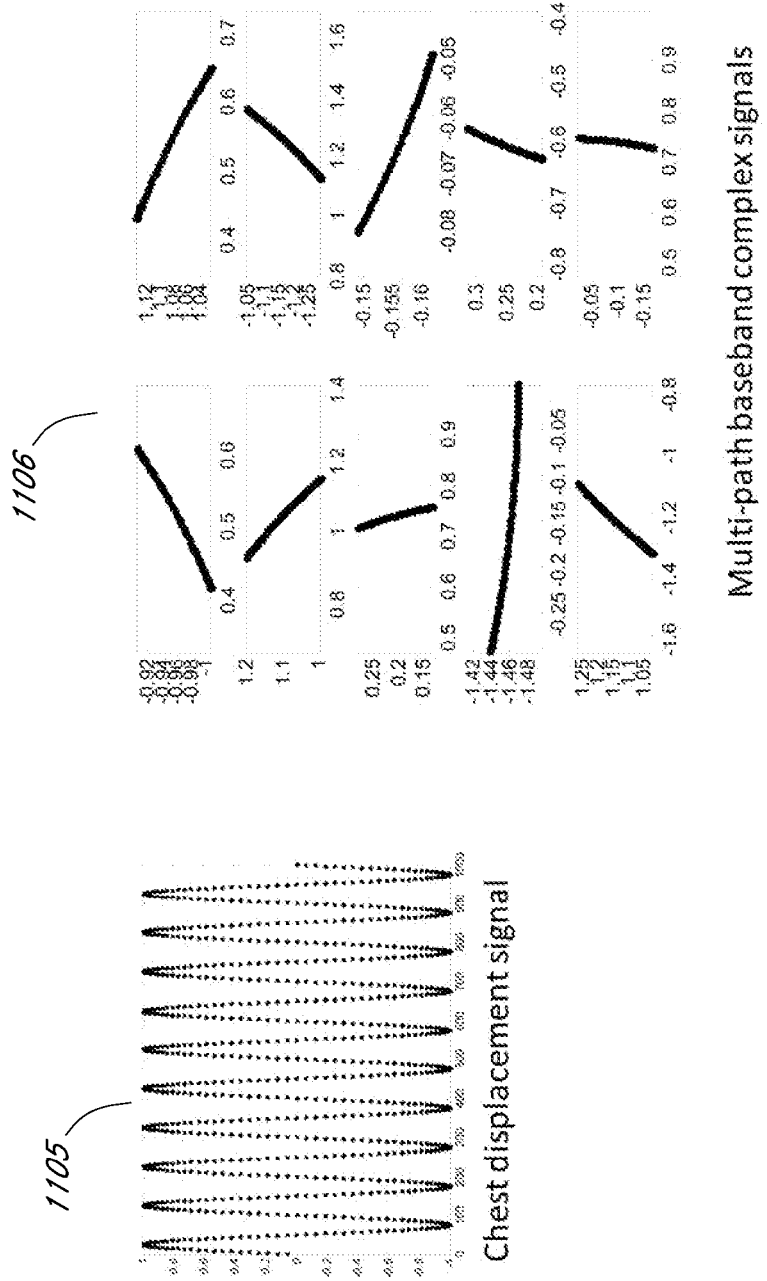
FIGS. 11F and 11G illustrate the baseband outputs with multi-path delayed signals when the body parts exhibit expand or contract with different phase delay.
Figure 11G:
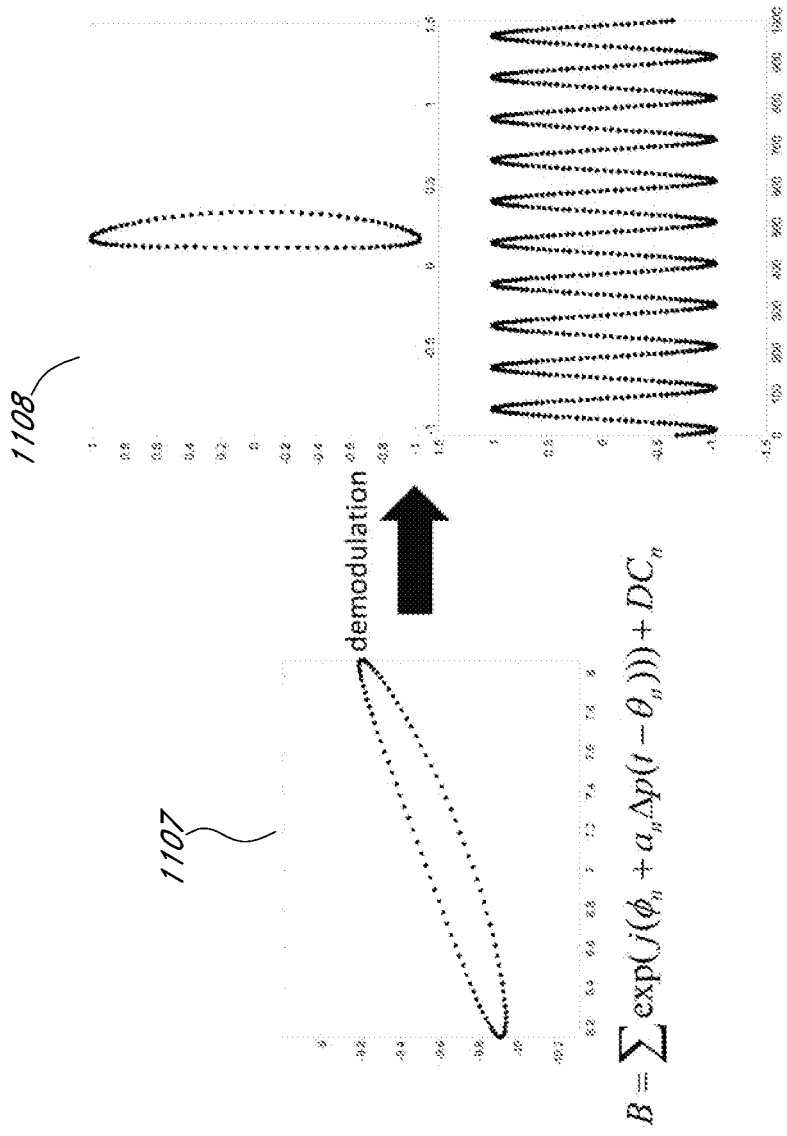

FIGS. 11D and 11E illustrate the baseband outputs with multi-path delayed signals when the body parts exhibit simultaneous body expansion and contraction motion while FIGS. 11F and 11G illustrate the baseband outputs with multi path delayed signals when the body parts expand or contract with different phase delays. Referring to FIGS. 11D and 11E, reference numeral 1101 of FIG. 11D illustrates a motion signal (e.g., chest displacement signal). The multi-path based complex signals are shown in plots identified by 1102. The summed multi-path signal is shown in plot 1103 of FIG. 11E. Plot 1104 shows the demodulation signal which is approximately linear indicating absence of abnormal breathing (e.g., paradoxical breathing).

Referring to FIGS. 11F and 11G, reference numeral 1105 of FIG. 11F illustrates a motion signal (e.g., chest displacement signal). The multi-path based complex signals are shown in plots identified by 1106. The summed multi-path signal is shown in plot 1107 of FIG. 11G. Plot 1108 shows the demodulation signal which is approximately linear indicating absence of abnormal breathing (e.g., paradoxical breathing).

In various embodiments, the radar-based physiological motion sensor can detect non-cardiopulmonary signals or motion events as described herein. In various embodiments, a signal with a single stable source can be considered as a cardiopulmonary signal and a signal that is unstable or has multiple sources can be considered a non-cardiopulmonary signal as disclosed in U.S. Provisional App. No. 61/123,017 which is incorporated herein by reference in its entirety and in U.S. Provisional App. No. 61/125,019, which is incorporated herein by reference in its entirety. In various embodiments, a signal with a single stable periodic scatterer can be considered a cardiopulmonary signal, and a signal that is unstable or has multiple scatterers can be considered to include non-cardiopulmonary motion or other signal interference.

In various embodiments, the physiological signals can be analyzed to determine the quality of the signal, including, but not limited to, detection of non-cardiopulmonary motion, detection of high signal-to-noise ratio, detection of low signal power, detection of RF interference, and detection of signal clipping. Additionally, signal quality can be measured by analyzing the signal in the complex plane to determine how much the scattered data samples are smeared with respect to an arc or a principle vector. The samples of a high-quality signal should lie very close to an arc or a principle vector, and significant deviation from that arc or vector can indicate a lower-quality signal. In some embodiments, the low-signal cutoff can be calculated based on a threshold, either in the spectral domain or the time domain. In some embodiments, the low signal power threshold can be calculated from the effective number of bits provided by the analog-to-digital converter and the full-scale voltage of the baseband circuit. In some embodiments, the clipping indicator can be triggered when the digitized voltage exceeds a maximum value as disclosed in U.S. Provisional App. No. 61/141,213 which is incorporated herein by reference in its entirety.

In various embodiments, non-cardiopulmonary motion (e.g., motion of objects in the vicinity of the subject or physical movement by the subject) may be detected in a variety of ways. For example, in some embodiments an excursion larger than the subject's maximum chest excursion due to cardiopulmonary motion (or breath) can be an indication of non-cardiopulmonary motion. Similarly, a significant increase in signal power can indicate motion.

In those systems where linear demodulation is suitable, significant changes to the best-fit vector, primary vector or eigenvector of the covariance matrices can indicate non-cardiopulmonary motion. The best-fit vector, primary vector or eigenvector is the vector on which the signals are projected. Significant changes to the best-fit vector, primary vector or eigenvector can also indicate a new relationship between the antenna and the subject and further indicates non-cardiopulmonary motion. Changes to the best-fit vector, the eigenvector or the primary vector can be detected by calculating the inner product of the normalized current vector and the normalized previous vector. If the inner product is below a threshold, then it is possible that non-cardiopulmonary motion is present. When linear demodulation is used, a significant change in the ratio of the eigenvalues, or of the RMS error of the data to the best-fit line, or of the RMS difference between the complex constellation of the signal and the best-fit vector, indicates that the detected motion does not fit the line well which can indicate presence of non-cardiopulmonary motion or signal interference as disclosed in U.S. Provisional App. No. 61/141,213 which is incorporated herein by reference in its entirety.

When arc-based demodulation is used, significant changes in the location of the origin, changes in the radius of the circle the arc is on, or changes in the position of the arc on the circle can indicate a change in the relationship between the antenna and subject, which can in turn indicate presence of non-cardiopulmonary motion. In those systems where arc-based demodulation is used, a change in the RMS error of the data to the best-fit arc or RMS difference between the complex constellation of the signal and the best-fit circle is an indication of a non-cardiopulmonary motion signal or other signal interference as disclosed in U.S. Provisional App. No. 61/141,213 which is incorporated herein by reference in its entirety.

In various embodiments, noise that affects the I and Q channels equally, including thermal noise and some types of noise from radio interference, can be estimated by the excursion of the signal from a line or arc in the complex plane, and the signal power can be calculated by the length of the line or arc. Thus, a signal-to-noise ratio can be estimated, and can be used as an indicator of the quality of the signal as disclosed in U.S. Provisional App. No. 61/141,213 which is incorporated herein by reference in its entirety.

In various embodiments, when motion or another non-respiratory signal is detected, the device can not display a respiratory rate as disclosed in U.S. Provisional App. No. 61/123,017 which is incorporated herein by reference in its entirety. The non-cardiopulmonary motion detection algorithm can be used to enable some embodiments to operate as an activity monitor.

Figure 12A:
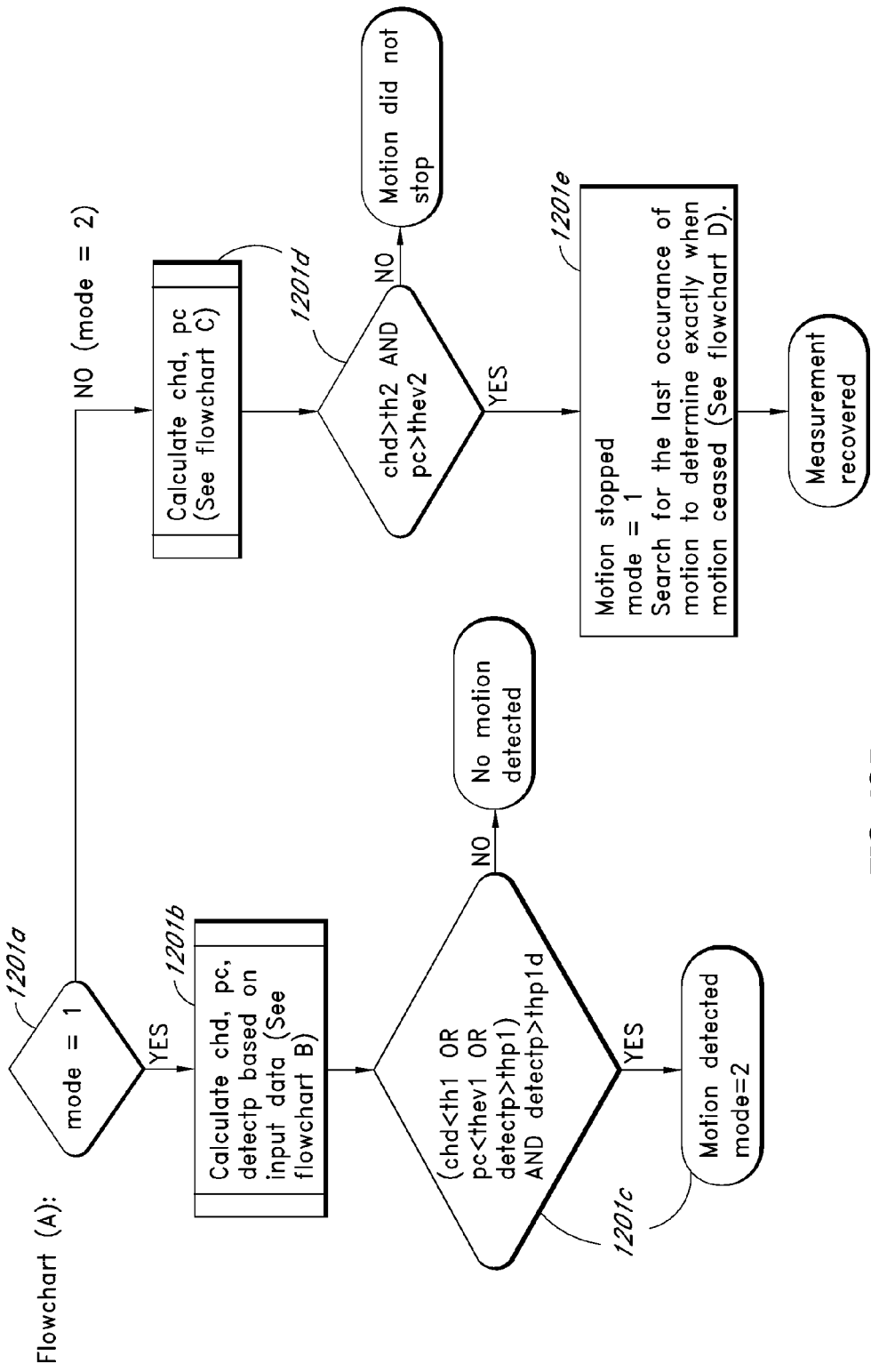
FIGS. 12A-12D illustrates an embodiment of a method configured to detect non-cardiopulmonary motion.
Figure 12B:
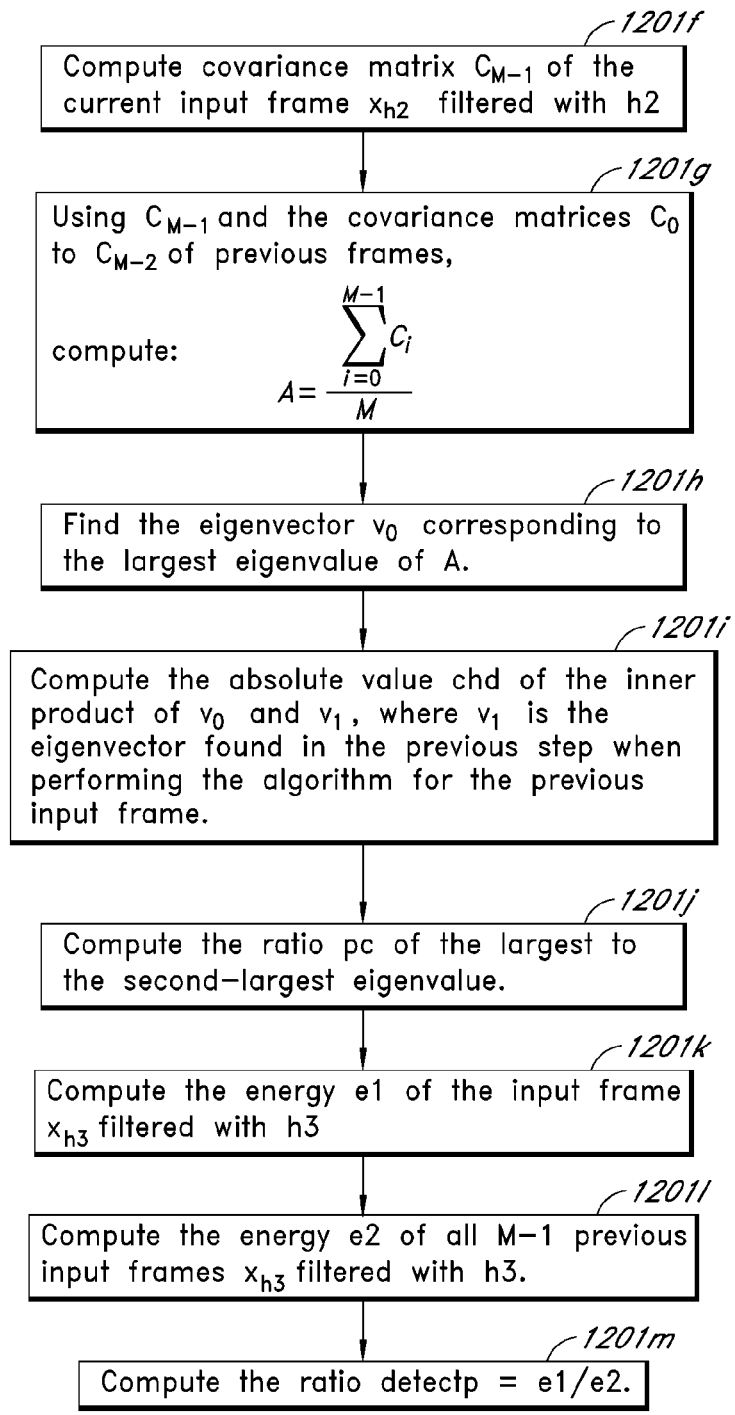

An example of a non-cardiopulmonary motion detection algorithm is further described below and illustrated in FIGS. 12A-12D. The algorithm can be executed by a processor and is configured to detect non-cardiopulmonary motion or other signal interference by looking at the change in direction of the eigenvectors, the ratio of the eigenvalues and the change of energy in the signal, as shown in block 1201*b*. The algorithm starts in mode 1, as shown in block 1201*a*, by assuming that no non-cardiopulmonary motion or other signal interference is present and switches to mode 2 as shown in block 1201*c* as soon as any non-cardiopulmonary motion or other signal interference is detected. When in mode 2, the algorithm similarly checks the change in direction of the eigenvectors and the ratio of eigenvalues, as shown in block 1201*a* to determine if the non-cardiopulmonary motion or other signal interference has ceased. If motion ceases, then the algorithm will find the earliest time (the retrospect) with no motion, as shown in block 1201*e*. The algorithm comprises the following steps:

Mode=1 a. Compute covariance matrix $C_{M-1}$ of the current input frame $x_{h2}$ filtered with a first filter having a filter function h2, as shown in block 1201*f* of FIG. 12B. In some embodiments, the first filter can be a low-pass filter.

b. Using $C_{M-1}$ and the covariance matrices $C_0$ to $C_{M-2}$ of previous frames, compute an A-matrix $$A = \frac{\sum_{i=0}^{M-1} C_i}{M},$$

as shown in block 1201*g* of FIG. 12B, where M is the number of preceding frames to consider and in some embodiments can be 32. In various embodiments M can be larger or smaller than 32.

c. Find the eigenvector $v_0$ corresponding to the largest eigenvalue of A, as shown in block 1201*h* of FIG. 12B.

d. Compute the absolute value chd of the inner product of $v_0$ and $v_1$, where $v_1$ is the eigenvector found in step c when performing the algorithm for the previous input frame, as shown in block 1201*i* of FIG. 12B.

e. Compute the ratio pc of the largest to the second-largest eigenvalue, as shown in block 1201*j* of FIG. 12B.

f. Compute the energy $e_1$ of the input frame $x_3$ filtered with a second filter having a filter function h3. In various embodiments, the second filter can be a high-pass filter, as shown in block 1201*k* of FIG. 12B.

g. Compute the average energy per frame $e_2$ of all M−1 previous input frames $x_3$ filtered with h3, as shown in block 1201*l* of FIG. 12B.

h. Compute the ratio detectp=$e_1/e_2$, as shown in block 1201*m* of FIG. 12B.

i. If (chd<th1 OR pc<thev1 OR detectp>thp1) AND detectp>thp1*d*), as shown in block 1201*b* and 1201*c* then non-cardiopulmonary motion or other signal interference is detected, switch to Mode=2. In various embodiments th1 can have a value between approximately 0.6 and approximately 1. In various embodiments, thev1 can have a value in the range 4 and 12. In various embodiments, thp1 can have a value in the range 4 and 20. In various embodiments, thp1$d$ can have a value between approximately 0.1 and approximately 0.8.

Figure 12C:
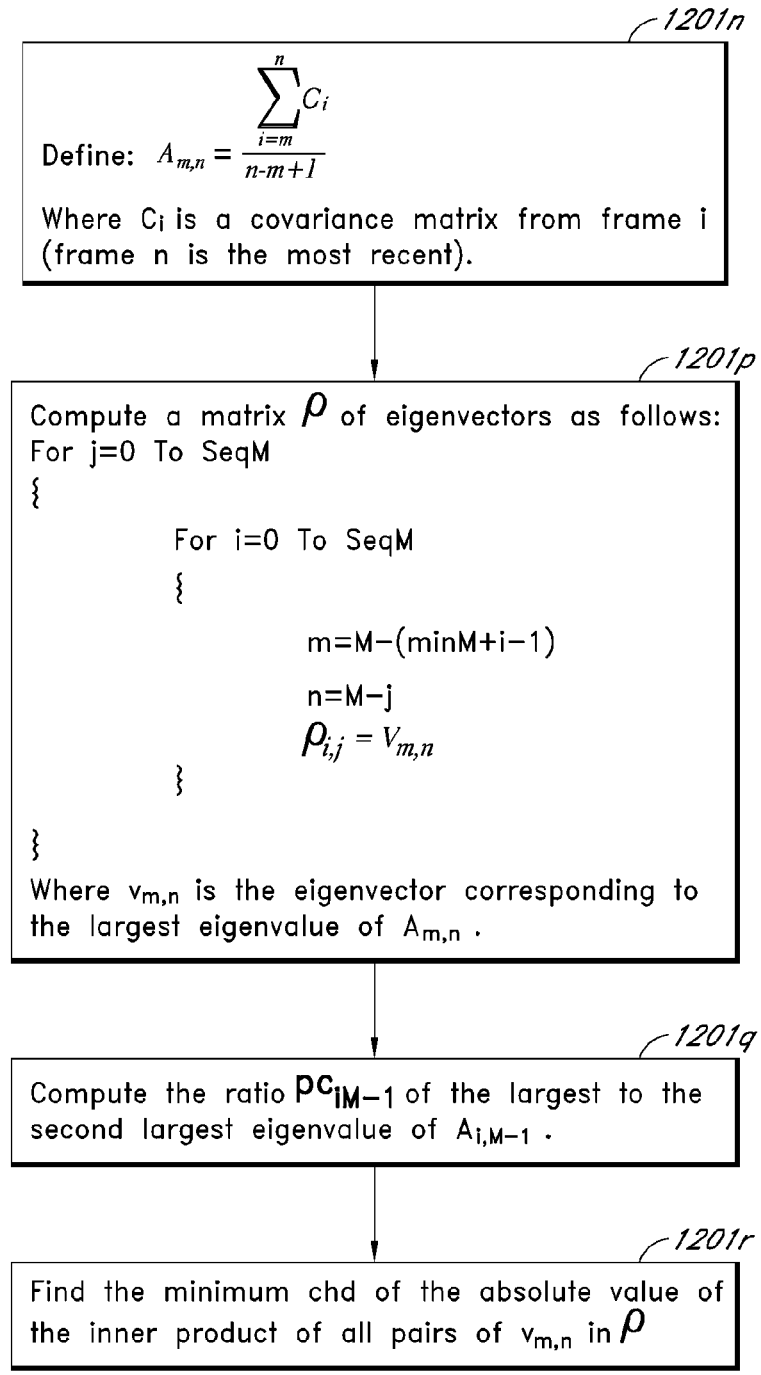
Figure 12D:
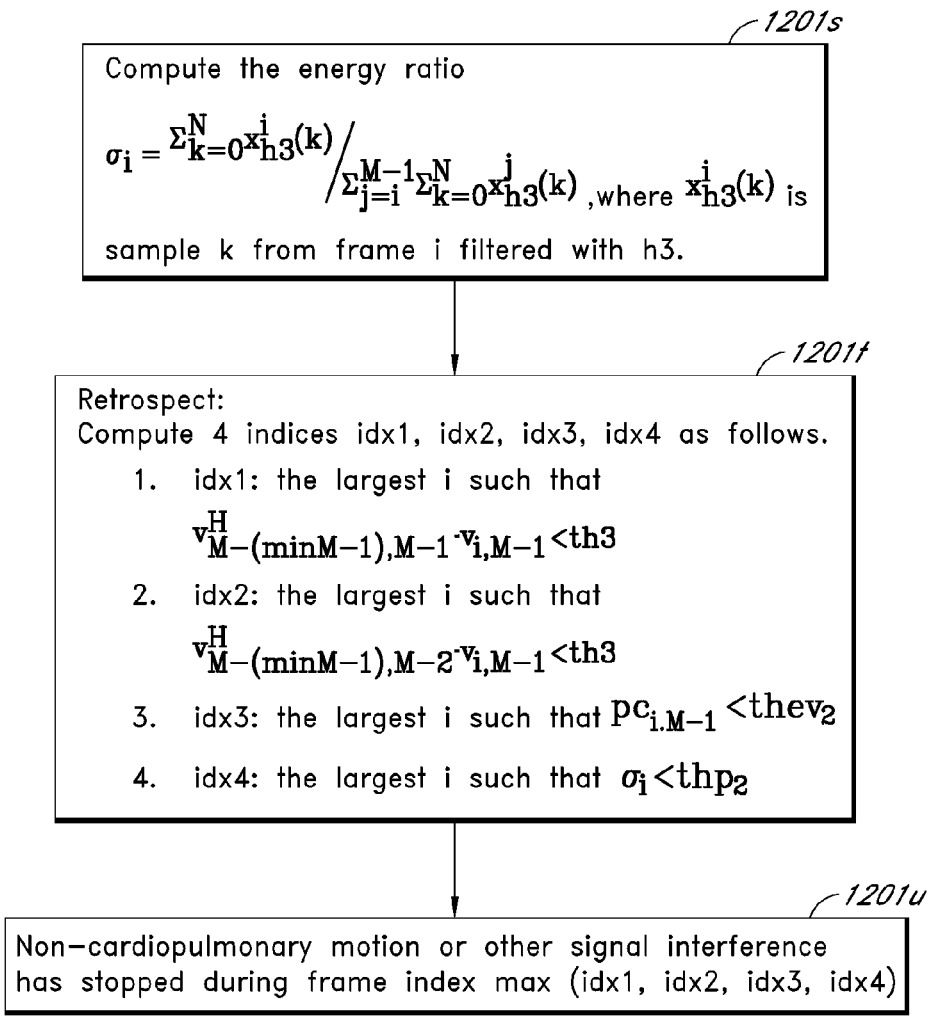

Mode=2 a. Calculate an A'-matrix given by the equation $$A_{m,n} = \frac{\sum_{i=m}^{n} C_i}{n - m + 1},$$

where $C_i$ is a covariance matrix from frame i (frame n being the most recent), as shown in block 1201$n$ of FIG. 12C.

b. Compute a matrix ρ of eigenvectors as follows, as shown in block 1201$p$ of FIG. 12C:

```
For j = 0 To SeqM
{
    For i = 0 To SeqM
    {
        m = M - (minM + i -1)
        n = M - j
        ρ_{i,j} = V_{m,n}
    }
}
```

$$\rho = \begin{bmatrix} V_{M-(minM-1),M-1} & \cdots & V_{M-(minM-1),M-SeqM} \\ \vdots & \ddots & \vdots \\ V_{M-(minM-SeqM-1),M-1} & \cdots & V_{M-(minM-SeqM-1),M-SeqM} \end{bmatrix},$$

where SeqM is about 5 in some embodiments and corresponds to the number of preceding frames to consider, where minM is the number of frames prior to current frame to consider and is about 8 in some embodiments, where $v_{m,n}$ is the eigenvector corresponding to the largest eigenvalue of $A_{m,n}$.

c. Compute the ratio $pc_{i,M-1}$ of the largest to the second largest eigenvalue of the matrix $A_{i,M-1}$, as shown in block 1201$q$ of FIG. 12C.

d. Find the minimum chd of the absolute value of the inner product of all pairs of $v_{m,n}$ in ρ, as shown in block 1201$r$ of FIG. 12C.

e. Compute the energy ratio $$\sigma_i = \frac{\sum_{k=0}^{N} x_{h3}^{(i)}(k)}{\sum_{j=i}^{M-1} \sum_{k=0}^{N} x_{h3}^{j}(k)},$$

where $x_{h3}^i(k)$ is sample k from frame i filtered with h3, as shown in block 1201$s$ of FIG. 12D.

f. If (chd>th2 AND $pc_{M-(minM-1),M-1}$>thev2) then non-cardiopulmonary motion or other signal interference has stopped, switch to Mode=1, as shown in blocks 1201$d$ and 1201$e$ of FIG. 12A. In various embodiments, th2 can have a value between approximately 0.6 and approximately 1. In various embodiments, thev2 can have a value between approximately 4 and approximately 12.

g. Retrospect: Compute 4 indices idx1, idx2, idx3, idx4 as follows, as shown in block 1201$t$.

i. idx1: the largest i such that $$v_{M-(minM-1),M-1}^H \cdot v_{i,M-1} < th_3.$$

ii. idx2: the largest i such that $$v_{M-(minM-1),M-2}^H \cdot v_{i,M-1} th_3.$$

iii. idx3: the largest i such that $pc_{i,M-1}$<thev2.
iv. idx4: the largest i such that $\sigma_i$<thp2.

In various embodiments, th3 can have a value between approximately 0.6 and approximately 1. In various embodiments, thp2 can have a value between approximately 4 and 12. In one embodiment, thp2 can be 5. In one embodiment, th3 can be approximately 0.97.

h. Then, non-cardiopulmonary motion or other signal interference has stopped during frame index max(idx1, idx2, idx3, idx4), as shown in block 1201$u$.

In various embodiments, three signal quality measures are computed before applying the rate estimation algorithm on the demodulated signal. First, an algorithm is used to highlight subset of samples of the demodulated signal with non-respiratory signal or interference. Secondly, an algorithm is used to highlight subsets of samples of the demodulated signal that have low power compared to a threshold. Thirdly, an algorithm is used to highlight subsets of samples with clipping. In various embodiments, the rate estimation algorithm also takes into account the low quality samples as determined by the three algorithms and flags them such that they would not affect the accuracy of the rate result. In various embodiments, the rate estimation algorithm uses only the samples that passed these quality checks and attempts to produce a rate based on these. In various embodiments, the rate estimation algorithm can set the flagged samples to zero. If too many of the samples are flagged, the system will not detect a sufficient number of breaths in the interval to for the time-domain rate estimation, and it will report an error. In various embodiments, the rate estimation further uses its own quality check measure. In various embodiments, the rate estimation algorithm is a cross-check of the rate results of a time domain approach and a frequency domain approach for rate estimation. In various embodiments, if the rate determined by the time domain approach differs from the rate determined by the frequency domain method by more than a threshold, the cross-check quality check fails. In various embodiments, if the cross-check quality check fails, the rate estimation communicates the possible reason for this failure. It will attribute the failure to one of these conditions when met in this order: low signal power, signal clipping, non-respiratory signal or interference. If none of these conditions are met, the rate estimation fails with a generic error.

In those embodiments of the system when the center of the circle is estimated from the arc, it is possible to distinguish between inhalation and exhalation by whether the phase of the signal viewed in the complex plane is moving clockwise or counter-clockwise (whether the phase is decreasing or increasing). Differentiation between inhale and exhale is important for some embodiments of triggering applications, some embodiments of synchronization applications, and for embodiments that require calculation of inhale time, exhale time, or the inhale time to exhale time ratio. Some examples of applications that would benefit from differentiation between inhale and exhale for inhale time/exhale time ratio include but are not limited to monitoring of chronic illness, biofeedback for management of chronic illness, and biofeedback for stress.

In various embodiments, the system 100 can perform a self-check to check for improper operation and/or environmental interference. In some embodiments, the self-check can be performed automatically. In various embodiments of the system, a self-test can be performed periodically to determine if portions of the hardware are malfunctioning. In various embodiments, the self-test can be performed by digitally controlling the activation of various components of the system and analyzing characteristics such as, but not limited to, channel noise level, channel imbalance and DC offset values. Although the self-test can be integrated as part of the system's start-up procedures, in various embodiments, the system 100 can require commands from the central controller to initiate the various self-test checks. In addition to hardware status, RF interference tests can be performed by comparing the normal transmitted RF power and reduced transmitted RF power. This can ensure that the received signal is not a result of an extra-sensor device producing cardio-pulmonary like signals.

Figure 13:
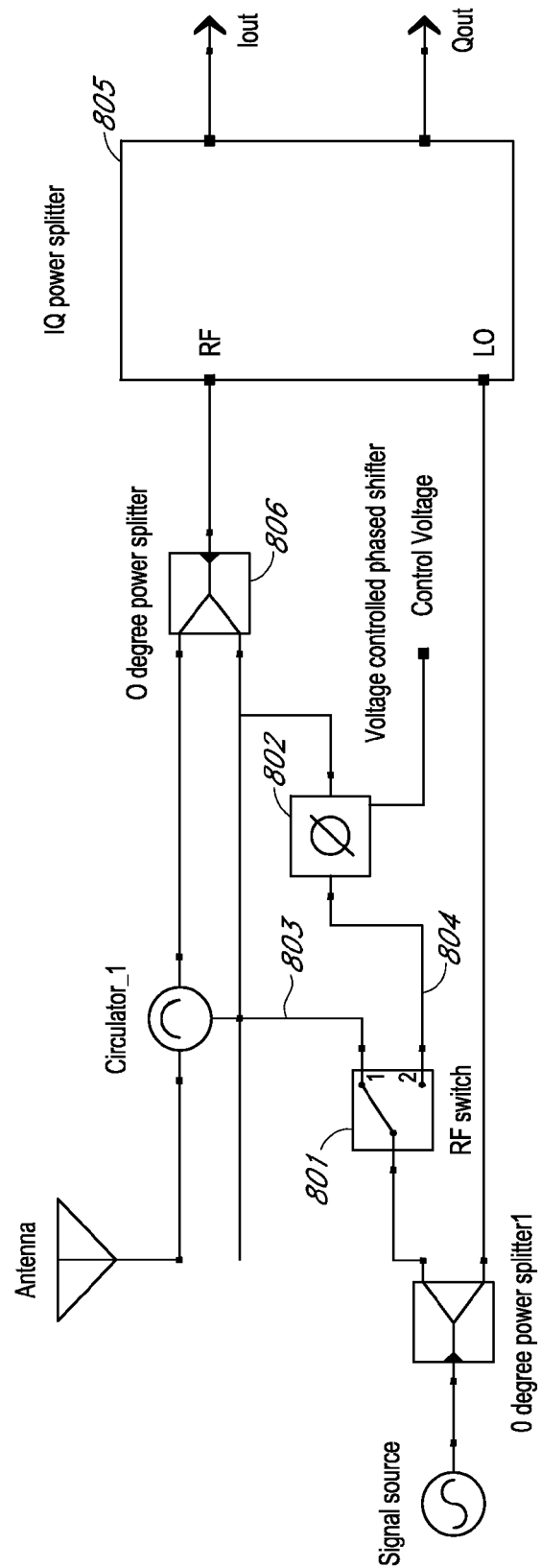
FIG. 13 schematically illustrates a block diagram of an embodiment of a self testing circuit.

FIG. 13 illustrates a block diagram of a self testing circuit 1300. In various embodiments, the self testing circuit includes an absorptive SPDT switch, 1301 and voltage controlled phase shifter 1302. The SPDT switch 1301 can be used for selecting either transmitting path 1303 or self testing path 1304. A voltage controlled phase shifter implemented on self testing path generates an artificial signal which is inputted in to RF input port of IQ demodulator 1305 through 0 degree power splitter 1306. The signal makes either full circle or partial of arc depending on the control voltage on complex constellation plot. The plot can be used to test the signal source, IQ imbalance, external interference, baseband signal conditioning, and data acquisition.

In various embodiments, a processor configured to execute a direction of arrival algorithm can be used to isolate cardiopulmonary motion from spatially separated non-cardiopulmonary motion based on their differing angles from the antenna as disclosed in U.S. Provisional App. No. 61/125,027, which is incorporated herein by reference in its entirety and in U.S. Provisional App. No. 61/125,020, which is incorporated herein by reference in its entirety. In various embodiments, a processor configured to execute a direction of arrival algorithm can be used to isolate separate two spatially separated cardiopulmonary motion signals based on their differing angles from the antenna. In various embodiments, a processor configured to execute a direction of arrival algorithm can be used to track the angle to a subject. To use direction of arrival, the radar-based physiological motion sensor includes at least two antennas in each plane in which it is desired to assess the direction of the source, and/or to separate spatially separated motion for subject separation and for non-cardiopulmonary motion cancellation.

In various embodiments, it is often desirable to have a wide antenna beam width, to ensure that the beam covers the subject in all probable positions. However, this wide beam width means that motion away from the subject can still be in the antenna's mean, and therefore can still affect the measurement. In various embodiments, direction of arrival (DOA) processing from multiple receive antennas can provide a wide angle of scanning to detect the subject, and then a narrower angle for measurement of a subject's physiological motion, avoiding interference from motion away from the subject. In some embodiments, the signals from the antennas can be processed as an antenna array, which has a narrower beam width than any of the individual antennas. Through processing, the beam of this array can be effectively steered towards the desired source, so the antenna beam is focused on the source and any motion outside the main beam will be attenuated according to the antenna pattern in that direction. Additionally in various embodiments, the angle to the target subject can be detected and presented in the interface, either as the angle or as a more general indication of the direction (i.e., straight, left, or right), effectively providing tracking of the subject.

In various embodiments, the signals from the different antennas can be used to detect and track the angle of an interfering source, and the signals from the antennas can be combined such that there is a null in the antenna pattern in the direction of the interfering motion, enabling continued detection of respiratory waveform in the presence of spatially separated motion. Any of several DOA algorithms can be used for this technique. These approaches can be used in a SIMO system including one transmitter and multiple receiver antennas. The DOA algorithms can be implemented in a MIMO system including multiple transmitters, each transmitting at a different frequency, and multiple receivers. Other advanced DOA algorithms including but not limited to MUSIC or ESPRIT could also be used to separate sources at different angles from the antenna.

In various embodiments, DOA processing can be used to isolate rib cage and abdominal breathing as disclosed in U.S. Provisional App. No. 61/125,020, which is incorporated herein by reference in its entirety. In various embodiments, DOA processing can be used to isolate leg motion from cardiopulmonary motion, enabling detection of restless leg syndrome during sleep. In various embodiments, multiple subjects can be monitored with one device using DOA processing as disclosed in U.S. Provisional App. No. 61/194,880 which is incorporated herein by reference in its entirety. As described above, in various embodiments, a Doppler radar system 100 can monitor a human's physiological signals such as respiration or heart waveforms, and respiratory and heart rates can be extracted. By employing multiple antennas in the system, direction of arrival (DOA) processing can be achieved, enabling detection of the angular direction of targets. In various embodiments, multiple targets' physiological signals can be separated based on DOA processing obtained by an arrayed Doppler radar. In various embodiments, separating these physiological signals can enable the waveforms of each target to be separated for the display or communication of waveforms and for the extraction of rates. If multiple people are within the antennas' field of view, each person's respiratory rates can be obtained with this signal processing scheme, as long as their angular separation is greater than the resolution of the array and there are no more people within the field of view than antennas and receivers in the plane the people and the antenna share is less than the number of antennas and receivers. In some embodiments, the multiple antennas can be separated by a distance $\lambda/2$. In various embodiments employing three antennas, two subjects who are separated by approximately 15 to 20 degrees can be simultaneously tracked and monitored. By increasing the number of antennas the angular separation between the two subjects can be further reduced.

Figure 14A:
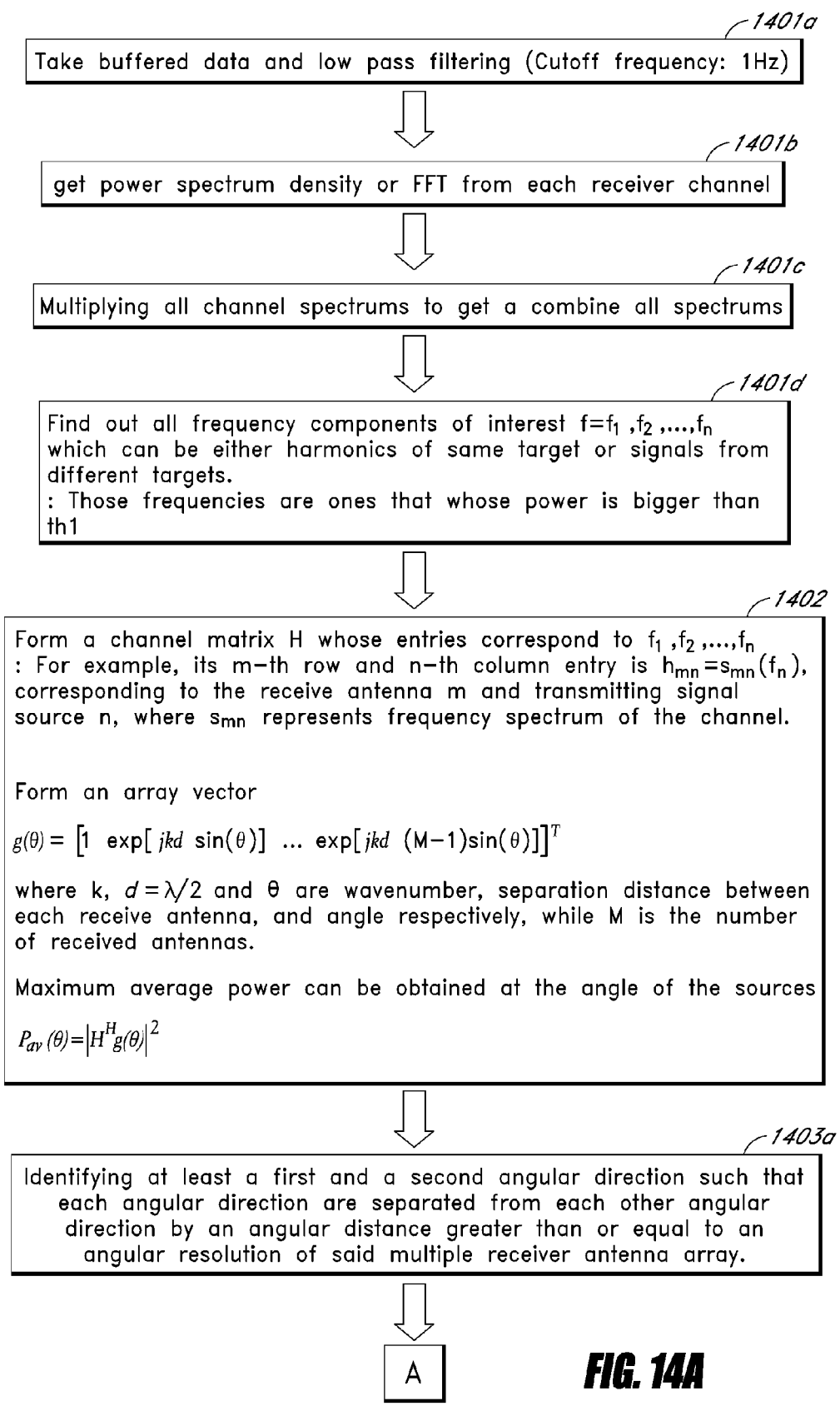
FIG. 14 (which consists of 14A and 14B) illustrate an embodiment of a method for separating multiple cardiopulmonary signals.

One embodiment of a method for separating multiple cardiopulmonary signals is illustrated in FIG. 14 and includes:

1. As illustrated in blocks 1401a-1401d, the method includes determining the frequency components f= $f_1, f_2, \ldots, f_n$ of the buffered data that are most likely to contain the cardiopulmonary signals. In some embodiments, these frequency components can be determined by measuring the power spectral density of the combination of the channels, and applying a cost function to the output. In some embodiments, the power spectrum density of the combination of channels can be determined by obtaining the power spectral density from each receiver and multiplying them to get a combined spectrum. In some embodiments, a low-pass filter is applied before obtaining the power spectral density from each receiver. In some embodiments, the cutoff frequency of said low-pass filter is 1 Hz.

2. As shown in block 1402, the method further includes identifying the angular direction of each frequency component. In some embodiments, the angular frequency components are identified by forming a channel matrix H whose entries correspond to the frequency components most likely to contain the cardiopulmonary signals found in Step 1, using this channel matrix and an array vector corresponding to each angle from the target to calculate the maximum average power at each angle. In some embodiments, the $m^{th}$ row and $n^{th}$ column of the channel matrix entry can be $h_{mn}=s_{mn}(f_n)$, corresponding to the receiver antenna m and moving scatterer, where $s_{mn}$ represents frequency spectrum of the channel. In some embodiments, an array vector corresponding to each angle from the target is formed. In some embodiments, the array vector is given by equation (1):

$$g(\theta)=[1\ \exp\ [jkd\sin(\theta)] \ldots \exp\ [jkd(M-1)\sin(\theta)]]^T \quad (1)$$

where k is the wavenumber, $d=\lambda/2$ is the separation distance between each receiver antenna and θ is the angle from the antenna normal vector to the target, while M is the number of received antennas. In some embodiments, the maximum average power that can be obtained at each the angle of the scatterers is given by equation (2):

$$P_{av}(\theta)=|H^H g(\theta)|^2 \quad (2)$$

3. As illustrated in blocks 1403a and 1403b, the method further includes eliminating angles that are separated from each other by an angular distance less than the angular resolution of the multiple receiver antenna array, and identifying at least a first and second angular direction such that each angular direction is separated from each other angular source by an angular distance greater than or equal to an angular resolution of said multiple receiver antenna array. 4. Generating a DOA vector with unity magnitude for each target in the said angular direction. In various embodiments, an M×N array matrix A is foamed, whose ith column is given by the equation (3)

$$g(\theta_i)=1\ \exp\ [jkd\sin\ [(\theta_i)] \ldots \exp\ [jdk(M-1)\sin(\theta_i)]]^T \quad (3)$$

where $d=\lambda/2$ and θ are the receive antenna separation and angle respectively, while M is the number of received antennas. In those embodiments where there are other moving objects in the vicinity of the subject which can scatter the radar signal and are separated by an angular distance greater than the angular resolution of the multiple receiver antenna array, N denotes the number of moving scatterers.

4. In various embodiments, smoothing the DOA vectors with a weighted average of the current DOA vectors and previous DOA vectors in a buffer, as shown in block 1405.

5. Separating the signal from each angular direction by steering spatial nulls towards the other angular directions, as shown in block 1404. In various embodiments, the signal separation can be achieved by steering spatial nulls toward unwanted signal sources by applying inverse of matrix A, estimated in step 4, to the conditioned channel data.

$$S=A^{-1}R_x \quad (4)$$

6. In various embodiments, applying the non-cardiopulmonary motion detector to each separated output, and if non-cardiopulmonary motion is detected, clearing the buffer of DOA vectors 7. In various embodiments, demodulating each of the separated signals individually, and processing each signal to obtain information corresponding to cardiopulmonary motion.

8. Outputting information on at least one of the angle to each target, cardiopulmonary motion related to the target.

Figure 15:
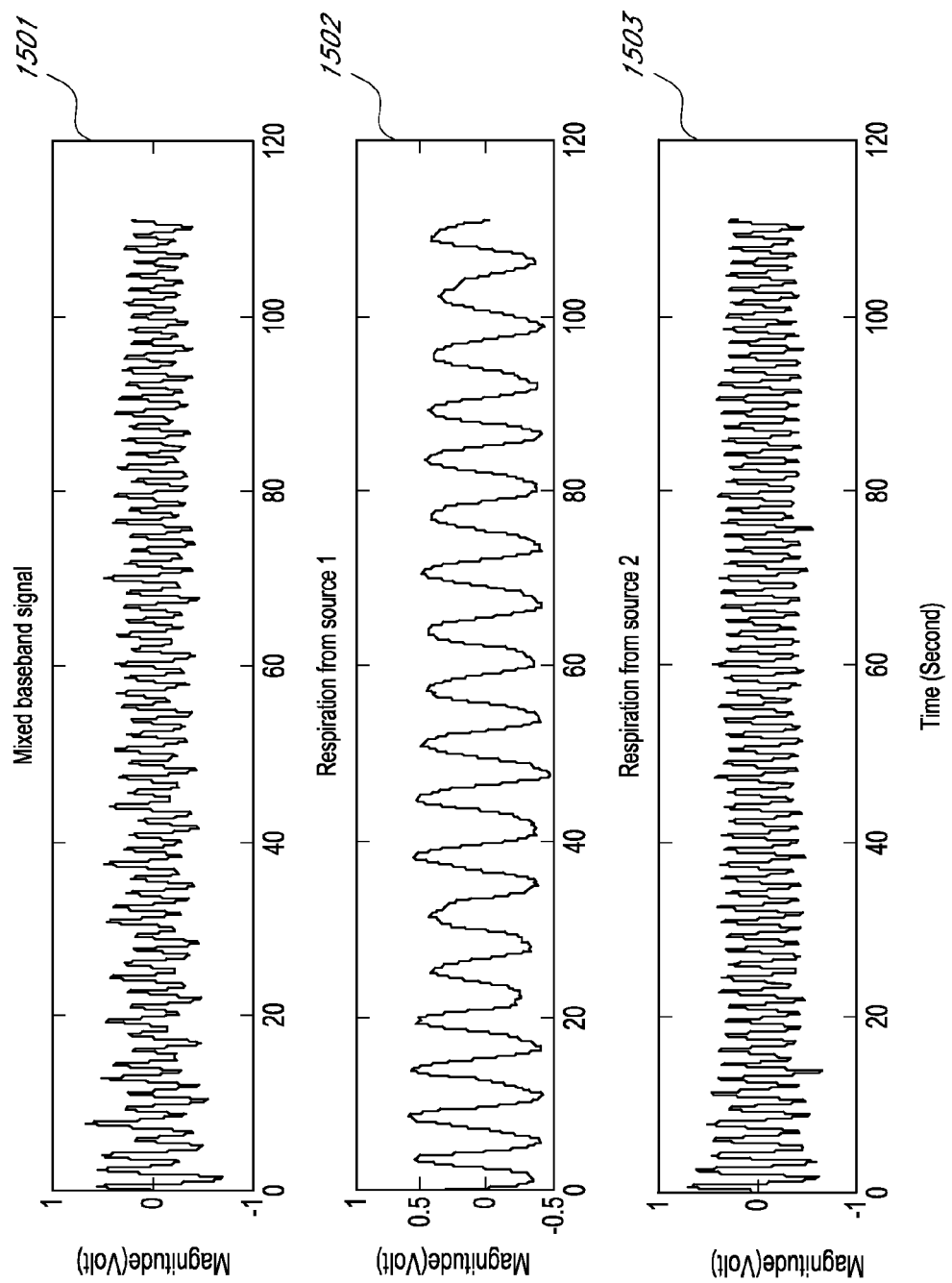
FIG. 15 illustrates measurements showing the separation of respiratory signals from two targets.

FIG. 15 illustrates the separation of respiratory signals from two targets. Plot 1501 illustrates a mixed baseband signal which is separated using DOA processing. Plot 1502 illustrates the respiratory signal from a first subject or source and plot 1503 illustrates the respiratory signal from a second source or subject. In various embodiments, a body-worn identification tag including a system configured to perform DOA processing can be used to help identify and enhance measurement of a targeted subject as disclosed in U.S. Provisional App. No. 61/200,876 which is incorporated herein by reference in its entirety.

Alternatively to separating and analyzing two distinct signals, in various embodiments of the device, the system 100 can use the DOA algorithm to track a single, desired, cardiopulmonary signal, while nulling one or more undesired cardiopulmonary or non-cardiopulmonary signals. In some embodiments, the desired subject can be tracked with an RFID tag. In some embodiments, the desired subject can be tracked with biometrics. In some embodiments, the desired subject can be tracked based on a known initial position. In this case, only the desired signal will be demodulated and only the angle information and/or cardiopulmonary information related to the desired target will be outputted. The various embodiments of the system 100 can include DOA processing algorithms to track a subject or patient as disclosed in U.S. Provisional App. No. 61/125,020, which is incorporated herein by reference in its entirety and in U.S. Provisional App. No. 61/194,836 which is incorporated herein by reference in its entirety. For example, in some embodiments, DOA processing can be used to track a sleeping subject throughout the night as the subject tosses and turns while sleeping.

Figure 16A:
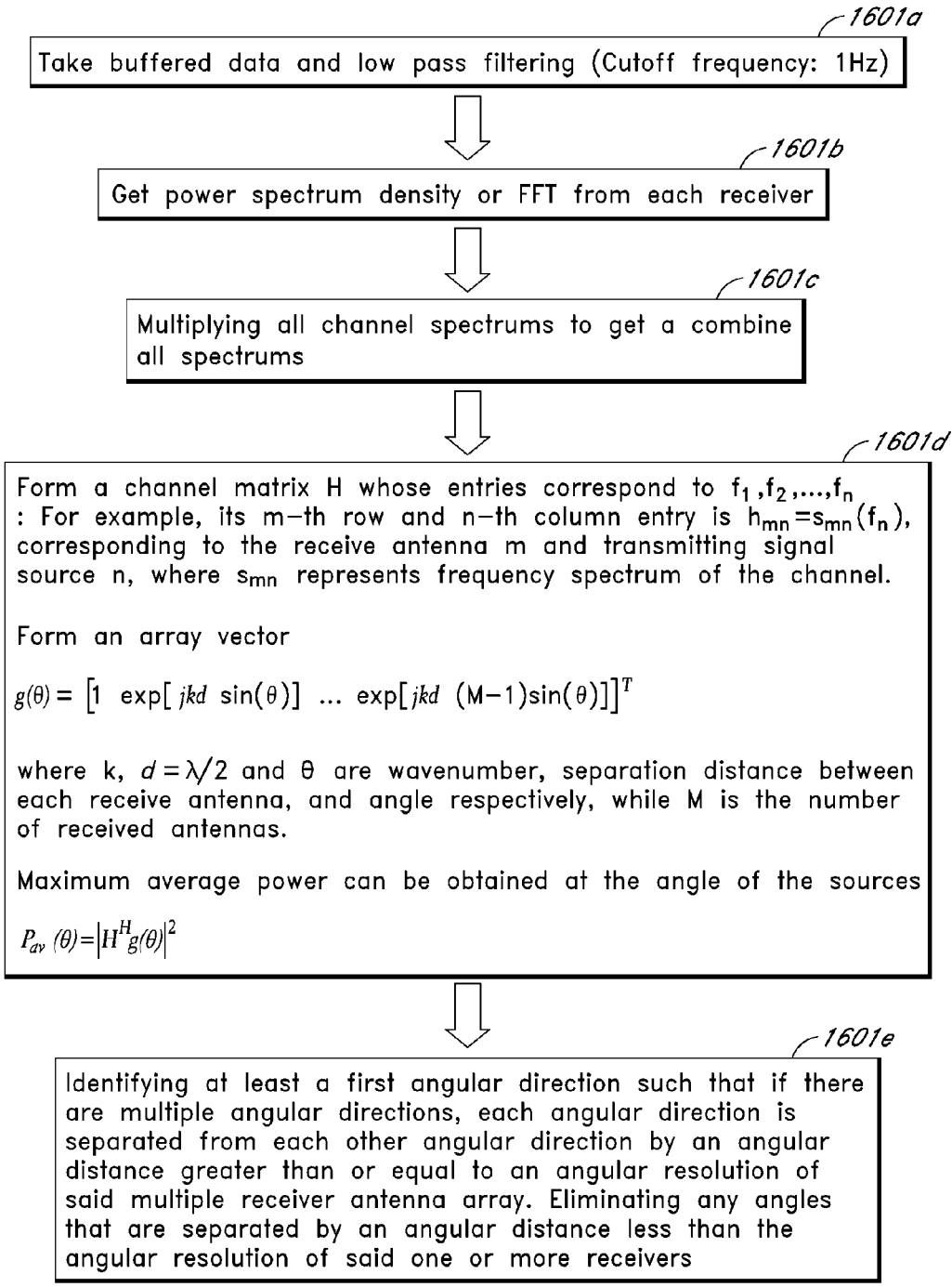
FIGS. 16 (which consists of 16A and 16B) illustrate an embodiment algorithm for tracking the direction of one or more cardiopulmonary signals.
Figure 16B:
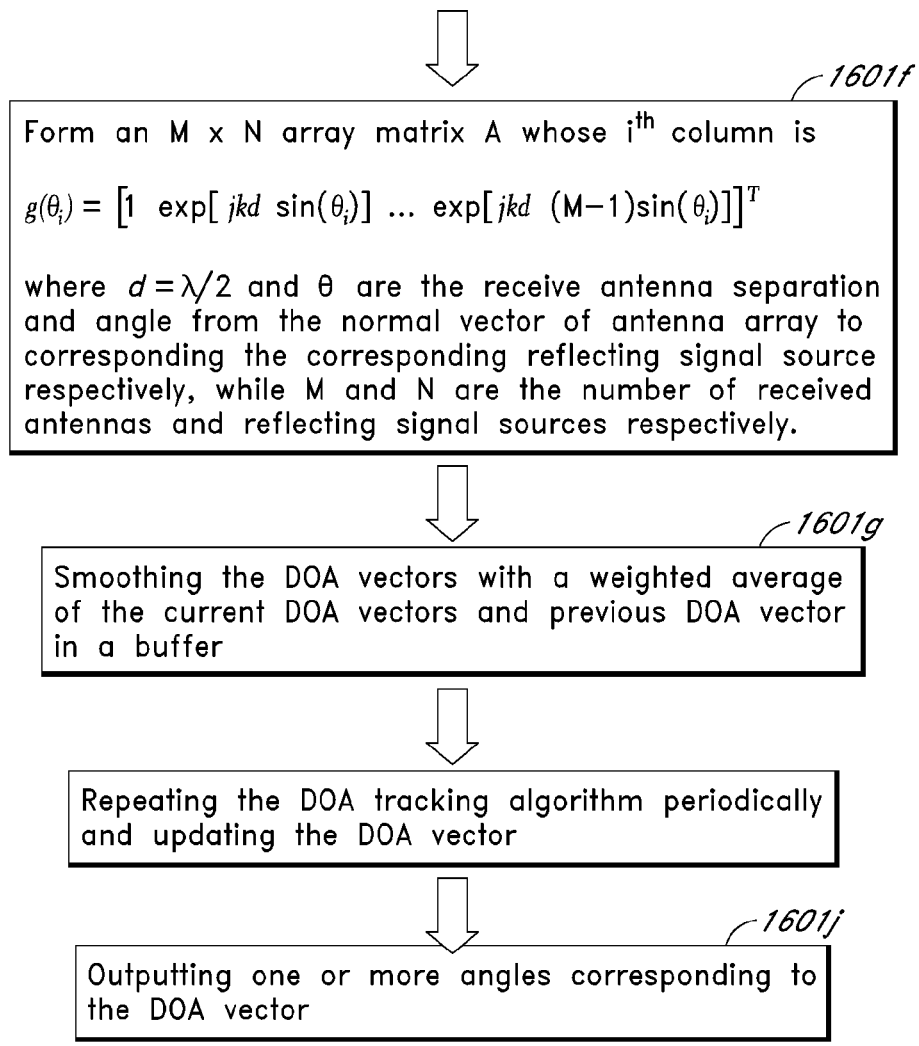

One embodiment algorithm for tracking the direction of one or more cardiopulmonary signals is described below as illustrated in FIG. 16 and includes 1. As illustrated in blocks 1601a-1601c, the method includes determining the frequency components f= $f_1, f_2, \ldots, f_n$ of the buffered data that are most likely to contain the cardiopulmonary signals. In some embodiments, these frequency components can be determined by measuring the power spectral density of the combination of the channels, and applying a cost function to the output. In some embodiments, the power spectrum density of the combination of channels can be determined by obtaining the power spectral density from each receiver and multiplying them to get a combined spectrum. In some embodiments, a low-pass filter is applied before obtaining the power spectral density from each receiver. In some embodiments, the cutoff frequency of said low-pass filter is 1 Hz.

2. As illustrated in step 1601d, the method further includes identifying the angular direction of each frequency component. In some embodiments, the angular frequency components are identified by forming a channel matrix H whose entries correspond to the frequency components most likely to contain the cardiopulmonary signals found in Step 1, using this channel matrix and an array vector corresponding to each angle from the target to calculate the maximum average power at each angle. In some embodiments, the $m^{th}$ row and $n^{th}$ column of the channel matrix entry can be $h_{mn}=s_{mn}(f_n)$, corresponding to the receiver antenna m and moving scatterer, where $s_{mn}$ represents frequency spectrum of the channel. In some embodiments, an array vector corresponding to each angle from the target is formed. In some embodiments, the array vector is given by equation (1):

$$g(\theta)=[1\ \exp\ [jkd\sin(\theta)] \ldots \exp\ [jkd(M-1)\sin(\theta)]]^T \quad (1)$$

where k is the wavenumber, $d=\lambda/2$ is the separation distance between each receiver antenna and $\theta$ is the angle from the antenna normal vector to the target, while M is the number of received antennas. In some embodiments, the maximum average power that can be obtained at each the angle of the scatterers is given by equation (2):

$$i\ P_{av}(\theta) = |H^H g(\theta)|^2 \quad (2)$$

3. As illustrated in block 1604e, the method further includes eliminating angles that are separated from each other by an angular distance less than the angular resolution of the multiple receiver antenna array, and identifying at least a first and second angular direction such that each angular direction is separated from each other angular source by an angular distance greater than or equal to an angular resolution of said multiple receiver antenna array.

4. Generating a DOA vector with unity magnitude for each target in the said angular direction. In various embodiments, an M×N array matrix A is formed, as shown in block 1601f, whose ith column is given by the equation (3)

$$g(\theta_i) = [1\ \exp\ [jkd\ \sin(\theta_i)] \ldots \exp\ [jkd(M-1)\ \sin(\theta_i)]]^T \quad (3)$$

where $d=\lambda/2$ and $\theta$ are the receive antenna separation and angle respectively, while M is the number of received antennas. In those embodiments where there are other moving objects in the vicinity of the subject which can scatter the radar signal and are separated by an angular distance greater than the angular resolution of the multiple receiver antenna array, N denotes the number of moving scatterers.

5. In various embodiments, smoothing the DOA vectors with a weighted average of the current DOA vectors and previous DOA vectors in a buffer, as shown in block 1601g.

6. Separating the signal from each angular direction by steering spatial nulls towards the other angular directions. In various embodiments, the signal separation can be achieved by steering spatial nulls toward unwanted signal sources by applying inverse of matrix A, estimated in step 4, to the conditioned channel data.

$$S = A^{-1} R_x \quad (4)$$

7. In various embodiments, applying the non-cardiopulmonary motion detector to each separated output, and if non-cardiopulmonary motion is detected, clearing the buffer of DOA vectors.

8. In various embodiments, demodulating each of the separated signals individually, and processing each signal to obtain information corresponding to cardiopulmonary motion.

9. Outputting information on at least one of the angle to each target, cardiopulmonary motion related to the target as shown in block 1601j.

In various embodiments, empirical mode decomposition (EMD) algorithms can be used to isolate the signal from motion as disclosed in U.S. Provisional App. No. 61/125,023, which is incorporated herein by reference in its entirety including motion due to but not limited to non-cardiopulmonary motion by the subject, cardiopulmonary motion of one or more people other than the intended subject, non-cardiopulmonary motion of another person or other people, motion of other objects in the environment, motion of the radar system.

Various embodiments of the system 100 can include a combination of Empirical Mode Decomposition and Direction of Arrival processing as disclosed in U.S. Provisional App. No. 61/125,027, which is incorporated herein by reference in its entirety. In some embodiments, the DOA processing can be used to separate motion signals that occur at different angles. Subsequently EMD processing can be used to extract the desired physiological motion signal from non-physiological motion and other signal interference that remains after DOA processing. Various embodiments can include a processor configured to execute a motion compensation algorithm. Motion compensation can suppress interference with cardiopulmonary signals caused by movement of other body parts or movement by another person in the antenna's field of view. The cardiopulmonary signal can be in a low frequency range e.g., from a few Hz to a few kHz even including harmonics, while other non-cardiopulmonary motion can be wideband because it moves more quickly; for example, an impulse response can include all frequency components. In some embodiments, the motion compensation algorithm can separate low pass filtered and high pass filtered versions of the data or signal and find at least two primary vectors (e.g., principle eigenvectors) for the high pass filtered data or signal. The low pass filtered data or signals which include the cardiopulmonary signal, can be projected on the orthogonal subspace spanned by these primary vectors of the high pass filtered signal. This subspace can contain reduced or minimal motion interference. This approach can provide information related to the respiratory signal with greater accuracy when used with multiple spatially separated antennas.

Noise reduction can be obtained through filtering, wherein the filter passes signals in the physiological band and attenuates signals outside of that band.

Since the cardiopulmonary signal has low frequency components, an oversampling and averaging method can be applied to reduce noise with inexpensive data acquisition devices. By oversampling, the uncorrelated noise power (such as AWGN) on baseband signals can be reduced by a factor of 1/N by averaging N samples, while keeping the same signal power, resulting in a SNR that is N times greater with oversampling and averaging than with Nyquist sampling.

Noise reduction can be obtained through performing empirical mode decomposition and selecting the one or more modes that contain the physiological signal(s) and using only those to reconstitute the signal. The empirical mode decomposition algorithm adaptively separates the signal into intrinsic mode functions (IMFs) which are adaptively created based on the highest-energy intrinsic time scales in the data, and thus capture the most important information in the signal. IMFs have well-defined Hilbert transforms. This empirical mode decomposition algorithm can be used to process the digitized output of a radar designed to measure cardiopulmonary motion of a subject. The quadrature outputs of the radar signal can be processed with an EMD algorithm including at least one of bivariate EMD, complex EMD, or rotation-variant EMD. The IMFs of the I and Q channels can be combined with a linear or nonlinear demodulation algorithm. Then a motion signal can be constructed from the IMFs containing the signal, without the IMFs that contain only noise, resulting in significant noise reduction as disclosed in U.S. Provisional App. No. 61/125,023, which is incorporated herein by reference in its entirety.

The system 100 including the radar-based physiological sensor can be configured in variety of ways as described below.

An example system configuration can include a Spot Check monitor configured as a single piece or a two piece system and adapted to operate at 2.4 GHz. The system 100 can further include a single antenna, direct conversion or a homodyne receiver and a high-pass filter. The system 100 can further include a processor configured to process signals using the linear demodulation algorithm described above. In various embodiments, the processor can also be configured to estimate the rate (e.g., respiratory rate, heart rate, etc.) using one or more rate finding algorithms.

As described above, in various embodiments, the monitor can include a homodyne receiver. In various embodiments, the homodyne receiver is used for its simplicity and for its phase noise cancellation property. In various embodiments, to eliminate mirror imaging at baseband after down converting the RF signal, the system includes complex demodulation, which provides quadrature analog outputs. In various embodiments, to get a focused beam, a 2 by 2 arrayed patch antennas are used. In various other embodiments, smaller or larger array patch antennas or a single (non-array) patch antenna can be used. For example, to get a more focused beam, more antennas can be used in the array. In various other embodiments, other (non-patch) antenna configurations can be used. In various embodiments, the quadrature outputs can be anti-alias filtered and the DC signal can be removed with a high-pass filter. The filtered signal can be sampled with an analog to digital converter (ADC) and the digitized data is subsequently processed in the processor. In some embodiments, the physiological motion signal is analyzed to determine whether the signal has low quality due to noise, interference, and/or non-physiological motion. In some embodiments, the physiological motion signal is separated from noise, interference and/or non-physiological motion. Then the physiological motion signal is processed to determine respiratory waveform, and the respiratory rate. In some embodiments, the respiratory rate is extracted from the respiratory rate waveform.

Figure 17:
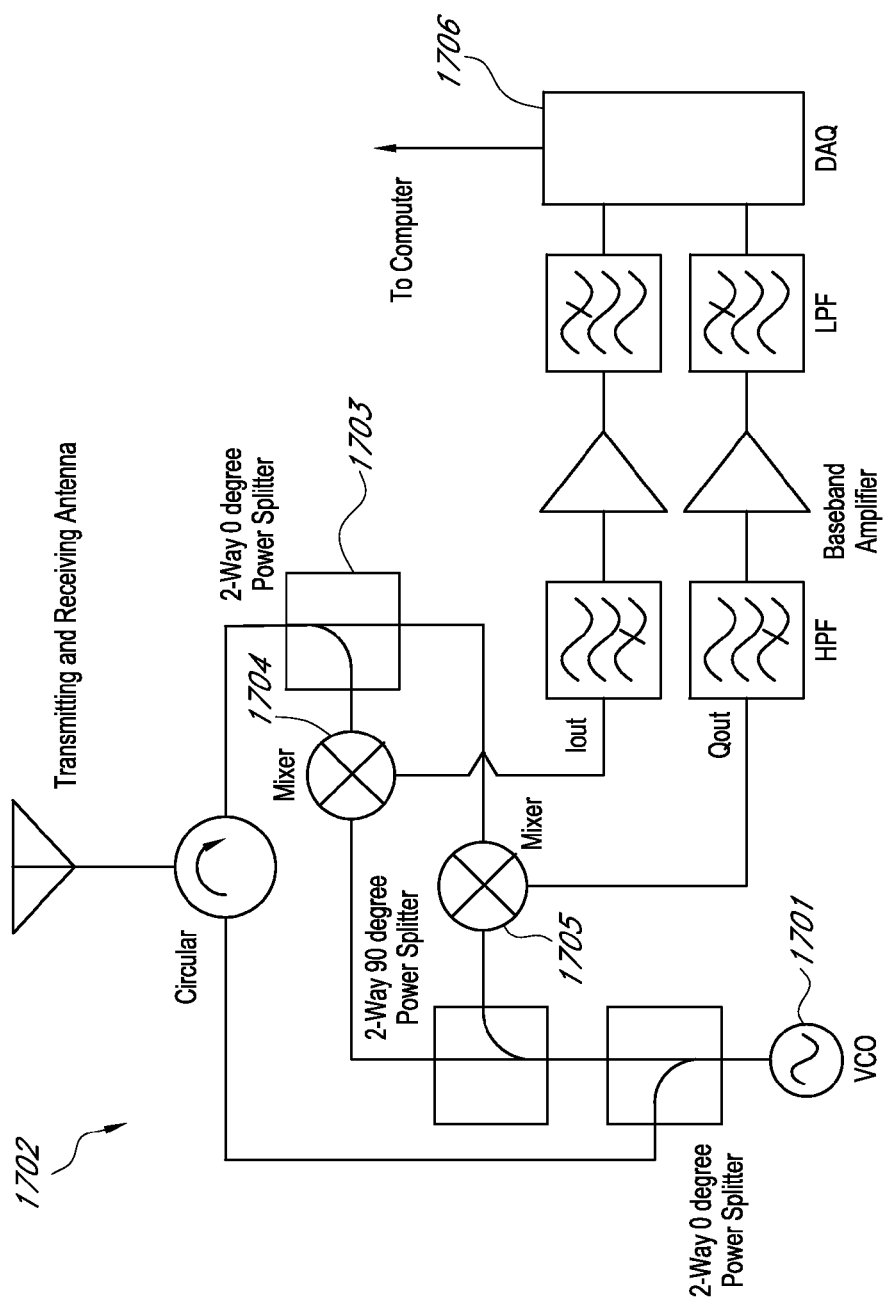
FIG. 17 illustrates an alternate embodiment of the radar-based physiological motion sensor system.

FIG. 17 illustrates an embodiment of the system 100 configured as respiratory rate spot check measurement device. The device illustrated in FIG. 17 includes a source of electromagnetic radiation 1701 (e.g., a voltage controlled oscillator) and a transceiver 1702. In some embodiments, the transceiver 1702 can include a single antenna to transmit and receive the signals. The signal received from said one or more objects that scatter radiation and have motion is directed to at least one mixer 1704 through a power splitter 1703. In some embodiments, the power splitter can be a 2-way 0 degree power splitter. In various embodiments, the signal from the source 1701 can be mixed with the received signal at the mixer. In various embodiments the system 100 can include two mixers (e.g., 1704 and 1705) that can output an in-phase and a quadrature-phase component. The signals output from the mixer can be conditioned and sampled by a data acquisition system (DAQ or DAS) 1706. In various embodiments, the signal can be conditioned to remove aliasing, for example by low-pass filtering. In various embodiments, the signal can be conditioned, for example, by high-pass filtering, low-pass filtering, DC-cancellation, amplifying, etc. The digital acquisition system 1706 can include multiplexers, analog-to-digital converter (ADC), digital-to-analog converter (DAC), timers, buffers, etc. The output of the digital acquisition system 1706 can be communicated to a computer or a processor for further signal processing. In some embodiments the computer or the processor can be in electronic communication with an output unit that is configured to perform an output action based on the information obtained after signal processing. For example, in some embodiments, the output unit can include a display unit configured to display. In some embodiments, the output unit can include a printer configured to print or an audible system configured to sound an alarm or and audible system configured to speak the respiratory read or a medical device (e.g., a defibrillator) configured to use the information or a home healthcare device configured to collect information from various medical devices and transmit the information to a central database or a health kiosk computer configured to transmit the information to a remote healthcare practitioner. In some embodiments, the computer or processor can be in electronic communication with an input unit that is configured to control system. In some embodiments, the input unit can be a start button or a health kiosk computer configured to allow a remote healthcare practitioner to initiate the measurement or a home healthcare device configured to initiate the measurement.

In various embodiments, the cardiopulmonary related motion of the body surface can be measured either from a distance or by contacting the body surface. In those embodiments, wherein the antenna is in contact with the body methods to isolate body surface reflections from internal reflections are used to enable measurement of the internal body motion. Various internal cardiopulmonary related changes can also be electromagnetically measured for surface and internal body parts and tissues, including impedance changes associated with heart beat.

Figure 18:
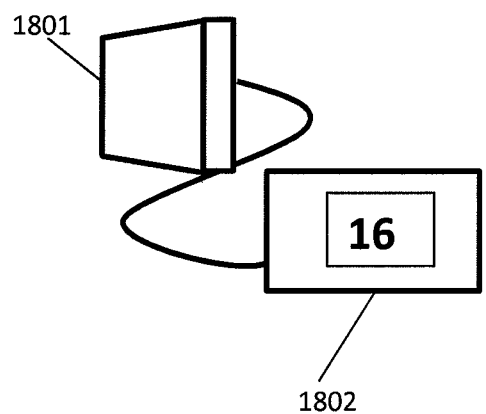
FIG. 18 illustrates an embodiment of the radar-based physiological motion sensor comprising a sensor unit, a computational unit and a display unit.

One embodiment of a respiration rate spot checker is illustrated in FIG. 18. The system includes a radar-based physiological sensor 1801 similar to the various embodiments described above, a computational unit, and a display unit. In various embodiments, the computational unit and the display unit can be housed together in single housing 1802 (e.g., a laptop, a handheld computer, a PDA, etc.). The sensor 1801 can communicate with the computation unit and/or the display unit wirelessly or over a wired connection using the various communication protocols discussed above. In various embodiments, the sensor 1801, the computation unit and the display unit can be housed together in a single housing. In certain embodiments, the sensor 1801 and the computational unit can be housed together in single unit and the display unit can be separate.

In various embodiments, the spot check monitor can be configured to operate when a start button is actuated. In various embodiments, the monitor can start measuring the physiological motion signal in the operational mode. In various embodiments, a user can select one of three modes: quick mode, extended mode, or continuous mode. Each of the three modes can require a different number of consecutive breaths without motion before providing a rate. For example, in the quick mode, approximately 2 consecutive breaths without motion can be required to calculate the rate, in the extended mode, approximately 6 consecutive breaths without motion can be required to calculate the rate while in the normal mode, approximately 3 consecutive breaths can be required to calculate the rate.

Figure 19:
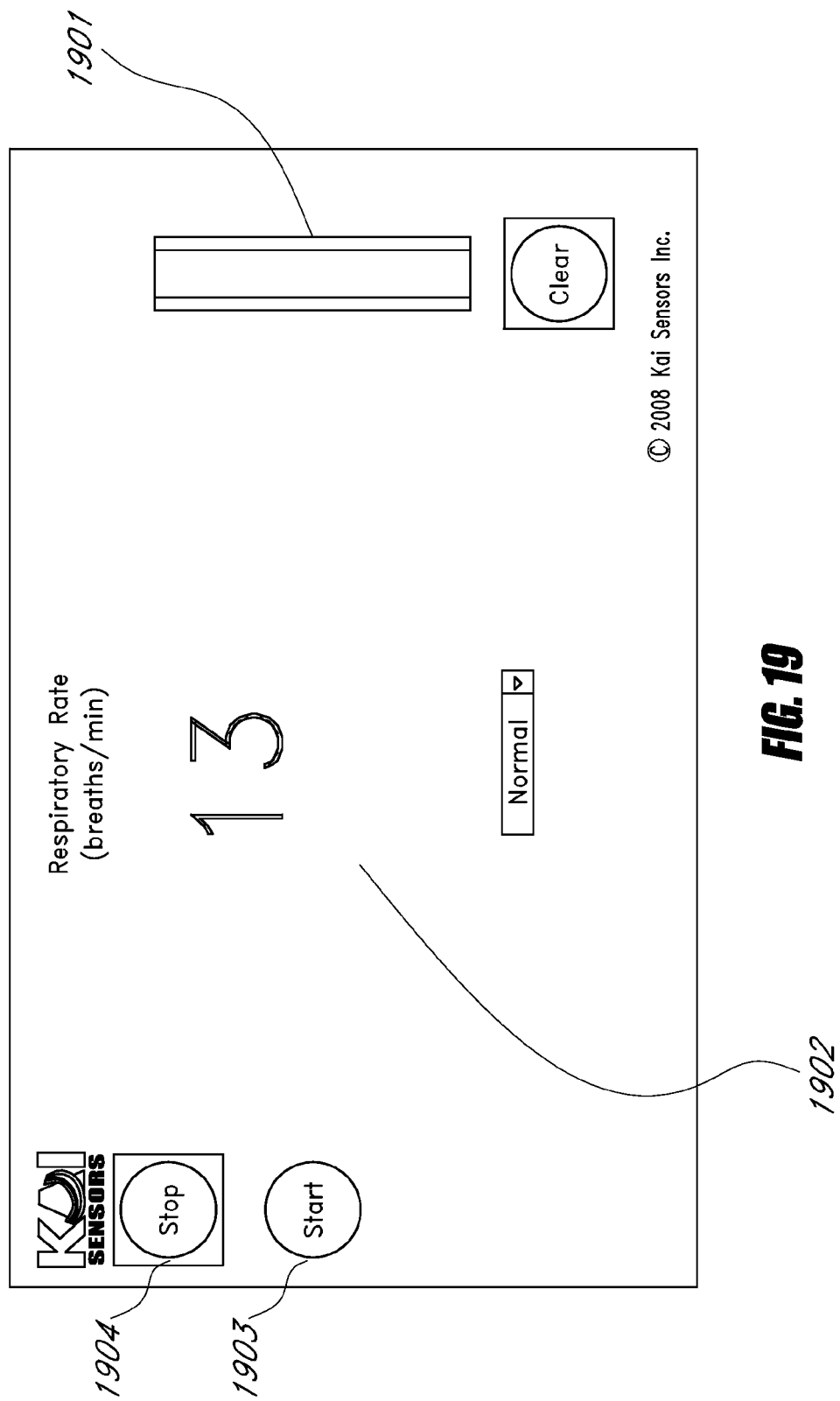
FIG. 19 illustrates an embodiment of an interface (e.g., a display screen) configured to output cardiopulmonary or cardiovascular related information.

FIG. 19 illustrates an embodiment of an interface (e.g., a display screen) configured to output cardiopulmonary or cardiovascular related information (e.g., respiration rate, respiratory waveform, heart rate, pulse rate, etc.). The embodiment illustrated in FIG. 19 is a screen shot of a display displaying the measured respiratory rate. In various embodiments, a signal processing unit (e.g., the computation unit of FIG. 18) can determine the peak inhalation points of the subject and count them over time using one or more algorithms. In various embodiments, the system 100 can buffer a respiration rate for every block of data. In various embodiments, if an interruption (e.g., interruption created due to non-cardiopulmonary motion or other signal interference) is detected during the reading, any respiration rate values stored in the buffer will be cleared and no values will be buffered until the interruption has ceased. Once the approximate required number of breaths is read consecutively, the device returns the median value recorded, to ensure that the reading is as accurate as possible. In some embodiments, the required number of breaths can be 3. In various embodiments, the required number of breaths can be 5, 10, 15, 20 or some other value in the range from 3-30. In various embodiments, the interface can have a status indicator 1901 configured to show a status. For example, the status indicator 1901 can be a bar which will grow as each consecutive breath is read. As soon as the required number of breaths is read, the status indicator can stop growing. The measured respiratory rate can be indicated in area 1902 of the display. In various embodiments, controls can be provided on the interface configured to control the system. For example, a start and a stop button 1903 and 1904 can be provided on the display interface illustrated in FIG. 19. In various embodiments, the measurement can be interrupted if the stop button is actuated, in which case no values can be returned.

In various embodiments of the system, the respiration rate can be determined by using a rate estimation algorithm which uses two processes, e.g., a time domain approach and/or a frequency domain approach to determine the respiration rate: a frequency domain estimate and a time domain estimate. A first advantage of employing two methods is that comparing the result of the two approaches can help to determine if breathing is regular. A second advantage is that the redundancy introduced by employing two algorithms can help in risk mitigation for inaccurate respiratory rates. In various embodiments, the time domain rate estimation uses the zero crossings with positive or negative slope in the signal to recognize a breath. The peak of the signal between two consecutive positive zero crossings or two consecutive zero crossings is compared against a threshold to determine if the two consecutive zero crossings actually include a breath. In some embodiments, the positive zero crossings will be used, and if there are not enough breaths for a rate to be calculated, the negative zero crossings will be used. Additionally, a Fourier transform is computed on all the samples to provide the signal spectrum. In various embodiments, the frequency domain estimate of the rate can be the largest magnitude frequency component in the signal. The time domain and the frequency domain rate estimates can be compared. In various embodiments, the difference between the two results can indicate the degree to which the signal does not fit the assumptions of either the time or frequency domain approaches. For example, a difference of 0 can indicate a perfect match between the time domain and the frequency domain approach. In various embodiments, the frequency domain calculation can serve as a cross check to the measurement obtained from the time domain approach or vice versa. In various embodiments, the two rates can serve as a cross check for accuracy. A mismatch between the frequency domain and time domain calculations can also indicate possible irregular breathing. Various embodiments of the device can require a low variability in the respiratory rate to provide a measurement or a reading to ensure that measurement or readings provided are accurate. In some embodiments, the system could display or otherwise communicate an indication of level of variability of the measured rate, i.e., how much the rate varied during the measurement interval. The variation in the measured rate can be used in medical analysis by the health care professional.

Figure 20:
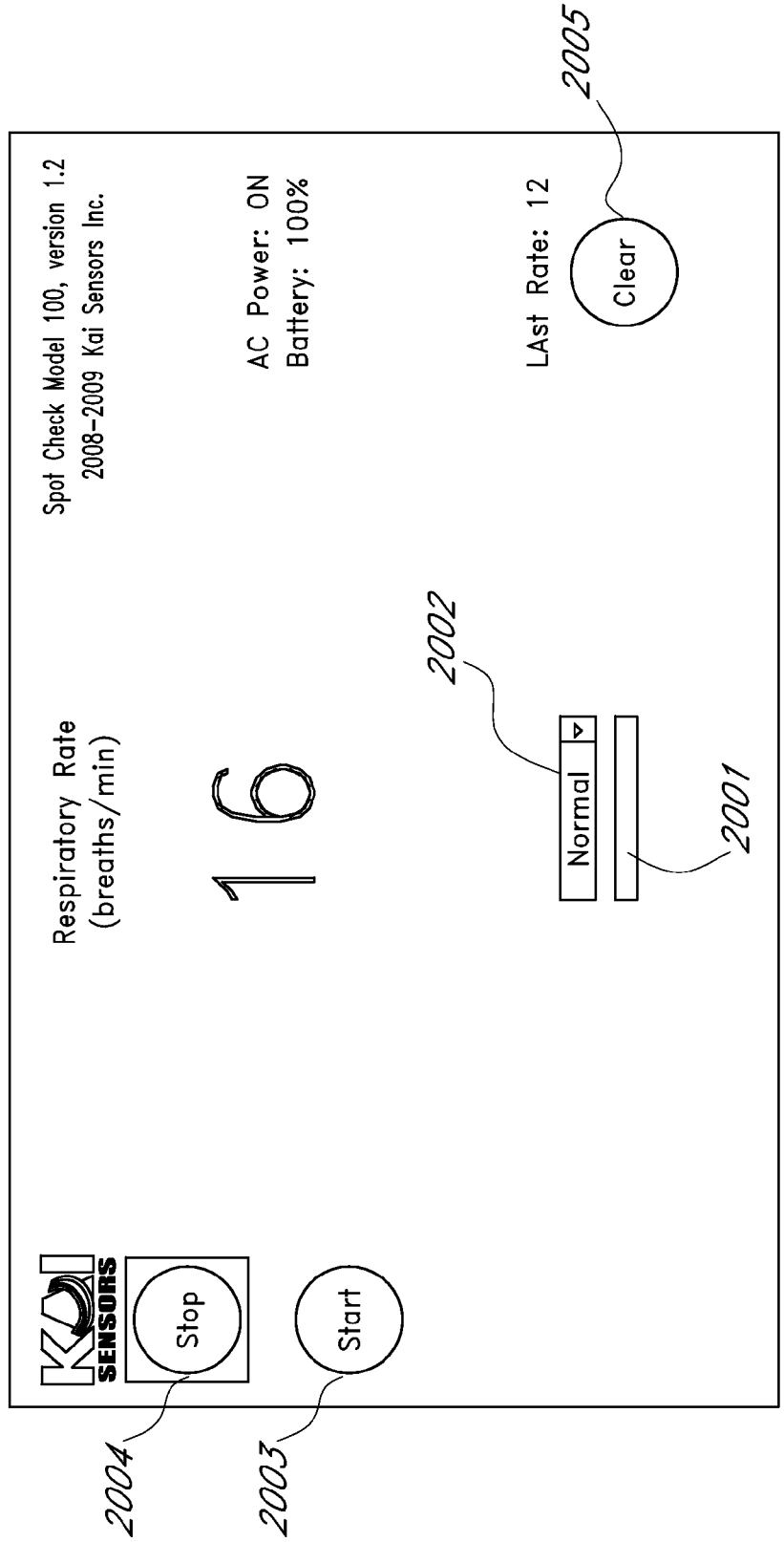
FIG. 20 illustrates a screen shot of a display device showing a respirator rate.

FIG. 20 illustrates a screen shot of a display device. The display device is in communication with a system 100 that uses both time domain approach and frequency domain approach to calculate the respiration rate as discussed above. The system 100 can be configured to perform the measurement over a fixed period in a range between approximately 15 seconds to approximately 1 minute. For example, in some embodiments, in the quick mode the system 100 can perform a measurement over a 15 second time interval, in the normal mode, the system 100 can perform a measurement over a 30 second time interval and in the extended mode, the system 100 can perform a measurement over a 60 second time interval. These time intervals correspond to intervals commonly used by healthcare practitioners when counting respiratory excursions to estimate respiratory rate. In other embodiments, the time intervals for the three modes can be different. A status indicator 2001 can indicate the time that has passed during the measurement and the time that remains for the measurement. In some embodiments, the display can also have a control button 2002 that can allow a user to choose a mode of operation (e.g., quick, normal or extended). Other controls such as a start button 2003 and a stop button 2004 can also be provided on the display to control the system. In some embodiments, the display can also provide a status indication of the system. For example, in FIG. 20, the display indicates the status of the power source and the battery power for the computation unit. In some embodiments, the previously measured rate can also be displayed. In some embodiments a clear button 2005 can also be include to remove the displayed respiratory rates from the screen. In various embodiments errors in estimating a respiration rate for example due to the presence of non-cardiopulmonary motion or other signal interference can also be displayed on the display device.

Figure 21:
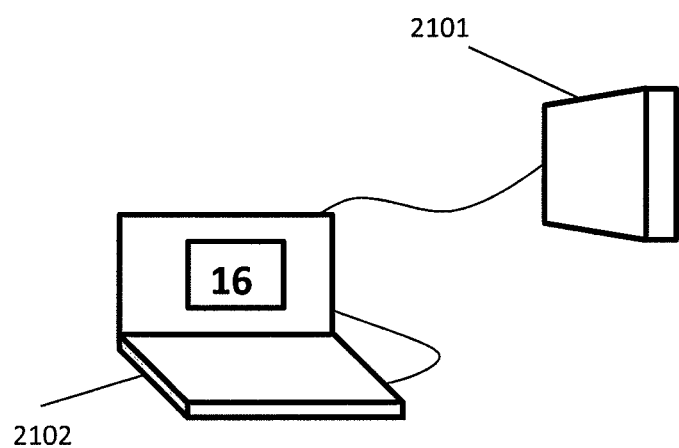
FIG. 21 illustrates an alternate embodiment of the radar-based physiological motion sensor comprising a sensor unit, a computational unit and a display unit.

FIG. 21 illustrates another embodiment of a system 100 including a sensor 2101, a computational unit and a display unit housed in a single housing 2102.

In various embodiments, the rate-estimation algorithm, described above, operates on all the data obtained during the measurement interval. In various embodiments, the rate-estimation algorithm can detect a non-respiratory signal (e.g., non-cardiopulmonary signal or other signal interference) and use this information to identify the signal quality. Samples of data having low signal quality can be rejected. For example, samples having an excursion larger than the subject's maximum breath can result from non-cardiopulmonary motion or other signal interference and thus can be rejected. In some embodiments, samples exhibiting a significant increase in signal power can also result from non-cardiopulmonary motion and thus can be rejected. In some embodiments, the non-cardiopulmonary motion detection algorithm described above can be used to detect non-respiratory signals or other signal interference. In various embodiments, additional inputs to signal quality indication can include low signal power, signal clipping due to high signal power, and low estimated signal to noise ratio. In various embodiments, the values that are rejected due to low signal quality can be set to zero before proceeding with rate estimation.

As discussed above, in various embodiments, the time domain rate estimation uses the zero crossings with positive or negative slope in the signal to recognize a breath. The peak of the signal between two consecutive positive zero crossings or two consecutive zero crossings is compared against a threshold to determine if the two consecutive zero crossings actually include a breath. In some embodiments, the positive zero crossings will be used, and if there are not enough breaths for a rate to be calculated, the negative zero crossings will be used. Additionally, a Fourier transform is computed on all the samples to provide the signal spectrum. In various embodiments, the frequency domain estimate of the rate can be the largest magnitude frequency component in the signal. The time domain and the frequency domain rate estimates can be compared and the accuracy of the estimated rate can be determined.

In various embodiments of the system (e.g., a system using a 2.4-GHz ISM band) using linear demodulation algorithm to demodulate the sample, significant changes to the best-fit vector or eigenvector on which the signals are projected can indicate a new relationship between the antenna and the subject, which can indicate the presence of non-cardiopulmonary motion or signal interference. When linear demodulation is used, a change in the ratio of the eigenvalues, or of the RMS error of the fit to the best-fit line, can also indicate that the detected motion does not fit the line well consequently indicating non-cardiopulmonary motion or other signal interference.

The various embodiments of the respiratory rate spot check measurement device described above can be adapted to be used in a health kiosk. The spot check measurement device described with reference to FIGS. 17-21 can be in communication with one or more master control systems such that the spot check monitor can be controlled by one or more master control systems. Various embodiments of the system initiate a measurement by at least one of a local operator by pressing a button on the device, remote activation by a healthcare practitioner, automatic initiation when the presence of the patient in the kiosk is sensed. Various embodiments of the device can sense the presence of a patient in the kiosk and communicate that information to the kiosk computer. Various embodiments of the device can take an input from another sensor, communicated through the kiosk computer that indicates the presence of the patient in the kiosk. Various embodiments of the system 100 can communicate with the one or more master control systems using any standard or proprietary communication protocol, or any combination thereof. Such protocols can include any communication technology, which can or cannot be included in TCP/IP or OSI network layers, including, but not limited to, serial, USB, Bluetooth, Zigbee, Wi-Fi, Cellular, WiMAX, Ethernet, and SOAP. For example, Ethernet can be used as the link layer protocol while TCP/IP is used for routing, and SOAP is used as an Application layer protocol. On the other hand, only TCP/IP over Ethernet can be used, without additional packaging at the Application level. In the later case, data collected from the radar system 100 can be formatted and directly packaged as TCP payload. This can include timestamp for when the data was collected, the data, and an indicator for the quality of the data. This data is attached with a TCP header and then becomes the IP payload. The IP header (addresses) is attached to the payload and then is encapsulated by Link layer headers and footers. Finally, physical layer header and footers are added and the packet is sent via the Ethernet connection. To access data from the connection, the client should have a program to listen to a specified port on their Ethernet connection where the packets are being sent. Various embodiments of the system 100 can comply with the Continua Health Alliance medical device communications guidelines, including control and communication via USB or Bluetooth.

An example configuration of system 100 can include spot check monitor configured in various embodiments as a single piece or a two piece system and adapted to operate at a radio frequency of approximately 5.8 GHz. Various embodiments of the system 100 can include DC-cancellation circuit to reduce the delay between the motion signal and the electronic indication of the motion. In various embodiments, DC-cancellation can enable faster synchronization between the motion sensor and the output device (e.g., a display or an imaging system). DC cancellation or low-IF at 5.8 GHz can make arc demodulation relatively more accurate. DC cancellation typically improves the synchronization time, which can be important for integration with an imaging system or a ventilator.

In embodiments using radio frequency in the 5.8 GHz range, the phase deviation due to the chest motion associated with cardiopulmonary activity can increase by more than two times when compared to embodiments using radio frequency in the 2.4 GHz range. In various embodiments, this phenomenon can result in non-linear baseband output such that the complex constellation more closely approximates an arc rather than a line. In these embodiments, arc-based demodulation algorithms can be preferred over other demodulation algorithms. In various embodiments, arc-based demodulation algorithms can provide results having greater accuracy by appropriately resolving this non-linear effect. In various embodiments, DC cancellation can be preferred over an AC coupled filter as DC cancellation can reduce signal distortion. In embodiments without DC cancellation, the origin of the circle where signal samples are scattered cannot be determined with sufficient accuracy.

When arctangent demodulation is used, significant changes in the location of the origin, or changes in the radius of the circle of the arc is on, or changes in the position of the arc on the circle can indicate a change in the relationship between the antenna and subject, which can indicate the presence of non-cardiopulmonary motion or other signal interference. In some embodiments, a change in the relationship between the subject and the antenna can be detected if the calculated inner product of the normalized current vector and the normalized previous vector is below a threshold. In a system where arctangent demodulation is used, a change in the RMS error of the fit to the best-fit arc can also indicate non-cardiopulmonary motion or other signal interference.

An example configuration of system 100 can include a continuous physiological monitor configured to operate in the frequency range of approximately 2.4 GHz and further configured as a two piece system. The continuous physiological monitor is configured to provide vital signs information and/or physiological waveforms over extended periods of time and not just periodic snapshots. Various embodiments of the continuous vital signs monitor can be configurable to operate in a spot check or a continuous mode. Various embodiments of the monitor can be configured to monitor at least one of the heart waveforms and variables and respiratory waveforms and variables. Various embodiments of the monitor can include a single antenna or an antenna array combined to operate as a single antenna, a direct-conversion or homodyne receiver and a high-pass filter. In various embodiments, multiple antennas can be used. Various embodiments of the monitor can include other electronic components such as filters, amplifiers, multiplexers, etc. In various embodiments, the system 100 can include a processor configured to execute the eigenvector-based linear demodulation algorithm or an arc-based demodulation algorithm other algorithm described above. In some embodiments, the system 100 can be configured to determine the heart rate and/or the respiratory rate.

Figure 22:
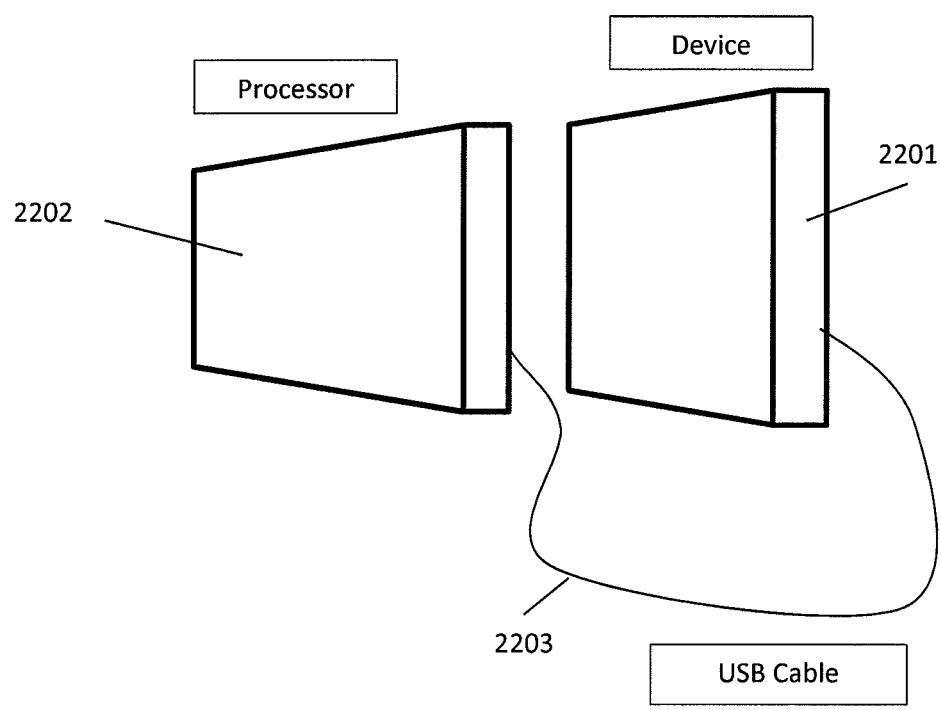
FIG. 22 illustrates an alternate embodiment of the radar-based physiological motion sensor comprising a sensor unit and a processor.

The system illustrated in FIG. 17 can be adapted to operate as a continuous vital signs monitor. The system illustrated in FIG. 17 is a continuous-wave radar transceiver with a homodyne receiver. One advantage of this configuration is the simplicity of the system. Another advantage of the system is its ability to cancel or reduce phase noise. In various embodiments, the transceiver 1702 can operate in the 2.4 GHz-2.5 GHz or the 5.8 GHz ISM band. In various embodiments, the transceiver can operate in a frequency range outside this band. In various embodiments, the source 1701 can be configured to generate both the transmitted signal and the local oscillator signal for the receiver. Such a configuration can be referred to as an internal voltage-controlled oscillator. In various embodiments, the oscillator can be free-running, phase-locked to a crystal, or phase-locked to an external reference. In other embodiments, the local oscillator can be generated externally to the rest of the circuit. In various embodiments, complex demodulation can be used to generate quadrature outputs. An advantage of this technique can be the elimination of mirror imaging at baseband after down converting the RF signal. In various embodiments, another advantage of this technique is the ability to use linear or nonlinear complex demodulation algorithms to avoid phase demodulation nulls that can plague single-mixer receivers used for this application. In some embodiments, the quadrature outputs can be amplified and anti-alias filtered before analog-to-digital conversion. To improve the dynamic range, in various embodiments, the DC offset can be removed with a high-pass filter, and variable gain amplifiers (VGAs) can be provided to ensure that the full input range of the ADC is utilized. In various embodiments, the VGAs can be controlled by digital control signals. In various embodiments, the gain levels of the VGA can be determined either by the user or dynamically by the processor through signal analysis. In various embodiments, DC-cancellation can be used instead of a high-pass filter. In various embodiments, after the signal is sampled by the analog to digital converter (ADC), it can transmitted over a wired or wireless communication link (e.g., Bluetooth, USB, etc.) to a processor that performs signal processing. In various embodiments, the processor can include a digital signal processor, a microprocessor or a computer. In various embodiments, the processor can be on the same board as the ADC, on a separate board, or in a separate unit. In various embodiments, the processor can use a linear demodulation algorithm to generate the combined physiological motion waveform. In various embodiments, the processor can use digital filters to further isolate respiration and heart signals from the combined physiological motion signal. In various embodiments, the respiration and heart signal can be isolated using with fixed digital filters. The signal processing algorithm can also determine a signal-quality parameter, including whether the signal has very low power (below 0.0001-0.0004 W) or very high power (above 5 to 10 W). In various embodiments, the algorithm can also determine if there is non-physiological motion. In various embodiments, the processor can stream data on a frame-by-frame basis over Ethernet using TCP/IP. In other embodiments, the processor can stream data with a protocol compliant with the Continua Health Alliance guidelines. In other embodiments the processor can stream data with a proprietary protocol. In various embodiments, each packet will contain a time stamp of when the data was taken, and at least one of the combined physiological waveform (heart and respiration before they are separated), respiration waveform, and heart waveform, respiration rate, heart rate, and signal-quality parameter. FIG. 22 illustrates an embodiment of a continuous wave monitor 2201 described above in communication with a processor 2202. As illustrated, in this embodiment, the continuous monitor 2201 communicates with the processor 2202 over a wired USB link 2203.

Figure 23:
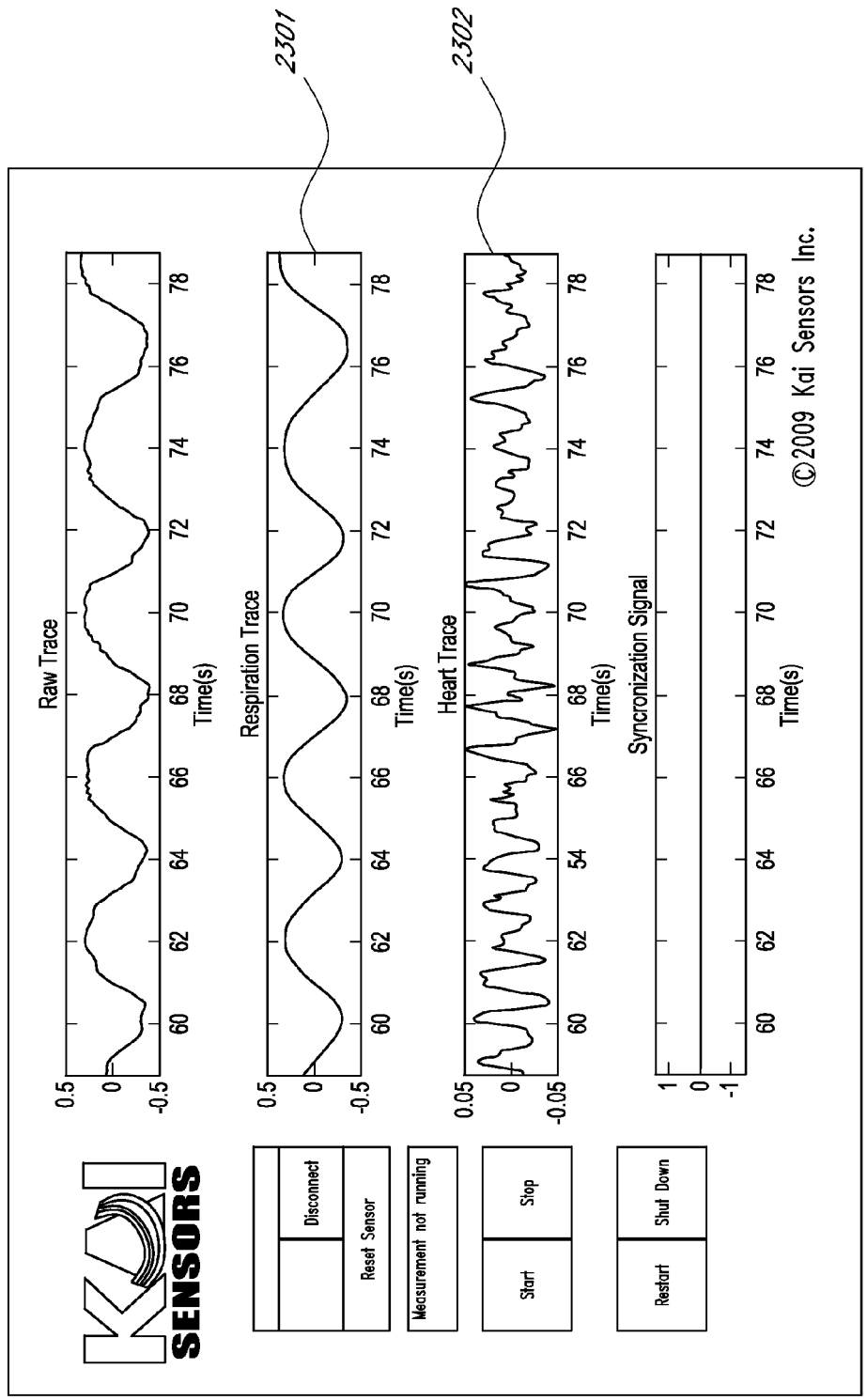
FIG. 23 shows a screen shot of an embodiment of a display device configured to display the respiration signal and the heart signal in addition to other information.

FIG. 23 shows a screen shot of an embodiment of a display device which displays the respiration signal and the heart signal in addition to other information to a user located locally or at a remote location. Plot 2301 shows the respiration trace obtained by the monitor 2301 while plot 2302 shows the heart trace obtained by the monitor 2301.

An example configuration of the system 100 can include a continuous physiological monitor including one or more antennas configured to operate in a radio frequency range of 2.4-2.5 GHz, a direct-conversion or a homodyne receiver and an anti-aliasing filter. Various embodiments include either a high-pass filter or a DC-cancellation circuit. In various embodiments, the system 100 can include a processor configured to execute a linear demodulation algorithm. In some embodiments, the processor can also be configured to execute the non-cardiopulmonary motion detection algorithm and/or a rate estimation algorithm. In some embodiments, multiple receive antennas and multiple receivers will be used such that the DOA algorithm described can be executed by the processor for separation and/or tracking purposes. In various embodiments, the rate estimation algorithm described above can be used herein to estimate the rate of respiration or cardiac activity. For example, in various embodiments, a frequency domain rate estimation algorithm, a time domain rate estimation algorithm, a peak detection algorithm or a combination of these can be used. In various embodiments, the accuracy of the determined respiration or cardiac activity can be improved by employing the methods listed above as disclosed in U.S. Provisional App. No. 61/204,881 which is incorporated herein by reference in its entirety. In some embodiments, the rate estimation algorithm can be performed periodically (e.g., every 10 seconds, every 20 seconds, every 30 seconds, etc.).

Figure 24:
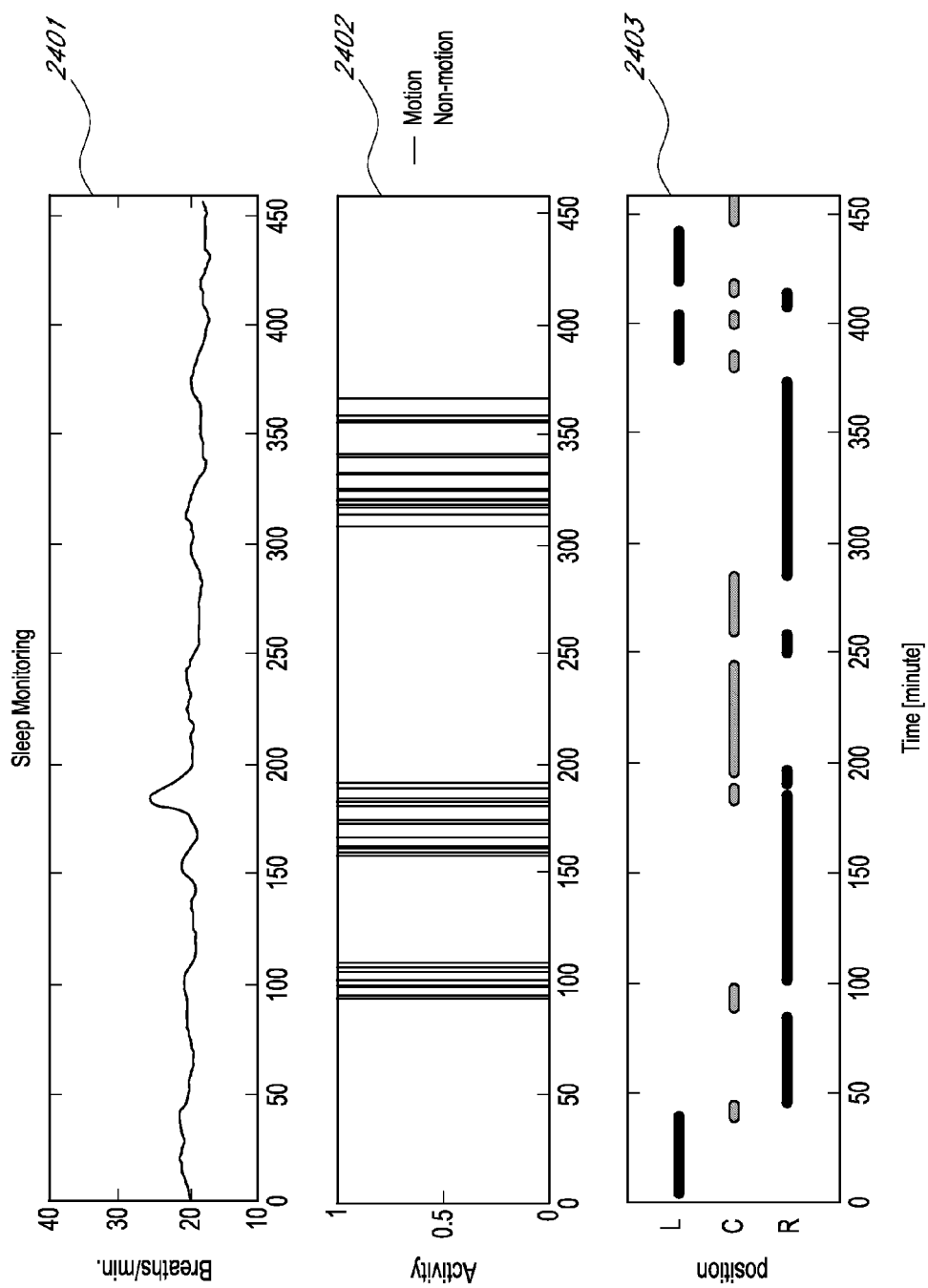
FIG. 24 is a screen shot of a display device or unit illustrating the respiratory rate, activity indicator and position of a sleeping subject.

In various embodiments, the continuous physiological monitor can include an activity monitor configured to provide an indication when and for how long the target subject performs a non-respiratory movement. In some embodiments, the activity monitor can be configured to provide an activity index that can provide an indication of the frequency and duration of motion over a measurement period. In various embodiments, provided with multiple antennas, DOA processing can enable determination of a subject's position and the frequency with which the subject changes position. For example, it is possible to determine whether the subject is rolling to the left, rolling to the right, or moving without changing position. FIG. 24 is a screen shot of a display device or unit illustrating the respiratory rate, activity indicator and position of a sleeping subject. Plot 2401 illustrates the breaths/minute as a function of time for the subject. Plot 2402 illustrates activity of the sleeping subject while plot 2403 shows the position of the subject while sleeping.

Figure 25A:
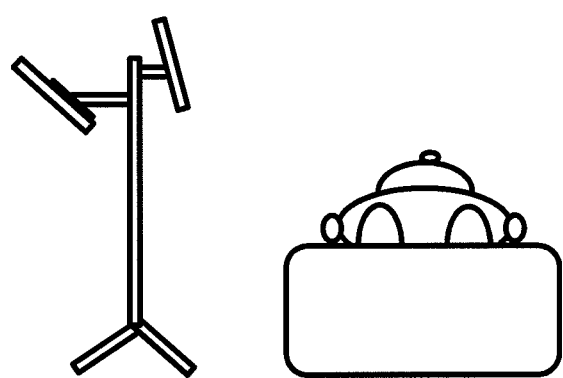
FIG. 25A shows the application of the system in a hospital environment to measure the respiratory and/or cardiac activity of a patient.
Figure 25B:
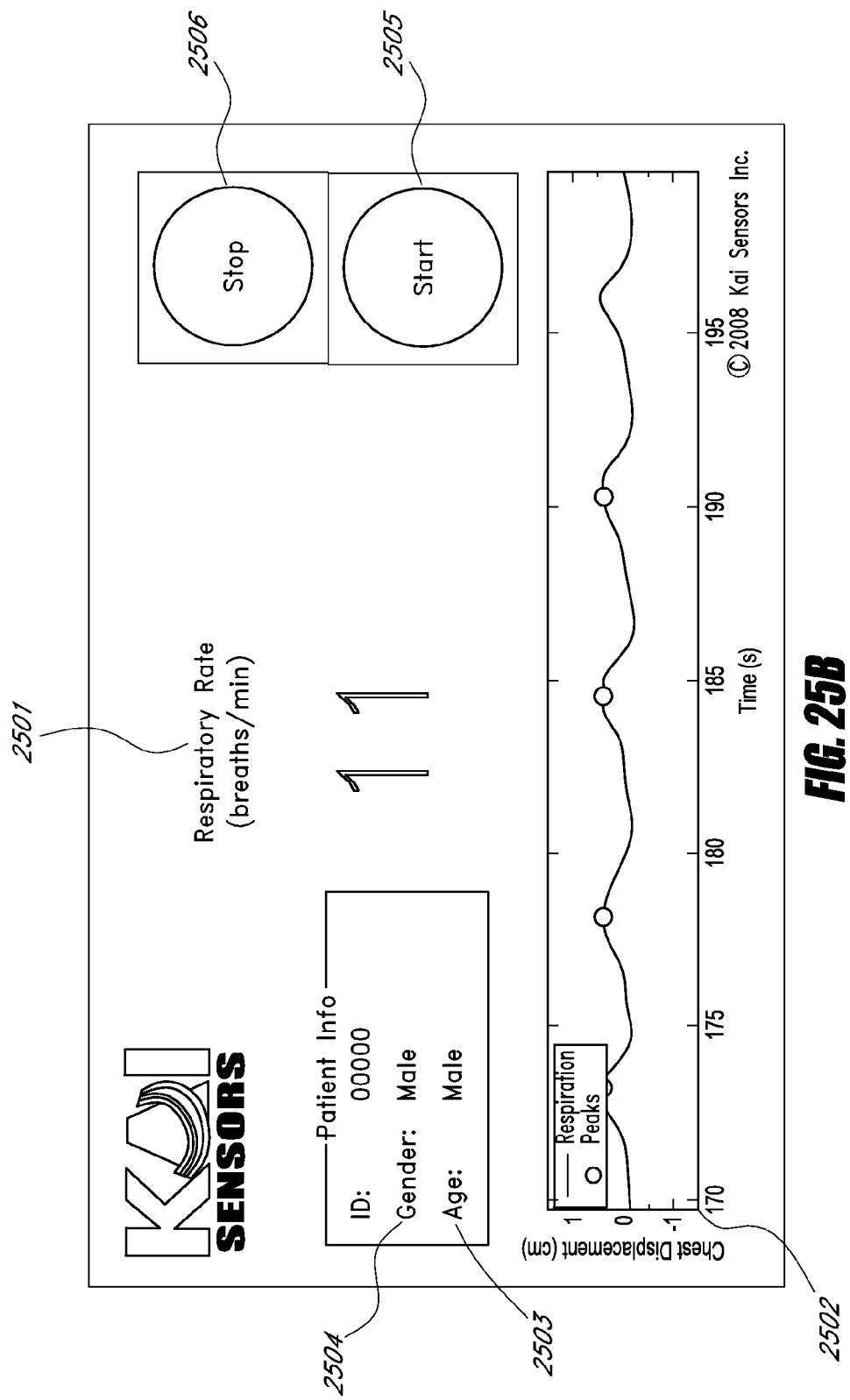
FIG. 25B is a screenshot of the display device illustrated in FIG. 25A.
Figure 26A:
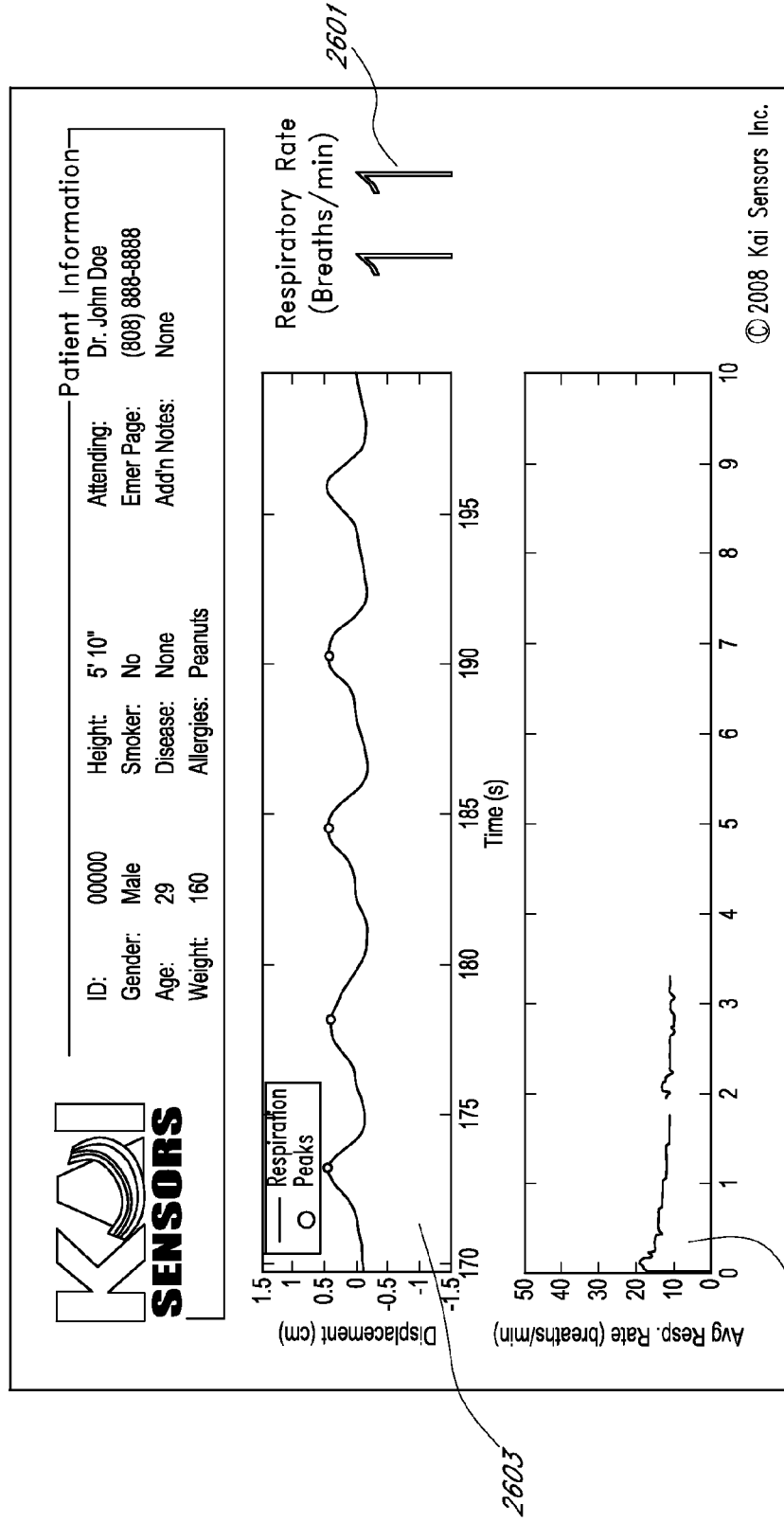
FIGS. 26A and 26B illustrate screen shots of a display device that can be used for viewing the vital signs provided by the device
Figure 26B:
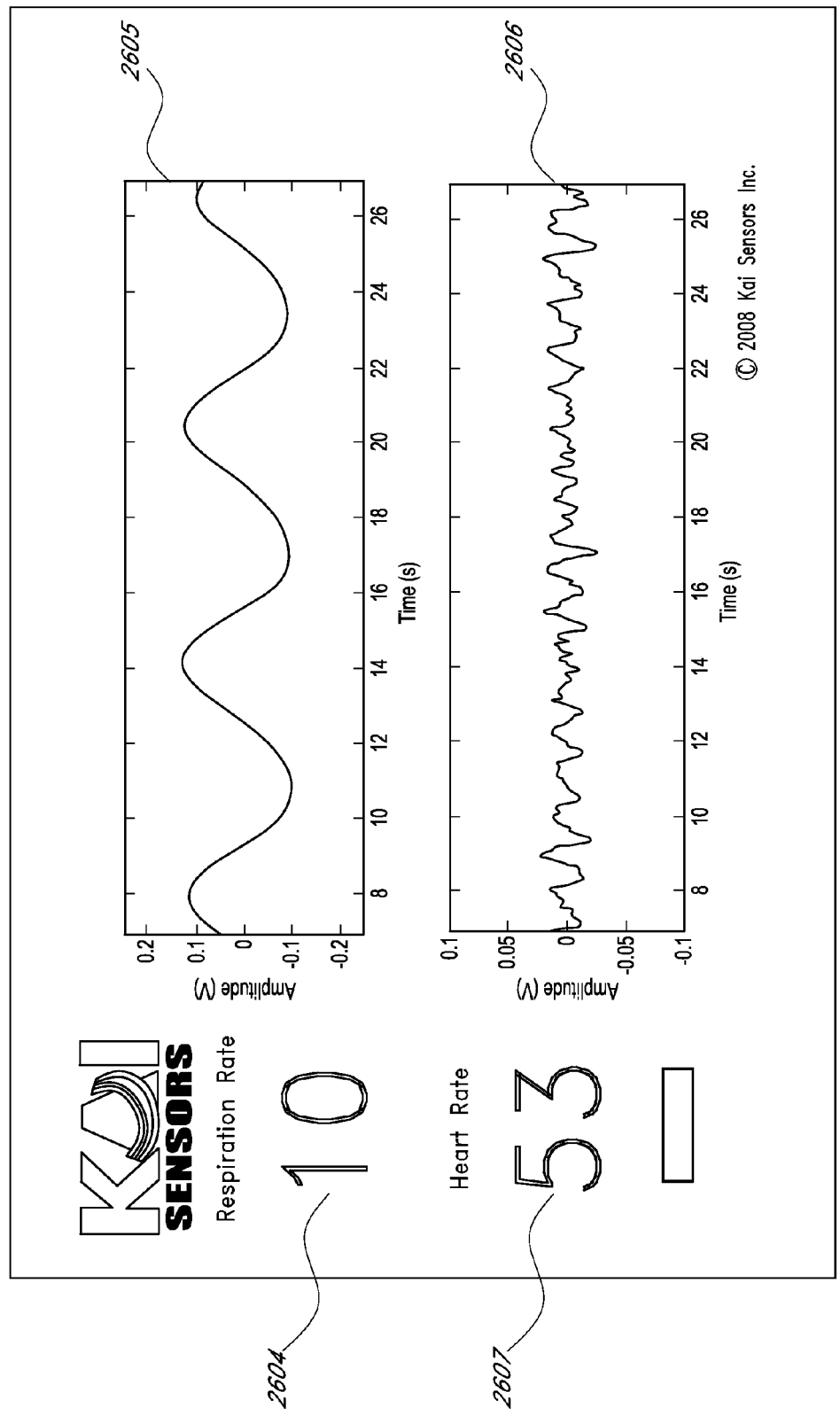

In various embodiments, the vital signs information (e.g., respiration rate or heart rate) can be buffered and plotted to provide historical data for the subject. FIG. 25A shows the application of the system in a hospital environment to measure the respiratory and/or cardiac activity of a patient. FIG. 25B is a screenshot of the display device illustrated in FIG. 25A. In some embodiments, the display device can display the respiratory or respiration rate 2501 and a waveform indicative of the respiratory activity 2502 (e.g., displacement of the chest over time). The display device can provide additional information related to the patient 2503 and 2504 (e.g., age, gender, etc.). The display device can also include a start and a stop button 2505 and 2506. In various embodiments, the display device can be a part of a device operated by health care professionals. FIGS. 26A and 26B illustrate screen shots of a display device that can be used for viewing the vital signs provided by the device. FIG. 26A shows an embodiment of a display device that displays a respiration rate 2601, average respiration rate over time 2602 and waveforms related to respiratory activity 2603 (e.g., chest displacement). FIG. 26B shows an embodiment of a display device that displays a respiration rate 2604, waveforms indicative of respiration activity 2605 and cardiac activity 2606 and a heart rate 2607.

An example system configuration includes a system configured to detect paradoxical breathing. The system includes a single antenna configured to operate in the radio frequency range of approximately 2.4 GHz, a direct conversion or homodyne receiver, and a DC-cancellation circuit. In various embodiments, the system can be configured to detect paradoxical breathing. In some embodiments, the system 100 can also include algorithms to estimate the rate of a respiratory activity or cardiac activity.

In various embodiments, the system 100 can include a continuous-wave radar transceiver with a direct conversion or homodyne receiver as described above with reference to FIGS. 17, 18, 19 and 20. As discussed above, advantages of this approach are the simplicity of the system and the ability to cancel or reduce phase noise. In various embodiments, the transceiver operates in a frequency range including, but not limited to, the 2.4 GHz-2.5 GHz ISM band. As discussed above, in various embodiments, a single signal source can be used to generate both the transmitted signal and the local oscillator signal for the receiver (e.g., source 1701 of FIG. 17). In various embodiments, the homodyne receiver can generate quadrature outputs using complex demodulation. In various embodiments, the quadrature outputs are amplified and anti-alias filtered before being input to a system configured to convert analog signals to digital signals.

Figure 27:
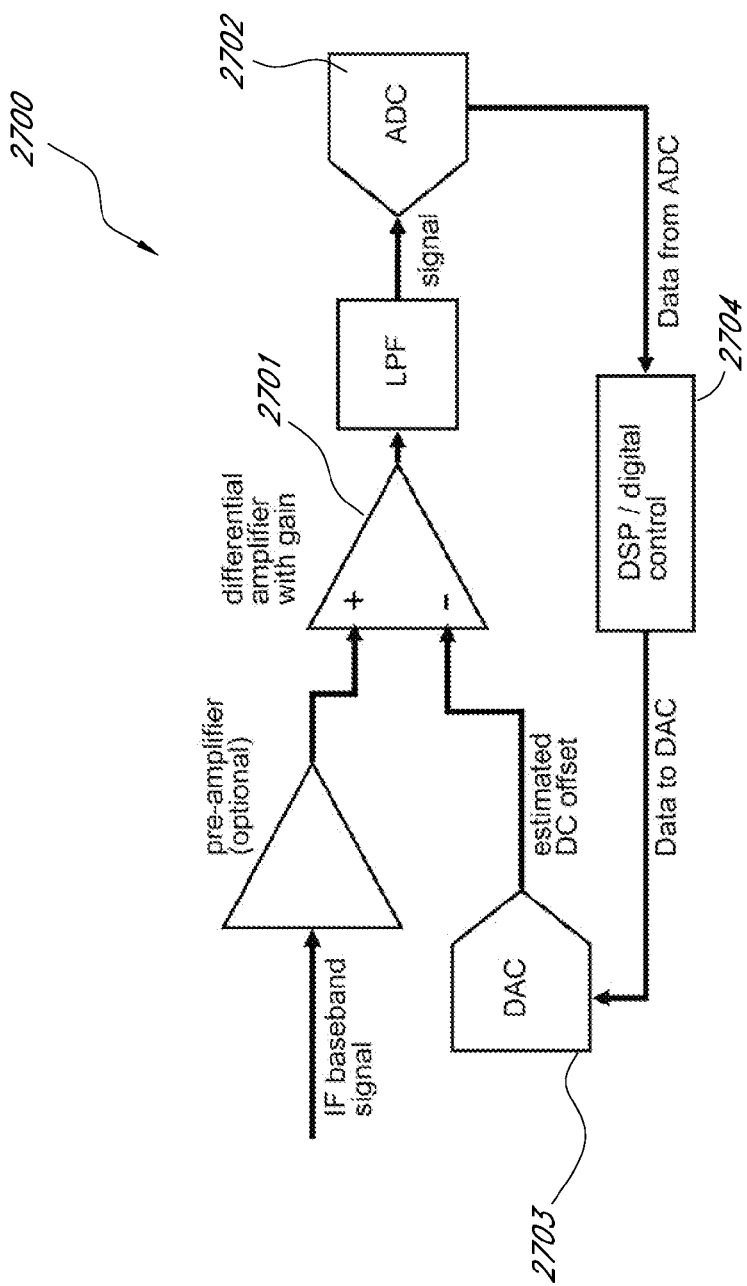
FIG. 27 illustrates an embodiment of a DC-cancellation circuit.

In various embodiments, to improve the dynamic range, the DC offset can be removed or reduced. In various embodiments, a conventional method of using an AC-coupling filter can be used to reduce or remove the DC offset. However, using an AC-coupled filter or a high-pass filtering can remove not only the DC offset itself but can also suppress low frequency components of the signal as well as distort their phase. Consequently, this causes an exponential attenuation of the static signal which is not DC offset, or distorts the phase of the signal. Additionally, a system having AC-coupling can generate or increase the group delay of the filtered signals, which causes a long settling time or a delayed version of the signal. These effects can result in the signal sample being distributed in a ribbon shape rather than an arc in the complex constellation. This distortion can adversely make the paradoxical breathing detection algorithm inaccurate. Some or all of these defects can be eliminated by using a DC cancellation circuit 2700, illustrated in FIG. 27, which is configured to subtract only DC value from the signals without distorting or adversely affecting the rest of the signal components. The DC cancellation circuit 2700 comprises a differential amplifier with gain 2701, an analog-to-digital converter 2702, a digital-to-analog converter 2703 and a DSP/digital control 2704. In various embodiments, the DC cancellation circuit can remove or reduce the DC offset by using feedback loops between ADC and DAC or voltage divider with digital potentiometer. Due to very small phase distortion, settling time, and group delay, systems including DC cancellation can be used to synchronize cardiopulmonary motion or other motion to imaging (e.g., CT scans or MRI) and to synchronize spontaneous respiratory effort to non-invasive or invasive assistive ventilation. The improved phase distortion and settling time also makes it easier to synchronize cardiopulmonary motion to questions asked and other sensors in polygraphs, to stimuli and other sensors for security screening, and for biofeedback applications, as disclosed in U.S. Provisional App. No. 61/204,881 which is incorporated herein by reference in its entirety.

In various embodiments, the system 100 can be configured to include an antenna array that can be used for transmitting and receiving radar signals. In some embodiments, a single antenna can be used for transmitting the radar signal, and an array of antennas can be used for receiving radar signals. The receiver can be configured as a homodyne receiver which is configured to generate quadrature outputs using complex demodulation algorithms. An advantage of this technique as discussed above is elimination of mirror imaging at baseband after down converting the RF signal. In various embodiments, the quadrature outputs are anti-alias filtered and the DC signal is removed or reduced with a DC-cancellation system similar to the one discussed above. The filtered signal is sampled by an analog to digital converter (ADC) and the digital data is processed to isolate physiological motion from noise, interference, and non-physiological motion. The physiological motion signal can be processed to extract the waveforms and parameter(s) of interest.

Figure 28:
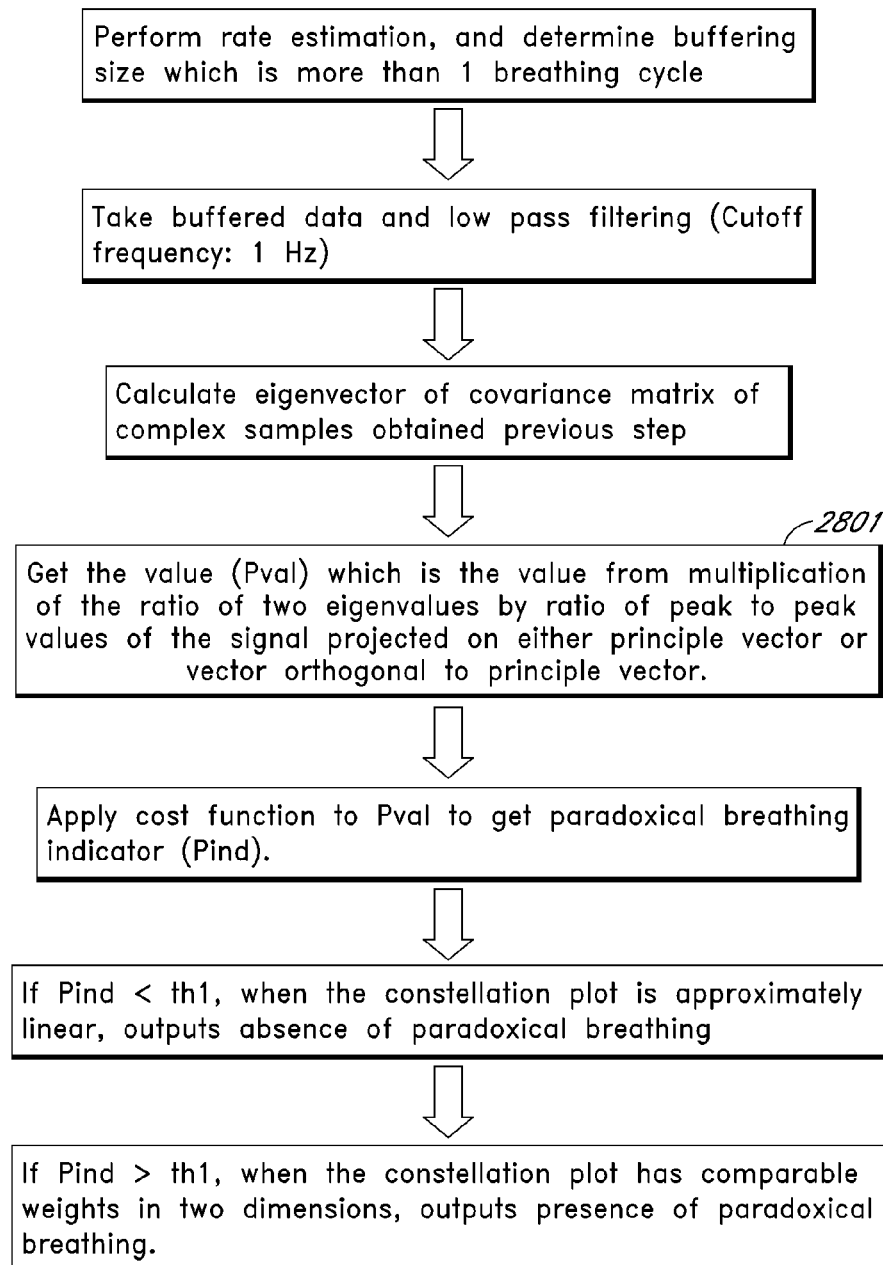
FIG. 28 illustrates an embodiment of a method to determine a paradoxical breathing indicator.

As discussed above, in various embodiments, the system 100 can be configured to detect the presence of or the degree of paradoxical breathing, which is a signature of obstructed breathing, respiratory muscle weakness, or respiratory failure. The system (e.g., a continuous monitor, quadrature continuous-wave Doppler radar system) can monitor the degree of paradoxical breathing based on analysis of the shape of the complex constellation and/or the trace of the plot of the in-phase (I) vs. quadrature (Q) signals from the quadrature radar receiver. An embodiment of a method to determine a paradoxical breathing indicator is illustrated in FIG. 28 and includes 1. The paradoxical factor can be estimated by multiplying the ratio of the biggest eigenvalue to the second biggest eigenvalue by the ratio of the maximum peak-to-peak value of the signal projected on the principal eigenvector to the maximum peak to peak value of the signal projected on the vector orthogonal to the principal vector, as illustrated in block 2801.
2. The paradox index can be calculated as a cost function performed on the paradoxical factor.
3. If the paradox index is compared with one or more thresholds, it can be interpreted as the absence or presence of paradoxical breathing or the degree of asynchronous respiration.

Figure 29:
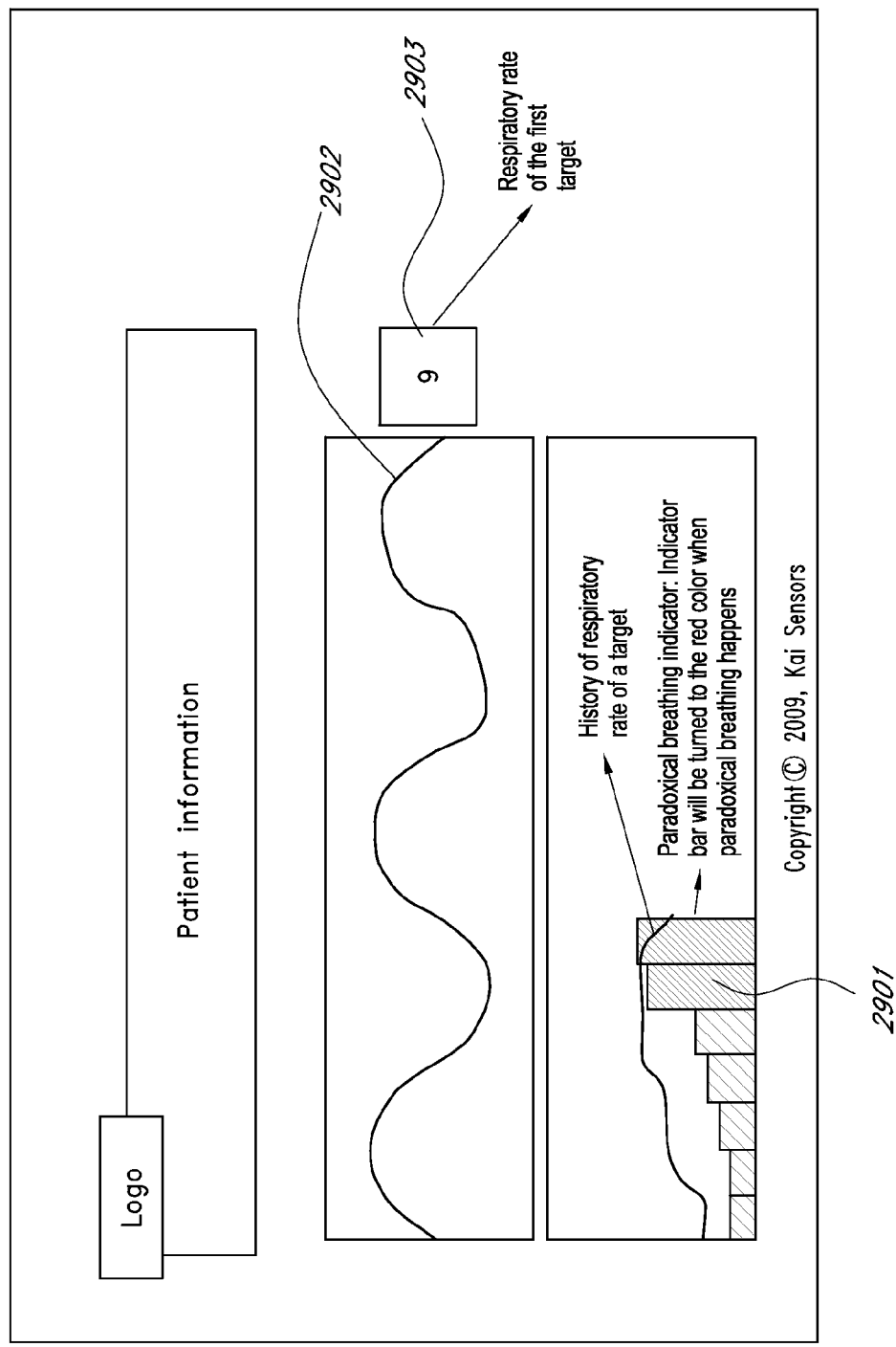
FIGS. 29 and 30 are screen shots of a display device configured to display the output from a system configured to detect paradoxical breathing
Figure 30:
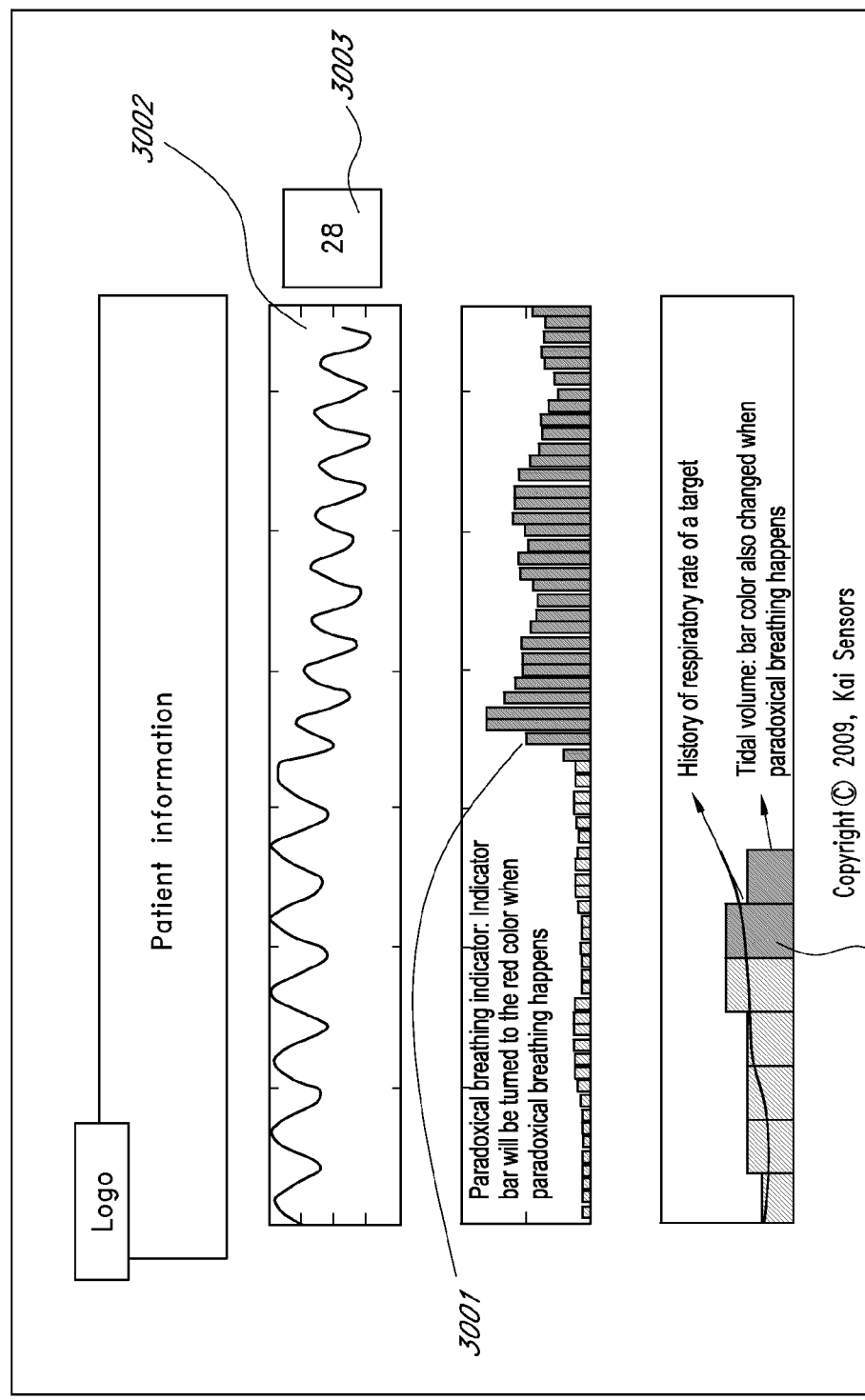

FIGS. 29 and 30 are screen shots of a display device configured to display the output from a system configured to detect paradoxical breathing. Information related to paradoxical breathing can be displayed graphically (e.g., as bars) 2901 and 3001. For example as illustrated in FIGS. 29 and 30, when paradoxical breathing is detected the bars indicating the average respiration rate can change color (e.g., from yellow to red, or green to red, or red to green, etc.). Other information such as respiratory waveform 2902 and 3002 or a respiratory rate 2903 and 3003 can also be displayed. The display of FIG. 30 also shows the tidal volume (amount of air flowing through the nasal passage at each breath) graphically (e.g., as a bar graph) 3004. The color of the bars representing tidal volume can also change colors (e.g., from yellow to red, or green to red) when paradoxical breathing is detected. Other ways of indicating paradoxical breathing can also be used.

An example configuration includes a system 100 configured to operate at a frequency of approximately 2.4 GHz. In some embodiments, the system includes a single antenna configured as a transmitter and three or more antennas configured as a receiver. In various embodiments, the receiver antennas can be spaced half wavelength apart. In various embodiments, a different number of transmitting and receiving antennas can be used. In some embodiments, the system further includes a quadrature direct conversion or homodyne receiver, a high-pass filter or a DC-cancellation circuit or both. The system 100 can further include a processor configured to execute linear demodulation algorithm as disclosed in U.S. Provisional App. No. 61/204,881 which is incorporated herein by reference in its entirety and in U.S. Provisional App. No. 61/137,519 which is incorporated herein by reference in its entirety.

Figure 31:
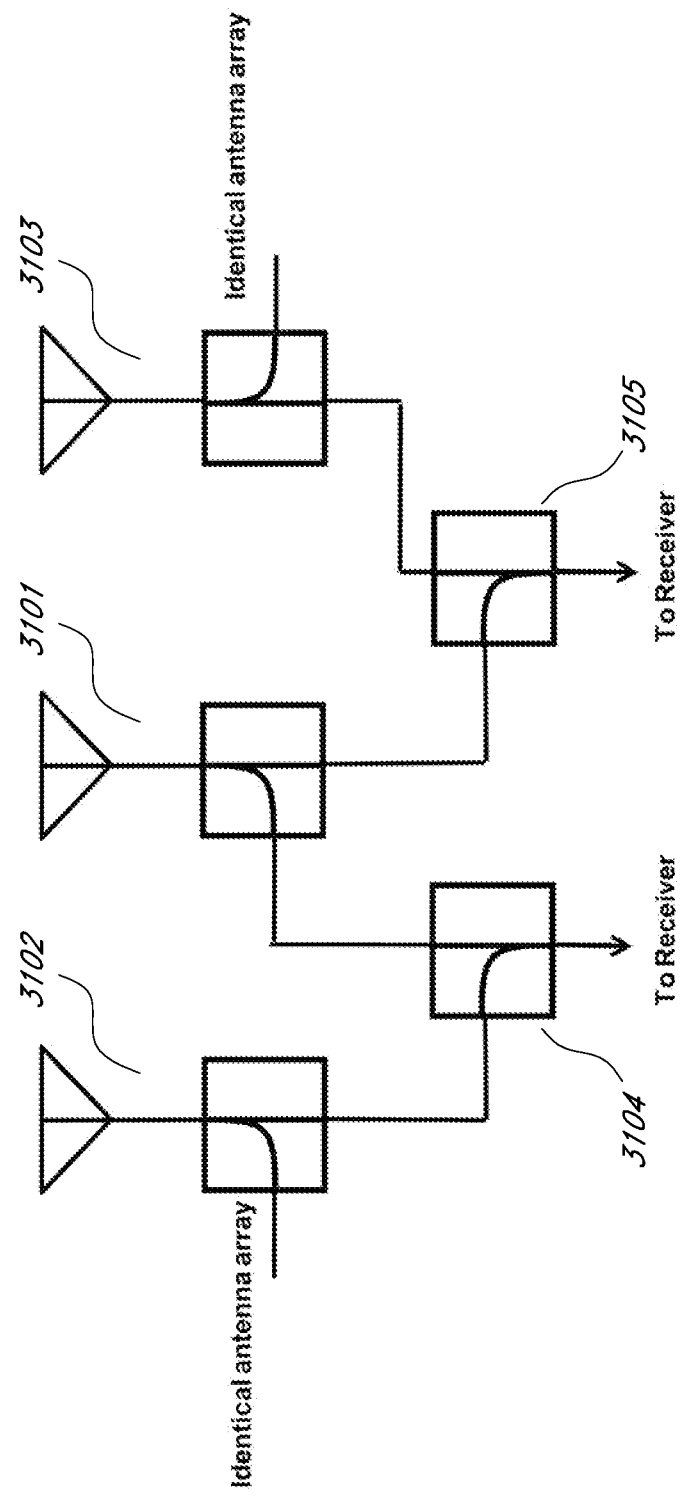
FIG. 31 illustrates an embodiment of a system including a compact antenna array.
Figure 32:
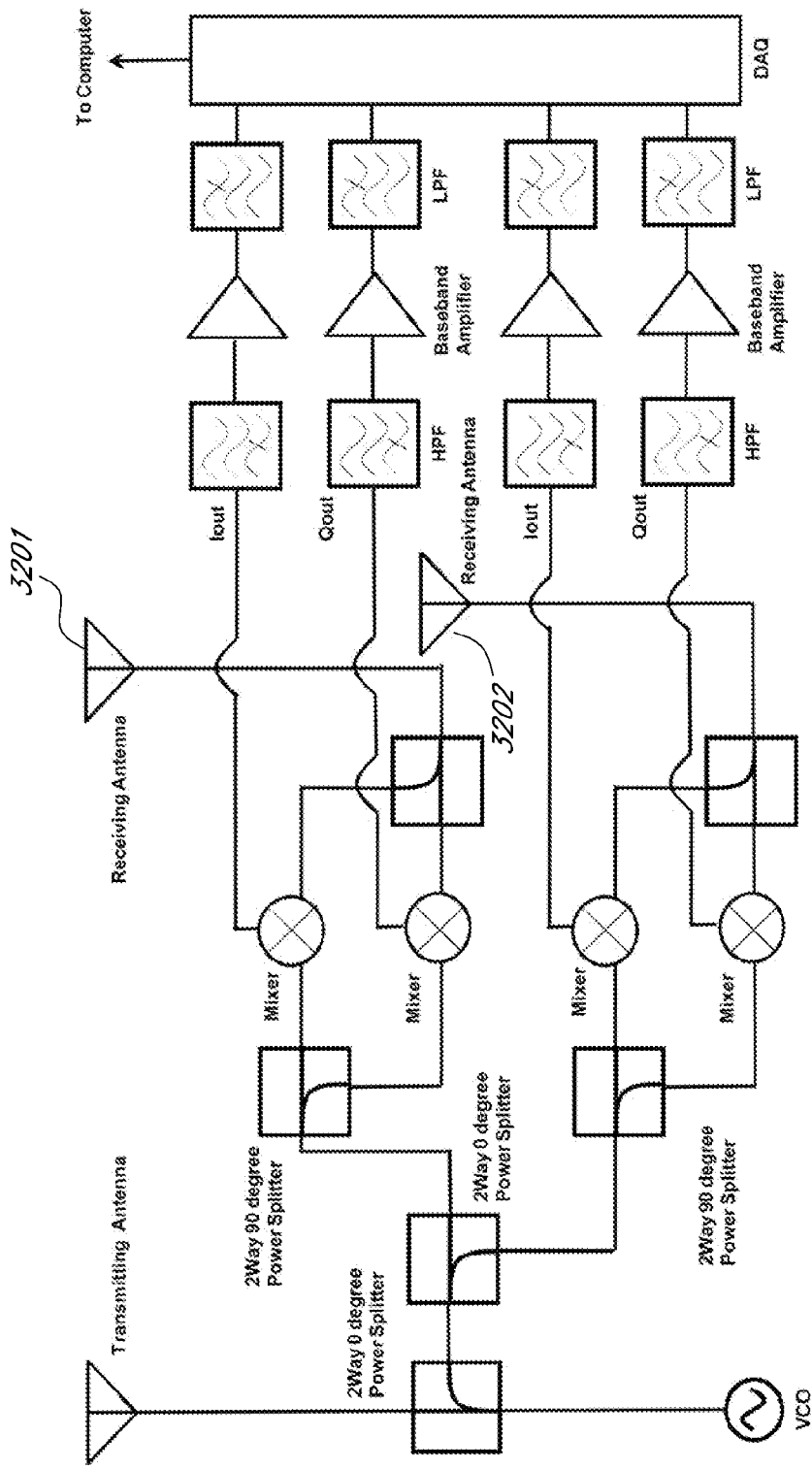
FIG. 32 illustrates an embodiment of a system including two receiving antennas.

As discussed above, in various embodiments, a homodyne receiver is used for its simplicity and for its phase noise cancellation or reduction property. To eliminate mirror imaging at baseband after down-converting the RF signal, the system includes complex demodulation, which provides quadrature outputs. In various embodiments, an antenna array can be used to transmit and receive radar signals. In some embodiments, a single antenna can be used to transmit, and an array of antennas can be used for receiving. In various embodiments, the system 100 can be configured to execute the Direction of Arrival (DOA) algorithm or processing can be provided with at least two receiver antennas in each plane of interest. In various embodiments, one or more receiver antenna arrays can be used to execute the DOA algorithm. Antenna arrays can be more compactly designed by sharing antennas for different array clusters as illustrated in FIG. 31. The system 3100 illustrated in FIG. 31 comprises a central antenna 3101, an antenna on left 3102 in communication with a receiver 3104 and an antenna on the right 3103 in communication with a receiver 3105. With reference to FIG. 31, the center antenna 3101 belongs to both left and right array clusters and is in communication with both the receiver 3104 and 3105 which results in two independent array clusters composed of two single elements. In one embodiment, this approach can reduce the number of antennas required as compared to a conventional antenna array design wherein each cluster is designed to have two elements, thereby reducing the total area required for the number of antennas. As discussed above, the quadrature outputs can be anti-alias filtered and in various embodiments, the DC signal can be removed either with a high-pass filter or a DC-cancellation system. The filtered signal can be sampled by an analog to digital converter (ADC) followed by signal processing, which can isolate the physiological motion signal from noise, interference, and non-physiological motion. The physiological motion signal can be processed to determine the cardiopulmonary parameter(s) of interest. FIG. 32 illustrates an embodiment of a system including two receiving antennas 3201 and 3202. The system of illustrated in FIG. 32 can be extended to any number of receiving antennas, or can be modified to include only one receiving antenna. In some embodiments, each receiver may have its own antenna.

In various embodiments that include multiple antennas and multiple receivers, DOA algorithm or processing can be used to provide several benefits in the detection of vital signs. When sensing physiological information with a radar system, it is desirable to have a wide antenna beam width to cover the subject in all probable positions. However, the wide beam can cause detection of motion away from the subject, which can affect the measurement. DOA processing from multiple antennas can provide the wide beam width needed to detect and track a subject as well as a way to steer a narrower beam to concentrate the radar signal on the physiological motion and avoid interfering motion from the surrounding. In order to focus the beam on the target, an array antenna configuration can be used as a transceiving antenna. In various embodiments, DOA processing can also null out angles with high amplitude interfering signals.

The radar system 100 can use DOA to separate sources of motion sensed by the radar system based on their differing angles from the antenna. Any of several DOA algorithms can be used for this technique. The signals from the antennas can be processed as an antenna array, which has a narrower beam width than any of the individual antennas. Through processing, the beam of this array can be effectively steered towards the desired source, so the antenna beam is focused on the source and any motion outside the beam will be attenuated according to the antenna pattern in that direction. Additionally, the angle to the target subject can be detected and presented in the interface, either as the angle or as a more general indication of the direction (i.e., straight, left, or right).

The multiple antennas can also be used to detect and track the angle of an interfering motion source. The signals from the antennas can then be combined such that there is a null in the antenna beam pattern in the direction of the interfering motion. This can be used to separate signal sources, by measuring one source while placing a null in the direction of the interfering motion.

One embodiment of an algorithm for separating multi physiological signals is described below and includes:

1. Determining the frequency components of interest $f=f_1, f_2, \ldots, f_n$. In some embodiments, this can be done by measuring combination of spectral power of multi-channels. A specified cost function can provide output that can distinguish frequency components from the targets' chest motion.

2. Forming a channel matrix H whose entries correspond to $f_1, f_2, \ldots, f_n$. For example, the $m^{th}$ row and $n^{th}$ column of the channel matrix entry can be $h_{mn}=s_{mn}(f_n)$, corresponding to the receiver antenna m and signal source n, where $s_{mn}$ represents frequency spectrum of the channel.

3. Forming an array vector given by equation (1):

$$g(\theta)=[1 \; \exp[jkd\sin(\theta)] \ldots \exp[jkd(M-1)\sin(\theta)]]^T \quad (1)$$

where k is the wavenumber, $d=\lambda/2$ is the separation distance between each receiver antenna and $\theta$ is the angle from the antenna normal vector to the target, while M is the number of received antennas.

4. Calculating the maximum average power that can be obtained at the angle of the sources and is given by equation (2):

$$P_{av}(\theta)=|H^H g(\theta)|^2 \quad (2)$$

5. Eliminating angles that are separated from each other by an angular distance less than the angular resolution of the multiple receiver antenna array, and identifying at least a first and second angular direction such that each angular direction is separated from each other angular source by an angular distance greater than or equal to an angular resolution of said multiple receiver antenna array.

6. Forming an M×N array matrix A whose ith column is given by the equation (3)

$$g(\theta_i)=[1 \; \exp[jkd\sin(\theta_i)] \ldots \exp[jkd(M-1)\sin(\theta_i)]]^T \quad (3)$$

where $d=\lambda/2$ and $\theta$ are the receive antenna separation and angle respectively, while M is the number of received antennas. In those embodiments where there are other moving objects in the vicinity of the subject which can scatter the radar signal, N denotes the number of moving objects.

7. Including signal separation that can be achieved by steering spatial nulls toward unwanted signal sources by multiplying inverse of matrix A, estimated in step 4, to the channel data.

$$S=A^{-1}R_x$$

In various embodiments, these approaches can be used as a SIMO (single input multiple output) system, with one transmitter and multiple receiver antennas, or could be implemented as a MIMO (multiple input multiple output) system, with multiple transmitters, each at a different frequency, and multiple receivers. In various embodiments, other DOA algorithms could also be used to separate sources at different angles from the antenna.

In various embodiments, after DOA processing, the subject's vital signs, such as respiratory rate, chest displacement, tidal volume, and/or heart rate can be extracted from the physiological motion waveform and output to the output device.

Figure 33:
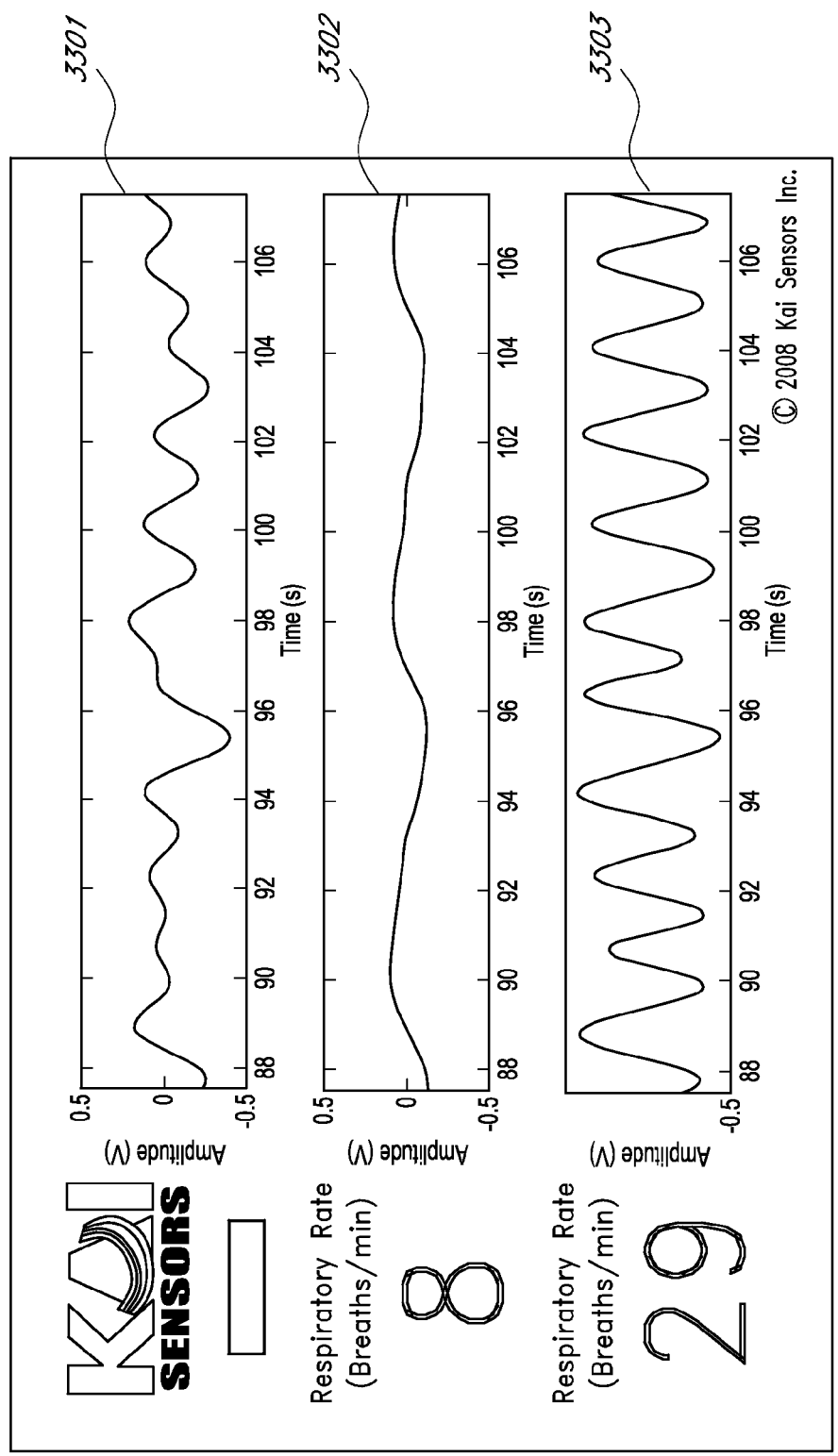
FIG. 33 illustrates the screen shot of a display device configured to output cardiopulmonary information of two people after DOA processing separated their respiratory signals.
Figure 34:
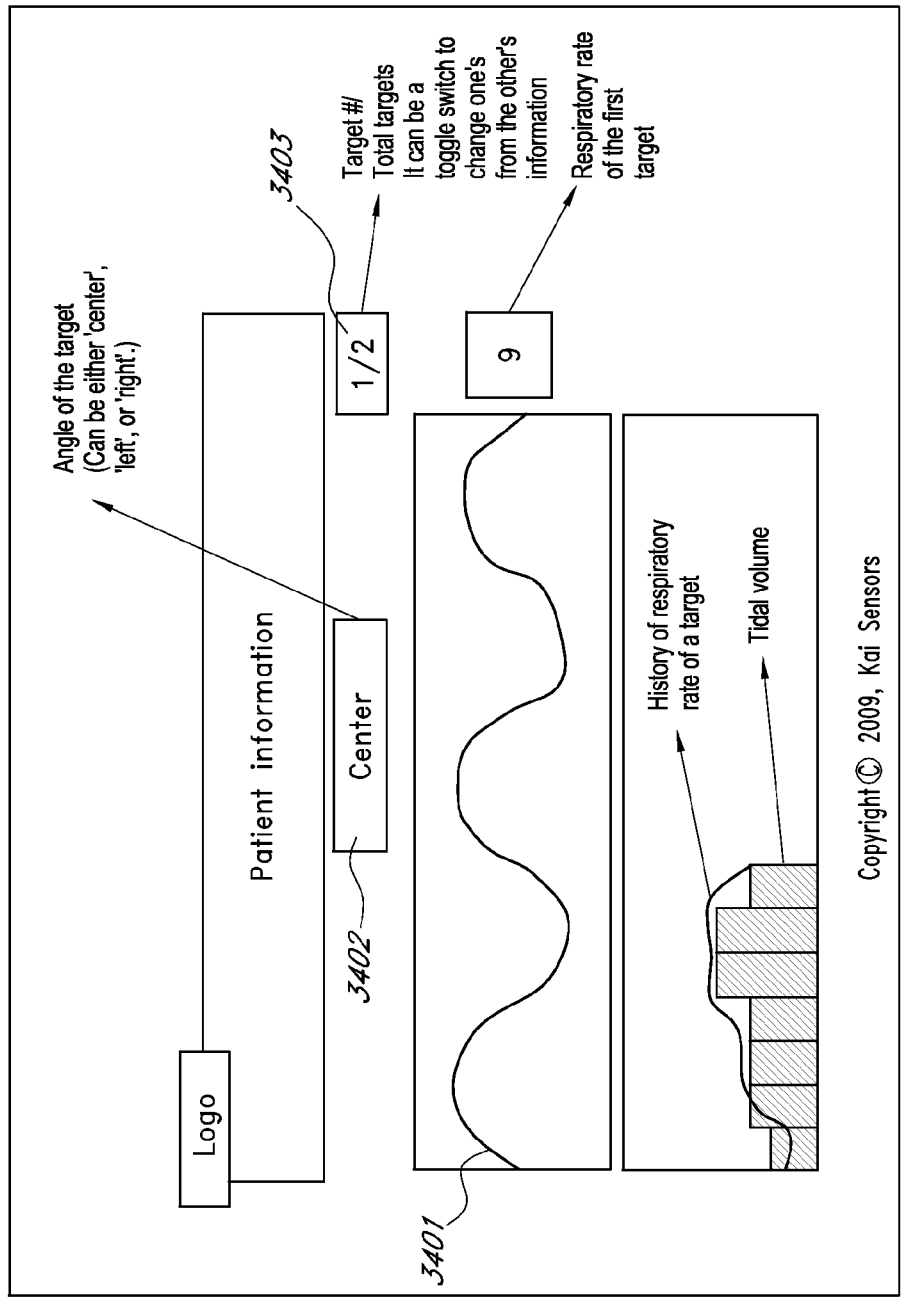
FIG. 34 illustrates a screen shot of a display device configured to display a respiratory waveform and tidal volume.

In various embodiments, the vital signs and/or directional information can be buffered and plotted to provide historical data for the subject. FIG. 33 shows the screen shot of a display device configured to output cardiopulmonary information of two people after DOA processing separated their respiratory signals. Plot 3301 shows the baseband signal obtained from both the subjects. Plot 3302 shows a waveform corresponding to a respiratory activity of a first subject while plot 3303 shows a waveform corresponding to a respiratory activity of a second subject. In various embodiments, the display device can be configured to display information related to respiratory activity (e.g., waveform related to respiration, average respiration rate, etc.). In various embodiments, other information such as tidal volume, heart and/or angle or position of the subject can also be displayed. FIG. 34, illustrates a screen shot of a display device configured to display the respiratory waveform 3401 and the tidal volume and a history of respiration rate. In some embodiments, the position of the target with reference to the sensor can also be displayed on the display 3402. In various embodiments, the display can include a control area 3403 to switch between patients. FIG. 35 illustrates a screen shot of a display device configured to display the respiratory motion waveforms for two people. Plot 3501 shows the mixed baseband signal obtained by the system from two subjects. The mixed baseband signal is processed using a DOA algorithm to extract information related to the respiratory activity of the two subjects. Plot 3502 shows the respiratory activity of a first subject positioned about 24 degrees to the right of the system and plot 3503 shows the respiratory activity of a second subject positioned about 13 degrees to the left of the system. A history of the respiratory rates for the two subjects is shown in plot 3504.

An example configuration includes a system 100 configured to operate at approximately 5.8 GHz with a low-IF receiver. In various embodiments, the system further includes a single antenna configured to transmit radar signals and a single antenna configured to receive radar signals. In various embodiments, the system includes a low-IF receiver configured to transform the received signal to a signal including frequencies in the range from a few Hz to a few kHz. For example, in some embodiments, the IF receiver can be configured to transform the received signal to a signal having a frequency in the range for about 1 Hz to 200 kHz. In various embodiments, the system's processor can be configured to execute an arc demodulation algorithm. In various embodiments, the system 100 can be configured as a spot check monitor or a continuous monitor.

In various embodiments, the system includes an oscillator (e.g., a voltage controlled oscillator) configured to operate at approximately 5.8 GHz and a stable crystal oscillator configured to generate radiation in the kHz to MHz range. The signal from the oscillator is split in by a power splitter. The signal from a first output of the power splitter is provided to the transmitting antenna and the signal from a second output of the power splitter is multiplied by the signal from the crystal oscillator to generate a reference signal for the receiver. Since the reference signal will still benefit from the range correlation effect, the phase noise of the reference signal will not adversely affect the residual phase noise; the residual phase noise will be limited by the crystal oscillator, which typically has a very low phase noise. In various embodiments, a low-IF receiver architecture can mitigate problems caused by 1/f noise, channel imbalance, and dc offset with low phase noise. In various embodiments, low-IF signals can be directly sampled by an ADC and down-converted to quadrature baseband signals in the digital domain.

Thus, when arctangent demodulation is used, significant changes in the location of the origin, changes in the radius of the circle the arc is on, or changes in the position of the arc on the circle can indicate a change in the relationship between the antenna and subject, which can indicate non-cardiopulmonary motion. As discussed above, non-cardiopulmonary motion can be detected by calculating the inner product of the normalized current vector and the normalized previous vector. A significant change in the relationship between the subject and the antenna is indicated if the value of the inner product is below a threshold. In those embodiments, where arctangent demodulation is used, a change in the RMS error of the fit to the best-fit arc can also indicate non-cardiopulmonary motion or other signal interference.

An example configuration includes a system 100 configured to operate at a radio frequency of approximately 5.8 GHz with a direct-conversion receiver and DC-offset cancellation. In various embodiments, the system 100 includes a single antenna to transmit radiation and a single antenna to receive radiation. In various embodiments, one or more antennas can be used to transmit and/or receive signals. In various embodiments, the system 100 can include a processor configured to execute an arc demodulation algorithm.

Figure 36A:
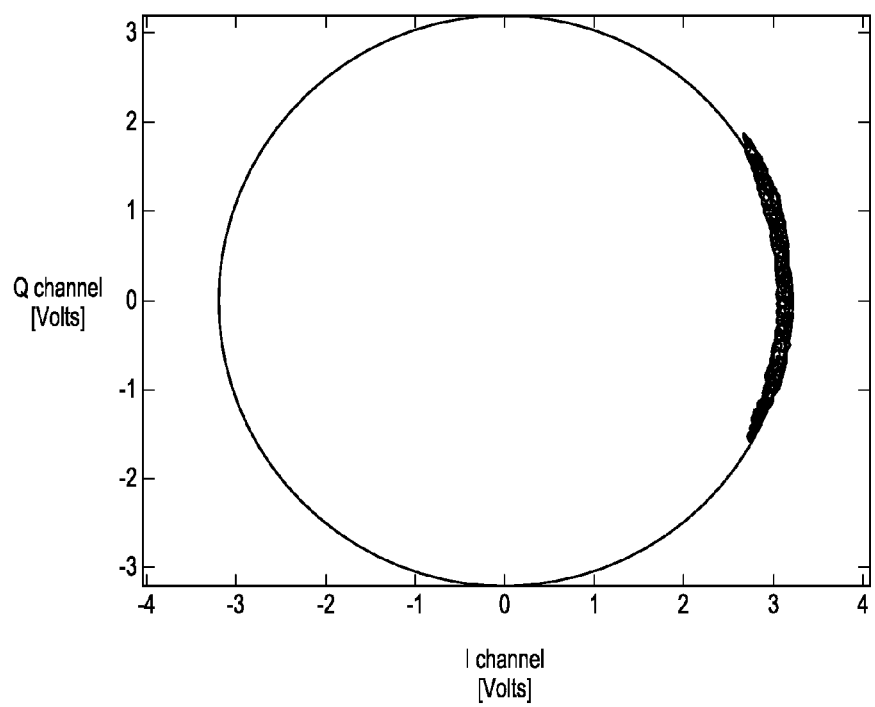
FIG. 36A shows a complex constellation plot of the quadrature phase component and the in-phase component of a signal.
Figure 36B:
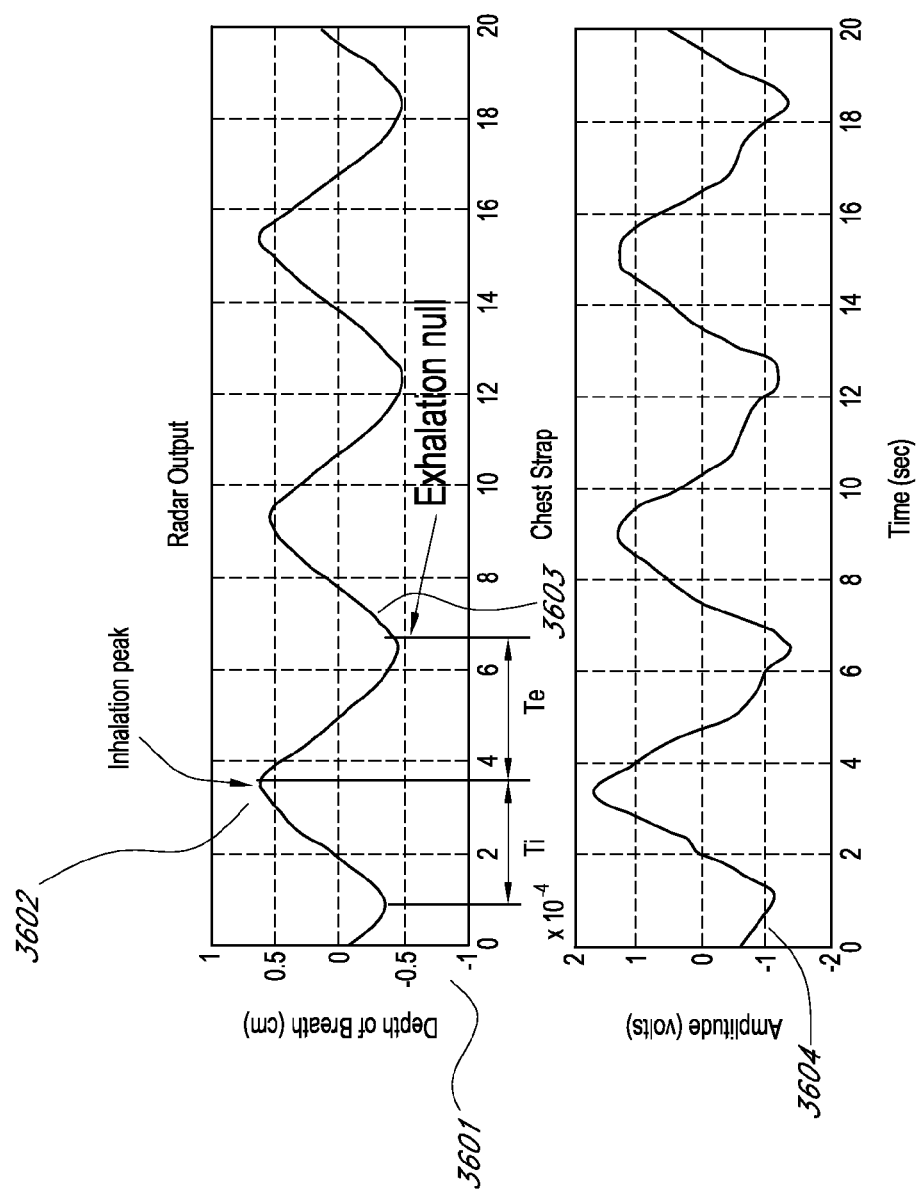
FIG. 36B shows a plot of depth of breath versus time as measured by a radar-based physiological motion sensor and a conventional motion sensor, e.g., chest strap.
Figure 36C:
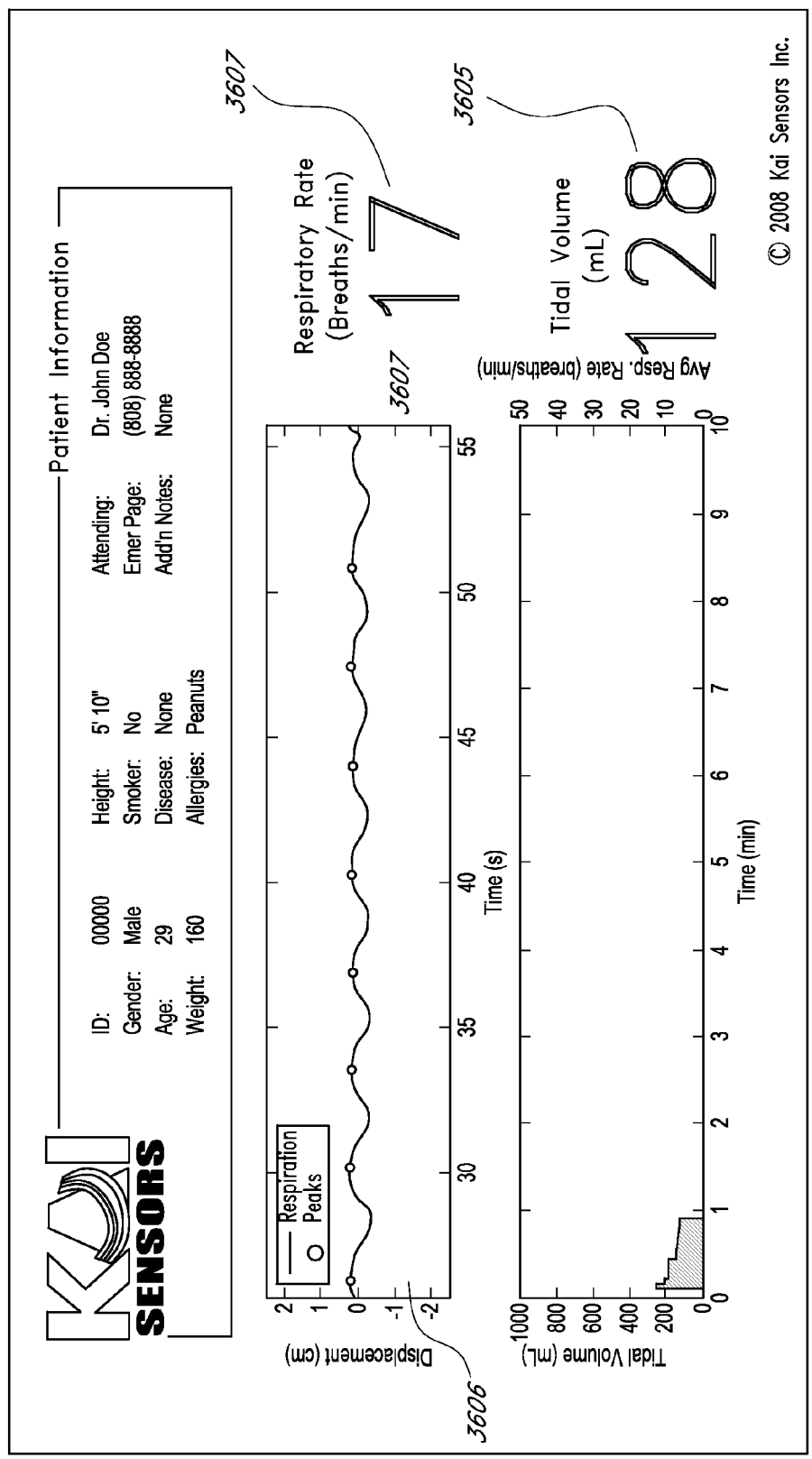
FIG. 36C shows a snapshot of a display device illustrating the tidal volume, a waveform corresponding to the respiratory activity and a respiratory rate.

In embodiments using a radio frequency of approximately 5.8 GHz, the phase deviation, can result in non-linear quadrature baseband output or an arc trace rather than a line in the complex constellation as shown in FIG. 36A. Consequently, arc demodulation can be preferred over other demodulation algorithms to obtain accurate signals in systems with 5.8-GHz carriers. Furthermore, DC cancellation rather than AC coupling filter can be preferred to reduce signal distortion, and to enable determination of the origin of the circle where signal samples are scattered with sufficient accuracy. Since arc demodulation can extract phase information from baseband signal which can be linearly proportional to the actual chest motion, it is possible to estimate depth of breath from arc demodulation. The depth of breath information obtained from arc demodulation can also be applied to tidal volume estimation; there can be a linear relationship between the linear chest excursion and the tidal volume. FIG. 36B shows a plot 3601 of the depth of breath versus time. The depth of breath shows an inhalation peak 3602 and an exhalation null 3603. From this plot the tidal volume (amount of air inhaled Ti and amount of air exhaled Te in each respiratory cycle) can be estimated. Plot 3604 shows a corresponding measurement obtained by a conventional sensor. FIG. 36C shows a snapshot of a display device illustrating the tidal volume 3605, a waveform corresponding to the respiratory activity 3606 and a respiratory rate 3607. In various embodiments, as the length of arc increases, the ambiguity in the signal polarity can be reduced which can enable estimation of inhaling and exhaling time duration, which enables estimation of the ratio between inhale time and exhale time. The cardiopulmonary related motion of the body surface can be measured either from a distance or in contact with the body. In those embodiments, wherein the antenna is in contact with the body, methods to isolate body surface reflections from internal reflections can be used and internal body motion can be measured. In various embodiments, other internal cardiopulmonary related changes can also be electromagnetically measured for surface and internal body parts and tissues, including impedance change associated with heart beat.

An example configuration includes a multi-receiver system configured to operate at a radio frequency in the 5.8 GHz band. The system includes a single antenna to transmit the radar signal and four or more antennas to receive the radar signals. In various embodiments, the receiver antennas can be placed a half wavelength apart. In some embodiments, the system 100 can include more than one transmitting antenna and less than four receiving antennas. The system further includes a direct conversion or homodyne receiver for each receiving antenna. In various embodiments, the system 100 can include a DC cancellation circuit to remove or reduce the DC offset. The system 100 can also include a processor configured to execute an arc demodulation algorithm.

Figure 37:
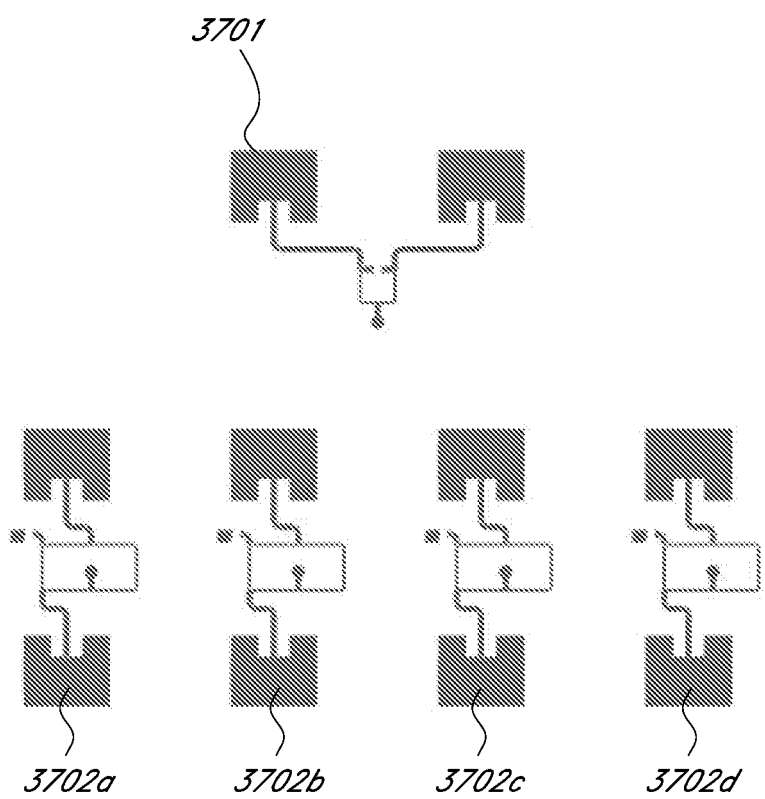
FIG. 37 illustrates a schematic layout of an array element including a transmitting antenna and at least four receiving antennas.

In embodiments of the system configured to operate in a frequency range of approximately 5.8 GHz, it is possible to design and manufacture compact antenna arrays. Thus, in systems configured to operate at approximately 5.8 GHz it is possible to get an increased number of arrayed elements within substantially the same area as a system configured to operate at approximately 2.4 GHz. In other words, it is possible to achieve higher spatial resolution in systems configured to operate at approximately 5.8 GHz as compared to systems configured to operate at approximately 2.4 GHz, with an antenna of the same footprint. FIG. 37 illustrates a schematic layout of an array element including a transmitting antenna 3701 and at least four receiving antennas 3702a-3702d. Thus embodiments of systems configured to operate at approximately 5.8 GHz can be advantageous when used for DOA processing because a given area can include a higher number of antennas as compared to a system configured to operate at approximately 2.4 GHz. An increase in the number of antennas can enable detection and tracking of subjects who are closely spaced (e.g., angular separation between two subjects can be less than 15 degrees with 4 antennas).

The DOA algorithm or processing technique described above can be employed to track subjects in various embodiments of the system. In some embodiments, arc demodulation can be employed after using DOA algorithms to tracking subject or suppress interference from non-cardiopulmonary motion or a cardiopulmonary motion of a second person. After signals from the multiple subjects are separated, non-cardiopulmonary motion detection algorithm can be employed. In various embodiments, the signal from each direction can be demodulated with an arc-based demodulation algorithm, which uses the parameters of the best-fit circle to obtain angular information from the complex constellation. Significant changes in the location of the origin if the best-fit circle, changes in the radius of the best-fit circle, or changes in the angular position of the arc on the circle can indicate a non-cardiopulmonary motion or other signal interference. The processor can then provide cardiopulmonary information on one or more subjects.

In various embodiments, a system 100 including a sensor placed on the body for measuring whether there is respiration and/or heart motion is described. The system 100 can be configured as wearable Microwave Doppler radar which can be placed in contact with a subject (e.g., in contact with a subject's chest). The wearable Microwave Doppler radar can be used to estimate a subject's respiratory rate and heart rate, and/or other vital signs, by detecting the motion of the body surface, motion of internal organs, or a combination of these motions. Various embodiments of this system 100 can operate at approximately 2.4 GHz, approximately 5.8 GHz or some other frequency band. In various embodiments, the system 100 can be configured as a stand alone device or can be integrated with a wireless communication system to communicate with other local devices and/or remote data centers or interfaces as disclosed in U.S. Provisional App. No. 61/194,838 which is incorporated herein by reference in its entirety.

In various embodiments a system comprising a sensor placed on the body for measuring a respiratory activity and/or heart motion is described. The system may comprise a wearable Microwave Doppler radar which can be placed in contact with a subject (e.g., in contact with a subject's chest). The wearable Microwave Doppler radar may be used to estimate a subject's respiratory rate and heart rate, and/or other vital signs, by detecting the motion of the body surface, motion of internal organs, or a combination of these motions. Various embodiments of this system can operate at approximately 2.4 GHz, approximately 5.8 GHz or some other frequency band. In various embodiments, the system may be configured as a stand alone device or can be integrated with a wireless communication system to communicate with other local devices and/or remote data centers or interfaces as disclosed in U.S. Provisional App. No. 61/194,838 which is incorporated herein by reference in its entirety.

Figure 38A:
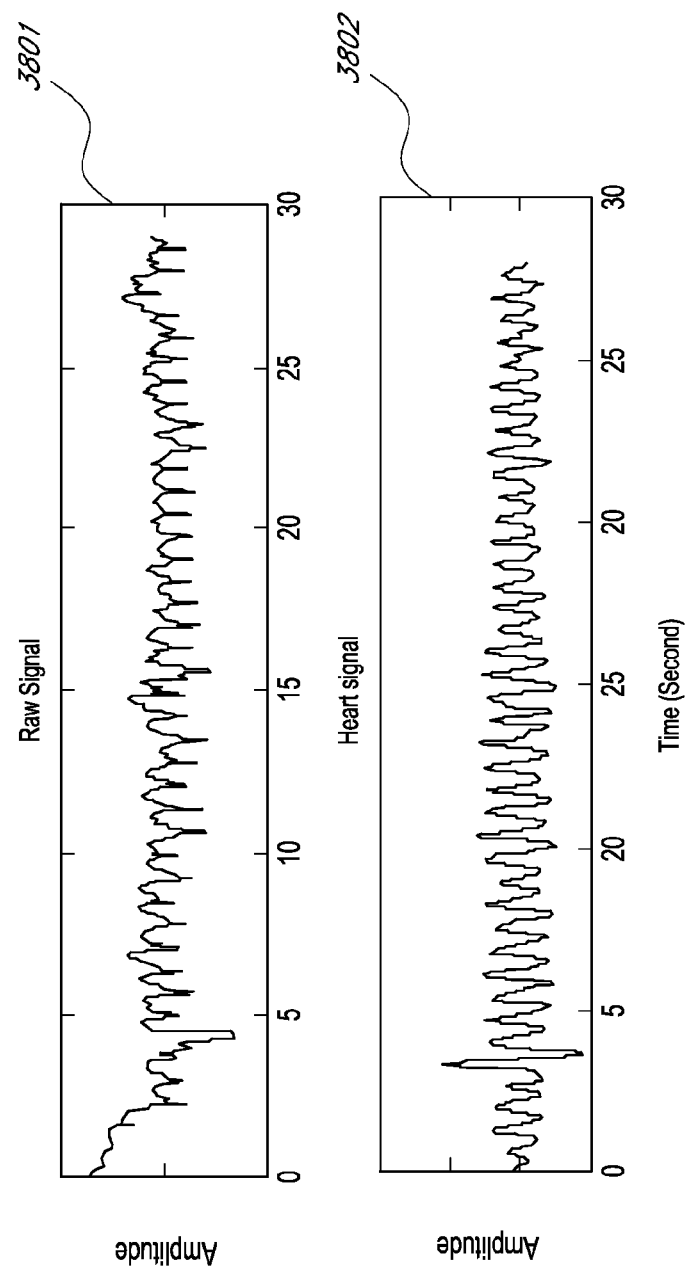
Figure 38B:
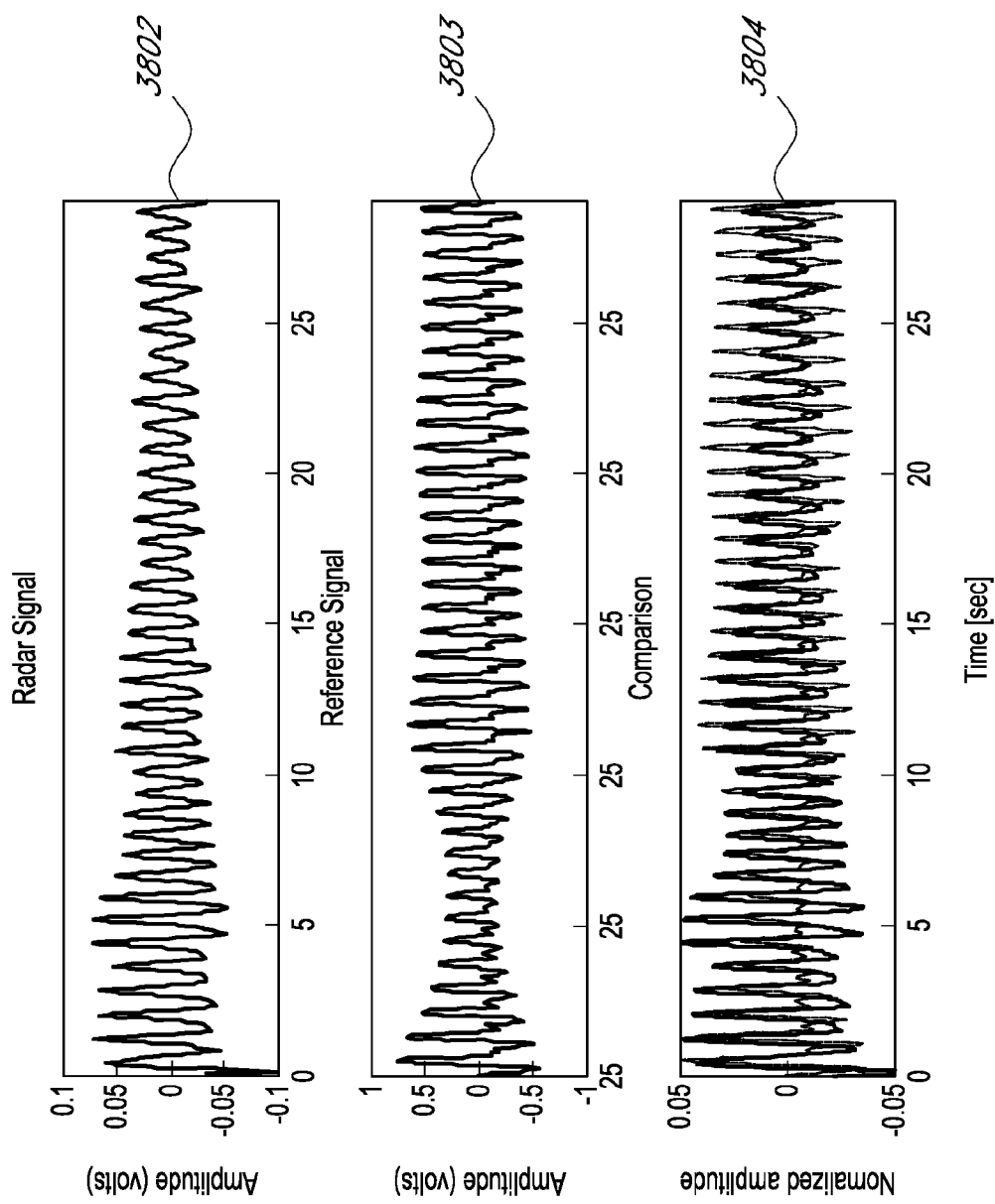

FIG. 38A shows the information related to cardiopulmonary activity when a wearable radar system similar to system 100 is placed in contact with a subject who is holding his/her breath. Plot 3801 illustrates a raw cardiopulmonary signal which has not been processed and plot 3802 illustrates a processed heart signal. FIG. 38B shows the information related to cardiopulmonary activity when a wearable radar system is placed in contact with the subject who is holding his/her breath in comparison to a reference signal. Plot 3802 shows the received radar signal and plot 3803 shows the reference signal. Plot 3804 shows the comparison between the radar signal and the reference signal.

FIG. 38C shows the information related to cardiopulmonary activity when a wearable radar system is placed in contact with a subject who is breathing normally. Plot 3805 shows the unprocessed signal and plot 3806 shows the respiration signal obtained after processing the raw signal. Plot 3807 is a heart signal obtained after processing the raw signal. The heart signal appears irregular due to coupling with breathing and/or harmonics of the breathing signal. However, a substantially accurate heart rate can be measured with the embodiments described in this application.

Figure 38D:
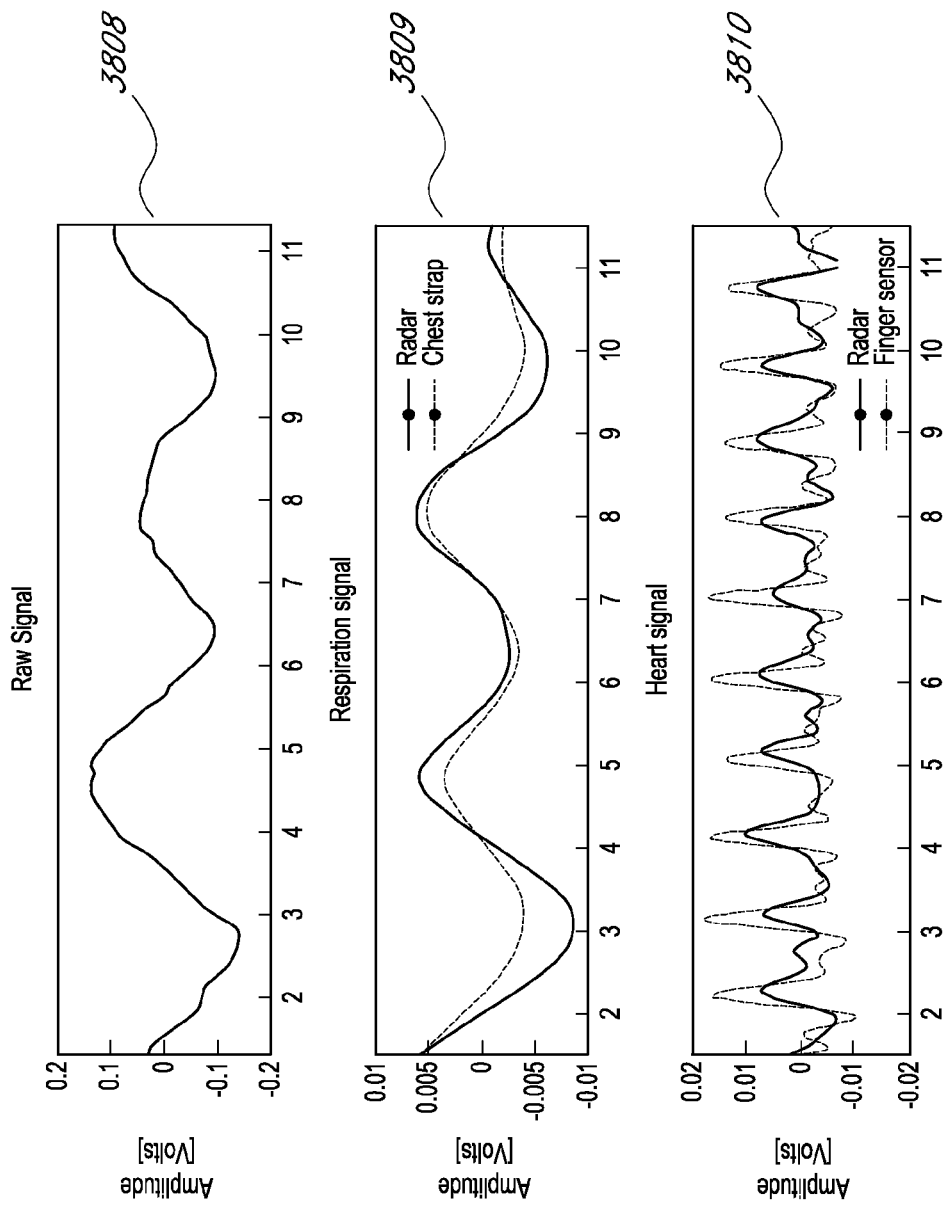
FIG. 38D illustrate information related to cardiopulmonary activity as measured by a non-contact Doppler radar system.

FIG. 38D shows the information related to cardiopulmonary activity as compared to a reference signal using a non-contact radar-based physiological sensor described above on a subject who is breathing normally. Plot 3808 shows the unprocessed signal and plot 3809 shows the respiration signal obtained after processing the raw signal. Also shown in plot 3809 is the respiration signal measured with a conventional sensor such as a chest strap. Plot 3810 is a heart signal obtained after processing the raw signal as compared to a heart signal obtained using a finger sensor.

Figure 38E:
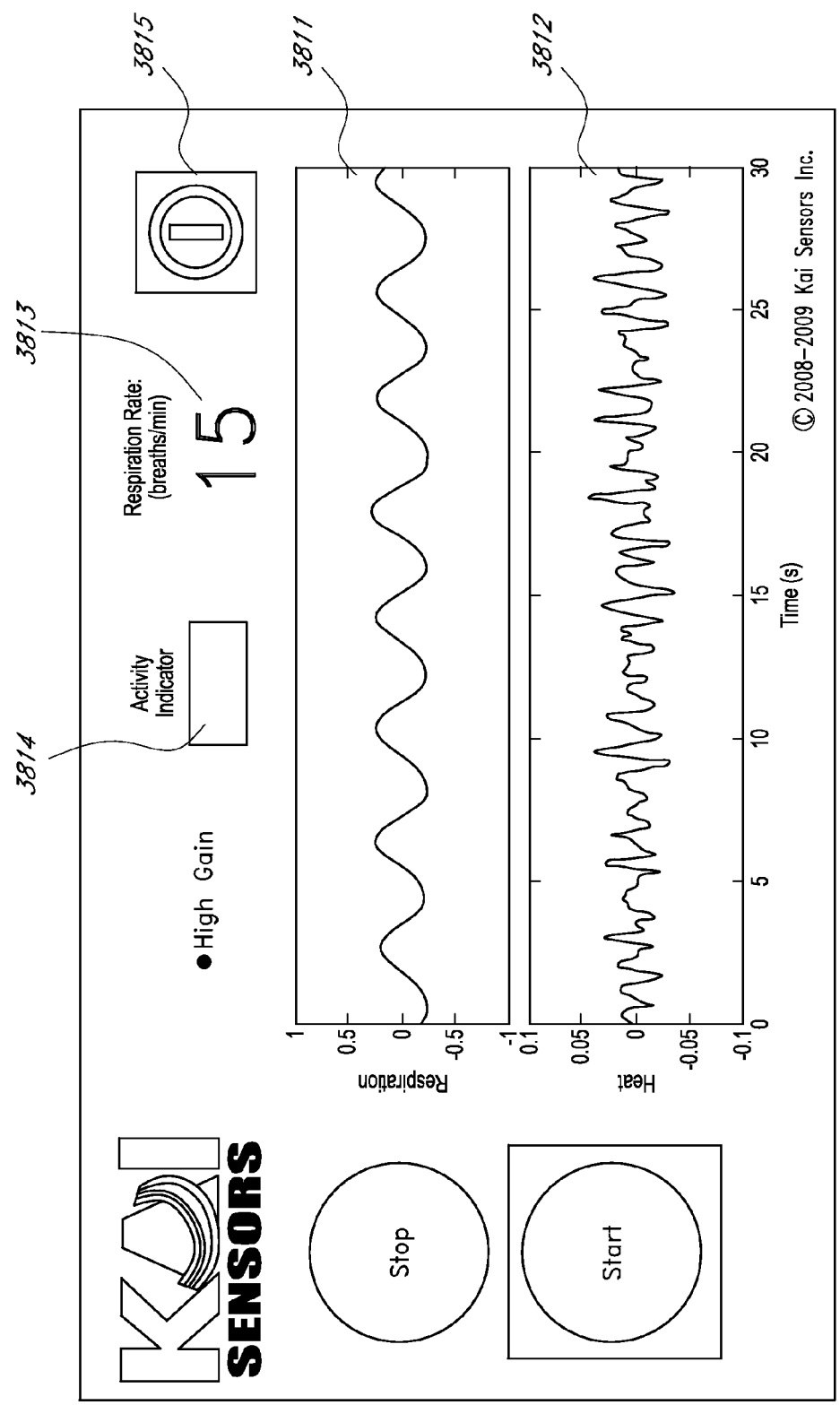
FIGS. 38E-38J show embodiments of a display device configured to display measurements related to cardiopulmonary activity and indicate presence of a subject.
Figure 38F:
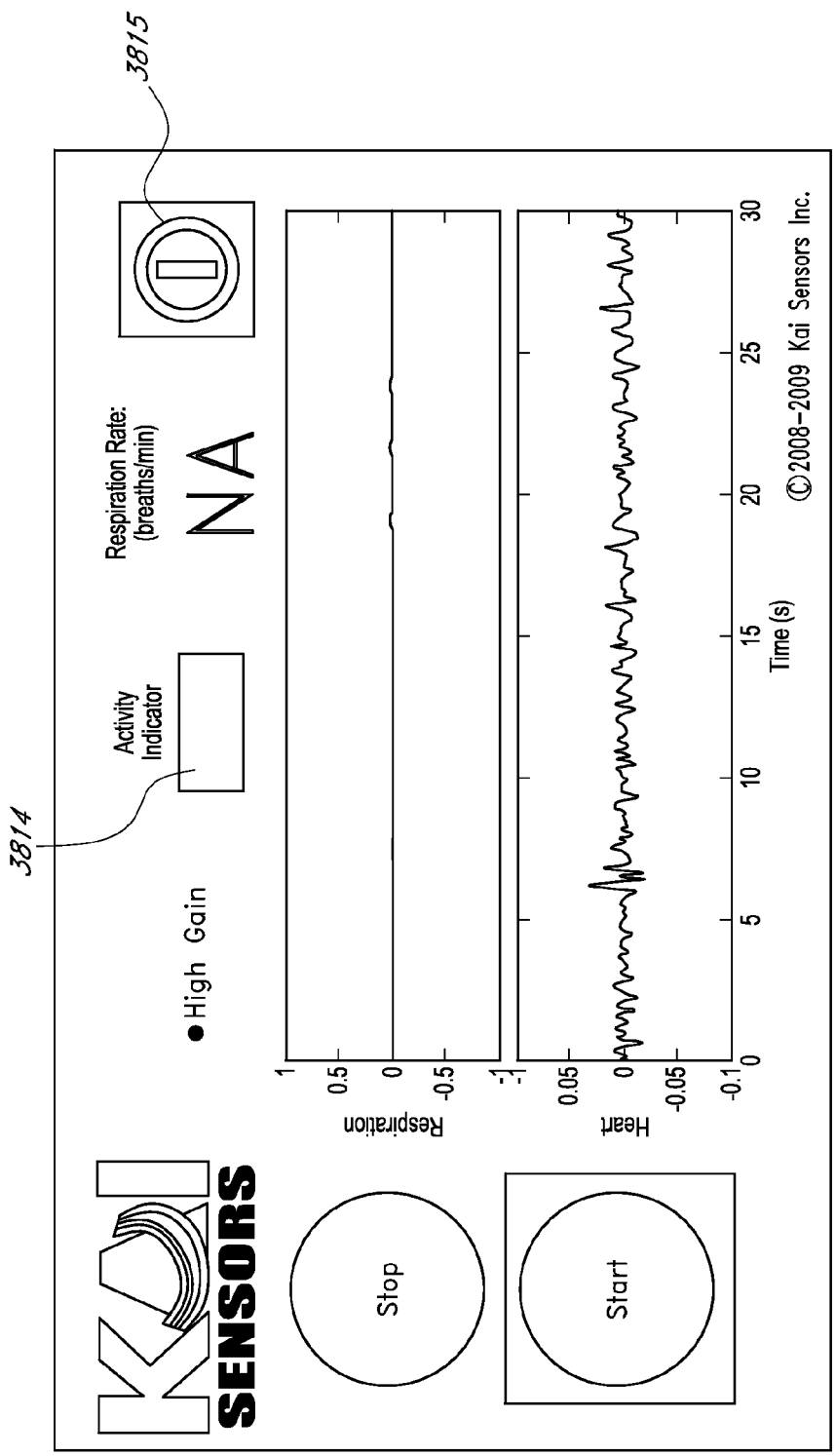
Figure 38G:
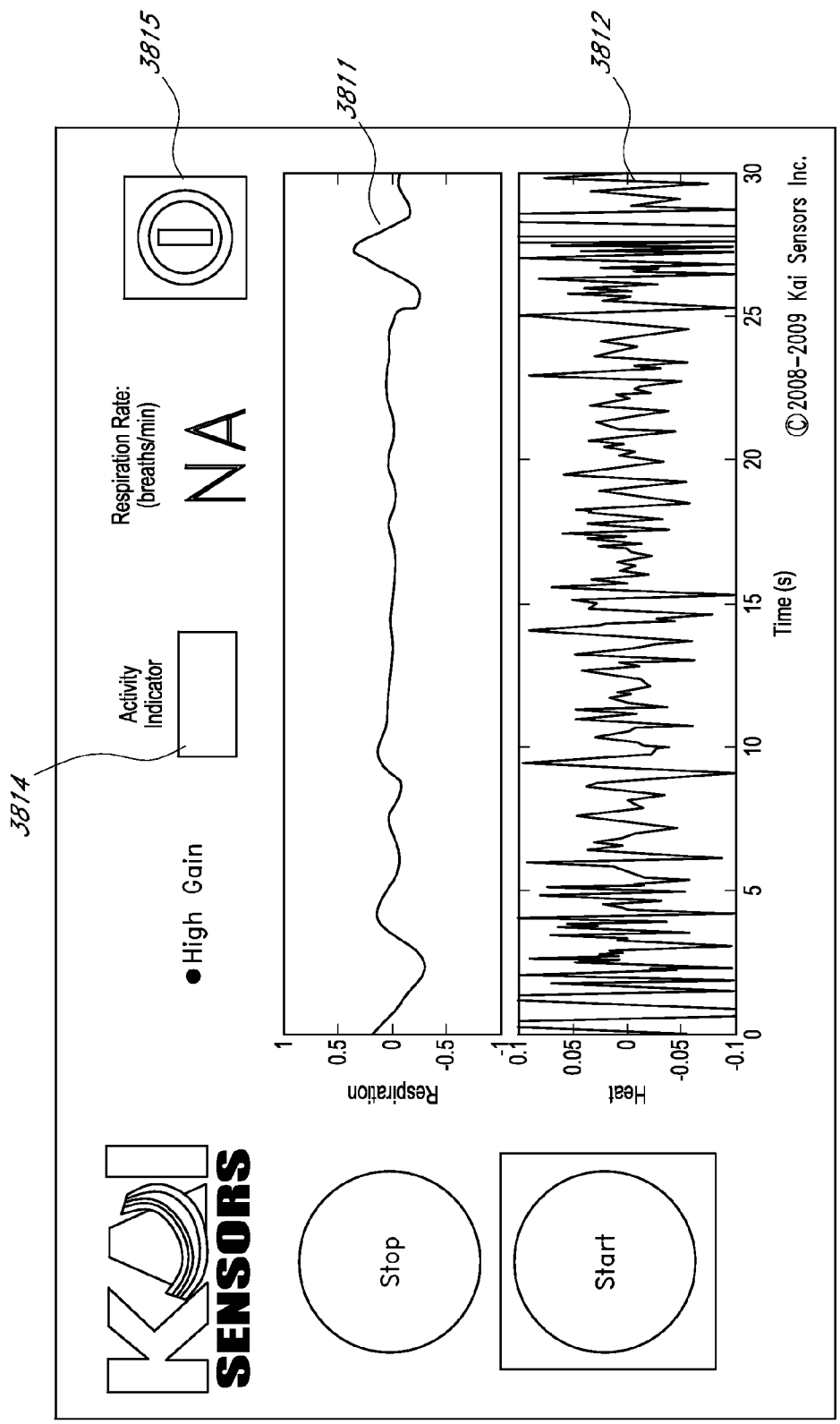
Figure 38H:
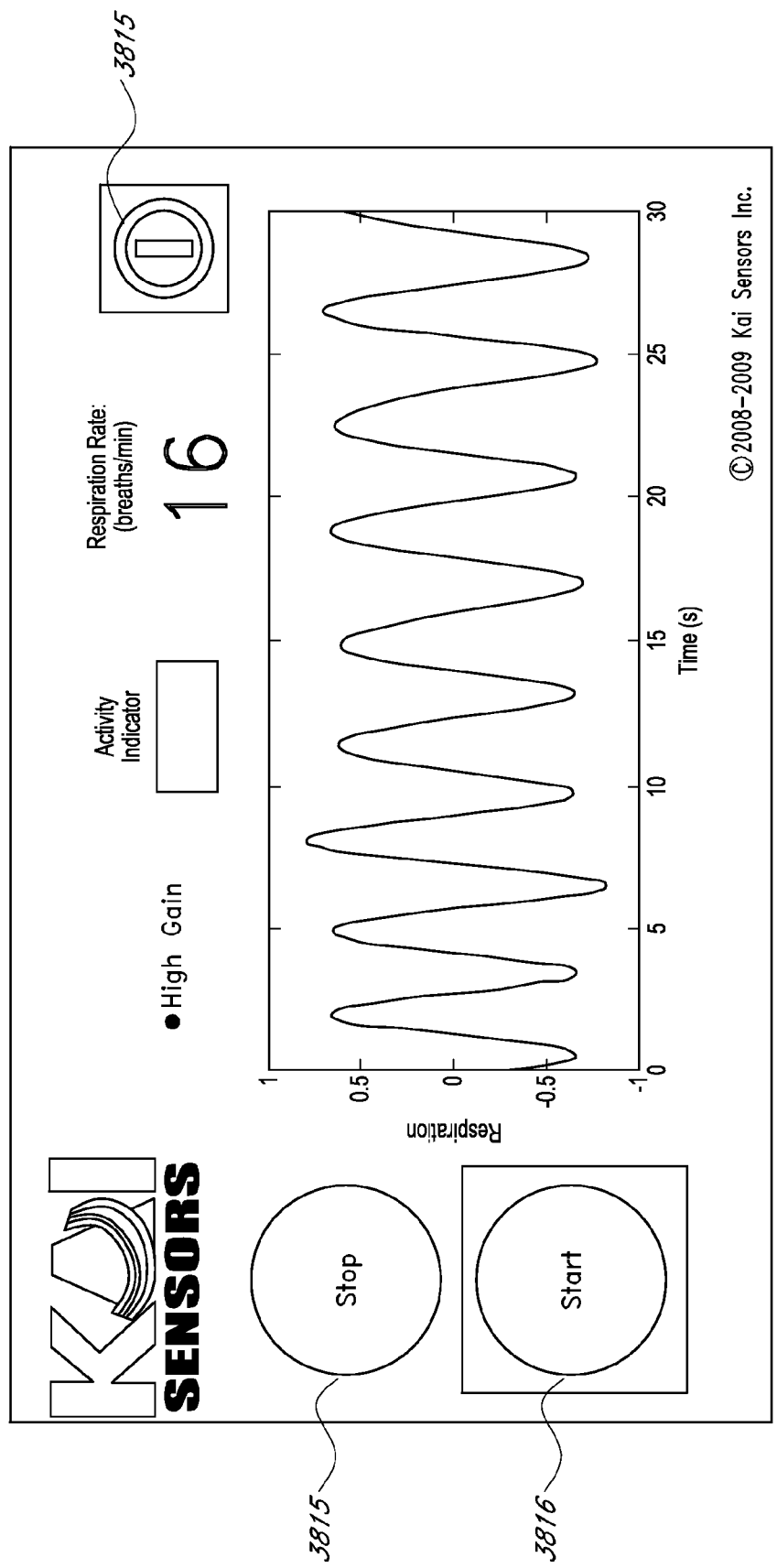

FIGS. 38E and 38F are embodiments of a display device configured to display respiration waveform 3811, heart waveform 3812, respiration rate 3813, and indication of activity 3814. In various embodiments, this user interface can be used for detecting the presence of a subject or for detecting whether or not a subject is breathing or a subject's heart is beating. In various embodiments, the display interface can be used for triage and resuscitation as well as detecting a subject's presence. In various embodiments, if activity or respiration or heart is detected, a subject is present; if neither is present, a subject is not detected. In various embodiments, the display interface can be used to detect whether or not a subject's heart is beating and/or the subject is breathing for triage and to determine whether CPR and/or defibrillation and/or other resuscitation is required. In various embodiments, if a subject's presence is detected, for example due to cardiopulmonary activity of the subject then an indication can be provided. For example, the 3815 may turn green if a subject is present. However, if a subject's presence is not detected then, the indicator 3815 may turn red and respiration waveform or respiration rate is not display as shown in FIG. 38F FIGS. 38G-38J are alternate embodiment of the display device shown in FIGS. 38E and 38F that are configured to display a respiration waveform, a respiration rate, a heart rate, a heart waveform, indication of activity, indication of subject's presence etc. In FIG. 38G, a subject's presence is detected by the heart signal 3812 and the respiration signal 3814 and is indicated by the indicator 3815 turning yellow and/or the activity indicator 3814 glowing. In FIG. 38H, a subject's respiration signal is detected as shown by the respiration waveform 3811 and can be indicated when the activity indicator turns green. Start and Stop controls can be provided on the display as shown by 3816 and 3815 respectively.

Figure 38I:
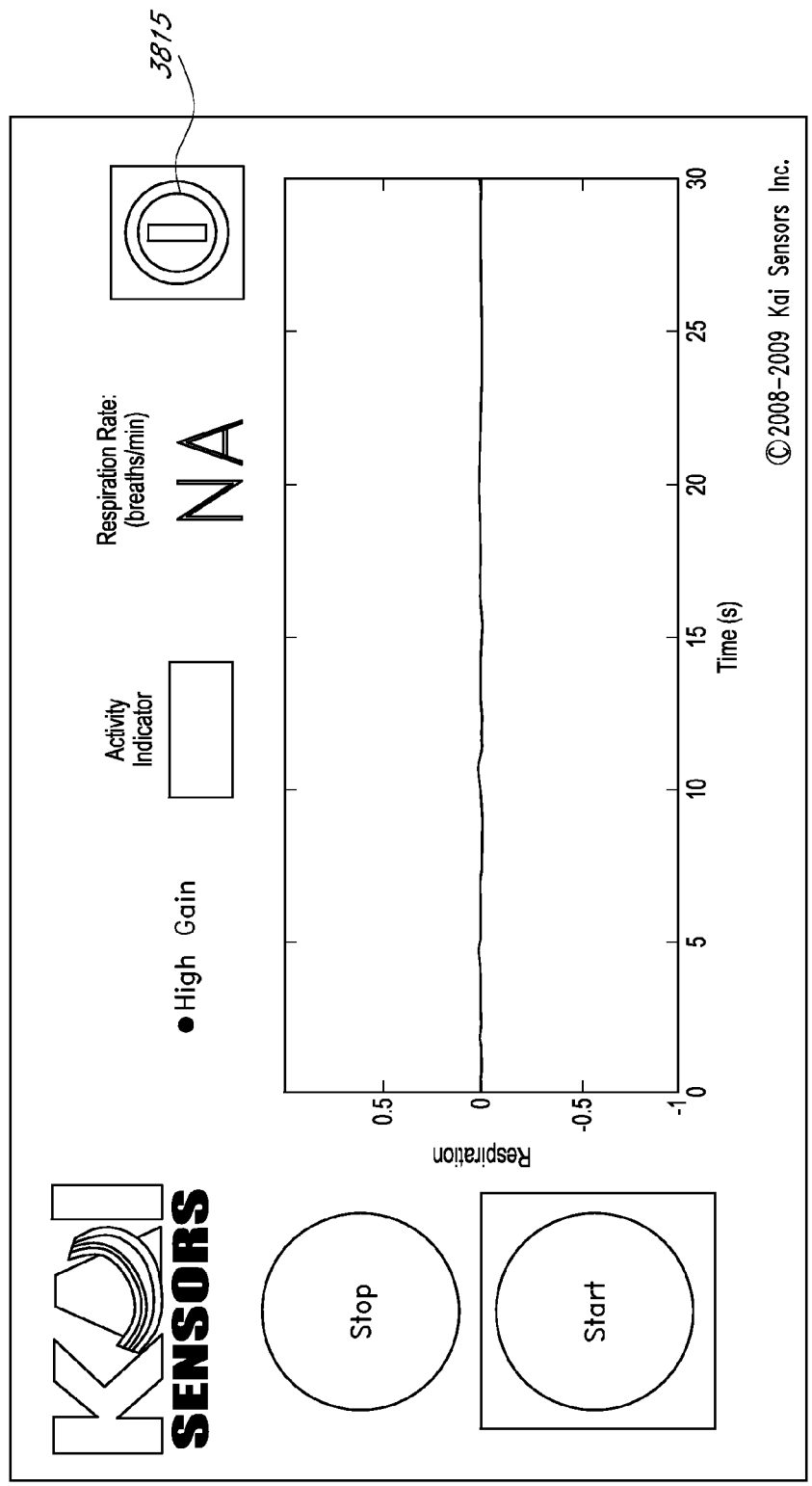
Figure 38J:
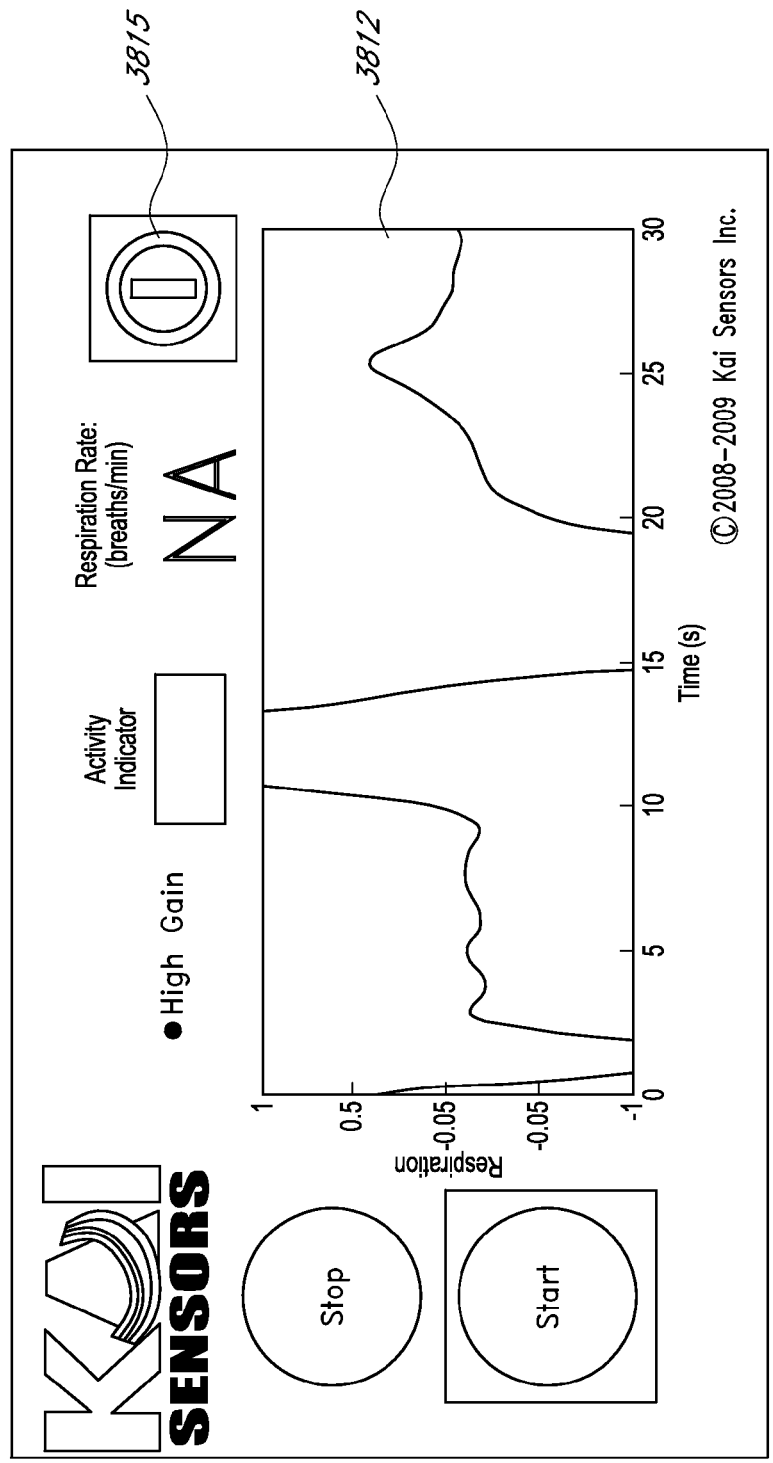

In FIG. 38I, no respiration signal is detected and so the indicator 3815 is red. In 38J a respiration signal 3812 is observed which indicates a subject's presence and by the activity indicator turning red.

In some embodiments, the sensor can also detect mechanical physiological motion including cardiopulmonary activity via direct contact with a subject's chest. When the sensor is not in contact, some of the signal emitting from an antenna is reflected on the surface of the chest, and some of the emitted signal can bypass the subject altogether, such that motion in the surrounding environment can interfere with the physiological motion signal. When the sensor is in contact, nearly all of the signal couples with the body, and almost none of the signal by passes the subject. In embodiments where the sensor does not contact the body, an antenna array is used so the antenna radiation pattern has a narrow beam width to enable focusing the transmitted signal in the desired direction to avoid sensing motion in the surrounding environment. In embodiments wherein the sensor contacts the body, nearly all of the transmitted signal couples with the body, so the antenna beam width is not an issue, and it is feasible to detect a cardiopulmonary signal with a single antenna (rather than an array) without any significant interference from the surrounding environment. The use of a single antenna rather than multiple antennas results in a more compact device.

When a sensor is in contact position with a subject's chest, chest motion due to cardiopulmonary activity can be amplitude modulated on the reflected signal. In some embodiments, this amplitude modulated signal, which is proportional to a subject's chest motion, corresponding to his/her cardiopulmonary activity, can be extracted by a low-IF single channel receiver architecture. In various embodiments, once the reflected signal is down converted to the low-IF, the signal will be sampled at higher than Nyquist rate to obtain non-aliased digital signal. In various embodiments, the Hilbert transform performed on the digitized input signal to obtain a complex signal where the in-phase part is the input signal while the quadrature part is the output of Hilbert transform.

In various embodiments, the envelope of the reflected signal, which is proportional to the cardiopulmonary activity, can be obtained by taking the absolute value of the complex value obtained in previous step. This method can achieve a compact device by using a single channel receiver without any concern of imbalance factors. The demodulation circuit is much simpler than that of quadrature architecture.

Figure 39A:
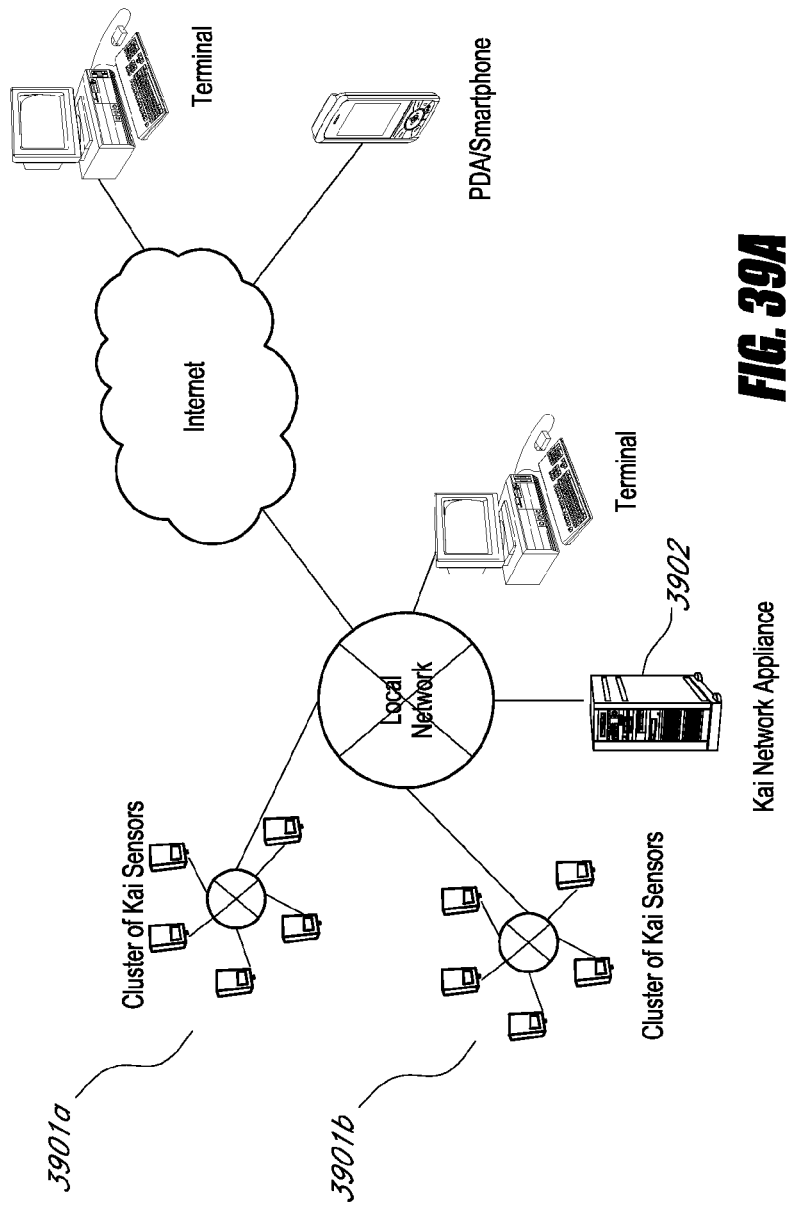

In various embodiments, a sensor network including many "thin" cardio pulmonary sensors works in conjunction with a centralized processing appliance. FIG. 39A describes a centralized topology such that many "thin" non-contact cardiopulmonary sensors form clusters 3901a and 3901b. The sensor clusters can be controlled by a network appliance 3902 where all processing will take place. Embodiments of this topology can be useful where sensors can be deployed in a dense area (i.e., one per hospital bed). In this case, rather than having each sensor be a full fledged cardio pulmonary monitor, each sensor will only possess minimal hardware, in some embodiments, only enough for data acquisition and forwarding a data stream. In various embodiments, each sensor will include a data acquisition module and a network module. In various embodiments, raw data will be streamed to the network appliance 3902 where further processing will be done. In various embodiments described above, the system can process the raw data internally. In various embodiments, processing will include the demodulation of the IQ channels, any DOA processing for tracking, respiration rate, etc. In various embodiments, the calculated statistics and processed data will then reside on the network appliance 3902 or they can be forwarded to an electronic health record server. A remote client can then access this data via a computer, mobile phone, PDA, etc. The data can also be viewed via a terminal locally or remotely in various embodiments. FIG. 39B shows an alternate embodiment of FIG. 39A showing the direction of information travel between the sensor cluster 3901a, the network appliance 3902 and various other components of the network.

The configuration above can also be useful in security applications where information needs to be processed at a centralized location. For example, in home security, the network appliance 3902 can be set to sound an alert if more than the set number of subjects is detected in the home. Another application for the various embodiment of the "thin sensor network" is homeland security, where many people need to be screened quickly such as at ports. A living database can be built and accessed in which biometrics information for certain individuals can be acquired, compared, and analyzed for security purposes."

Although certain preferred embodiments and examples are disclosed above, inventive subject matter extends beyond the specifically disclosed embodiments to other alternative embodiments and/or uses and to modifications and equivalents thereof. Thus, the scope of the claims appended hereto is not limited by any of the particular embodiments described. For example, in any method or process disclosed herein, the acts or operations of the method or process can be performed in any suitable sequence and are not necessarily limited to any particular disclosed sequence. Various operations can be described as multiple discrete operations in turn, in a manner that can be helpful in understanding certain embodiments; however, the order of description should not be construed to imply that these operations are order dependent. Additionally, the structures, systems, and/or devices described herein can be embodied as integrated components or as separate components. For purposes of comparing various embodiments, certain aspects and advantages of these embodiments are described. Not necessarily all such aspects or advantages are achieved by any particular embodiment. Thus, for example, various embodiments can be carried out in a manner that achieves or optimizes one advantage or group of advantages as taught herein without necessarily achieving other aspects or advantages as can also be taught or suggested herein. Thus, the invention is limited only by the claims that follow.

What is claimed is:

1. A method of sensing motion using a motion sensor, the method comprising:

generating electromagnetic radiation from a source of radiation, wherein the frequency of the electromagnetic radiation is in the radio frequency range;

transmitting the electromagnetic radiation towards a subject using one or more transmitters;

receiving a radiation scattered at least by the subject using one or more receivers;

extracting a Doppler shifted signal from the scattered radiation;

transforming the Doppler shifted signal to a digitized motion signal, said digitized motion signal comprising one or more frames, wherein the one or more frames comprise time sampled quadrature values of the digitized motion signal;

demodulating said one or more frames using a demodulation algorithm executed by a processor to isolate a signal corresponding to a physiological movement of the subject or a part of the subject;

analyzing the signal to obtain information corresponding to a non-cardiopulmonary motion or other signal interference;

processing the signal to obtain information corresponding to the physiological movement of the subject or a part of the subject, substantially separate from said non-cardiopulmonary motion or other signal interference; and communicating the information to an output system that is configured to perform an output action, wherein demodulating said one or more frames comprises:
- computing in the processor a first set of covariance matrices of a first subset of frames selected from said one or more frames and a second set of covariance matrices of a second subset of frames selected from said one or more frames;
- determining a first A-matrix, wherein the first A-matrix comprises a weighted sum of the first set of covariance matrices;
- determining a first parameter vector corresponding to a first primary value of the first A matrix;
- storing the first parameter vector in a memory device which is in communication with the processor
- determining a second A-matrix, wherein the second A-matrix comprises a weighted sum of the second set of covariance matrices;
- determining a second parameter vector corresponding to a second primary value of the second A-matrix;
- calculating an inner product of the first parameter vector and the second parameter vector;
- multiplying the second parameter vector by the sign of the inner product and
- projecting the values of the second frame on the second parameter vector to obtain the demodulated signal.

2. The method of claim 1, wherein the output system comprises a display unit configured to display the information.

3. The method of claim 1, wherein the output system comprises an audible system that is configured to report information or alerts audibly based on the information.

4. The method of claim 1, wherein the output system comprises an external medical system that is configured to perform an action based on the information.

5. The method of claim 1, wherein the demodulating algorithm comprises a linear demodulation algorithm, an arc-based demodulation algorithm or a non-linear demodulation algorithm.

6. The method of claim 1, wherein the information is displayed at least alphanumerically, graphically and as a waveform.

7. The method of claim 1, wherein the subject is a human being or an animal and the physiological movement comprises at least one of a motion due to respiratory activity of the subject, motion due to a cardiopulmonary activity of the subject, motion due to a cardiac activity of the subject, motion due to a cardiovascular activity of the subject, and motion due to a physical activity of the subject.

8. The method of claim 1, wherein the demodulating algorithm comprises projecting the signal in a complex plane on a best-fit line, projecting the signal in a complex plane on a principal eigenvector, or aligning a signal arc to a best-fit circle and using the best-fit circle parameters to extract the angular information from the signal arc.

9. The method of claim 1, wherein the first primary value comprises the largest eigenvalue of the first A-matrix and the first primary vector comprises an eigenvector corresponding to said eigenvalue.

10. The method of claim 1, wherein the second primary value comprises the largest eigenvalue of the second A-matrix and the second primary vector comprises an eigenvector corresponding to said eigenvalue.

11. The method of claim 1, wherein the source of radiation comprises an oscillator.

12. The method of claim 1, wherein said one or more transmitters comprise one or more antennae.

13. The method of claim 1, wherein said one or more receivers comprise one or more antennae or arrays of antennae.

14. The method of claim 1, wherein said transmitting and receiving antennae are the same antennae.

15. The method of claim 1, wherein the receiver comprises a homodyne receiver.

16. The method of claim 1, wherein the receiver comprises a heterodyne receiver.

17. The method of claim 1, wherein the receiver comprises a low-IF receiver configured to transform the Doppler-shifted signal to a Doppler-shifted signal comprising frequencies in a low intermediate frequency range, which is digitized and digitally transformed to a digitized motion signal.

18. The method of claim 1, wherein the processor comprises at least one of a digital signal processor, a microprocessor and a computer.

19. The method of claim 18, further comprising a controller configured to control the processor.

20. The method of claim 1, wherein the output system comprises a display unit configured to display information regarding the physiological movement of a user at a remote location.

21. The method of claim 1, wherein analyzing the signal comprises executing a non-cardiopulmonary motion detection algorithm configured to detect the absence of non-cardiopulmonary motion is detected if the signal comprises a single stable source or the presence of non-cardiopulmonary signal if at least the signal is unstable or at least the signal has multiple sources.

22. The method of claim 1, wherein analyzing the signal comprises executing a non-cardiopulmonary motion detection algorithm configured to detect the presence of non-cardiopulmonary motion if the signal indicates an excursion larger than the subject's maximum chest excursion from cardiopulmonary activity.

23. The method of claim 1, wherein analyzing the signal comprises executing a non-cardiopulmonary motion detection algorithm configured to detect the presence of non-cardiopulmonary motion if a best-fit vector related to linear demodulation changes significantly.

24. The method of claim 1, wherein analyzing the signal comprises executing a non-cardiopulmonary motion detection algorithm configured to detect the presence of non-cardiopulmonary motion if a RMS difference between a complex constellation of the signal and a best fit vector related to linear demodulation changes significantly.

25. The method of claim 1, wherein analyzing the signal comprises executing a non-cardiopulmonary motion detection algorithm configured to detect the presence of non-cardiopulmonary motion if an origin or radius of a best-fit circle related to arc-based demodulation changes significantly.

26. The method of claim 1, wherein analyzing the signal comprises executing a non-cardiopulmonary motion detection algorithm configured to detect the presence of non-cardiopulmonary motion if a RMS difference between a complex constellation of the signal and a best-fit circle related to arc-based demodulation changes significantly.

27. The method of claim 1, further comprising communicating information related to a signal quality of a cardiopulmonary motion signal, based on at least one of: a presence of non-cardiopulmonary motion or other signal interference, an absence of non-cardiopulmonary motion or other signal interference, a degree of non-cardiopulmonary motion or other signal interference, an assessment of the signal-to-noise ratio, a detection of low signal power, or a detection of signal clipping or other signal interference, to an output system configured to output the information.

28. A method of sensing motion using a motion sensor, the method comprising:
generating electromagnetic radiation from a source of radiation wherein the frequency of the electromagnetic radiation is in the radio frequency range;
transmitting the electromagnetic radiation towards a subject using one or more transmitters;
receiving a radiation scattered at least b the subject using one or more receivers;
extracting a Doppler shifted signal from the scattered radiation;
transforming the Doppler shifted signal to a digitized motion signal, said digitized motion signal comprising one or more frames, wherein the one or more frames comprise time sampled quadrature values of the digitized motion signal,
demodulating said one or more frames using a demodulation algorithm executed by a processor to isolate a signal corresponding to a physiological movement of the subject or a part of the subject:
analyzing the signal to obtain information corresponding to a non-cardiopulmonary motion or other signal interference, wherein analyzing the signal comprises executing a non-cardiopulmonary motion detection algorithm by a processor to detect the presence or absence of non-cardiopulmonary motion or other signal interference from the digitized motion signal, wherein the non-cardiopulmonary motion detection algorithm comprises a first mode which detects a presence of non-cardiopulmonary motion or other signal interference and a second mode which detects a cessation of non-cardiopulmonary motion or other signal interference;
processing the signal to obtain information corresponding to the physiological movement of the subject or a part of the subject, substantially separate from said non-cardiopulmonary motion or other signal interference; and
communicating the information to an output system that is configured to perform an output action.

29. The method of claim 28, wherein the first mode comprises:
selecting a first subset of frames from said one or more frames and computing in the processor a first set of covariance matrices of the first subset of frames filtered by a low-pass filter;
determining a first A-matrix wherein the A-matrix comprises a weighted sum of the first set of covariance matrices;
determining a first parameter vector corresponding to a first primary value of the first A matrix; and
storing the first parameter vector in a memory device which is in communication with the processor.

30. The method of claim 29, further comprising
computing in the processor a second set of covariance matrices of a second subset of frames filtered by the low-pass filter;
determining a second A-matrix, wherein the A-matrix comprises a weighted sum value of the second set of covariance matrices;
determining a first and a second primary value of the second A-matrix;
determining a second parameter vector corresponding to the first primary value of the second A-matrix;
calculating an inner product of the first parameter vector and the second parameter vector;
calculating a ratio of the first primary value of the second A matrix to the second primary value of the second A matrix;
calculating a first energy corresponding to the average energy of a third subset of frames filtered by a high-pass filter and a second energy corresponding to the average energy of a fourth subset of frames filtered by a high-pass filter; and
calculating a ratio of the second energy to the first energy.

31. The method of claim 29, wherein the first primary value of the first A-matrix comprises the largest eigenvalue of the first A-matrix and the first primary vector comprises an eigenvector corresponding to said eigenvalue.

32. The method of claim 30, wherein the first primary value of the second A-matrix comprises the largest eigenvalue of the second A-matrix, the second primary value of the second A-matrix comprises the second largest eigenvalue of the second A-matrix and the second primary vector of the second A-matrix comprises an eigenvector corresponding to said first primary value of the second A-matrix.

33. The method of claim 28, wherein the method further comprises:
computing in the processor a first condition, said first condition being the inner product is less than a first threshold value or the ratio of the first primary value of the second A-matrix to the second primary value of the second A-matrix is less than a second threshold value or the ratio of the second energy to the first energy is greater than a third threshold value,
wherein the presence of non-cardiopulmonary motion or other signal interference is detected if the first condition is true and the ratio of the second energy to the first energy is greater than a fourth threshold value.

34. The method of claim 33, wherein the first threshold value is approximately between 0.6 and 1.

35. The method of claim 33, wherein the second threshold value is approximately between 4 and 12.

36. The method of claim 33, wherein the third threshold value is approximately between 4 and 20.

37. The method of claim 33, wherein the fourth threshold value is approximately between 0.1 and 0.8.

38. The method of claim 28, wherein the second mode comprises:
selecting in the processor each and every consecutive subset of frames within a fifth subset of frames;
computing in the processor covariance matrices for every subset of frames;
computing in the processor an A'-matrix for each subset of frames, wherein the A'-matrix is the average of the covariance matrices in the subset;
computing in the processor a ρ- matrix, wherein each element of the ρ-matrix corresponds to a first primary vector of the corresponding A'-matrix;

computing the inner product of each pair of primary vectors in the ρ- matrix and selecting a minimum absolute value of the inner products;
calculating an A matrix which is the sum of the covariance matrices in a sixth subset of frames;
determining a first and a second primary value of the A-matrix; and
calculating the ratio of the first primary value of the A matrix to the second primary value of the A matrix.

39. The method of claim 38, wherein the method further comprises:
computing in the processor a second condition, said second condition being the minimum absolute value of the inner products is greater than a first threshold value and the ratio of the first primary value to the second primary value is greater than a second threshold value,
wherein the cessation of non-cardiopulmonary motion or other signal interference is detected if the second condition is true.

40. The method of claim 39, wherein the fifth threshold value is approximately between 0.6 and 1.

41. The method of claim 39, wherein the sixth threshold value is approximately between 4 and 12.

42. The method of claim 38, wherein the first primary vector comprises an eigenvector corresponding to the largest eigenvalue of the corresponding A'-matrix 43. The method of claim 38, wherein the first primary value comprises the largest eigenvalue of the A-matrix and the second primary value comprises the second largest eigenvalue of the A-matrix.

44. The method of claim 38, further comprising a retrospect step configured to determine a frame from said one or more frames when the non-cardiopulmonary motion substantially ceased.

45. The method of claim 44, wherein one or more frames preceding said frame are discarded.

46. The method of claim 29, wherein the weighted sum is an arithmetic mean.

* * * * *